United States Patent
Benjahad et al.

(10) Patent No.: US 9,168,245 B2
(45) Date of Patent: Oct. 27, 2015

(54) SELECTIVE PROTEIN KINASE INHIBITORS

(75) Inventors: Abdellah Benjahad, Champigny sur Marne (FR); Alain Moussy, Paris (FR); Emmanuel Chevenier, Les Ulis (FR); Willy Picoul, Lyons (FR); Anne Lermet, Paris (FR); Didier Pez, Nievroz (FR); Jason Martin, Fresnes (FR); Franck Sandrinelli, Balan (FR)

(73) Assignee: AB SCIENCE, Paris (FR)

( * ) Notice: Subject to any disclaimer, the term of this patent is extended or adjusted under 35 U.S.C. 154(b) by 0 days.

(21) Appl. No.: 14/234,935

(22) PCT Filed: Jul. 24, 2012

(86) PCT No.: PCT/EP2012/064539
§ 371 (c)(1),
(2), (4) Date: Jan. 24, 2014

(87) PCT Pub. No.: WO2013/014170
PCT Pub. Date: Jan. 31, 2013

(65) Prior Publication Data
US 2014/0179698 A1    Jun. 26, 2014

Related U.S. Application Data

(60) Provisional application No. 61/512,165, filed on Jul. 27, 2011.

(51) Int. Cl.
| | |
|---|---|
| C07D 413/14 | (2006.01) |
| C07D 417/14 | (2006.01) |
| C07D 413/10 | (2006.01) |
| C07D 417/10 | (2006.01) |
| A61K 31/535 | (2006.01) |
| A61K 31/42 | (2006.01) |
| A61K 31/445 | (2006.01) |
| A61K 31/497 | (2006.01) |
| A61K 31/505 | (2006.01) |
| A61K 31/422 | (2006.01) |
| A61K 31/454 | (2006.01) |
| A61K 31/4545 | (2006.01) |
| A61K 31/496 | (2006.01) |
| A61K 31/506 | (2006.01) |
| A61K 31/5377 | (2006.01) |

(52) U.S. Cl.
CPC ............ *A61K 31/422* (2013.01); *A61K 31/454* (2013.01); *A61K 31/4545* (2013.01); *A61K 31/496* (2013.01); *A61K 31/506* (2013.01); *A61K 31/5377* (2013.01); *C07D 413/10* (2013.01); *C07D 413/14* (2013.01); *C07D 417/10* (2013.01); *C07D 417/14* (2013.01)

(58) Field of Classification Search
USPC .................... 548/234, 193; 546/271.4, 269.7; 544/369, 137, 331, 364, 131
See application file for complete search history.

(56) References Cited

U.S. PATENT DOCUMENTS

| | | |
|---|---|---|
| 2004/0110810 A1 | 6/2004 | Ciufolini et al. |
| 2005/0239852 A1 | 10/2005 | Ciufolini et al. |
| 2007/0135368 A1 | 6/2007 | Knapp et al. |
| 2008/0242704 A1 | 10/2008 | Grierson et al. |
| 2008/0255141 A1 | 10/2008 | Ciufolini et al. |
| 2010/0298331 A1 | 11/2010 | Lee et al. |
| 2012/0053186 A1 | 3/2012 | Ciufolini et al. |
| 2012/0108616 A1 | 5/2012 | Grierson et al. |

FOREIGN PATENT DOCUMENTS

| | | |
|---|---|---|
| WO | WO 03/002105 | 1/2003 |
| WO | WO 03/002106 | 1/2003 |
| WO | WO 03/002107 | 1/2003 |

(Continued)

OTHER PUBLICATIONS

Kim et al.: "Inhibition of vascular endothelial growth factor-induced angiogenesis suppresses tumour growth in vivo"; Nature, vol. 362, Apr. 1993, pp. 841-844.

(Continued)

*Primary Examiner* — Nyeemah A Grazier
(74) *Attorney, Agent, or Firm* — Hamre, Schumann, Mueller & Larson, P.C.

(57) ABSTRACT

The present invention relates to compounds of formula I or pharmaceutically acceptable salts thereof:

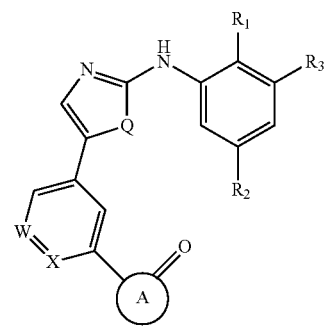

wherein $R_1$, $R_2$, $R_3$, A, Q, W and X are as defined in the description.

These compounds selectively modulate, regulate, and/or inhibit signal transduction mediated by certain native and/or mutant protein kinases implicated in a variety of human and animal diseases such as cell proliferative, metabolic, allergic, and degenerative disorders. More particularly, these compounds are potent and selective native and/or mutant c-kit inhibitors.

15 Claims, No Drawings

(56) References Cited

FOREIGN PATENT DOCUMENTS

| | | |
|---|---|---|
| WO | WO 03/002108 | 1/2003 |
| WO | WO 03/002109 | 1/2003 |
| WO | WO 03/002114 | 1/2003 |
| WO | WO 03/003004 | 1/2003 |
| WO | WO 03/003006 | 1/2003 |
| WO | WO 03/004006 | 1/2003 |
| WO | WO 03/004007 | 1/2003 |
| WO | WO 03/035049 | 5/2003 |
| WO | WO 03/035050 | 5/2003 |
| WO | WO 03/039550 | 5/2003 |
| WO | WO 2004/014903 | 2/2004 |
| WO | WO 2004/080462 | 9/2004 |
| WO | WO 2005/039586 | 5/2005 |
| WO | WO 2006/106437 | 10/2006 |
| WO | WO 2006/135721 | 12/2006 |
| WO | WO 2007/065939 | 6/2007 |
| WO | WO 2007/089069 | 8/2007 |
| WO | WO 2007/124369 | 11/2007 |
| WO | WO 2008/011080 | 1/2008 |
| WO | WO 2008/063888 | 5/2008 |
| WO | WO 2008/118391 | 10/2008 |
| WO | WO 2008/137794 | 11/2008 |
| WO | WO 2009/109071 | 9/2009 |
| WO | WO 2010/096395 | 8/2010 |

OTHER PUBLICATIONS

Broudy: "Stem Cell Factor and Hematopoiesis"; Blood 1997, 90: pp. 1345-1364.

Beghini et al.: "C-kit *mutations in core binding factor leukemias*"; Blood 2000, 95: pp. 726-728.

Longley et al.: "Classes of c-*KIT* activating mutations: proposed mechanisms of action and implications for disease classification and therapy"; PERGAMON, Leukemia Research 25 (2001), pp. 571-576.

Longley et al.: "Somatic c-*KIT* activating mutation in urticaria pigmentosa and aggressive mastocytosis: establishment of clonality in a human mast cell neoplasm"; Nature Genetics vol. 12, Mar. 1996, pp. 312-314.

Van Leusen et al.: "A Novel and Efficient Synthesis of Oxazoles from Tosylmethylisocyanide and Carbonyl Compounds"; Tetrahedron Letters, No. 23, 1972, pp. 2369-2372.

Frey et al.: "Practical routes toward the synthesis of 2-halo- and 2-alkylamino-4-pyridinecarboxaldehydes"; Tetrahedron Letters, 42 (2001), pp. 6815-6818.

Iwao et al.: "Design and Synthesis of Lamellarin D Analogues Targeting Topoisomerase I"; J. Org. Chem. 2009, 74, pp. 8143-8153.

Zhao et al.: "A new facile synthesis of 2-aminothiazole-5-carboxylates"; Tetrahedron Letters 42 (2001), pp. 2101-2102.

Beslu et al.: "Phosphatidylinositol-3' Kinase Is Not Required for Mitogenesis or Internalization of the Flt3/Flk2 Receptor Tyrosine Kinase"; The Journal of Biological Chemistry, vol. 271, No. 33, Aug. 1996, pp. 20075-20081.

SELECTIVE PROTEIN KINASE INHIBITORS

The present invention relates to compounds of formula I or pharmaceutically acceptable salts thereof, that selectively modulate, regulate, and/or inhibit signal transduction mediated by certain native and/or mutant protein kinases implicated in a variety of human and animal diseases such as cell proliferative, metabolic, allergic, and degenerative disorders. More particularly, these compounds are potent and selective native and/or mutant c-kit inhibitors.

BACKGROUND OF THE INVENTION

Protein Kinases are receptor type or non-receptor type proteins, which transfer the terminal phosphate of ATP to aminoacid residues, such as tyrosine, threonine, serine residues, of proteins, thereby activating or inactivating signal transduction pathways. These proteins are known to be involved in many cellular mechanisms, which in case of disruption, lead to disorders such as abnormal cell proliferation and migration as well as inflammation.

As of today, there are over 500 known Protein kinases. Included are the well-known Ab1, Akt1, Akt2, Akt3, ALK, Alk5, A-Raf, Axl, B-Raf, Brk, Btk, Cdk2, Cdk4, CdkS, Cdk6, CHK1, c-Raf-1, Csk, EGFR, EphA1, EphA2, EphB2, EphB4, Erk2, Fak, Fes, Fer, FGFR1, FGFR2, FGFR3, FGFR4, Flt-3, Fms, Frk, Fyn, Gsk3α, Gsk β, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mer, MNK1, MLK1, mTOR, p38, PDGFRα, PDGFRβ, PDPK1, PI3Kα, PI3Kβ, PI3Kγ, PI3Kδ, Pim1, Pim2, Pim3, PKC alpha, PKC beta, PKC theta, Plk1, Pyk2, Ret, ROCK1, ROCK2, RON, Src, Stk6, Syk, TEC, Tie2, TrkA, TrkB, Tyk2, VEGFR1/Flt-1, VEGFR2/Kdr, VEGFR3/Flt-4, Yes, and Zap70.

Abnormal cellular responses triggered by protein kinase-mediated events produce a variety of diseases. These include autoimmune diseases, inflammatory diseases, neurological and neurodegenerative diseases, cancer, cardiovascular diseases, allergies and asthma, Alzheimer's disease and hormone-related diseases.

Tyrosine kinases are receptor type or non-receptor type proteins, which transfer the terminal phosphate of ATP to tyrosine residues of proteins thereby activating or inactivating signal transduction pathways. These proteins are known to be involved in many cellular mechanisms, which in case of disruption, lead to disorders such as abnormal cell proliferation and migration as well as inflammation.

As of today, there are about 58 known receptor tyrosine kinases. Included are the well-known VEGF receptors (Kim et al., Nature 362, pp. 841-844, 1993), PDGF receptors, c-kit, Flt-3 and the FLK family. These receptors can transmit signals to other tyrosine kinases including Src, Raf, Frk, Btk, Csk, Abl, Fes/Fps, Fak, Jak, Ack, etc.

Among tyrosine kinase receptors, c-kit is of special interest. Indeed, c-kit is a key receptor activating mast cells, which have proved to be directly or indirectly implicated in numerous pathologies for which the Applicant filed WO 03/004007, WO 03/004006, WO 03/003006, WO 03/003004, WO 03/002114, WO 03/002109, WO 03/002108, WO 03/002107, WO 03/002106, WO 03/002105, WO 03/039550, WO 03/035050, WO 03/035049, U.S. 60/359,652, U.S. 60/359,651 and U.S. 60/449,861, WO 04/080462, WO 05/039586, WO 06/135721, WO 07/089,069, WO 07/124,369, WO 08/137,794, WO 08/063,888, WO 08/011,080, WO 09/109,071, WO 10/096,395.

It was found that mast cells present in tissues of patients are implicated in or contribute to the genesis of diseases such as autoimmune diseases (rheumatoid arthritis, inflammatory bowel diseases (IBD)), allergic diseases, bone loss, cancers such as solid tumors, leukaemia and GIST, tumor angiogenesis, inflammatory diseases, interstitial cystitis, mastocytosis, graft-versus-host diseases, infection diseases, metabolic disorders, fibrosis, diabetes and CNS diseases. In these diseases, it has been shown that mast cells participate in the destruction of tissues by releasing a cocktail of different proteases and mediators such as histamine, neutral proteases, lipid-derived mediators (prostaglandins, thromboxanes and leukotrienes), and various cytokines (IL-1, IL-2, IL-3, IL-4, IL-5, IL-6, IL-8, TNF-α, GM-CSF, MIP-1a, MIP-1b, MIP-2 and IFN-γ).

The c-kit receptor also can be constitutively activated by mutations leading to abnormal cell proliferation and development of diseases such as mastocytosis (D816V mutation) and various cancers such as GIST (c-kitΔ27, a juxtamembrane deletion).

Sixty to 70% of patients presenting with AML have blasts which express c-kit, the receptor for stem cell factor (SCF) (Broudy, 1997). SCF promotes growth of hematopoietic progenitors, and act as a survival factor for AML blasts. In some cases (1 to 2%) of AML, a mutation in a conserved residue of the kinase domain (Kit816) resulting in constitutive activation of c-kit has been described (Beghini et al., 2000; Longley et al., 2001). This gain of function mutation (Asp to Val/Tyr substitution) has been identified in mast cell leukemic cell lines and in samples derived from patients with mastocytosis (Longley et al., 1996). Preliminary results show that this mutation is expressed in most cases of systemic mastocytosis ([~60%], P Dubreuil, AFIRMM, study in progress on about 300 patients).

GOAL OF THE INVENTION

The main objective underlying the present invention is therefore to find potent and selective compounds capable of inhibiting wild type and/or mutated protein kinase, in particular wild type and/or mutated tyrosine kinase, and more particularly wild type and/or mutated c-kit.

In connection with the present invention, we have discovered that compounds of formula I are potent and selective inhibitors of certain protein kinases such as wild type and/or mutated c-kit. These compounds are good candidates for treating diseases such as autoimmunes diseases, inflammatory diseases, cancers and mastocytosis.

DESCRIPTION OF THE INVENTION

Compounds of the present invention were screened for their ability to inhibit a protein kinase and in particular a tyrosine kinase, and more particularly c-Kit and/or mutant c-Kit (especially c-Kit D816V).

In a first embodiment, the invention is aimed at compounds of formula I, which may represent either free base forms of the substances or pharmaceutically acceptable salts thereof:

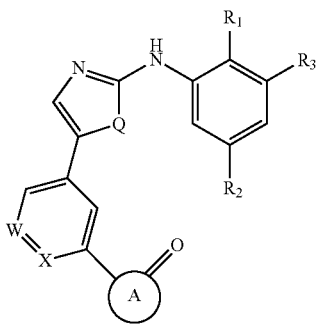

Wherein

A is five or six member heterocycle ring;

R₁ is hydrogen, halogen (selected from F, Cl, Br or I), an alkyl group containing from 1 to 10 carbon atoms, a thioalkyl group or an alkoxy group;

R₂ is halogen (selected from F, Cl, Br or I), an aryl group, an haloalkyl or alkyl group containing from 1 to 10 carbon atoms optionally substituted with at least one heteroatom, notably sulfur, oxygen or nitrogen, optionally substituted with an haloalkyl or alkyl group containing from 1 to 10 carbon atoms optionally substituted with a solubilising group; as well as an alkoxy group, a thioalkyl group or an haloalkoxy group; as well as a —COOR, —NRR', —NR—CO—R', —CONRR', —SO₂NRR' or —NR—SO₂—R' group wherein R and R' are each independently selected from hydrogen, aryl group, heteroaryl group, alkyl group optionally substituted with at least one heteroatom, notably oxygen or nitrogen, optionally substituted with an alkyl group containing from 1 to 10 carbon atoms optionally substituted with a solubilising group; as well as a heterocycle group or a solubilising group;

R₃ is hydrogen, halogen (selected from F, Cl, Br or I), cyano, an alkyl group containing from 1 to 10 carbon atoms or an alkoxy group; as well as CF₃, —NRR', —NR—CO—R', —CONRR', —SO₂NRR' group wherein R and R' are each independently selected from hydrogen, alkyl group optionally substituted with at least one heteroatom, notably sulfur, oxygen or nitrogen, optionally substituted with an alkyl group containing from 1 to 10 carbon atoms optionally substituted with a solubilising group; as well as a heterocycle group or a solubilising group;

Q is O or S;

W is N or CR₄;

R₄ is hydrogen, cyano, CF₃, halogen (selected from F, Cl, Br or I), a thioalkyl group, an alkyl group containing from 1 to 10 carbon atoms optionally substituted with at least one heteroatom, notably sulfur, oxygen or nitrogen, optionally substituted with an alkyl group containing from 1 to 10 carbon atoms optionally substituted with a solubilising group; as well as an alkoxy group or an haloalkoxy group, a solubilising group, an heterocycle, —CO—NRR', —SO₂—NRR', —NRR', —NR—CO—R' or —NR—SO₂R' group wherein R and R' are each independently selected from hydrogen, alkyl group optionally substituted with at least one heteroatom, notably oxygen or nitrogen, optionally substituted with an alkyl group containing from 1 to 10 carbon atoms optionally substituted with a solubilising group or heterocycle group;

X is N or CR₅;

R₅ is hydrogen, cyano, halogen (selected from F, Cl, Br or I), an alkyl group containing from 1 to 10 carbon atoms, an alkoxy group, —CO—OR, —CO—NRR' group wherein R and R' are each independently selected from hydrogen, alkyl group optionally substituted with at least one heteroatom, notably sulfur, oxygen or nitrogen, optionally substituted with an alkyl group containing from 1 to 10 carbon atoms optionally substituted with a solubilising group or heterocycle group.

In one embodiment, the invention relates to compounds of formula I or pharmaceutically acceptable salts thereof, wherein R₂ is halogen (selected from F, Cl, Br or I), an aryl group, an haloalkyl or alkyl group containing from 1 to 10 carbon atoms optionally substituted with at least one heteroatom, notably sulfur, oxygen or nitrogen, optionally substituted with an haloalkyl or alkyl group containing from 1 to 10 carbon atoms optionally substituted with a solubilising group; as well as an alkoxy group, a thioalkyl group or an haloalkoxy group; as well as a —NRR', —NR—CO—R', —CONRR', —SO₂NRR' or —NR—SO₂—R' group wherein R and R' are each independently selected from hydrogen, alkyl group optionally substituted with at least one heteroatom, notably oxygen or nitrogen, optionally substituted with an alkyl group containing from 1 to 10 carbon atoms optionally substituted with a solubilising group; as well as a heterocycle group or a solubilising group.

Unless otherwise specified, the below terms used herein are defined as follows.

As used herein, the term "alkyl" means a saturated straight chain or branched non-cyclic hydrocarbon having from 1 to 10 carbon atoms, preferably from 1 to 6 carbon atoms, more preferably from 1 to 4 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be optionally substituted with one or more substituents. Alkyl groups included in compounds of this invention may be optionally substituted with a solubilising group.

As used herein, the term "aryl" means a monocyclic or polycyclic-aromatic radical comprising carbon and hydrogen atoms. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents. Aryl groups included in compounds of this invention may be optionally substituted with a solubilising group.

As used herein, the term "alkoxy" refers to an alkyl group as defined above which is attached to another moiety by an oxygen atom. Examples of alkoxy groups include methoxy, isopropoxy, ethoxy, tert-butoxy, and the like. Alkoxy groups may be optionally substituted with one or more substituents. Alkoxy groups included in compounds of this invention may be optionally substituted with a solubilising group.

As used herein, the term "thioalkyl" refers to an alkyl group as defined above which is attached to another moiety by a sulfur atom. Thioalkyl groups may be optionally substituted with one or more substituents. Thioalkyl groups included in compounds of this invention may be optionally substituted with a solubilising group.

As used herein, the term "heterocycle" refers collectively to heterocycloalkyl groups and heteroaryl groups.

As used herein, the term "heterocycloalkyl" means a monocyclic or polycyclic group having at least one heteroatom selected from O, N or S, and which has from 2 to 11 carbon atoms, which may be saturated or unsaturated, but is not aromatic. Examples of heterocycloalkyl groups including (but not limited to): piperidinyl, piperazinyl, 2-oxopiperazinyl, 2-oxopiperidinyl, 2-oxopyrrolidinyl, 4-piperidonyl, pyrrolidinyl, hydantoinyl, valerolactamyl, oxiranyl, oxetanyl, tetrahydropyranyl, tetrahydrothiopyranyl, tetrahydropyrindinyl, tetrahydropyrimidinyl, tetrahydrothiopyranyl sulfone, tetrahydrothiopyranyl sulfoxide, morpholinyl, thiomorpholinyl, thiomorpholinyl sulfoxide, thiomorpholinyl sulfone, 1,3-dioxolane, tetrahydrofuranyl, dihydrofuranyl-2-one, tetrahydrothienyl, and tetrahydro-1,1-dioxothienyl. Typically, monocyclic heterocycloalkyl groups have 3 to 7 members. Preferred 3 to 7 membered monocyclic heterocycloalkyl groups are those having 5 or 6 ring atoms. A heteroatom may be substituted with a protecting group known to those of ordinary skill in the art, for example, the hydrogen on a nitrogen may be substituted with a tert-butoxycarbonyl group. Furthermore, heterocycloalkyl groups may be optionally substituted with one or more substituents. In addition, the point of attachment of a heterocyclic ring to another group may be at either a carbon atom or a heteroatom of a heterocyclic ring. Only stable isomers of such substituted heterocyclic groups are contemplated in this definition.

As used herein, the term "heteroaryl" or like terms means a monocyclic or polycyclic heteroaromatic ring comprising carbon atom ring members and one or more heteroatom ring members (such as, for example, oxygen, sulfur or nitrogen). Typically, a heteroaryl group has from 1 to about 5 heteroatom ring members and from 1 to about 14 carbon atom ring members. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzo(b)thienyl. A heteroatom may be substituted with a protecting group known to those of ordinary skill in the art, for example, the hydrogen on nitrogen may be substituted with a tert-butoxycarbonyl group. Heteroaryl groups may be optionally substituted with one or more substituents. In addition, nitrogen or sulfur heteroatom ring members may be oxidized. In one embodiment, the heteroaromatic ring is selected from 5-8 membered monocyclic heteroaryl rings. The point of attachment of a heteroaromatic or heteroaryl ring to another group may be at either a carbon atom or a heteroatom of the heteroaromatic or heteroaryl rings.

As used herein, the term "haloalkyl" means an alkyl group as defined above in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like. Haloalkyl groups may be optionally substituted with one or more substituents. Haloalkyl groups included in compounds of this invention may be optionally substituted with a solubilising group.

As used herein, the term "haloalkoxy" means an alkoxy group as defined above in which one or more (including all) the hydrogen radicals are replaced by a halo group, wherein each halo group is independently selected from —F, —Cl, —Br, and —I. Representative haloalkoxy groups include trifluoromethoxy, bromomethoxy, 1,2-dichloroethoxy, 4-iodobutoxy, 2-fluoropentoxy, and the like. Haloalkoxy groups may be optionally substituted with one or more substituents. Haloalkoxy groups included in compounds of this invention may be optionally substituted with a solubilising group.

As used herein the term "substituent" or "substituted" means that a hydrogen radical on a compound or group is replaced with any desired group that is substantially stable to reaction conditions in an unprotected form or when protected using a protecting group. Examples of preferred substituents are those found in the exemplary compounds and embodiments disclosed herein, as well as halogen; alkyl as defined above; hydroxy; alkoxy as defined above; nitro; thiol; thioalkyl as defined above; cyano; haloalkyl as defined above; haloalkoxy as defined above; cycloalkyl, which may be monocyclic or fused or non-fused polycyclic (e.g., cyclopropyl, cyclobutyl, cyclopentyl, or cyclohexyl) or a solubilising group.

As used herein, the term "solubilising" group means a group which has a hydrophilic character sufficient to improve or increase the water-solubility of the compound in which it is included, as compared to an analog compound that does not include the group. The hydrophilic character can be achieved by any means, such as by the inclusion of functional groups that ionize under the conditions of use to form charged moieties (e.g., carboxylic acids, sulfonic acids, phosphoric acids, amines, etc.); groups that include permanent charges (e.g., quaternary ammonium groups); and/or heteroatoms or heteroatomic groups (e.g., O, S, N, NH, N—$(CH_2)_zR$, N—$(CH_2)_z$—$C(O)R$, N—$(CH_2)_z$—$C(O)OR$, N—$(CH_2)_z$—$S(O)_2R$, N—$(CH_2)_z$—$S(O)_2OR$, N—$(CH_2)_z$—$C(O)NRR'$, where z is an integer ranging from 0 to 6, R and R' each independently are selected from hydrogen, an alkyl group containing from 1 to 10 carbon atoms and optionally substituted with one or more hetereoatoms such as halogen (selected from F, Cl, Br or I), oxygen, and nitrogen; as well as alkoxy group containing from 1 to 10 carbon atoms; as well as aryl and heteroaryl group.

In some embodiments, the solubilising group is a heterocycloalkyl that optionally includes from 1 to 5 substituents, which may themselves be solubilising groups. In a specific embodiment, the solubilising group is of the formula:

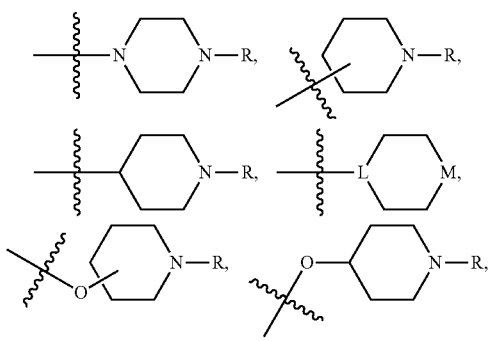

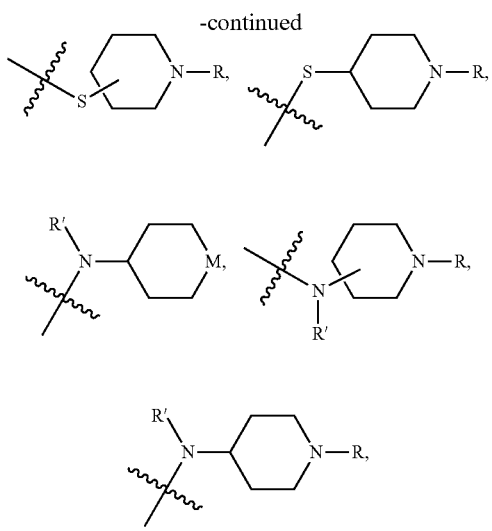

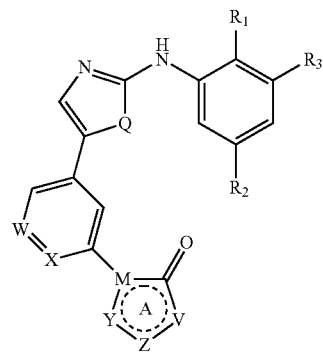

where L is selected from the group consisting of CH and N, M is selected from the group consisting of —CH(R)—, —CH$_2$—, —O—, —S—, —NH, —N(—(CH$_2$)$_z$—R)—, —N(—(CH$_2$)$_z$—C(O)R)—, —N(—(CH$_2$)$_z$—C(O)OR)—, —N(—(CH$_2$)$_z$—S(O)$_2$R)—, —N(—(CH$_2$)$_z$—S(O)$_2$OR)— and —N(—(CH$_2$)$_z$—C(O)NRR')—, where z is an integer ranging from 0 to 6, R and R' each independently are selected from hydrogen, an alkyl group containing from 1 to 10 carbon atoms and optionally substituted with one or more hetereoatoms such as halogen (selected from F, Cl, Br or I), oxygen, and nitrogen; as well as alkoxy group containing from 1 to 10 carbon atoms, NRR' group wherein R and R' are each independently selected from hydrogen, alkyl group as defined above optionally substituted with at least one heteroatom, notably oxygen or nitrogen optionally substituted with an alkyl group containing from 1 to 10 carbons optionally substituted; as well as aryl and heteroaryl group, with the proviso that L and M are not both simultaneously CH and CH$_2$, respectively.

In another specific embodiment, the solubilising group is selected from the group consisting of morpholinyl, piperidinyl, N—(C$_1$-C$_6$)alkyl piperidinyl, in particular N-methyl piperidinyl and N-ethyl piperidinyl, N-(4-piperidinyl)piperidinyl, 4-(1-piperidinyl)piperidinyl, 1-pyrrolidinylpiperidinyl, 4-morpholinopiperidinyl, 4-(N-methyl-1-piperazinyl)piperidinyl, piperazinyl, N—(C$_1$-C$_6$)alkylpiperazinyl, in particular N-methylpiperazinyl and N-ethyl piperazinyl, N—(C$_3$-C$_6$)cycloalkyl piperazinyl, in particular N-cyclohexyl piperazinyl, pyrrolidinyl, N—(C$_1$-C$_6$)alkyl pyrrolidinyl, in particular N-methyl pyrrolidinyl and N-ethyl pyrrolidinyl, diazepinyl, N—(C$_1$-C$_6$)alkyl azepinyl, in particular N-methyl azepinyl and N-ethyl azepinyl, homopiperazinyl, N-methyl homopiperazinyl, N-ethyl homopiperazinyl, imidazolyl, and the like.

Among the compounds of formula I in which ring A is depicted above, the present invention is directed to compounds of the following formula II:

Wherein:

A ring is a five member heterocycle ring;

$R_1$ is hydrogen, halogen (selected from F, Cl, Br or I), an alkyl group containing from 1 to 10 carbon atoms or an alkoxy group;

$R_2$ is halogen (selected from F, Cl, Br or I), an aryl group, an haloalkyl or alkyl group containing from 1 to 10 carbon atoms optionally substituted with at least one heteroatom, notably oxygen or nitrogen, optionally substituted with an haloalkyl or alkyl group containing from 1 to 10 carbon atoms optionally substituted with a solubilising group; as well as an alkoxy group or an haloalkoxy group; as well as a —COOR, —NRR', —NR—CO—R', —CONRR' or —NR—SO$_2$—R' group wherein R and R' are each independently selected from hydrogen, aryl group, heteroaryl group, alkyl group optionally substituted with at least one heteroatom, notably oxygen or nitrogen, optionally substituted with an alkyl group containing from 1 to 10 carbon atoms optionally substituted with a solubilising group; as well as a heterocycle group or a solubilising group;

$R_3$ is hydrogen, halogen (selected from F, Cl, Br or I), cyano, an alkyl group containing from 1 to 10 carbon atoms or an alkoxy group; as well as CF$_3$, —NRR', —NR—CO—R', —CONRR' group wherein R and R' are each independently selected from hydrogen, alkyl group optionally substituted with at least one heteroatom, notably oxygen or nitrogen, optionally substituted with an alkyl group containing from 1 to 10 carbon atoms optionally substituted with a solubilising group; as well as a heterocycle group or a solubilising group;

Q is O or S;

W is N or CR$_4$;

$R_4$ is hydrogen, cyano, CF$_3$, halogen (selected from F, Cl, Br or I), an alkyl group containing from 1 to 10 carbon atoms optionally substituted with at least one heteroatom, notably oxygen or nitrogen, optionally substituted with an alkyl group containing from 1 to 10 carbon atoms optionally substituted with a solubilising group; as well as an alkoxy group or an haloalkoxy group, a solubilising group, an heterocycle, —CO—NRR', SO$_2$—NRR', —NRR', —NR—CO—R' or —NR—SO$_2$R' group wherein R and R' are each independently selected from hydrogen, alkyl group optionally substituted with at least one heteroatom, notably oxygen or nitrogen, optionally substituted with an alkyl group containing from 1 to 10 carbon atoms optionally substituted with a solubilising group or heterocycle group;

X is N or CR$_5$;

$R_5$ is hydrogen, cyano, halogen (selected from F, Cl, Br or I), an alkyl group containing from 1 to 10 carbon atoms, an alkoxy group, —CO—OR, —CO—NRR' group wherein R and R' are each independently selected from hydrogen, alkyl group optionally substituted with at least one heteroatom, notably oxygen or nitrogen, optionally substituted with an alkyl group containing from 1 to 10 carbon atoms optionally substituted with a solubilising group or heterocycle group;

M is C or N;
V is $CH_2$, $CR_2$ or $NR_2$;
$R_7$ is hydrogen or an alkyl group containing from 1 to 10 carbon atoms optionally substituted with a solubilising group or heterocycle group;
Y is N, $CR_8$ or $CR_8R_9$;
Z is N, $NR_B$, $CR_8$ or $CR_8R_9$;
$R_8$ is hydrogen, an alkyl group containing from 1 to 10 carbon atoms or an alkoxy group;
$R_9$ is hydrogen or an alkyl group containing from 1 to 10 carbon atoms.

In one embodiment, the invention relates to compounds of formula II or pharmaceutically acceptable salts thereof, wherein $R_2$ is halogen (selected from F, Cl, Br or I), an aryl group, an haloalkyl or alkyl group containing from 1 to 10 carbon atoms optionally substituted with at least one heteroatom, notably oxygen or nitrogen, optionally substituted with an haloalkyl or alkyl group containing from 1 to 10 carbon atoms optionally substituted with a solubilising group; as well as an alkoxy group or an haloalkoxy group; as well as a —NRR', —NR—CO—R', —CONRR' or —NR—$SO_2$—R' group wherein R and R' are each independently selected from hydrogen, alkyl group optionally substituted with at least one heteroatom, notably oxygen or nitrogen, optionally substituted with an alkyl group containing from 1 to 10 carbon atoms optionally substituted with a solubilising group; as well as a heterocycle group or a solubilising group.

Examples of preferred compounds of the above formula are depicted in table 1 below:

TABLE 1

| Ex # | Chemical structure | Name | $^1$H NMR/LCMS |
|---|---|---|---|
| 001 | 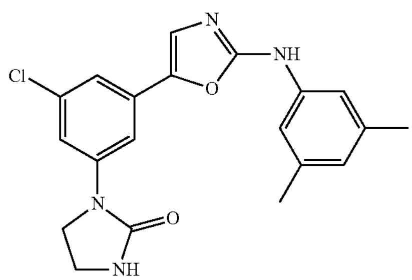 [SMILES: Cc1cc(C)cc(Nc2ncc(-c3cc(Cl)cc(N4CCNC4=O)c3)o2)c1] | 1-{3-Chloro-5-[2-(3,5-dimethyl-phenylamino)-oxazol-5-yl]-phenyl}-imidazolidin-2-one | (300 MHz, DMSO-$d_6$) δ 10.26 (br s, 1H), 7.70 (br s, 1H), 7.60-7.53 (d, J = 5.3 Hz, 2H), 7.38-7.16 (m, 4H), 6.61 (br s, 1H), 3.96-3.82 (m, 2H), 3.52-3.40 (m, 2H), 2.26 (s, 6H). (APCI+) m/z 383 (M + H)$^+$ Retention time = 3.76 min (method 2) |
| 002 | 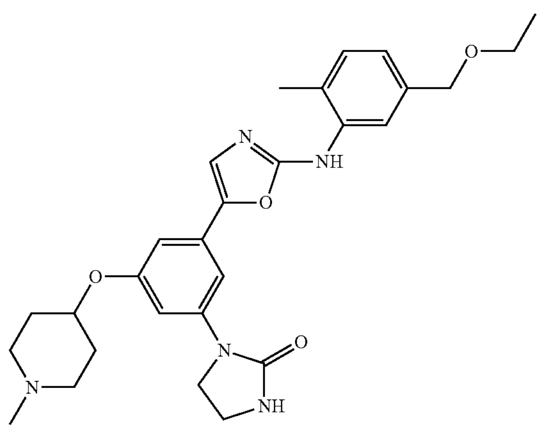 [SMILES: CCOCc1ccc(C)c(Nc2ncc(-c3cc(OC4CCN(C)CC4)cc(N4CCNC4=O)c3)o2)c1] | 1-[3-[2-((5-Ethoxymethyl)-2-methyl-phenylamino)-oxazol-5-yl]-5-(1-methyl-piperidin-4-yloxy)-phenyl]-imidazolidin-2-one | (300 MHz, DMSO-$d_6$) δ 9.26 (s, 1H), 7.82 (s, 1H), 7.42 (s, 1H), 7.29 (s, 1H), 7.20-7.12 (m, 1H), 7.14 (s, 1H), 7.02 (s, 1H), 6.93 (d, J = 7.6 Hz, 1H), 6.80 (s, 1H), 4.50-435 (m, 1H), 4.41 (s, 3H), 3.96-3.76 (m, 2H), 3.50-3.20 (m, 4H), 2.60-2.50 (m, 2H), 2.27 (s, 3H), 2.20-2.10 (m, 2H), 2.18 (s, 3H), 2.00-1.85 (m, 2H), 1.70-1.55 (m, 2H), 1.14 (t, J = 7.0 Hz, 3H). (APCI+) m/z 506 (M + H)$^+$ Retention time = 2.36 min (method 2) |
| 003 | 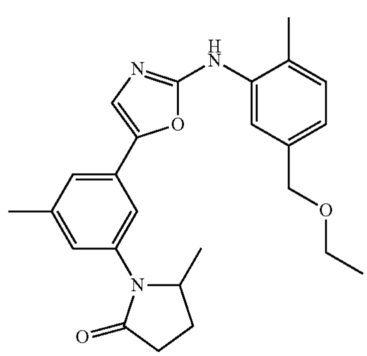 [SMILES: CCOCc1ccc(C)c(Nc2ncc(-c3cc(C)cc(N4C(=O)CCC4C)c3)o2)c1] | 1-{3-[2-((5-Ethoxymethyl)-2-methyl-phenylamino)-oxazol-5-yl]-5-methyl-phenyl}-5-methyl-pyrrolidin-2-one | $^1$H NMR (300 MHz, CDCl$_3$) ä 7.92 (s, 1H), 7.33 (s, 1H), 7.18-7.09 (m, 3H), 7.05-6.95 (m, 2H), 4.50 (s, 2H), 4.28 (dq, J = 12.2, 6.1 Hz, 1H), 3.58-3.47 (m, 2H), 2.69-2.43 (m, 2H), 2.34 (s, 3H), 2.30 (s, 3H), 1.81-1.65 (m, 2H), 1.27-1.16 (m, 6H). (APCI+) m/z 421 (M + H)$^+$ Retention time = 3.13 min (method 2) |

TABLE 1-continued

| Ex # | Chemical structure | Name | $^1$H NMR/LCMS |
|---|---|---|---|
| 004 | 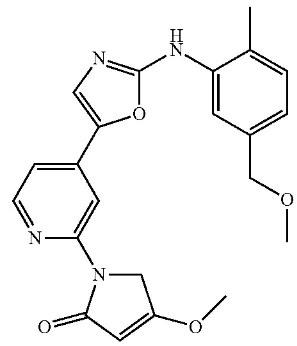 [SMILES: COCc1ccc(C)c(Nc2ncc(-c3ccnc(N4CC(OC)=CC4=O)c3)o2)c1] | 4-Methoxy-1-{4-[2-((5-methoxymethyl)-2-methyl-phenylamino)-oxazol-5-yl]-pyridin-2-yl}-1,5-dihydro-pyrrol-2-one | (300 MHz, DMSO-d$_6$) δ 9.63 (br s, 1H), 8.43 (s, 1H), 8.27 (dd, J = 5.4, 0.6 Hz, 1H), 7.79 (d, J = 1.3 Hz, 1H), 7.71 (s, 1H), 7.26 (dd, J = 5.4, 1.4 Hz, 1H), 7.19 (d, J = 7.7 Hz, 1H), 6.97 (dd, J = 7.7, 1.4 Hz, 1H), 5.41 (s, 1H), 4.55 (s, 2H), 4.39 (s, 2H), 3.88 (s, 3H), 3.29 (s, 3H), 2.30 (s, 3H). (APCI+) m/z 407 (M + H)$^+$ Retention time = 3.13 mins (method 2) |
| 005 | 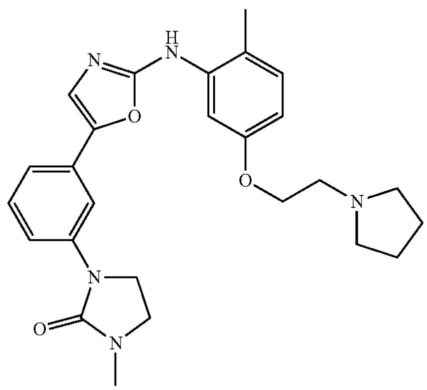 [SMILES: Cc1ccc(OCCN2CCCC2)cc1Nc1ncc(-c2cccc(N3CCN(C)C3=O)c2)o1] | 1-Methyl-3-(3-{2-[2-methyl-5-(2-pyrrolidin-1-yl-ethoxy)-phenylamino]-oxazol-5-yl}-phenyl)-imidazolidin-2-one | $^1$H NMR (300 MHz, CDCl$_3$) ä 8.09 (d, J = 1.1 Hz, 1H), 8.00 (d, J = 2.5 Hz, 1H), 7.51 (dd, J = 4.1, 1.3 Hz, 2H), 7.42-7.36 (m, 1H), 7.34 (s, 1H), 7.24 (d, J = 8.4 Hz, 1H), 6.92 (s, 1H), 6.74 (dd, J = 8.3, 2.6 Hz, 1H), 4.34 (t, J = 6.1 Hz, 2H), 4.04 (dd, J = 9.0, 6.8 Hz, 2H), 3.73-3.67 (m, 2H), 3.15-3.02 (m, 5H), 2.87-2.77 (m, 4H), 2.45 (s, 3H), 2.03-1.93 (m, 3H). (ES+) m/z 463 (M + H)$^+$ Retention time = 2.20 min (method 2) |
| 006 | 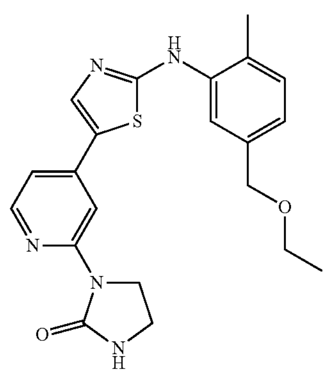 | 1-{4-[2-((5-Ethoxymethyl)-2-methyl-phenylamino)-thiazol-5-yl]-pyridin-2-yl}-imidazolidin-2-one | (300 MHz, DMSO-d$_6$) δ 9.64 (s, 1H), 8.20-8.15 (m, 2H), 7.84 (s, 1H), 7.75 (s, 1H), 7.28-7-18 (m, 3H), 7.02 (d, J = 7.8 Hz, 1H), 4.42 (s, 2H), 4.03-3.94 (m, 2H), 3.47 (q, J = 7.0 Hz, 2H), 3.39 (t, J = 8.0 Hz, 2H), 2.26 (s, 3H), 1.15 (t, J = 7.0 Hz, 3H). (APCI+) m/z 410 (M + H)$^+$ Retention time = 2.69 min (method 2) |
| 007 | 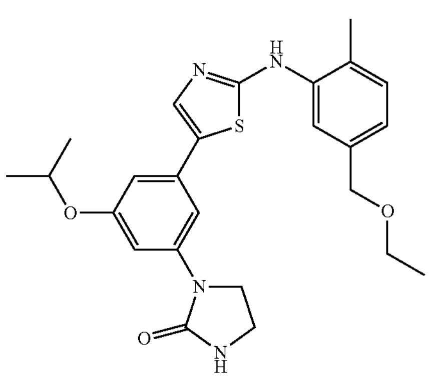 | 1-{3-[2-((5-Ethoxymethyl)-2-methyl-phenylamino)-thiazol-5-yl]-5-isopropoxy-phenyl}-imidazolidin-2-one | (300 MHz, DMSO-d$_6$) δ 9.37 (s, 1H), 7.78 (s, 1H), 7.61 (s, 1H), 7.22-7.16 (m, 2H), 7.04 (s, 1H), 7.03-6.95 (m, 3H), 6.70 (s, 1H), 4.63 (m, 1H), 4.41 (s, 2H), 3.92-3.79 (m, 2H), 3.47 (q, J = 7.0 Hz, 2H), 3.43-3.35 (m, 2H), 2.25 (s, 3H), 1.27 (d, J = 6.0 Hz, 6H), 1.14 (t, J = 7.0 Hz, 3H). (APCI+) m/z 467 (M + H)$^+$ Retention time = 3.64 min (method 2) |

TABLE 1-continued

| Ex # | Chemical structure | Name | $^1$H NMR/LCMS |
|---|---|---|---|
| 008 | 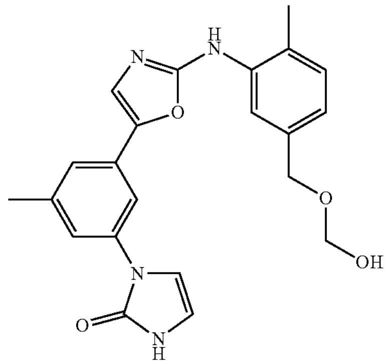 [SMILES: Cc1cc(-c2cnc(Nc3cc(COCO)ccc3C)o2)cc(-n2cc[nH]c2=O)c1] | 1-(3-{2-[5-(2-Hydroxy-ethoxy)-2-methyl-phenylamino]-oxazol-5-yl}-5-methyl-phenyl)-1,3-dihydro-imidazol-2-one | (300 MHz, DMSO-d$_6$) δ 10.35 (br s, 1H), 9.28 (s, 1H), 7.78 (s, 1H), 7.67 (d, J = 2.4 Hz, 1H), 7.47 (s, 1H), 7.41 (s, 1H), 7.29 (s, 1H), 7.07 (d, J = 8.3 Hz, 1H), 6.98 (br s, 1H), 6.70-6.48 (m, 2H), 4.87 (t, J = 5.6 Hz, 1H), 3.95 (t, J = 5.0 Hz, 2H), 3.82-3.65 (m, 2H), 2.37 (s, 3H), 2.23 (s, 3H). (APCI+) m/z 407 (M + H)$^+$ Retention time = 2.85 min (method 2) |
| 009 | 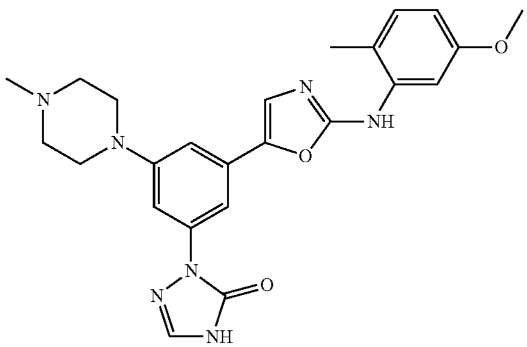 | 2-[3-[2-(5-Methoxy-2-methyl-phenylamino)-oxazol-5-yl]-5-(4-methyl-piperazin-1-yl)-phenyl]-2,4-dihydro-[1,2,4]triazol-3-one | (300 MHz, DMSO-d$_6$) δ 12.07 (br s, 1H), 9.30 (s, 1H), 8.13 (s, 1H), 7.64 (d, J = 2.5 Hz, 1H), 7.57 (s, 1H), 7.48 (s, 2H), 7.10-7.04 (m, 2H), 6.54 (dd, J = 8.3, 2.5 Hz, 1H), 3.72 (s, 3H), 3.24 (m, 4H), 2.60 (m, 2H), 2.32 (m, 2H), 2.22 (s, 3H). (APCI+) m/z 462 (M + H)$^+$ Retention time = 1.96 min (method 2) |
| 010 | 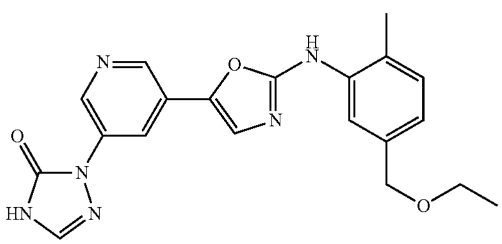 [SMILES: CCOCc1ccc(C)c(Nc2ncc(-c3cncc(-n4nc[nH]c4=O)c3)o2)c1] | 2-{5-[2-((5-Ethoxymethyl)-2-methyl-phenylamino)-oxazol-5-yl]-pyridin-3-yl}-2,4-dihydro-[1,2,4]triazol-3-one | (300 MHz, DMSO-d$_6$) δ 9.50 (s, 1H), 9.00 (s, 1H), 8.72 (s, 1H), 8.38 (s, 1H), 8.21 (s, 1H), 7.83 (s, 1H), 7.66 (s, 1H), 7.17 (d, J = 8.0 Hz, 1H), 6.95 (d, J = 7.5 Hz, 1H), 4.41 (s, 2H), 3.47 (dd, J = 13.9, 6.9 Hz, 2H), 2.28 (s, 3H), 1.13 (t, J = 7.0 Hz, 3H). (APCI+) m/z 393 (M + H)$^+$ Retention time = 4.53 min (method 2) |
| 011 | 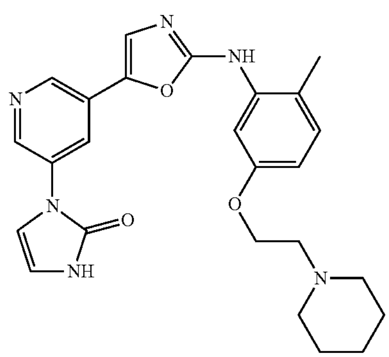 [SMILES: Cc1ccc(OCCN2CCCCC2)cc1Nc1ncc(-c2cncc(-n3cc[nH]c3=O)c2)o1] | 1-(5-{2-[2-Methyl-5-(2-piperidin-1-yl-ethoxy)-phenylamino]-oxazol-5-yl}-pyridin-3-yl)-1,3-dihydro-imidazol-2-one | (300 MHz, MeOH-d$_4$) δ 8.83 (br s, 1H), 8.76 (br s, 1H), 8.48 (s, 1H), 7.61 (s, 1H), 7.57 (d, J = 2.5 Hz, 1H), 7.22 (d, J = 8.5 Hz, 1H), 7.07 (d, J = 3.1 Hz, 1H), 6.78 (dd, J = 8.3, 2.5 Hz, 1H), 6.70 (d, J = 3.1 Hz, 1H), 4.46-4.36 (m, 2H), 3.71-3.54 (m, 4H), 3.17-3.05 (m, 2H), 2.33 (s, 3H), 2.05-1.80 (m, 6H). (APCI+) m/z 461 (M + H)$^+$ Retention time = 0.43 min (method 2) |
| 012 | 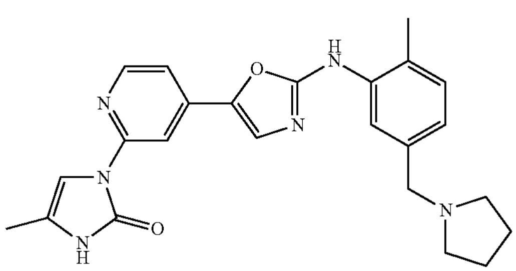 [SMILES: Cc1cn(-c2cc(-c3cnc(Nc4cc(CN5CCCC5)ccc4C)o3)ccn2)c(=O)[nH]1] | 4-Methyl-1-{4-[2-(2-methyl-5-pyrrolidin-1-ylmethyl-phenylamino)-oxazol-5-yl]-pyridin-2-yl}-1,3-dihydro-imidazol-2-one | (300 MHz, DMSO-d$_6$) δ 10.89 (br s, 1H), 10.52 (br s, 1H), 9.95 (br s, 1H), 8.50 (s, 1H), 8.36 (d, J = 5.4 Hz, 1H), 7.95 (s, 1H), 7.83 (s, 1H), 7.40 (dd, J = 5.3, 1.5 Hz, 1H), 7.37-7.27 (m, 2H), 7.03 (d, J = 1.4 Hz, 1H), 4.37-4.30 (m, 2H), 3.47-3.24 (m, 2H), 3.19-2.91 (m, 2H), 2.34 (s, 3H), 2.09-1.78 (m, 7H). (APCI+) m/z 431 (M + H)$^+$ Retention time = 0.55 min (method 2) |

TABLE 1-continued

| Ex # | Chemical structure | Name | ¹H NMR/LCMS |
|---|---|---|---|
| 013 | 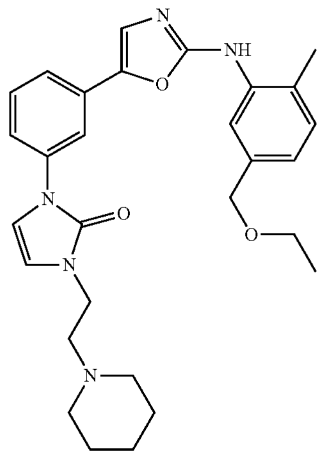 [SMILES: CCOCc1ccc(C)c(Nc2ncc(-c3cccc(-n4ccn(CCN5CCCCC5)c4=O)c3)o2)c1] | 1-{3-[2-((5-Ethoxymethyl)-2-methyl-phenylamino)-oxazol-5-yl]-phenyl}-3-(2-piperidin-1-yl-ethyl)-1,3-dihydro-imidazol-2-one | (300 MHz, CDCl₃) δ 8.06 (br s, 1H), 7.91 (br s, 1H), 7.47-7.40 (m, 2H), 7.22 (s, 1H), 7.19 (d, J = 7.6 Hz, 1H), 7.03 (d, J = 7.6 Hz, 1H), 6.75 (br s, 1H), 6.63 (d, J = 3.1 Hz, 1H), 6.59 (d, J = 3.0 Hz, 1H), 4.55 (s, 2H), 3.97-3.91 (m, 2H), 3.57 (q, J = 7.0 Hz, 2H), 2.83-2.74 (m, 2H), 2.67-2.57 (m, 4H), 2.35 (s, 3H), ), 1.77-1.65 (m, 4H), 1.55-1.46 (m, 2H), 1.26 (t, J = 7.0 Hz, 3H). (APCI+) m/z 502 (M + H)⁺ Retention time = 2.58 min (method 2) |
| 014 | 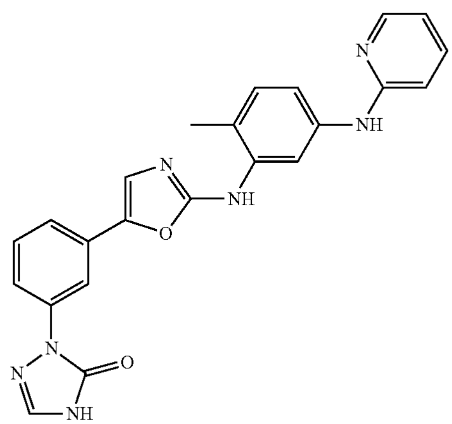 [SMILES: Cc1ccc(Nc2ccccn2)cc1Nc1ncc(-c2cccc(-n3nc[nH]c3=O)c2)o1] | 2-(3-{2-[2-Methyl-5-(pyridin-2-ylamino)-phenylamino]-oxazol-5-yl}-phenyl)-2,4-dihydro-[1,2,4]triazol-3-one | (300 MHz, DMSO-d₆) δ 9.30 (s, 1H), 8.96 (s, 1H), 8.13 (s, 1H), 8.12-8.06 (m, 2H), 8.01 (d, J = 2.1 Hz, 1H), 7.86-7.80 (m, 1H), 7.56-7.40 (m, 4H), 7.45 (m, 1H), 7.06 (d, J = 8.4 Hz, 1H), 6.85 (d, J = 8.4 Hz, 1H), 6.67 (dd, J = 6.3, 5.1 Hz, 1H), 2.23 (s, 3H). (APCI+) m/z 426 (M + H)⁺ Retention time = 2.11 min (method 2) |
| 015 | 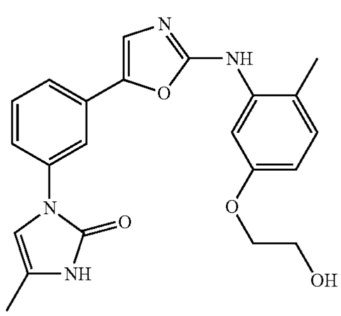 [SMILES: Cc1cn(-c2cccc(-c3cnc(Nc4cc(OCCO)ccc4C)o3)c2)c(=O)[nH]1] | 1-(4-{2-[5-(2-Hydroxy-ethoxy)-2-methyl-phenylamino]-oxazol-5-yl}-pyridin-2-yl)-4-methyl-1,3-dihydro-imidazol-2-one | (300 MHz, MeOH-d₄) δ 8.46 (br s, 1H), 8.33 (d, J = 5.1 Hz, 1H), 7.53 (br s, 1H), 7.41 (d, J = 2.4 Hz, 1H), 7.33 (d, J = 4.8 Hz, 1H), 7.14 (d, J = 8.3 Hz, 1H), 7.02 (s, 1H), 6.70 (dd, J = 8.3, 2.4 Hz, 1H), 4.13-4.06 (m, 2H), 3.95-3.87 (m, 2H), 2.29 (s, 3H), 2.12 (s, 3H). (APCI+) m/z 408 (M + H)⁺ Retention time = 2.89 min (method 2) |
| 016 | 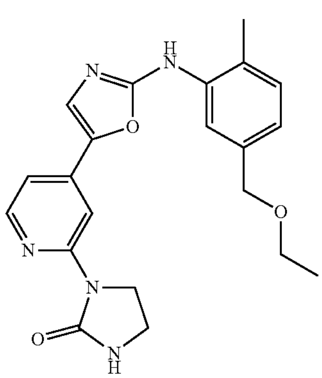 [SMILES: CCOCc1ccc(C)c(Nc2ncc(-c3ccnc(N4CCNC4=O)c3)o2)c1] | 1-{4-[2-((5-Ethoxymethyl)-2-methyl-phenylamino)-oxazol-5-yl]-pyridin-2-yl}-imidazolidin-2-one | ¹H NMR (300 MHz, CDCl₃) ä 8.23 (s, 1H), 8.13 (d, J = 5.5 Hz, 1H), 7.73 (s, 1H), 7.33 (s, 1H), 7.13 (d, J = 7.7 Hz, 1H), 6.98 (t, J = 5.1 Hz, 2H), 4.46 (s, 2H), 4.15-4.07 (m, 2H), 3.55-3.42 (m, 4H), 2.26 (s, 3H), 1.13 (t, J = 7.0 Hz, 3H). (ES+) m/z 394 (M + H)⁺ Retention time = 2.35 min (method 2) |

TABLE 1-continued

| Ex # | Chemical structure | Name | $^1$H NMR/LCMS |
|---|---|---|---|
| 017 | 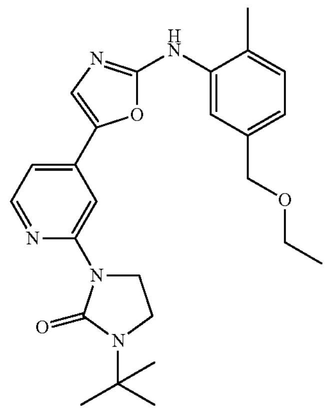 [SMILES: CCOCc1ccc(C)c(Nc2ncc(-c3ccnc(N4CCN(C(C)(C)C)C4=O)c3)o2)c1] | 1-tert-Butyl-3-{4-[2-((5-ethoxymethyl)-2-methyl-phenylamino)-oxazol-5-yl]-pyridin-2-yl}-imidazolidin-2-one | (300 MHz, DMSO-d$_6$) δ 9.60 (s, 1H), 8.35 (s, 1H), 8.23 (d, J = 5.4 Hz, 1H), 7.80 (s, 1H), 7.67 (s, 1H), 7.23-7.12 (m, 2H), 6.96 (d, J = 7.6 Hz, 1H), 4.42 (s, 2H), 3.85 (t, J = 7.8 Hz, 2H), 3.48 (dt, J = 14.0, 5.4 Hz, 4H), 2.28 (s, 3H), 1.37 (s, 9H), 1.14 (dd, J = 12.3, 5.3 Hz, 3H). (APCI+) m/z 450 (M + H)$^+$ Retention time = 3.28 min (method 2) |
| 018 | 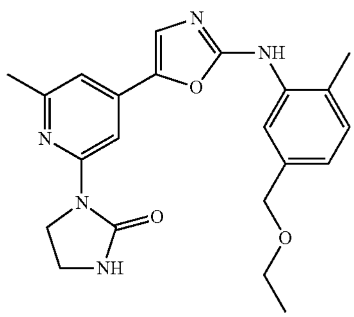 | 1-{4-[2-((5-Ethoxymethyl)-2-methyl-phenylamino)-oxazol-5-yl]-6-methyl-pyridin-2-yl}-imidazolidin-2-one | (300 MHz, DMSO-d$_6$) δ 9.55 (br s, 1H), 8.16 (s, 1H), 7.78 (s, 1H), 7.60 (s, 1H), 7.21 (s, 1H), 7.17 (d, J = 7.6 Hz, 1H), 7.06 (s, 1H), 6.96 (d, J = 7.6 Hz, 1H), 4.42 (s, 2H), 4.00 (t, J = 8.0 Hz, 2H), 3.52-3.36 (m, 4H), 2.39 (s, 3H), 2.28 (s, 3H), 1.14 (t, J = 7.0 Hz, 3H). (APCI+) m/z = 408 (M + H)$^+$ Retention time = 2.69 min (method 2) |
| 019 | 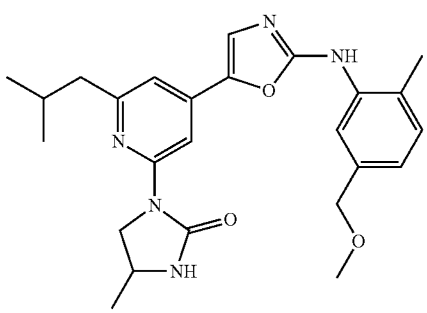 [SMILES: COCc1ccc(C)c(Nc2ncc(-c3cc(CC(C)C)nc(N4CC(C)NC4=O)c3)o2)c1] | 1-{6-Isobutyl-4-[2-((5-methoxymethyl)-2-methyl-phenylamino)-oxazol-5-yl]-pyridin-2-yl}-4-methyl-imidazolidin-2-one | (300 MHz, DMSO-d$_6$) δ 9.54 (br s, 1H), 8.15 (s, 1H), 7.80 (s, 1H), 7.61 (s, 1H), 7.37 (s, 1H), 7.18 (d, J = 7.7 Hz, 1H), 7.02 (s, 1H), 6.95 (d, J = 7.7 Hz, 1H), 4.38 (s, 2H), 4.18-4.09 (m, 1H), 3.89-3.72 (m, 1H), 3.52 (dd, J = 10.6, 6.4 Hz, 1H), 3.28 (s, 3H), 2.28 (s, 3H), 2.14-2.05 (m, 1H), 1.20 (d, J = 6.1 Hz, 3H), 0.91 (d, J = 6.0 Hz, 6H). (APCI+) m/z 450 (M + H)$^+$ Retention time = 3.17 min (method 2) |
| 020 | 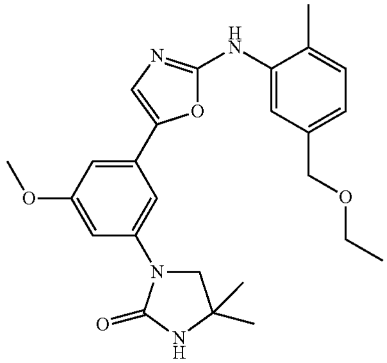 [SMILES: CCOCc1ccc(C)c(Nc2ncc(-c3cc(OC)cc(N4CC(C)(C)NC4=O)c3)o2)c1] | 1-{3-[2-((5-Ethoxymethyl)-2-methyl-phenylamino)-oxazol-5-yl]-5-methoxy-phenyl}-4,4-dimethyl-imidazolidin-2-one | (300 MHz, DMSO-d$_6$) δ 9.26 (br s, 1H), 7.84 (s, 1H), 7.41 (s, 1H), 7.29 (s, 1H), 7.24 (s, 1H), 7.18-7.12 (m, 2H), 6.93 (d, J = 7.7 Hz, 1H), 6.79 (s, 1H), 4.41 (s, 2H), 3.78 (s, 3H), 3.62 (s, 2H), 3.47 (q, J = 7.0 Hz, 2H), 2.28 (s, 3H), 1.28 (s, 6H), 1.14 (t, J = 7.0 Hz, 3H). (APCI+) m/z 451 (M + H)$^+$ Retention time = 3.49 min (method 2) |

TABLE 1-continued

| Ex # | Chemical structure | Name | $^1$H NMR/LCMS |
|---|---|---|---|
| 021 | 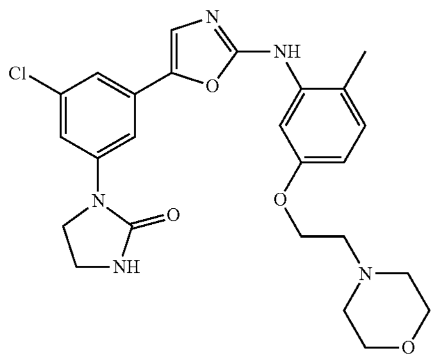 [SMILES: Cc1ccc(OCCN2CCOCC2)cc1Nc1ncc(-c2cc(Cl)cc(N3CCNC3=O)c2)o1] | 1-(3-Chloro-5-{2-[2-methyl-5-(2-morpholin-4-yl-ethoxy)-phenylamino]-oxazol-5-yl}-phenyl)-imidazolidin-2-one | (300 MHz, DMSO-d$_6$) δ 9.33 (br s, 1H), 7.64-7.62 (m, 2H), 7.60 (d, J = 2.5 Hz, 1H), 7.55 (s, 1H), 7.28 (br s, 1H), 7.21 (s, 1H), 7.07 (d, J = 8.3 Hz, 1H), 6.57 (dd, J = 8.4, 2.5 Hz, 1H), 4.04 (t, J = 5.8 Hz, 2H), 3.94-3.86 (m, 2H), 3.61-3.55 (m, 4H), 3.48-3.40 (m, 2H), 2.68 (t, J = 5.7 Hz, 2H), 2.49-2.44 (m, 4H), 2.22 (s, 3H). (APCI+) m/z 498 (M + H)$^+$ Retention time = 2.43 min (method 2) |
| 022 | 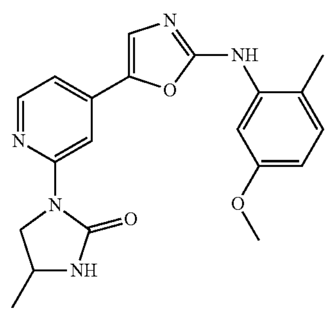 | 1-{4-[2-(5-Methoxy-2-methyl-phenylamino)-oxazol-5-yl]-pyridin-2-yl}-4-methyl-imidazolidin-2-one | (300 MHz, DMSO-d$_6$) δ 9.58 (br s, 1H), 8.34 (s, 1H), 8.24 (d, J = 5.4 Hz, 1H), 7.68 (s, 1H), 7.54 (d, J = 2.6 Hz, 1H), 7.44 (s, 1H), 7.19 (dd, J = 5.4, 1.4 Hz, 1H), 7.10 (d, J = 8.4 Hz, 1H), 6.60 (dd, J = 8.4, 2.6 Hz, 1H), 4.18-4.08 (m, 1H), 3.88-3.75 (m, 1H), 3.73 (s, 3H), 3.54 (dd, J = 10.6, 6.1 Hz, 1H), 2.23 (s, 3H), 1.21 (d, J = 6.1 Hz, 3H). (APCI+) m/z 380 (M + H)$^+$ Retention time = 2.76 min (method 2) |
| 023 | 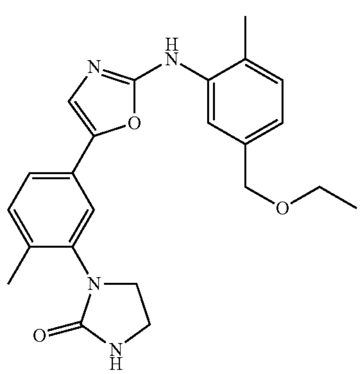 [SMILES: CCOCc1ccc(C)c(Nc2ncc(-c3ccc(C)c(N4CCNC4=O)c3)o2)c1] | 1-{5-[2-((5-Ethoxymethyl)-2-methyl-phenylamino)-oxazol-5-yl]-2-methyl-phenyl}-imidazolidin-2-one | $^1$H NMR (300 MHz, CDCl$_3$) ä 7.92 (s, 1H), 7.40-7.32 (m, 2H), 7.24 (d, J = 9.3 Hz, 2H), 7.16 (d, J = 7.7 Hz, 2H), 7.10 (s, 1H), 7.01 (d, J = 7.5 Hz, 2H), 5.58 (s, 1H), 4.51 (s, 2H), 3.82 (t, J = 7.8 Hz, 2H), 3.64-3.48 (m, 4H), 2.31 (s, 6H), 1.24 (t, J = 7.0 Hz, 3H). (AES+) m/z 407 (M + H)$^+$ Retention time = 3.54 min (method 2) |
| 024 | 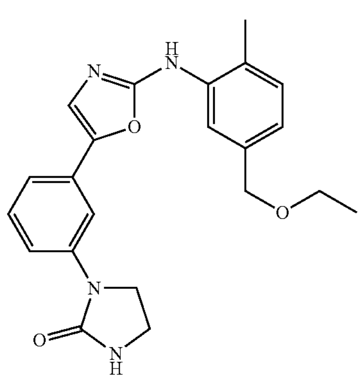 [SMILES: CCOCc1ccc(C)c(Nc2ncc(-c3cccc(N4CCNC4=O)c3)o2)c1] | 1-{3-[2-((5-Ethoxymethyl)-2-methyl-phenylamino)-oxazol-5-yl]-phenyl}-imidazolidin-2-one | $^1$H NMR (300 MHz, DMSO-d$_6$) ä 9.29 (s, 1H), 7.81 (d, J = 6.8 Hz, 2H), 7.46-7.29 (m, 3H), 7.18 (dd, J = 17.6, 7.7 Hz, 2H), 7.02 (s, 1H), 6.93 (d, J = 7.6 Hz, 1H), 4.41 (s, J = 5.3 Hz, 2H), 3.92-3.83 (m, 2H), 3.45 (m, 4H), 2.28 (s, 3H), 1.14 (t, J = 7.0 Hz, 3H). (ES+) m/z 393 (M + H)$^+$ Retention time = 2.76 min (method 2) |

TABLE 1-continued

| Ex # | Chemical structure | Name | ¹H NMR/LCMS |
|---|---|---|---|
| 025 | 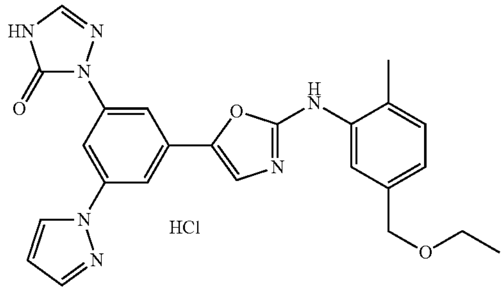 [SMILES: CCOCc1ccc(C)c(Nc2ncc(-c3cc(-n4cccn4)cc(-n4nc[nH]c4=O)c3)o2)c1 ; Cl] | 2-{3-[2-((5-Ethoxymethyl)-2-methyl-phenylamino)-oxazol-5-yl]-5-pyrazol-1-yl-phenyl}-2,4-dihydro-[1,2,4]triazol-3-one hydrochloride | (300 MHz, DMSO-$d_6$) δ 12.16 (s, 1H), 9.78 (s, 1H), 8.57 (d, J = 2.5 Hz, 1H), 8.35 (t, J = 1.9 Hz, 1H), 8.21 (s, 1H), 8.05 (d, J = 7.4 Hz, 1H), 7.93 (s, 1H), 7.79 (d, J = 1.7 Hz, 2H), 7.70 (s, 1H), 7.19 (d, J = 7.7 Hz, 1H), 6.98 (d, J = 7.5 Hz, 1H), 6.65-6.50 (m, 1H), 4.42 (s, 2H), 3.52-3.39 (m, 2H), 2.29 (s, 3H), 1.12 (t, J = 7.0 Hz, 3H). (APCI+) m/z =458 (M + H)⁺ Retention time = 3.44 min (method 2) |
| 026 | 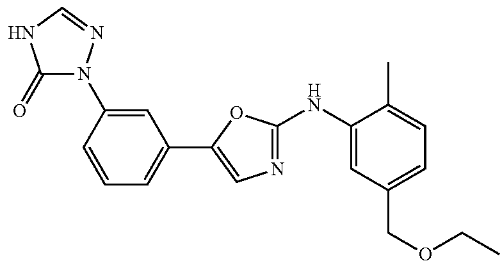 [SMILES: CCOCc1ccc(C)c(Nc2ncc(-c3cccc(-n4nc[nH]c4=O)c3)o2)c1] | 2-{3-[2-((5-Ethoxymethyl)-2-methyl-phenylamino)-oxazol-5-yl]-phenyl}-2,4-dihydro-[1,2,4]triazol-3-one | (300 MHz, DMSO-$d_6$) δ 12.11 (s, 1H), 10.30 (s, 1H), 8.15 (d, J = 12.0 Hz, 2H), 7.88 (d, J = 7.3 Hz, 1H), 7.71 (d, J = 10.1 Hz, 2H), 7.58-7.43 (m, 2H), 7.22 (d, J = 7.7 Hz, 1H), 7.04 (d, J = 7.6 Hz, 1H), 4.43 (s, 2H), 3.48 (q, J = 6.9 Hz, 2H), 2.29 (s, 3H), 1.13 (t, J = 7.0 Hz, 3H). (APCI+) m/z 392 (M + H)⁺ Retention time = 3.56 min (method 2) |
| 027 | 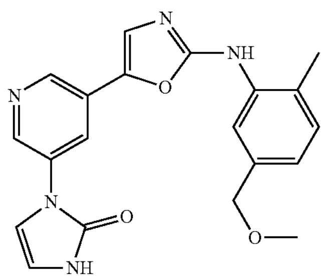 | 1-{5-[2-((5-Methoxymethyl)-2-methyl-phenylamino)-oxazol-5-yl]-pyridin-3-yl}-2,4-dihydro-imidazol-2-onehydrochloride | (300 MHz, DMSO-$d_6$) δ 10.64 (br s, 1H), 9.82 (br s, 1H), 8.95 (s, 1H), 8.75 (s, 1H), 8.59 (s, 1H), 7.81 (s, 1H), 7.79 (s, 1H), 7.27-7.15 (m, 2H), 6.99 (d, J = 7.8 Hz, 1H), 6.75 (br s, 1H), 4.39 (s, 3H), 3.28 (s, 3H), 2.29 (s, 3H). (APCI+) m/z 378 (M + H)⁺ Retention time = 4.25 min (method 2) |
| 028 | 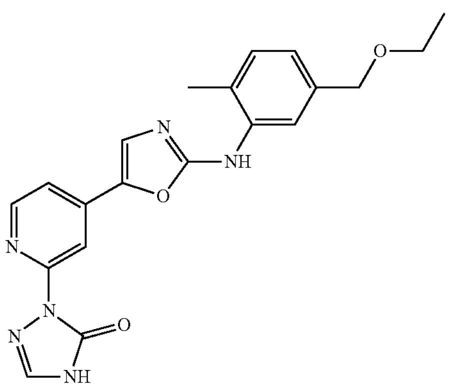 [SMILES: CCOCc1ccc(C)c(Nc2ncc(-c3ccnc(-n4nc[nH]c4=O)c3)o2)c1] | 2-{4-[2-(5-Ethoxymethyl-2-methyl-phenylamino)-oxazol-5-yl]-pyridin-2-yl}-2,4-dihydro-[1,2,4]triazol-3-one | (300 MHz, DMSO-$d_6$) δ 9.67 (s, 1H), 8.42 (d, J = 5.3 Hz, 1H), 8.10 (s, 1H), 8.05 (s, 1H), 7.79 (s, 1H), 7.77 (s, 1H), 7.44 (dd, J = 5.2, 1.4 Hz, 1H), 7.18 (d, J = 7.7 Hz, 1H), 6.97 (d, J = 7.2 Hz, 1H), 4.42 (s, 2H), 3.47 (t, J =7.0 Hz, 2H), 2.28 (s, 3H), 1.13 (t, J = 7.0 Hz, 3H). (APCI+) m/z 393 (M + H)⁺ Retention time = 4.49 min (method 2) |
| 029 | 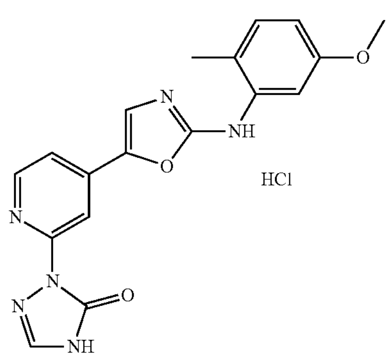 [SMILES: COc1ccc(C)c(Nc2ncc(-c3ccnc(-n4nc[nH]c4=O)c3)o2)c1 ; Cl] | 2-{4-[2-(5-Methoxy-2-methyl-phenylamino)-oxazol-5-yl]-pyridin-2-yl)-2,4-dihydro-[1,2,4]triazol-3-onehydrochloride | (300 MHz, DMSO-$d_6$) δ 12.40 (s, 1H), 10.02 (s, 1H), 8.42 (d, J = 5.5 Hz, 1H), 8.30 (s, 1H), 8.14 (s, 1H), 8.05 (s, 1H), 7.58 (d, J = 5.5 Hz, 2H), 7.46 (s, 1H), 7.12 (d, J = 8.4 Hz, 1H), 6.65 (d, J = 8.3 Hz, 1H), 3.73 (s, 3H), 2.22 (s, 3H). (APCI+) m/z 365 (M + H)⁺ Retention time = 4.82 min (method 2) |

TABLE 1-continued

| Ex # | Chemical structure | Name | ¹H NMR/LCMS |
|---|---|---|---|
| 030 | 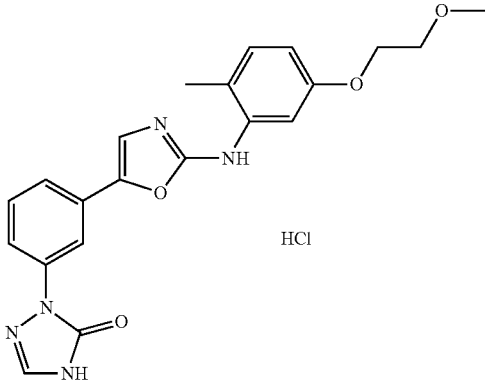 [SMILES: COCCOc1ccc(C)c(Nc2ncc(-c3cccc(-n4nc[nH]c4=O)c3)o2)c1 ; Cl] | 2-(4-{2-[5-(2-Methoxy-ethoxy)-2-methyl-phenylamino]-oxazol-5-yl}-pyridin-2-yl)-2,4-dihydro-[1,2,4]triazol-3-onehydrochloride | (300 MHz, DMSO-d₆) δ 12.38 (s, 1H), 9.98 (s, 1H), 8.43 (d, J = 5.7 Hz, 1H), 8.29 (s, 1H), 8.14 (s, 1H), 8.04 (s, 1H), 7.58 (d, J = 5.7 Hz, 1H), 7.49 (s, 1H), 7.11 (d, J = 8.4 Hz, 1H), 6.65 (d, J = 8.5 Hz, 1H), 4.05 (d, J = 4.5 Hz, 2H), 3.65 (d, J = 4.5 Hz, 2H), 3.30 (s, 3H), 2.22 (s, 3H). (APCI+) m/z = 409 (M + H)⁺ Retention time = 2.52 min (method 2) |
| 031 | 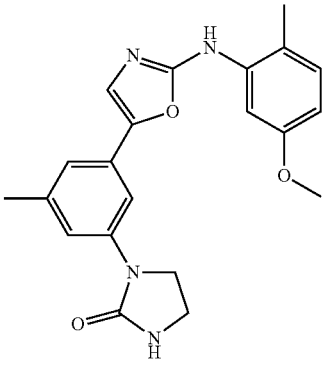 | 1-{3-[2-(5-Methoxy-2-methyl-phenylamino)-oxazol-5-yl]-5-methyl-phenyl}-imidazolidin-2-one | ¹H NMR (300 MHz, DMSO-d₆) ä 9.25 (s, 1H), 7.62 (d, J = 2.6 Hz, 1H), 7.37 (s, 1H), 7.27 (s, 1H), 7.11-7.04 (m, 1H), 6.99 (s, 1H), 6.55 (dd, J = 8.3, 2.6 Hz, 1H), 3.92-3.81 (m, 2H), 3.72 (s, 3H), 3.45-3.37 (m, 2H), 2.31 (s, 3H), 2.22 (s, 3H). (ES+) m/z 380 (M + H)⁺ Retention time = 3.28 min (method 2) |
| 032 | 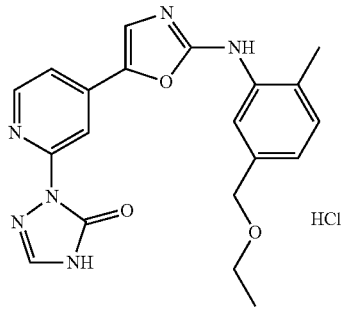 | 1-{4-[2-(5-(Ethoxymethyl)-2-methyl-phenylamino)-oxazol-5-yl]-pyridin-2-yl}-1,3-dihydro-imidazol-2-one hydrochloride | (300 MHz, MeOH-d₄) δ 8.40 (d, J = 5.7 Hz, 1H), 8.29 (br s, 1H), 8.00 (br s, 1H), 7.59 (br s, 1H), 7.49 (d, J = 5.4 Hz, 1H), 7.35 (d, J = 7.9 Hz, 1H), 7.25 (d, J = 6.6 Hz, 1H), 7.08 (br s, 1H), 4.55 (s, 2H), 3.63 (q, J = 7.0 Hz, 2H), 2.38 (s, 3H), 2.15 (s, 3H), 1.27 (t, J = 7.0 Hz, 3H). (APCI+) m/z 407 (M + H)⁺ Retention time = 2.99 min (method 2) |
| 033 | 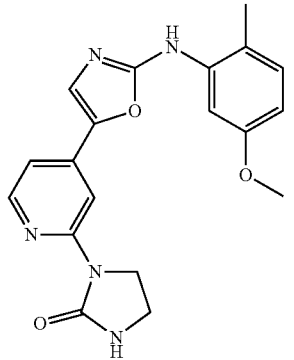 [SMILES: COc1ccc(C)c(Nc2ncc(-c3ccnc(N4CCNC4=O)c3)o2)c1] | 1-{4-[2-(5-Methoxy-2-methyl-phenylamino)-oxazol-5-yl]-pyridin-2-yl}-imidazolidin-2-one | ¹H NMR (300 MHz, DMSO-d₆) ä 9.57 (s, 1H), 8.33 (s, 1H), 8.24 (d, J = 4.8 Hz, 1H), 7.67 (s, 1H), 7.53 (s, 1H), 7.27 (s, 1H), 7.19 (d, J = 5.3 Hz, 1H), 7.09 (d, J = 8.5 Hz, 1H), 4.06-3.96 (m, 2H), 3.72 (s, 3H), 3.46-3.37 (m, 2H), 2.22 (s, 3H). (ES+) m/z = 366 (M + H)⁺ Retention time = 2.36 min (method 2) |

TABLE 1-continued

| Ex # | Chemical structure | Name | $^1$H NMR/LCMS |
|---|---|---|---|
| 034 | 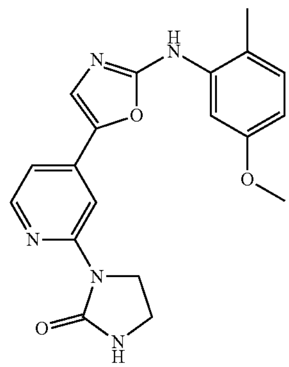 [SMILES: COc1ccc(C)c(Nc2ncc(-c3ccnc(N4CCNC4=O)c3)o2)c1] | 1-{4-[2-((5-Hydroxymethyl)-2-methyl-phenylamino)-oxazol-5-yl]-pyridin-2-yl}-imidazolidin-2-one | $^1$H NMR (300 MHz, DMSO-d$_6$) ä 9.55 (s, 1H), 8.33 (s, 1H), 8.23 (d, J = 5.4 Hz, 1H), 7.74 (s, 1H), 7.64 (s, 1H), 7.26 (s, 1H), 7.17 (dd, J = 8.9, 4.7 Hz, 1H), 6.97 (d, J = 8.0 Hz, 1H), 5.12 (t, J = 5.7 Hz, 1H), 4.46 (d, J = 5.7 Hz, 2H), 4.06-3.96 (m, 2H), 3.41 (t, J = 8.0 Hz, 2H), 2.27 (s, 3H). (ES+) m/z 366 (M + H)$^+$ Retention time = 1.91 min (method 2) |
| 035 | 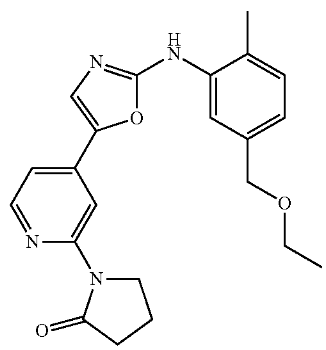 [SMILES: CCOCc1ccc(C)c(Nc2ncc(-c3ccnc(N4CCCC4=O)c3)o2)c1] | 1-{4-[2-((5-Ethoxymethyl)-2-methyl-phenylamino)-oxazol-5-yl]-pyridin-2-yl}-pyrrolidin-2-one | (300 MHz, DMSO-d$_6$) δ 9.62 (s, 1H), 8.43 (s, 1H), 8.33 (d, J = 5.4 Hz, 1H), 7.75 (s, 1H), 7.70 (s, 1H), 7.31 (dd, J = 5.3, 1.5 Hz, 1H), 7.18 (d, J = 7.7 Hz, 1H), 6.97 (d, J = 7.6 Hz, 1H), 4.42 (s, 2H), 4.00 (t, J = 7.1 Hz, 2H), 3.47 (dd, J = 14.0, 7.0 Hz, 2H), 2.59 (t, J = 8.0 Hz, 2H), 2.28 (s, 3H), 2.04 (dt, J = 15.5, 7.7 Hz, 2H), 1.14 (t, J = 7.0 Hz, 3H). (APCI+) m/z 393 (M + H)$^+$ Retention time = 3.29 min (method 2) |
| 036 | 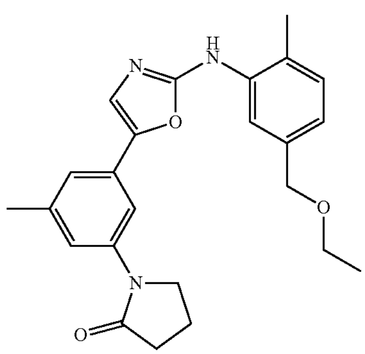 [SMILES: CCOCc1ccc(C)c(Nc2ncc(-c3cc(C)cc(N4CCCC4=O)c3)o2)c1] | 1-{3-[2-((5-Ethoxymethyl)-2-methyl-phenylamino)-oxazol-5-yl]-5-methyl-phenyl}-pyrrolidin-2-one | $^1$H NMR (300 MHz, CDCl$_3$) ä 7.97 (s, 1H), 7.60 (s, 1H), 7.27 (s, 1H), 7.17-7.07 (m, 3H), 6.98 (d, J = 7.7 Hz, 1H), 4.50 (s, 2H), 3.85 (t, J = 7.0 Hz, 2H), 3.52 (q, J = 7.0 Hz, 2H), 2.59 (dd, J = 10.2, 5.9 Hz, 2H), 2.34 (s, 3H), 2.30 (s, 3H), 2.18-2.05 (m, 2H), 1.22 (t, J = 7.1 Hz, 3H). (ES+) m/z 407 (M + H)$^+$ Retention time = 2.52 min (method 2) |
| 037 | 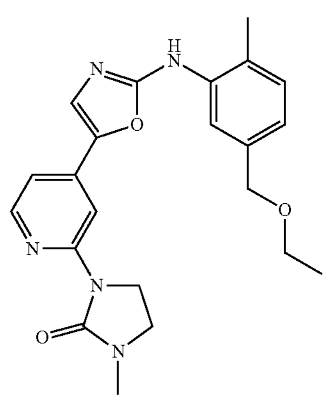 [SMILES: CCOCc1ccc(C)c(Nc2ncc(-c3ccnc(N4CCN(C)C4=O)c3)o2)c1] | 1-{4-[2-((5-Ethoxymethyl)-2-methyl-phenylamino)-oxazol-5-yl]-pyridin-2-yl}-3-methyl-imidazolidin-2-one | $^1$H NMR (300 MHz, CDCl$_3$) ä 8.35 (s, 1H), 8.09 (d, J = 5.4 Hz, 1H), 7.89 (s, 1H), 7.17 (s, 1H), 7.05 (d, J = 7.1 Hz, 2H), 6.90 (dd, J = 5.5, 4.0 Hz, 2H), 4.40 (d, J = 9.9 Hz, 2H), 3.98 (t, J = 7.2 Hz, 2H), 3.45-3.39 (m, 4H), 2.81 (s, 3H), 2.21 (s, 3H), 1.13 (t, J = 7.1 Hz, 3H). (ES+) m/= 409 (M + H)$^+$ Retention time = 2.58 min (method 2) |

TABLE 1-continued

| Ex # | Chemical structure | Name | $^1$H NMR/LCMS |
|---|---|---|---|
| 038 | 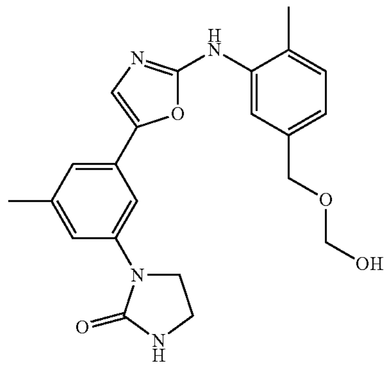 [SMILES: Cc1cc(-c2cnc(Nc3cc(COCO)ccc3C)o2)cc(N2CCNC2=O)c1] | 1-(3-{2-[5-(2-Hydroxy-ethoxy)-2-methyl-phenylamino]-oxazol-5-yl}-5-methyl-phenyl)-imidazolidin-2-one | (300 MHz, DMSO-d$_6$) δ 9.23 (s, 1H), 7.66 (d, J = 2.5 Hz, 1H), 7.61 (s, 1H), 7.37 (s, 1H), 7.28 (s, 1H), 7.06 (d, J = 8.8 Hz, 2H), 7.00 (s, 1H), 6.54 (dd, J = 8.3, 2.6 Hz, 1H), 4.86 (t, J = 5.6 Hz, 1H), 3.94 (t, J = 5.0 Hz, 2H), 3.91-3.81 (m, 2H), 3.71 (dd, J = 10.2, 5.2 Hz, 2H), 3.47-3.37 (m, 2H), 2.30 (d, J = 8.8 Hz, 3H), 2.22 (s, 3H). (APCI+) m/z 409 (M + H)$^+$ Retention time = 2.91 min (method 2) |
| 039 | 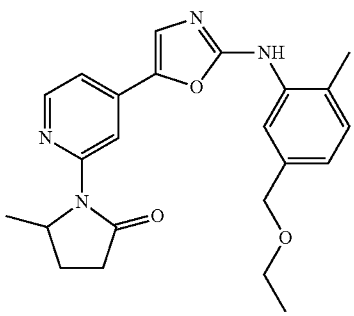 | 1-{4-[2-((5-Ethoxymethyl)-2-methyl-phenylamino)-oxazol-5-yl]-pyridin-2-yl}-5-methyl-pyrrolidin-2-one | $^1$H NMR (300 MHz, CDCl$_3$) ä 8.33 (s, 1H), 8.24 (d, J = 5.3 Hz, 1H), 7.85 (s, 1H), 7.32 (s, 1H), 7.32 (s, 1H), 7.10 (d, J = 7.7 Hz, 1H), 7.04 (dd, J = 5.3, 1.2 Hz, 1H), 6.95 (d, J = 8.2 Hz, 1H), 4.81 (ddq, J = 12.0, 6.1, 3.1 Hz, 1H), 4.45 (s, 2H), 3.49 (q, J = 7.0 Hz, 2H), 2.81-2.41 (m, 2H), 2.26 (s, J = 8.0 Hz, 3H), 1.70 (m, 2H), 1.28 (d, J = 6.3 Hz, 3H), 1.16 (t, J = 7.8 Hz, 3H). (ES+) m/z 407 (M + H)$^+$ Retention time = 3.05 min (method 2) |
| 040 | 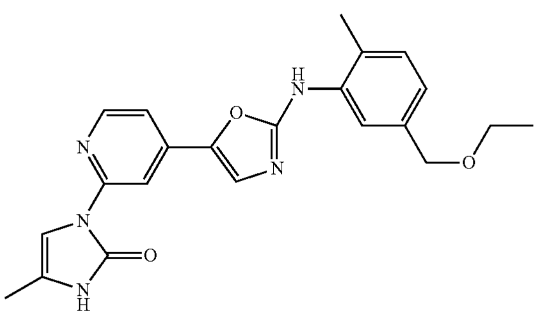 [SMILES: CCOCc1ccc(C)c(Nc2ncc(-c3ccnc(-n4cc(C)[nH]c4=O)c3)o2)c1] | 1-{4-[2-((5-Ethoxymethyl)-2-methyl-phenylamino)-oxazol-5-yl]-pyridin-2-yl}-4-methyl-1,3-dihydro-imidazol-2-one | (300 MHz, MeOH-d$_4$) δ 8.40 (d, J = 5.7 Hz, 1H), 8.20 (br s, 1H), 8.00 (br s, 1H), 7.50 (br s, 1H), 7.49 (d, J = 5.4 Hz, 1H), 7.35 (d, J = 7.9 Hz, 1H), 7.25 (d, J = 6.6 Hz, 1H), 7.08 (br s, 1H), 4.55 (s, 2H), 3.63 (q, J = 7.0 Hz, 2H), 2.38 (s, 3H), 2.15 (s, 3H), 1.27 (t, J = 7.0 Hz, 3H). (APCI+) m/z 407 (M + H)$^+$ Retention time = 2.99 min (method 2) |
| 041 | 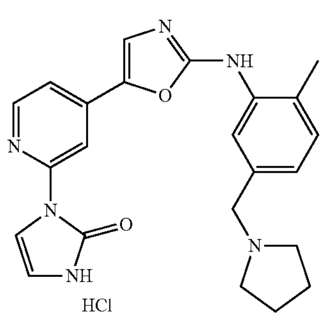 [SMILES: Cc1ccc(CN2CCCC2)cc1Nc1ncc(-c2ccnc(-n3cc[nH]c3=O)c2)o1 ; Cl] | 1-{4-[2-(2-Methyl-5-pyrrolidin-1-ylmethyl-phenylamino)-oxazol-5-yl]-pyridin-2-yl}-1,3-dihydro-imidazol-2-one | (300 MHz, DMSO-d$_6$) δ 10.83 (br s, 1H), 10.53 (br s, 1H), 9.91 (br s, 1H), 8.53 (s, 1H), 8.39 (d, J = 4.3 Hz, 1H), 7.95 (s, 1H), 7.82 (s, 1H), 7.53 7.20 (m, 4H), 6.65 (br s, 1H), 4.34 (s, 2H), 3.46 3.30 (m, 2H), 3.14-2.98 (m, 2H), 2.34 (s, 3H), 2.02-1.82 (m, 4H). (APCI+) m/z 417 (M + H)$^+$ Retention time = 0.41 min (method 2) |

TABLE 1-continued

| Ex # | Chemical structure | Name | $^1$H NMR/LCMS |
|---|---|---|---|
| 042 | 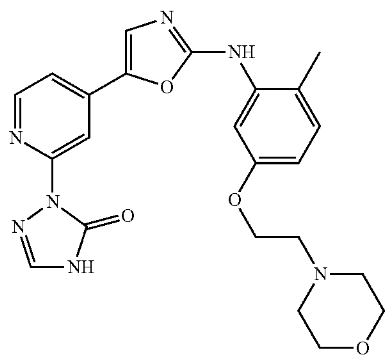 [SMILES: Cc1ccc(OCCN2CCOCC2)cc1Nc1ncc(-c2ccnc(-n3nc[nH]c3=O)c2)o1] | 1-(4-{2-[2-Methyl-5-(2-morpholin-4-yl-ethoxy)-phenylamino]-oxazol-5-yl}-pyridin-2-yl)-1,3-dihydro-imidazol-2-one | (300 MHz, CDCl$_3$) δ 9.15 (br s, 1H) 8.59 (s, 1 H), 8.37 (d, J = 5.2 Hz, 1H), 7.78 (br s, 1H), 7.46 (s, 1H), 7.38 (br s, 1H), 7.22 (d, J = 5.2 Hz, 1H), 7.10 (d, J = 8.2 Hz, 1H), 7.04 (br s, 1H), 6.60 (d, J = 8.2 Hz, 1H), 6.45 (br s, 1H), 4.22 (t, J = 5.3 Hz, 1H), 3.86-3.76 (m, 4H), 3.00-2.90 (m, 2H), 2.80-2.65 (m, 4H), 2.31 (s, 3H). (APCI+) m/z 463 (M + H)$^+$ Retention time = 0.52 min (method 2) |
| 043 | 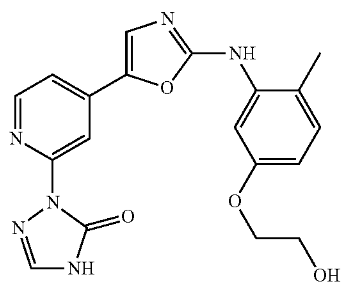 [SMILES: Cc1ccc(OCCO)cc1Nc1ncc(-c2ccnc(-n3nc[nH]c3=O)c2)o1] | 1-(4-{2-[5-(2-Hydroxy-ethoxy)-2-methyl-phenylamino]-oxazol-5-yl}-pyridin-2-yl)-1,3-dihydro-imidazol-2-one | (300 MHz, MeOD-d$_4$) δ 8.50 (s, 1H), 8.37 (d, J = 5.0 Hz, 1H), 7.55 (s, 1H), 7.42 (d, J = 2.5 Hz, 1H), 7.37 (dd, J = 5.0, 1.5 Hz, 1H), 7.34 (d, J = 3.1 Hz, 1H), 7.15 (d, J = 8.4 Hz, 1H), 6.71 (dd, J = 8.4, 2.5 Hz, 1H), 6.55 (d, J = 3.1 Hz, 1H), 4.11 (t, J = 4.5 Hz, 2H), 3.91 (t, J = 4.5 Hz, 2H), 2.30 (s, 3H). (APCI+) m/z 394 (M + H)$^+$ Retention time = 2.45 min (method 2) |
| 044 | 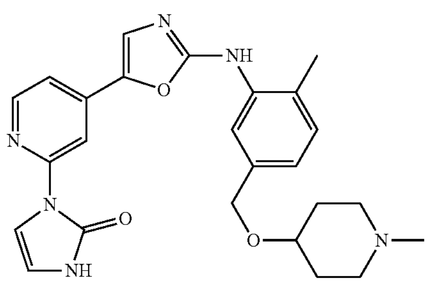 [SMILES: Cc1ccc(COC2CCN(C)CC2)cc1Nc1ncc(-c2ccnc(-n3cc[nH]c3=O)c2)o1] | 1-(4-{2-[2-Methyl-5-(1-methyl-piperidin-4-yloxymethyl)-phenylamino]-oxazol-5-yl}-pyridin-2-yl)-1,3-dihydro-imidazol-2-one | (300 MHz, MeOH-d$_4$) δ 8.48 (br s, 1H), 8.34 (d, J = 5.3 Hz, 1H), 7.70 (br s, 1H), 7.49 (s, 1H), 7.35 - 7.28 (m, 2H), 7.23 (d, J = 7.3 Hz, 1H), 7.08 (d, J = 7.3 Hz, 1H), 6.50 (d, J = 3.1 Hz, 1H), 4.57 (s, 1H), 3.60-3.45 (m, 1H), 2.80-2.66 (m, 2H), 2.35 (s, 3H), 2.29-2.20 (m, 5H), 2.02 1.90 (m, 2H), 1.80-1.66 (m, 2H). (APCI+) m/z 461 (M + H)$^+$ Retention time = 2.27 min (method 2) |
| 045 | 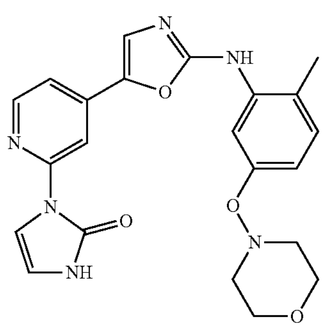 [SMILES: Cc1ccc(ON2CCOCC2)cc1Nc1ncc(-c2ccnc(-n3cc[nH]c3=O)c2)o1] | 1-{4-[2-(2-Methyl-5-morpholm-4-ylmethyl-phenylamino)-oxazol-5-yl]-pyridin-2-yl}-1,3-dihydro-imidazol-2-one | (300 MHz, MeOH-d$_4$) δ 8.49 (br s, 1H), 8.36 (d, J = 5.3 Hz, 1H), 7.66 (s, 1H), 7.52 (s, 1H), 7.36-7.31 (m, 2H), 7.23 (d, J = 7.7 Hz, 1H), 7.09 (d, J = 7.7 Hz, 1H), 6.53 (d, J = 3.1 Hz, 1H), 3.79-3.66 (m, 4H), 3.57 (s, 2H), 2.57-2.49 (s, 4H), 2.35 (s, 3H). (APCI+) m/z 433 (M + H)$^+$ Retention time = 2.21 min (method 2) |
| 046 | 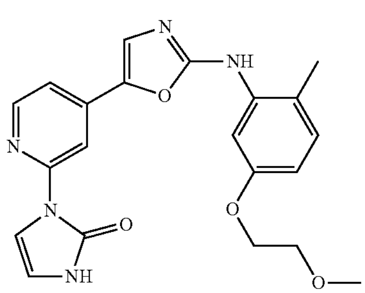 [SMILES: COCCOc1ccc(C)c(Nc2ncc(-c3ccnc(-n4cc[nH]c4=O)c3)o2)c1] | 1-(4-{2-[5-(2-Methoxy-ethoxy)-2-methyl-phenylamino]-oxazol-5-yl}-pyridin-2-yl)-1,3-dihydro-imidazol-2-one | (300 MHz, DMSO-d$_6$) δ 10.49 (br s, 1H), 9.65 (br s, 1H), 8.53 (s, 1H), 8.38 (d, J = 5.4 Hz, 1H), 7.78 (s, 1H), 7.56 (d, J = 2.1 Hz, 1H), 7.42 (d, J = 5.3 Hz, 1H), 7.27 (br s, 1H), 7.10 (d, J = 8.3 Hz, 1H), 6.70-6.55 (m, 2H), 4.12-3.99 (m, 2H), 3.70-3.61 (m, 2H), 3.31 (s, 3H), 2.24 (s, 3H). (APCI+) m/z 408 (M + H)$^+$ Retention time = 3.01 min (method 2) |

TABLE 1-continued

| Ex # | Chemical structure | Name | $^1$H NMR/LCMS |
|---|---|---|---|
| 047 | 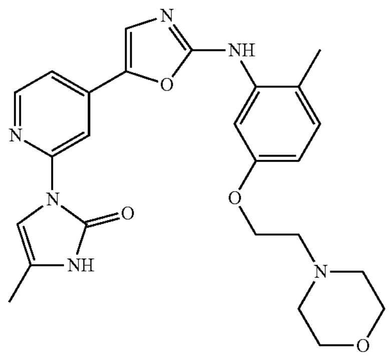 [SMILES: Cc1cn(-c2cc(-c3cnc(Nc4cc(OCCN5CCOCC5)ccc4C)o3)ccn2)c(=O)[nH]1] | 4-Methyl-1-(4-{2-[2-methyl-5-(2-morpholin-4-yl-ethoxy)-phenylamino]-oxazol-5-yl}-pyridin-2-yl)-1,3-dihydro-imidazol-2-one | (300 MHz, DMSO-$d_6$) δ 10.45 (br s, 1H), 9.63 (br s, 1H), 8.50 (s, 1H), 8.34 (d, J = 5.4 Hz, 1H), 7.76 (s, 1H), 7.55 (d, J = 2.5 Hz, 1H), 7.37 (dd, J = 5.3, 1.5 Hz, 1H), 7.09 (d, J = 8.4 Hz, 1H), 7.01 (br s, 1H), 6.61 (dd, J = 8.4, 2.6 Hz, 1H), 4.05 (t, J = 5.8 Hz, 2H), 3.60-3.54 (m, 4H), 2.68 (t, J = 5.8 Hz, 2H), 2.49-2.42 (m, 4H), 2.23 (s, 3H), 2.00 (s, 3H). (APCI+) m/z 477 (M + H)$^+$ Retention time = 2.44 min (method 2) |
| 048 | 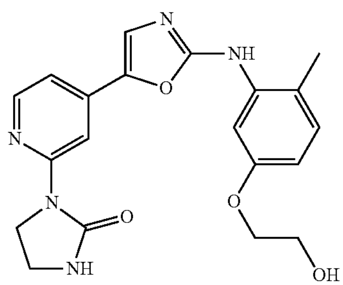 [SMILES: Cc1ccc(OCCO)cc1Nc1ncc(-c2ccnc(N3CCNC3=O)c2)o1] | 1-(4-{2-[5-(2-Hydroxy-ethoxy)-2-methyl-phenylamino]-oxazol-5-yl}-pyridin-2-yl)-imidazolidin-2-one | (300 MHz, DMSO-$d_6$) δ 9.54 (br s, 1H), 8.35 (br s, 1H), 8.25 (d, J = 5.4 Hz, 1H), 7.67 (s, 1H), 7.57 (d, J = 2.4 Hz, 1H), 7.25 (s, 1H), 7.19 (d, J = 5.3 Hz, 1H), 7.09 (d, J = 8.3 Hz, 1H), 6.60 (d, J = 5.7 Hz, 1H), 4.83 (t, J = 5.6 Hz, 1H), 4.05 3.99 (m, 2H), 3.95 (t, J = 5.0 Hz, 2H), 3.75-3.70 (m, 2H), 3.42 (t, J = 8.0 Hz, 2H), 2.23 (s, 3H). (APCI+) m/z 396 (M + H)$^+$ Retention time = 2.44 min (method 2) |
| 049 | 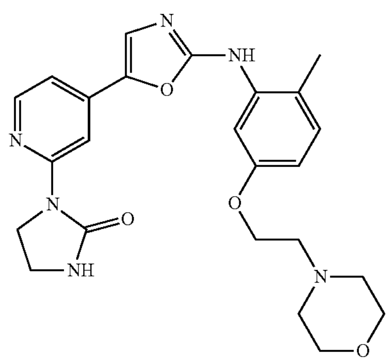 [SMILES: Cc1ccc(OCCN2CCOCC2)cc1Nc1ncc(-c2ccnc(N3CCNC3=O)c2)o1] | 1-(4-{2-[2-Methyl-5-(2-morpholin-4-yl-ethoxy)-phenylamino]-oxazol-5-yl}-pyridin-2-yl)-imidazolidin-2-one | (300 MHz, DMSO-$d_6$) δ 9.57 (br s, 1H), 8.35 (br s, 1H), 8.25 (d, J = 5.4 Hz, 1H), 7.68 (s, 1H), 7.56 (br s, 1H), 7.27 (br s, 1H), 7.20 (d, J = 5.3 Hz, 1H), 7.09 (d, J = 8.3 Hz, 1H), 6.61 (d, J = 8.3 Hz, 1H), 4.11-3.93 (m, 4H), 3.63-3.54 (m, 4H), 3.46-3.38 (m, 2H), 2.69 (t, J = 5.7 Hz, 2H), 2.52-2.45 (m, 4H), 2.23 (s, 3H). (APCI+) m/z 465 (M + H)$^+$ Retention time = 2.05 min (method 2) |
| 050 | 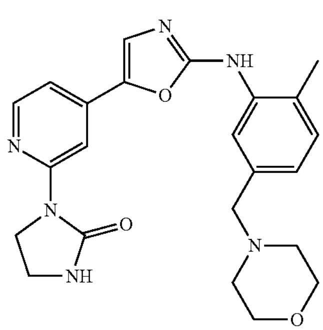 [SMILES: Cc1ccc(CN2CCOCC2)cc1Nc1ncc(-c2ccnc(N3CCNC3=O)c2)o1] | 1-{4-[2-(2-Methyl-5-morpholin-4-ylmethyl-phenylamino)-oxazol-5-yl]-pyridin-2-yl}-imidazolidin-2-one | (300 MHz, DMSO-$d_6$) δ 9.57 (br s, 1H), 8.32 (br s, 1H), 8.24 (d, J = 5.3 Hz, 1H), 7.72 (s, 1H), 7.66 (s, 1H), 7.26 (br s, 1H), 7.20-7.12 (m, 2H), 6.96 (d, J = 7.5 Hz, 1H), 4.01 (t, J = 7.9 Hz, 2H), 3.60-3.52 (s, 4H), 3.46-3.37 (m, 4H), 2.40-2.32 (m, 4H), 2.27 (s, 3H). (APCI+) m/z 435 (M + H)$^+$ Retention time = 2.00 min (method 2) |

TABLE 1-continued

| Ex # | Chemical structure | Name | ¹H NMR/LCMS |
|------|-------------------|------|-------------|
| 051 | 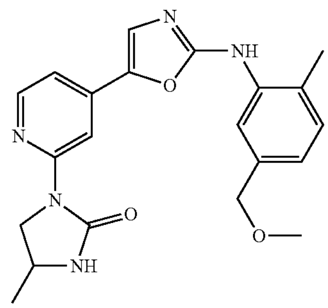 | 1-{4-[2-((5-Methoxymethyl)-2-methyl-phenylamino)-oxazol-5-yl]-pyridin-2-yl}-4-methyl-imidazolidin-2-one | (300 MHz, DMSO-$d_6$) δ 9.59 (br s, 1H), 8.32 (br s, 1H), 8.22 (d, J = 5.5 Hz, 1H), 7.78 (br s, 1H), 7.65 (s, 1H), 7.43 (br s, 1H), 7.20-7.14 (m, 2H), 6.96 (d, J = 7.6 Hz, 1H), 4.38 (s, 2H), 4.17-4.07 (m, 1H), 3.83-3.73 (m, 1H), 3.53 (dd, J = 10.5, 6.0 Hz, 1H), 3.28 (s, 3H), 2.28 (s, 3H), 1.20 (d, J = 6.1 Hz, 3H).<br>(APCI+) m/z 394 (M + H)⁺<br>Retention time = 2.69 min (method 2) |
| 052 | 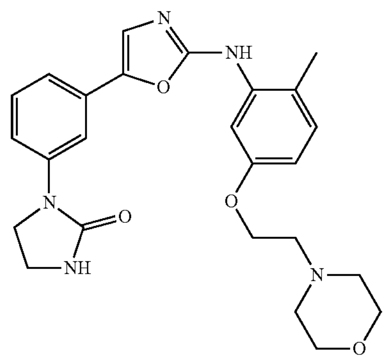 [SMILES: Cc1ccc(OCCN2CCOCC2)cc1Nc1ncc(-c2cccc(N3CCNC3=O)c2)o1] | 1-(3-{2-[2-Methyl-5-(2-morpholin-4-yl-ethoxy)-phenylamino]-oxazol-5-yl}-phenyl)-imidazolidin-2-one | (300 MHz, DMSO-$d_6$) δ 9.26 (s, 1H), 7.80 (s, 1H), 7.61 (d, J = 2.5 Hz, 1H), 7.43 (d, J = 9.2 Hz, 1H), 7.40 (s, 1H), 7.34 (t, J = 7.9 Hz, 1H), 7.23 (d, J = 7.6 Hz, 1H), 7.06 (d, J = 8.5 Hz, 1H), 7.02 (br s, 1H), 6.55 (dd, J = 8.3, 2.6 Hz, 1H), 4.04 (t, J = 5.8 Hz, 2H), 3.94-3.83 (m, 2H), 3.63-3.52 (m, 4H), 3.42 (t, J = 8.0 Hz, 2H), 2.68 (t, J = 5.8 Hz, 2H), 2.49-2.41 (m, 4H), 2.22 (s, 3H).<br>(APCI+) m/z 464 (M + H)⁺<br>Retention time = 2.27 min (method 2) |
| 053 | 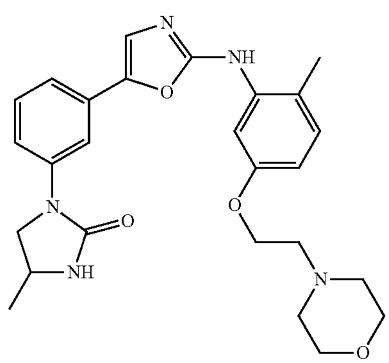 [SMILES: Cc1ccc(OCCN2CCOCC2)cc1Nc1ncc(-c2cccc(N3CC(C)NC3=O)c2)o1] | 4-Methyl-1-(4-{2-[2-methyl-5-(2-morpholin-4-yl-ethoxy)-phenylamino]-oxazol-5-yl}-pyridin-2-yl)-imidazolidin-2-one | (300 MHz, DMSO-$d_6$) δ 9.56 (br s, 1H), 8.33 (s, 1H), 8.23 (d, J = 5.4 Hz, 1H), 7.68 (s, 1H), 7.55 (d, J = 2.5 Hz, 1H), 7.43 (s, 1H), 7.19 (dd, J = 5.3, 1.5 Hz, 1H), 7.08 (d, J = 8.3 Hz, 1H), 6.60 (dd, J = 8.3, 2.5 Hz, 1H), 4.14 (dd, J = 10.5, 8.7 Hz, 1H), 4.05 (t, J = 5.7 Hz, 2H), 3.85-3.75 (m, 1H), 3.60-3.50 (m, 5H), 2.69 (t, J = 5.7 Hz, 2H), 2.49-2.44 (m, 4H), 2.23 (s, 3H), 1.21 (d, J = 6.1 Hz, 3H).<br>(APCI+) m/z 479 (M + H)⁺<br>Retention time = 2.13 min (method 2) |
| 054 | 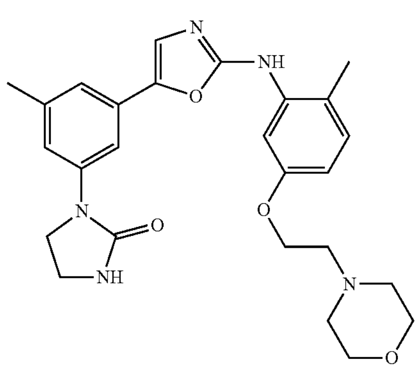 [SMILES: Cc1cc(-c2cnc(Nc3cc(OCCN4CCOCC4)ccc3C)o2)cc(N2CCNC2=O)c1] | 1-(3-Methyl-5-{2-[2-methyl-5-(2-morpholin-4-yl-ethoxy)-phenylamino]-oxazol-5-yl}-phenyl)-imidazolidin-2-one | (300 MHz, DMSO-$d_6$) δ 9.23 (s, 1H), 7.63 (d, J = 2.6 Hz, 2H), 7.37 (s, 1H), 7.27 (s, 1H), 7.06 (dd, J = 6.0, 4.6 Hz, 2H), 7.00 (s, 1H), 6.55 (dd, J = 8.3, 2.6 Hz, 1H), 4.09-3.99 (m, 2H), 3.92-3.80 (m, 2H), 3.63-3.53 (m, 4H), 3.41 (t, J = 7.9 Hz, 2H), 2.68 (t, J = 5.7 Hz, 2H), 2.48-2.42 (m, 4H), 2.31 (s, 3H), 2.22 (s, 3H).<br>(APCI+) m/z 478 (M + H)⁺<br>Retention time = 2.33 min (method 2) |

TABLE 1-continued

| Ex # | Chemical structure | Name | ¹H NMR/LCMS |
|---|---|---|---|
| 055 | 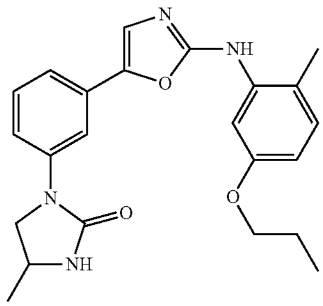 [SMILES: CCCOc1ccc(C)c(Nc2ncc(-c3cccc(N4CC(C)NC4=O)c3)o2)c1] | 1-{3-[2-((5-Ethoxymethyl)-2-methyl-phenylamino)-oxazol-5-yl]-phenyl}-4-methyl-imidazolidin-2-one | (300 MHz, DMSO-d$_6$) δ 9.29 (br s, 1H), 7.84 (br s, 1H), 7.77 (s, 1H), 7.44 (d, J = 7.8 Hz, 1H), 7.39 (s, 1H), 7.34 (t, J = 7.8 Hz, 1H), 7.22-7.13 (m, 3H), 6.94 (d, J = 7.5 Hz, 1H), 4.42 (s, 2H), 4.01 (t, J = 8.8 Hz, 1H), 3.88-3.76 (m, 1H), 3.54-3.38 (m, 3H), 2.29 (s, 3H), 1.22 (d, J = 6.1 Hz, 3H), 1.15 (t, J = 7.0 Hz, 3H). (APCI+) m/z 407 (M + H)⁺ Retention time = 3.08 min (method 2) |
| 056 | 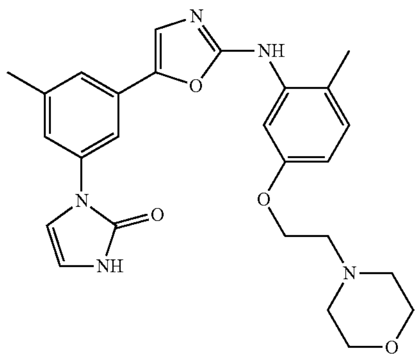 | 1-(3-Methyl-5-{2-[2-methyl-5-(2-morpholin-4-yl-ethoxy)-phenylamino]-oxazol-5-yl}-phenyl)-1,3-dihydro-imidazol-2-one | (300 MHz, CDCl$_3$) δ 10.36 (br s, 1H), 7.86 (d, J = 2.1 Hz, 1H), 7.72 (s, 1H), 7.36-7.28 (m, 3H), 7.15 (d, J = 8.4 Hz, 1H), 6.99 (br s, 1H), 6.67-6.61 (m, 2H), 6.52 (d, J = 2.1 Hz, 1H), 4.29 (t, = 5.3 Hz, 2H), 3.90-3.83 (m, 4H), 3.06-2.95 (m, 2H), 2.88-2.743 (s, 4H), 2.50 (s, 3H), 2.35 (s, 3H). (APCI+) m/z 476 (M + H)⁺ Retention time = 2.17 min (method 2) |
| 057 | 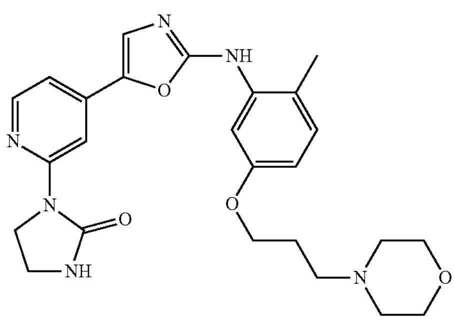 [SMILES: Cc1ccc(OCCCN2CCOCC2)cc1Nc1ncc(-c2ccnc(N3CCNC3=O)c2)o1] | 1-(4-{2-[2-Methyl-5-(3-morpholin-4-yl-propoxy)-phenylamino]-oxazol-5-yl}-pyridin-2-yl)-imidazolidin-2-one | (300 MHz, DMSO-d$_6$) δ 9.57 (br s, 1H), 8.35 (s, 1H), 8.25 (d, J = 5.4 Hz, 1H), 7.68 (s, 1H), 7.54 (d, J = 2.5 Hz, 1H), 7.28 (br s, 1H), 7.20 (dd, J = 5.3, 1.5 Hz, 1H), 7.08 (d, J = 8.4 Hz, 1H), 6.59 (dd, J = 8.4, 2.5 Hz, 1H), 4.06-3.93 (m, 4H), 3.60-3.54 (m, 4H), 3.47-3.38 (m, 2H), 2.47-2.32 (m, 6H), 2.23 (s, 3H), 1.93-1.83 (m, 2H). (APCI+) m/z 479 (M + H)⁺ Retention time = 1.95 min (method 2) |
| 058 | 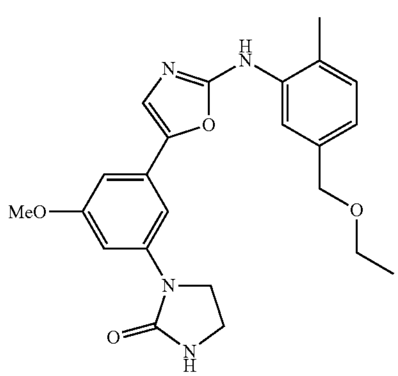 [SMILES: CCOCc1ccc(C)c(Nc2ncc(-c3cc(OC)cc(N4CCNC4=O)c3)o2)c1] | 1-{3-[2-((5-Ethoxymethyl)-2-methyl-phenylamino)-oxazol-5-yl]-5-methoxy-phenyl}-imidazolidin-2-one | (300 MHz, DMSO-d$_6$) δ 9.29 (s, 1H), 7.83 (d, J = 1.2 Hz, 1H), 7.41 (s, 1H), 7.38-7.31 (m, 1H), 7.15 (d, J = 8.0 Hz, 1H), 7.14-7.11 (m, 1H), 7.04 (s, 1H), 6.93 (dd, J = 7.7, 1.4 Hz, 1H), 6.82-6.79 (m, 1H), 4.41 (s, 2H), 3.87 (dd, J = 9.1, 6.7 Hz, 2H), 3.78 (s, 3H), 3.47 (q, J = 7.0 Hz, 2H), 3.43, (m, 1H), 2.28 (s, 3H), 1.14 (t, J = 7.0 Hz, 3H). (APCI+) m/z 423 (M + H)⁺ Retention time = 3.03 min (method 2) |

TABLE 1-continued

| Ex # | Chemical structure | Name | ¹H NMR/LCMS |
|---|---|---|---|
| 059 | 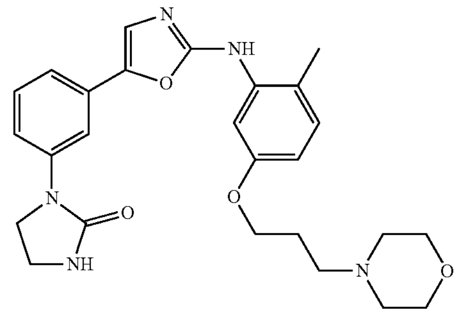 [SMILES: Cc1ccc(OCCCN2CCOCC2)cc1Nc1ncc(-c2cccc(N3CCNC3=O)c2)o1] | 1-(3-{2-[2-Methyl-5-(3-morpholin-4-yl-propoxy)-phenylamino]-oxazol-5-yl}-phenyl)-imidazolidin-2-one | (300 MHz, CDCl₃) δ 8.05 (s, 1H), 7.89 (d, J = 2.5 Hz, 1H), 7.53-7.43 (m, 2H), 7.38 (dd, J = 7.2, 1.4 Hz, 1H), 7.32 (s, 1H), 7.21 (d, J = 8.4 Hz, 1H), 7.10 (br s, 1H), 6.68 (dd, J = 8.3, 2.5 Hz, 1H), 5.67 (br s, 1H), 4.22 (t, J = 6.1 Hz, 2H), 4.12 (dd, J = 9.1, 6.7 Hz, 2H), 4.00-3.87 (m, 4H), 3.83 3.68 (m, 2H), 2.88-2.60 (m, 6H), 2.42 (s, 3H), 2.28-2.12 (m, 2H).<br>(APCI+) m/z 478 (M + H)⁺<br>Retention time = 2.16 min (method 2) |
| 060 | 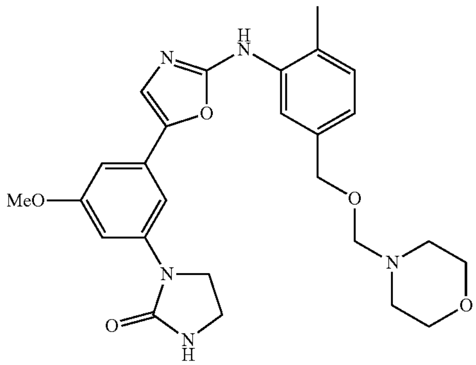 [SMILES: COc1cc(-c2cnc(Nc3cc(COCN4CCOCC4)ccc3C)o2)cc(N2CCNC2=O)c1] | 1-(3-Methoxy-5-{2-[2-methyl-5-(2-morpholin-4-yl-ethoxy)-phenylamino]-oxazol-5-yl}-phenyl)-imidazolidin-2-one | (300 MHz, DMSO-d₆) δ 9.26 (s, 1H), 7.61 (d, J = 2.5 Hz, 1H), 7.43 (s, 1H), 7.34 (s, 1H), 7.14 (t, J = 2.0 Hz, 1H), 7.06 (d, J = 8.8 Hz, 2H), 6.81 (s, 1H), 6.55 (dd, J = 8.3, 2.5 Hz, 1H), 4.04 (t, J = 5.9 Hz, 2H), 3.86 (dd, J = 14.9, 6.4 Hz, 2H), 3.78 (s, 3H), 3.60-3.53 (m, 4H), 3.41 (t, J = 8.0 Hz, 2H), 2.68 (t, J = 5.7 Hz, 2H), 2.49-2.38 (m, 4H), 2.22 (s, 3H).<br>(APCI+) m/z 494 (M + H)⁺<br>Retention time = 2.35 min (method 2) |
| 061 | 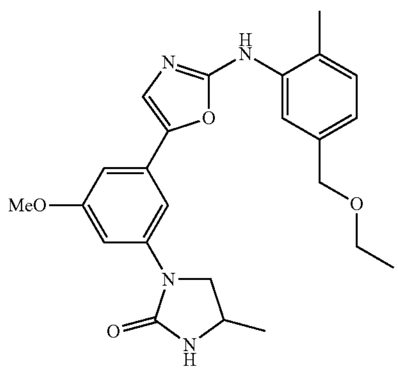 [SMILES: CCOCc1ccc(C)c(Nc2ncc(-c3cc(OC)cc(N4CC(C)NC4=O)c3)o2)c1] | 1-{3-[2-((5-Ethoxymethyl)-2-methyl-phenylamino)-oxazol-5-yl]-5-methoxy-phenyl}-4-methyl-imidazolidin-2-one | (300 MHz, DMSO-d₆) δ 9.27 (s, 1H), 7.83 (s, 1H), 7.41 (s, 1H), 7.31 (s, 1H), 7.20 (s, 1H), 7.15 (d, J = 8.3 Hz, 2H), 6.93 (d, J = 7.7 Hz, 1H), 6.80 (d, J = 1.3 Hz, 1H), 4.41 (s, 2H), 4.00 (dd, J = 16.1, 7.9 Hz, 1H), 3.87-3.73 (m, 4H), 3.45 (dt, J = 7.1, 4.9 Hz, 3H), 2.28 (s, 3H), 1.21 (d, J = 6.0 Hz, 3H), 1.18-1.06 (m, 3H).<br>(APCI+) m/z 437(M + H)⁺<br>Retention time = 3.43 min (method 2) |
| 062 | 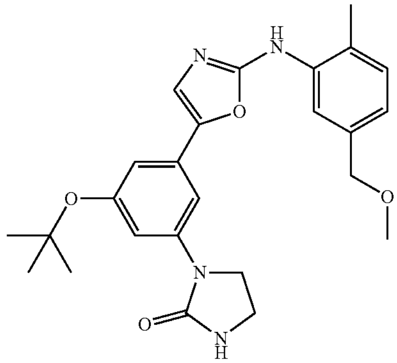 [SMILES: COCc1ccc(C)c(Nc2ncc(-c3cc(OC(C)(C)C)cc(N4CCNC4=O)c3)o2)c1] | 1-{3-tert-Butoxy-5-[2-((5-methoxymethyl)-2-methyl-phenylamino)-oxazol-5-yl]-phenyl}-imidazolidin-2-one | (300 MHz, DMSO-d₆) δ 9.43 (s, 1H), 8.00 (s, 1H), 7.57 (s, 1H), 7.55 (d, J = 1.6 Hz, 1H), 7.42 (t, J = 2.0 Hz, 1H), 7.33 (d, J = 7.7 Hz, 1H), 7.19 (s, 1H), 7.09 (dd, J = 7.6, 1.3 Hz, 1H), 7.02 6.96 (m, 1H), 4.54 (s, 2H), 4.10-3.98 (m, 2H), 3.58 (t, J = 7.9 Hz, 2H), 3.45 (s, 3H), 2.45 (s, 3H), 1.51 (s, 9H).<br>(APCI+) m/z 451 (M + H)⁺<br>Retention time = 3.98 min (method 2) |

TABLE 1-continued

| Ex # | Chemical structure | Name | ¹H NMR/LCMS |
|---|---|---|---|
| 063 | 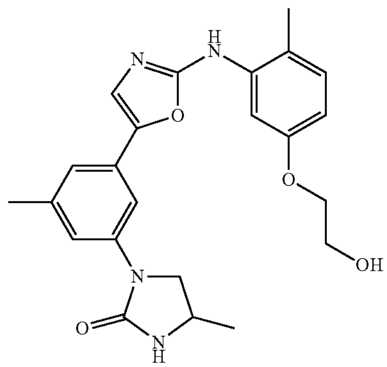 [SMILES: Cc1cc(-c2cnc(Nc3cc(OCCO)ccc3C)o2)cc(N2CC(C)NC2=O)c1] | 1-(3-{2-[5-(2-Hydroxy-ethoxy)-2-methyl-phenylamino]-oxazol-5-yl}-5-methyl-phenyl)-4-methyl-imidazolidin-2-one | (300 MHz, MeOH-d$_4$) δ 7.64 (br s, 1H), 7.43 (d, J = 2.5 Hz, 1H), 7.18 (br s, 1H), 7.15 (s, 1H), 7.14-7.08 (m, 2H), 6.65 (dd, J = 8.3, 2.6 Hz, 1H), 4.13-4.04 (m, 3H), 4.00-3.88 (m, 3H), 3.54 (dd, J = 8.8, 6.2 Hz, 1H), 2.38 (s, 3H), 2.28 (s, 3H), 1.36 (d, J = 6.1 Hz, 3H). (APCI+) m/z 422 (M + H)⁺ Retention time = 3.05 min (method 2) |
| 064 | 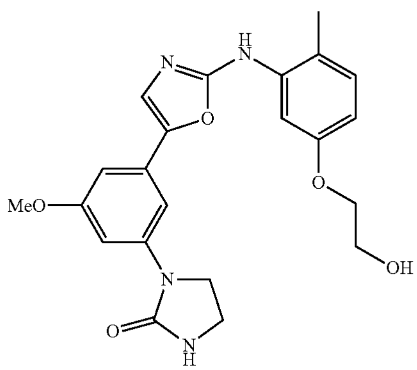 [SMILES: COc1cc(-c2cnc(Nc3cc(OCCO)ccc3C)o2)cc(N2CCNC2=O)c1] | 1-(3-{2-[5-(2-Hydroxy-ethoxy)-2-methyl-phenylamino]-oxazol-5-yl}-5-methoxy-phenyl)-imidazolidin-2-one | (300 MHz, DMSO-d$_6$) δ 9.26 (s, 1H), 7.64 (d, J = 2.6 Hz, 1H), 7.43 (s, 1H), 7.34 (s, 1H), 7.14 (t, J = 2.1 Hz, 1H), 7.08-7.02 (m, 2H), 6.82 (d, J = 1.4 Hz, 1H), 6.55 (dd, J = 8.3, 2.6 Hz, 1H), 4.86 (t, J = 5.6 Hz, 1H), 3.96-3.82 (m, 4H), 3.78 (s, 3H), 3.70 (dd, J = 10.3, 5.2 Hz, 2H), 3.45-3.37 (m, 2H), 2.22 (s, 3H). (APCI+) m/z 425 (M + H)⁺ Retention time = 2.58 min (method 2) |
| 065 | 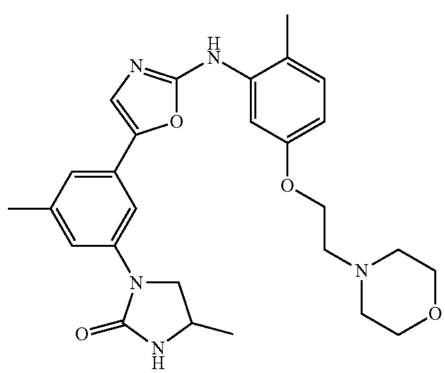 [SMILES: Cc1cc(-c2cnc(Nc3cc(OCCN4CCOCC4)ccc3C)o2)cc(N2CC(C)NC2=O)c1] | 4-Methyl-1-(3-methyl-5-{2-[2-methyl-5-(2-morpholin-4-yl-ethoxy)-phenylamino]-oxazol-5-yl}-phenyl)-imidazolidin-2-one | (300 MHz, DMSO-d$_6$) δ 9.24 (br s, 1H), 7.65 (d, J = 2.4 Hz, 1H), 7.60 (br s, 1H), 7.38 (s, 1H), 7.28 (br s, 1H), 7.18 (br s, 1H), 7.112-7.03 (m, 2H), 6.56 (d, J = 5.9 Hz, 1H), 4.12-3.92 (m, 3H), 3.91 3.76 (m, 1H), 3.63 3.53 (m, 4H), 3.42 (dd, J = 9.0, 6.2 Hz, 1H), 2.69 (t, J = 5.7 Hz, 2H), 2.50-2.43 (d, J = 4.4 Hz, 2H), 2.32 (s, 3H), 2.23 (s, 3H), 1.22 (d, J = 6.0 Hz, 3H). (APCI+) m/z 492 (M + H)⁺ Retention time = 2.46 min (method 2) |
| 066 | 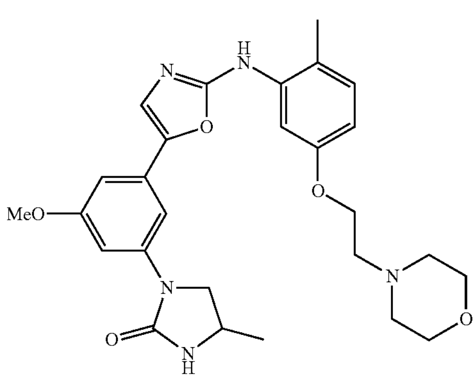 [SMILES: COc1cc(-c2cnc(Nc3cc(OCCN4CCOCC4)ccc3C)o2)cc(N2CC(C)NC2=O)c1] | 1-(3-Methoxy-5-{2-[2-methyl-5-(2-morpholin-4-yl-ethoxy)-phenylamino]-oxazol-5-yl}-phenyl)-4-methyl-imidazolidin-2-one | (300 MHz, DMSO-d$_6$) δ 9.25 (s, 1H), 7.63 (d, J = 2.3 Hz, 1H), 7.43 (s, 1H), 7.32 (s, 1H), 7.21 (s, 1H), 7.15 (s, 1H), 7.06 (d, J = 8.4 Hz, 1H), 6.81 (s, 1H), 6.56 (dd, J = 8.3, 2.5 Hz, 1H), 4.11 3.94 (m, 3H), 3.82 (m, 1H), 3.78 (s, 3H), 3.64 3.52 (m, 4H), 3.47-3.37 (m, 1H), 2.68 (m, 2H), 2.50-2.40 (m, 4H), 2.22 (s, 3H), 1.21 (d, J = 6.1 Hz, 3H). (APCI+) m/z 508 (M + H)⁺ Retention time = 2.61 min (method 2) |

TABLE 1-continued

| Ex # | Chemical structure | Name | $^1$H NMR/LCMS |
|---|---|---|---|
| 067 | 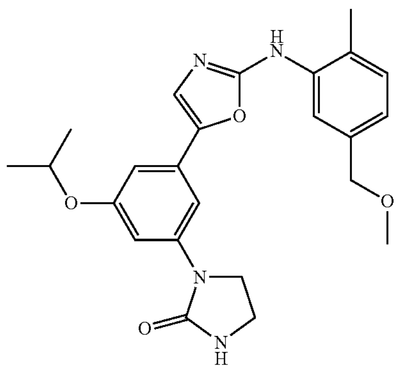 [SMILES: COCc1ccc(C)c(Nc2ncc(-c3cc(OC(C)C)cc(N4CCNC4=O)c3)o2)c1] | 1-{3-Isopropoxy-5-[2-((5-methoxymethyl)-2-methyl-phenylamino)-oxazol-5-yl]-phenyl}-imidazolidin-2-one | (300 MHz, DMSO-$d_6$) δ 9.27 (s, 1H), 7.84 (s, 1H), 7.41 (s, 1H), 7.29 (s, 1H), 7.23-7.09 (m, 2H), 7.02 (s, 1H), 6.92 (d, J = 7.6 Hz, 1H), 6.79 (d, J = 1.3 Hz, 1H), 4.63 (m, 1H), 4.37 (s, 2H), 3.93-3.81 (m, 2H), 3.46-3.36 (m, 2H), 3.28 (s, 3H), 2.28 (s, 3H), 1.28 (d, J = 6.0 Hz, 6H). (APCI+) m/z 437 (M + H)$^+$ Retention time = 3.79 min (method 2) |
| 068 | 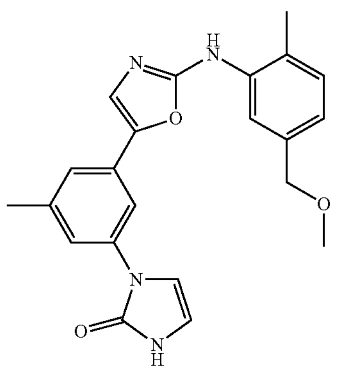 | 1-{3-[2-((5-Methoxymethyl)-2-methyl-phenylamino)-oxazol-5-yl]-5-methyl-phenyl}-1,3-dihydro-imidazol-2-one | (300 MHz, DMSO-$d_6$) δ 10.35 (br s, 1H), 9.31 (br s, 1H), 7.88 (s, 1H), 7.77 (s, 1H), 7.45 (s, 1H), 7.41 (s, 1H), 7.28 (s, 1H), 7.17 (d, J = 7.6 Hz, 1H), 7.00-6.96 (m, 1H), 6.93 (d, J = 7.7 Hz, 1H), 6.64-6.59 (m, 1H), 4.38 (s, 2H), 3.28 (s, 3H), 2.37 (s, .3H), 2.29 (s, 3H). (APCI+) m/z 391 (M + H)$^+$ Retention time = 3.46 min (method 2) |
| 069 | 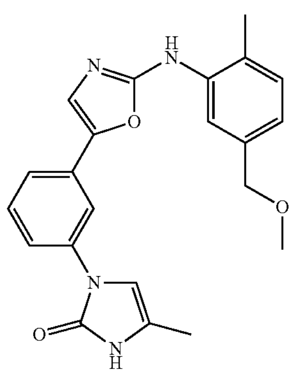 [SMILES: COCc1ccc(C)c(Nc2ncc(-c3cccc(-n4cc(C)[nH]c4=O)c3)o2)c1] | 1-{3-[2-((5-Methoxymethyl)-2-methyl-phenylamino)-oxazol-5-yl]-phenyl}-4-methyl-1,3-dihydro-imidazol-2-one | (300 MHz, DMSO-$d_6$) δ 10.34 (br s, 1H), 9.34 (br s, 1H), 7.94 (s, 1H), 7.87 (s, 1H), 7.60-7.34 (m, 4H), 7.17 (d, J = 7.4 Hz, 1H), 6.94 (d, J = 7.4 Hz, 1H), 6.71 (s, 1H), 4.38 (s, 2H), 3.28 (s, 3H), 2.29 (s, 3H), 2.00 (s, 3H). (APCI+) m/z 391 (M + H)$^+$ Retention time = 3.17 min (method 2) |
| 070 | 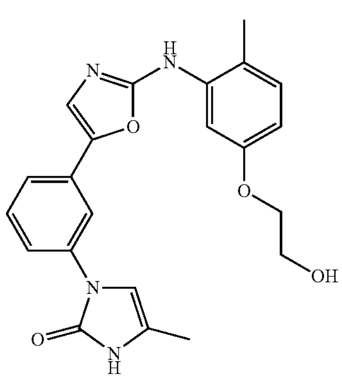 [SMILES: Cc1cn(-c2cccc(-c3cnc(Nc4cc(OCCO)ccc4C)o3)c2)c(=O)[nH]1] | 1-(3-{2-[5-(2-Hydroxy-ethoxy)-2-methyl-phenylamino]-oxazol-5-yl}-phenyl)-4-methyl-1,3-dihydro-imidazol-2-one | (300 MHz, DMSO-$d_6$) δ 10.35 (br s, 1H), 9.30 (br s, 1H), 7.95 (s, 1H), 7.67 (s, 1H), 7.57-7.41 (m, 4H), 7.08 (d, J = 8.3 Hz, 1H), 6.72 (br s, 1H), 6.57 (d, J= 8.3 Hz, 1H), 4.87 (t, J = 5.6 Hz, 1H), 3.95 (t, J = 4.9 Hz, 2H), 3.76-3.69 (m, 2H), 2.24 (s, 3H), 2.00 (s, 3H). (APCI+) m/z 407 (M + H)$^+$ Retention time = 2.85 min (method 2) |

TABLE 1-continued

| Ex # | Chemical structure | Name | $^1$H NMR/LCMS |
|---|---|---|---|
| 071 | 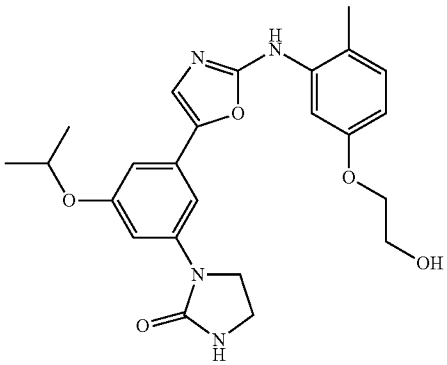 [SMILES: Cc1ccc(OCCO)cc1Nc1ncc(-c2cc(OC(C)C)cc(N3CCNC3=O)c2)o1] | 1-(3-{2-[5-(2-Hydroxy-ethoxy)-2-methyl-phenylamino]-oxazol-5-yl}-5-isopropoxy-phenyl)-imidazolidin-2-one | (300 MHz, DMSO-d$_6$) δ 9.23 (s, 1H), 7.63 (d, J = 2.5 Hz, 1H), 7.43 (s, 1H), 7.29 (s, 1H), 7.13 (d, J = 2.0 Hz, 1H), 7.10-6.99 (m, 2H), 6.80 (s, 1H), 6.55 (dd, J = 8.3, 2.5 Hz, 1H), 4.85 (t, J = 5.6 Hz, 1H), 4.63 (m, 1H), 3.94 (t, J = 5.0 Hz, 2H), 3.91-3.82 (m, 2H), 3.71 (m, 2H), 3.45-3.37 (m, 2H), 2.22 (s, 3H), 1.28 (d, J = 6.0 Hz, 6H). (APCI+) m/z 453 (M + H)$^+$ Retention time = 3.12 min (method 2) |
| 072 | 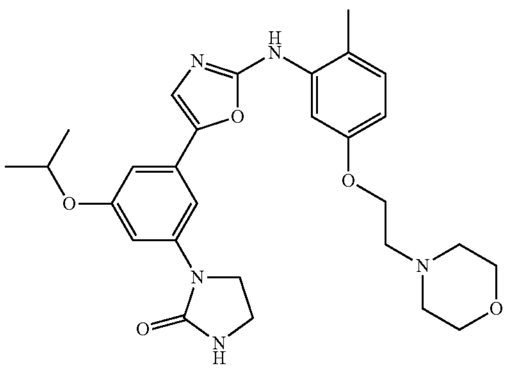 [SMILES: Cc1ccc(OCCN2CCOCC2)cc1Nc1ncc(-c2cc(OC(C)C)cc(N3CCNC3=O)c2)o1] | 1-(3-Isopropoxy-5-{2-[2-methyl-5-(2-morpholin-4-yl-ethoxy)-phenylamino]-oxazol-5-yl}-phenyl)-imidazolidin-2-one | (300 MHz, DMSO-d$_6$) δ 9 35 (s, 1H), 7.74 (s, 1H), 7.55 (s, 1H), 7.42 (s, 1H), 7.24 (s, 1H), 7.21-7.11 (m, 2H), 6.93 (s, 1H), 6.67 (dd, J = 8.3, 2.3 Hz, 1H), 4.84-4.66 (m, 1H), 4.16 (t, J = 5.8 Hz, 2H), 4.06-3.92 (m, 2H), 3.79-3.64 (m, 4H), 3.52 (dd, J = 15.7, 6.8 Hz, 2H), 2.80 (t, J = 5.7 Hz, 2H), 2.59 (d, J = 4.4 Hz, 4H), 2.34 (s, 3H). 1.42 (t, J = 7.0 Hz, 6H). (APCI+) m/z 522 (M + H)$^+$ Retention time = 2.46 min (method 2) |
| 073 | 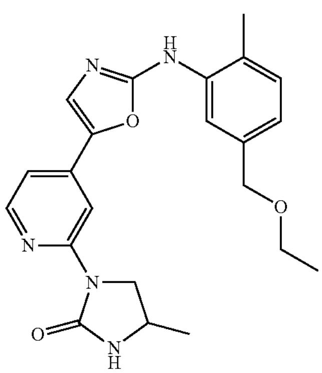 [SMILES: CCOCc1ccc(C)c(Nc2ncc(-c3ccnc(N4CC(C)NC4=O)c3)o2)c1] | 1-{4-[2-((5-Ethoxymethyl)-2-methyl-phenylamino)-oxazol-5-yl]-pyridin-2-yl}-4-methyl-imidazolidin-2-one | (300 MHz, DMSO-d$_6$) δ 9.59 (br s, 1H), 8.32 (br s, 1H), 8.22 (d, J = 5.4 Hz, 1H), 7.76 (s, 1H), 7.65 (s, 1H), 7.43 (br s, 1H), 7.21-7.15 (m, 2H), 6.97 (d, J = 7.5 Hz, 1H), 4.42 (s, 2H), 4.13 (t, J = 9.7 Hz, 1H), 3.85-3.75 (m, 1H), 3.59-3.42 (m, 3H), 2.28 (s, 3H), 1.20 (d, J = 6.0 Hz, 3H), 1.14 (t, J = 7.0 Hz, 3H). (APCI+) m/z 408 (M + H)$^+$ Retention time = 2.85 min (method 2) |
| 074 | 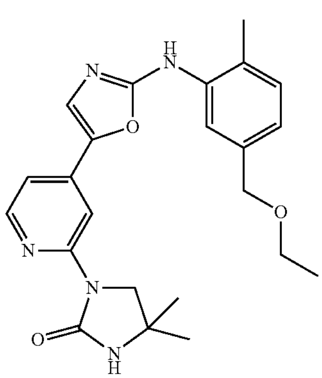 [SMILES: CCOCc1ccc(C)c(Nc2ncc(-c3ccnc(N4CC(C)(C)NC4=O)c3)o2)c1] | 1-{4-[2-((5-Ethoxymethyl)-2-methyl-phenylamino)-oxazol-5-yl]-pyridin-2-yl}-4,4-dimethyl-imidazolidin-2-one | (300 MHz, DMSO-d$_6$) δ 9.59 (br s, 1H), 8.33 (br s, 1H), 8.22 (d, J = 5.4 Hz, 1H), 7.77 (s, 1H), 7.66 (s, 1H), 7.48 (s, 1H), 7.20-7.13 (m, 2H), 6.97 (d, J = 7.8 Hz, 1H), 4.43 (s, 2H), 3.75 (s, 2H), 3.48 (q, J = 7.0 Hz, 2H), 2.29 (s, 3H), 1.29 (s, 6H), 1.15 (t,J = 7.0 Hz, 3H). (APCI+) m/z 422 (M + H)$^+$ Retention time = 2.98 min (method 2) |

TABLE 1-continued

| Ex # | Chemical structure | Name | ¹H NMR/LCMS |
|------|-------------------|------|-------------|
| 075 | 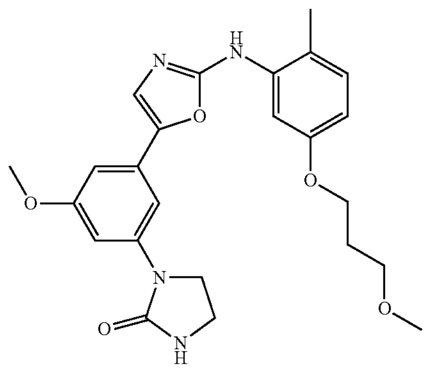 | 1-(3-Methoxy-5-{2-[5-(3-methoxy-propoxy)-2-methyl-phenylamino]-oxazol-5-yl}-phenyl)-imidazolidin-2-one | (300 MHz, DMSO-$d_6$) δ 9.25 (s, 1H), 7.61 (d, J = 2.5 Hz, 1H), 7.44 (s, 1H), 7.34 (s, 1H), 7.14 (t, J = 2.0 Hz, 1H), 7.08-7.02 (m, 2H), 6.82 (s, 1H), 6.54 (dd, J = 8.3, 2.6 Hz, 1H), 3.97(t, J = 6.4 Hz, 2H), 3.92-3.83 (m, 2H), 3.78 (s, 3H), 3.51-3.36 (m, 4H), 3.24 (s, 3H), 2.22 (s, 3H), 1.93 (m, 2H). (APCI+) m/z 453 (M + H)$^+$ Retention time = 3.38 min (method 2) |
| 076 | 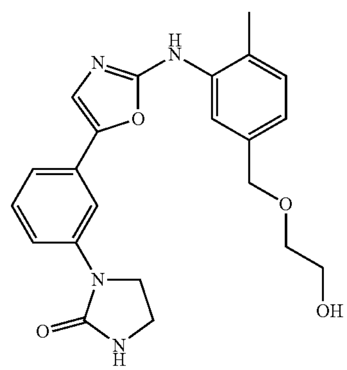 [SMILES: Cc1ccc(COCCO)cc1Nc1ncc(-c2cccc(N3CCNC3=O)c2)o1] | 1-(3-{2-[(5-(2-Hydroxy-ethoxymethyl))-2-methyl-phenylamino]-oxazol-5-yl}-phenyl)-imidazolidin-2-one | (300 MHz, DMSO-$d_6$) δ 9.30 (br s, 1H), 7.84-7.78 (m, 2H), 7.43 (d, J = 8.2 Hz, 1H), 7.38 (s, 1H), 7.35 (t, J = 7.6 Hz, 1H), 7.22 (d, J = 7.6 Hz, 1H), 7.17 (d, J = 7.7 Hz, 1H), 7.03 (s, 1H), 6.97 (d, J = 7.8 Hz, 1H), 4.62 (t, J = 5.5 Hz, 1H), 4.46 (s, 2H), 3.94-3.84 (m, 2H), 3.58-3.38 (m, 4H), 2.29 (s, 3H). (APCI+) m/z 409 (M + H)$^+$ Retention time = 2.80 min (method 2) |
| 077 | 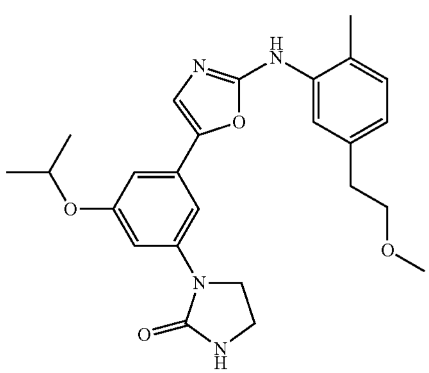 [SMILES: COCCc1ccc(C)c(Nc2ncc(-c3cc(OC(C)C)cc(N4CCNC4=O)c3)o2)c1] | 1-(3-Isopropoxy-5-{2-[5-(2-methoxy-ethyl)-2-methyl-phenylamino]-oxazol-5-yl}-phenyl)-imidazolidin-2-one | (400 MHz, DMSO-$d_6$) δ 9.22 (s, 1H), 7.70 (s, 1H), 7.41 (s, 1H), 7.29 (s, 1H), 7.19-7.06 (m, 2H), 7.03 (s, 1H), 6.86 (d, J = 7.5 Hz, 1H), 6.79 (s, 1H), 4.72-4.57 (m, 1H), 3.98-3.74 (m, 2H), 3.52 (t, J = 6.9 Hz, 2H), 3.46-3.38 (m, 2H), 2.77 (t, J = 6.6 Hz, 2H), 2.25 (s, 3H), 1.29 (d, J = 6.0 Hz, 6H). (ESI+) m/z 451 (M + H)$^+$ Retention time = 3.94 min (method 1) |
| 078 | 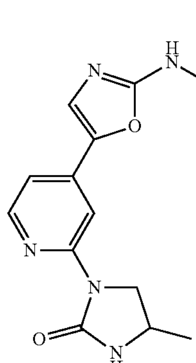 | 1-(4-{2-[5-(2-Methoxy-ethoxy)-2-methyl-phenylamino]-oxazol-5-yl}-pyridin-2-yl)-4-methyl-imidazolidin-2-one | (300 MHz, DMSO-$d_6$) δ 9.56 (br t, 1H), 8.33 (br s, 1H), 8.23 (d, J = 5.4 Hz, 1H), 7.67 (s, 1H), 7.56 (d, J = 2.5 Hz, 1H), 7.43 (s, 1H), 7.19 (d, J = 4.1 Hz, 1H), 7.08 (d, J = 8.3 Hz, 1H), 6.59 (dd, J = 8.3, 2.5 Hz, 1H), 4.17-4.08 (m, 1H), 4.08-4.01 (m, 2H), 3.87-3.73 (m, 1H), 3.67-3.63 (m, 2H), 3.54 (dd, J = 10.6, 6.1 Hz, 1H), 3.31 (s, 3H), 2.22 (s, 3H), 1.20 (d, J = 6.1 Hz, 3H). (APCI+) m/z 424 (M + H)$^+$ Retention time = 2.76 min (method 2) |

TABLE 1-continued

| Ex # | Chemical structure | Name | ¹H NMR/LCMS |
|---|---|---|---|
| 079 | 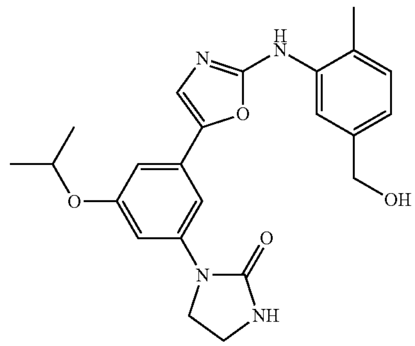 [SMILES: Cc1ccc(CO)cc1Nc1ncc(-c2cc(OC(C)C)cc(N3CCNC3=O)c2)o1] | 1-{3-[2-(5-Hydroxymethyl-2-methyl-phenylamino)-oxazol-5-yl]-5-isopropoxy-phenyl}-imidazolidin-2-one | (300 MHz, DMSO) δ 9.22 (s, 1H), 7.80 (s, 1H), 7.39 (s, 1H), 7.29 (s, 1H), 7.12 (m, 2H), 7.02 (s, 1H), 6.92 (d, J = 7.7 Hz, 1H), 6.79 (s, 1H), 5.12 (t, J = 5.7 Hz, 1H), 4.63 (m, 1H), 4.45 (d, J = 5.7 Hz, 2H), 3.94-3.78 (m, 2H), 3.40 (t, J = 8.0 Hz, 2H), 2.26 (s, 3H), 1.28 (d, J = 6.0 Hz, 6H). (ESI+) m/z 423 (M + H)+ Retention time = 4.82 min (method 2) |
| 080 | 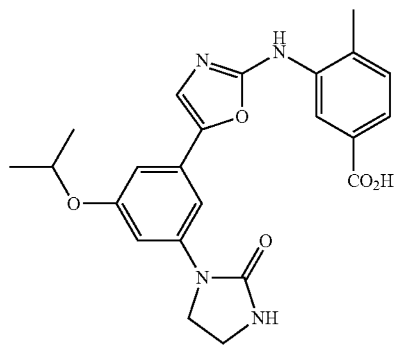 [SMILES: Cc1ccc(C(=O)O)cc1Nc1ncc(-c2cc(OC(C)C)cc(N3CCNC3=O)c2)o1] | 3-{5-[3-Isopropoxy-5-(2-oxo-imidazolidin-1-yl)-phenyl]-oxazol-2-ylamino}-4-methyl-benzoic acid | (300 MHz, DMSO) δ 9.58 (brs, 1H), 8.54 (d, J = 1.5 Hz, 1H), 7.56 (dd, J = 7.8, 1.6 Hz, 1H), 7.49 (s, 1H), 7.36-7.27 (m, 2H), 7.14 (s, 1H), 7.04 (brs, 1H), 6.82 (s, 1H), 4.63 (m, 1H), 3.95-3.80 (m, 2H), 3.49-3.32 (m, 2H), 2.36 (s, 3H), 1.28 (d, J = 6.0 Hz, 6H). (ESI+) m/z 437 (M + H)+ Retention time = 5.01 min (method 2) |
| 081 | 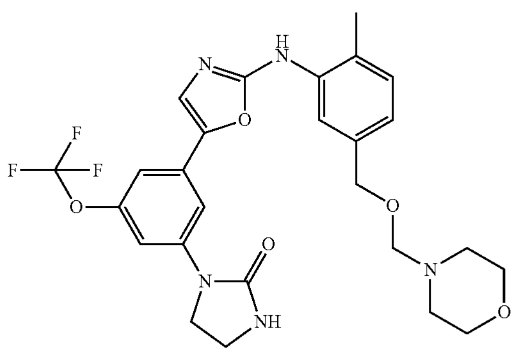 [SMILES: Cc1ccc(COCN2CCOCC2)cc1Nc1ncc(-c2cc(OC(F)(F)F)cc(N3CCNC3=O)c2)o1] | 1-(3-(2-(2-methyl-5-(2-morpholinoethoxy)phenylamino)oxazol-5-yl)-5-(trifluoromethoxy)phenyl)imidazolidin-2-one | ¹H NMR (300 MHz, DMSO) δ 9.34 (s, 1H), 7.68 (s, 1H), 7.59 (d, J = 2.5 Hz, 3H), 7.23 (s, 1H), 1.16 (s, 1H), 7.07 (d, J = 8.4 Hz, 1H), 6.57 (dd, J = 8.3, 2.6 Hz, 1H), 4.04 (t, J = 5.8 Hz, 2H), 3.97-3.85 (m, 2H), 3.57 (dd, J = 5.5, 3.8 Hz, 4H), 3.43 (dd, J = 15.9, 8.0 Hz, 2H), 2.68 (t, J = 5.8 Hz, 2H), 2.48-2.43 (m, 4H), 2.22 (s, 3H). (ESI+) m/z 548.2 (M + H)+ Retention time = 2.43 min (method 2) |
| 082 | 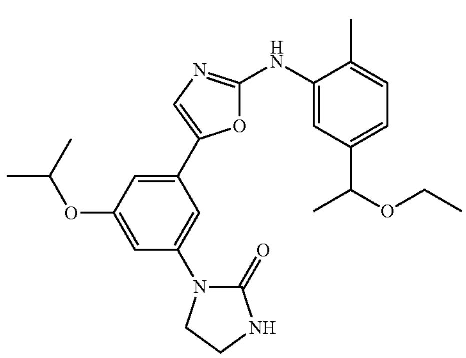 [SMILES: CCOC(C)c1ccc(C)c(Nc2ncc(-c3cc(OC(C)C)cc(N4CCNC4=O)c3)o2)c1] | 1-(3-{2-[5-(1-Ethoxy-ethyl)-2-methyl-phenylamino]-oxazol-5-yl}-5-isopropoxy-phenyl)-imidazolidin-2-one | (300 MHz, DMSO) δ 9.25 (s, 1H), 7.79 (s, 1H), 7.41 (s, 1H), 7.21-7.08 (m, 2H), 7.01 (s, 1H), 6.91 (d, J = 8.1 Hz, 1H), 6.78 (s, 1H), 4.62 (m, 1H), 4.37 (q, J = 6.1 Hz, 1H), 3.94-3.79 (m, 2H), 3.40 (m, 2H), 3.30 (m, 2H), 2.27 (s, 3H), 1.32 (d, J = 6.4 Hz, 2H), 1.28 (d, J = 6.0 Hz, 3H), 1.08 (t, J = 7.0 Hz, 3H). (ESI+) m/z 465 (M + H)+ Retention time = 3.58 min (method 2) |

TABLE 1-continued

| Ex # | Chemical structure | Name | ¹H NMR/LCMS |
|------|-------------------|------|-------------|
| 083 | 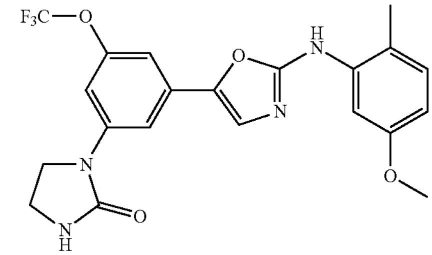 [SMILES: COc1ccc(C)c(Nc2ncc(-c3cc(OC(F)(F)F)cc(N4CCNC4=O)c3)o2)c1] | 1-(3-(2-(5-methoxy-2-methylphenylamino)oxazol-5-yl)-5-(trifluoromethoxy)phenyl)imidazolidin-2-one | (300 MHz, DMSO) δ 9.36 (s, 1H), 7.68 (s, 1H), 7.59 (d, J = 2.0 Hz, 3H), 7.25 (s, 1H), 7.16 (s, 1H), 7.08 (d, J = 8.4 Hz, 1H), 6.57 (dd, J = 8.3, 2.6 Hz, 1H), 3.98-3.86 (m, 2H), 3.72 (s, 3H), 3.51-3.38 (m, 2H), 2.22 (s, 3H).<br>(ESI+) m/z 449 (M + H)+<br>Retention time = 3.55 min (method 2) |
| 084 | 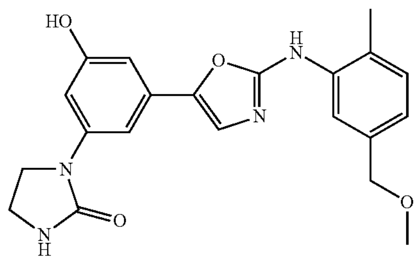 [SMILES: COCc1ccc(C)c(Nc2ncc(-c3cc(O)cc(N4CCNC4=O)c3)o2)c1] | 1-(3-hydroxy-5-(2-(5-methoxymethyl)-2-methylphenylamino)oxazol-5-yl)phenyl)imidazolidin-2-one | (300 MHz, DMSO) δ 9.51 (s, 1H), 9.24 (s, 1H), 7.83 (s, 1H), 7.30 (s, 1H), 7.19-7.11 (m, 2H), 7.08 (s, 1H), 6.97 (s, 1H), 6.92 (d, J = 7.7 Hz, 1H), 6.62 (s, 1H), 4.37 (s, 2H), 3.89-3.78 (m, 2H), 3.46-3.36 (m, 2H), , 3.27 (s, 3H), 2.28 (s, 3H).<br>(ESI+) m/z 395 (M + H)+<br>Retention time = 2.76 min (method 2) |
| 085 | 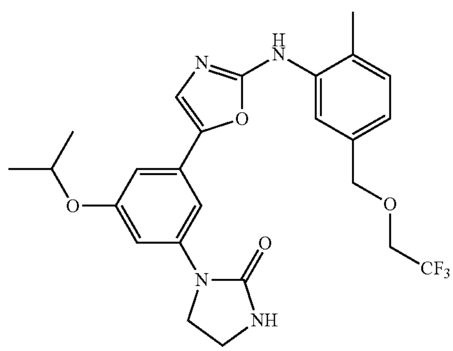 [SMILES: Cc1ccc(COCC(F)(F)F)cc1Nc1ncc(-c2cc(OC(C)C)cc(N3CCNC3=O)c2)o1] | 1-(3-Isopropoxy-5-{2-[2-methyl-5-(2,2,2-trifluoro-ethoxymethyl)-phenylamino]-oxazol-5-yl)-phenyl)-imidazolidin-2-one | (300 MHz, DMSO) δ 9.30 (s, 1H), 7.88 (s, 1H), 7.41 (s, 1H), 7.31 (s, 1H), 7.20 (d, J = 7.8 Hz, 1H), 7.11 (t, J = 2.1 Hz, 1H), 7.01 (s, 1H), 6.97 (d, J = 7.7 Hz, 1H), 6.79 (s, 1H), 4.62 (s, 2H), 4.62 (m, 1H), 4.08 (q, J = 9.4 Hz, 2H), 3.94-3.81 (m, 2H), 3.40 (m, 2H), 2.29 (s, 3H), 1.28 (d, J = 6.0 Hz, 6H).<br>(ESI+) m/z 505 (M + H)+<br>Retention time = 3.63 min (method 2) |
| 086 | 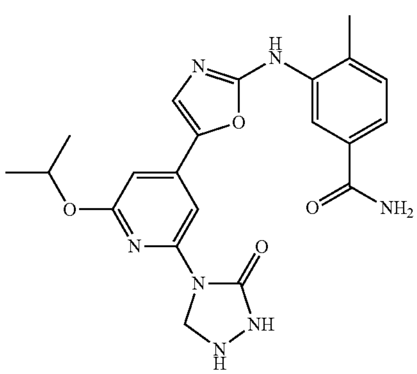 [SMILES: Cc1ccc(C(N)=O)cc1Nc1ncc(-c2cc(OC(C)C)nc(N3CNNC3=O)c2)o1] | 3-{5-[3-Isopropoxy-5-(2-oxo-imidazolidin-1-yl)-phenyl]-oxazol-2-ylamino}-4-methyl-benzamide | (300 MHz, DMSO) δ 9.39 (s, 1H), 8.35 (s, 1H), 7.88 (s, 1H), 7.49 (d, J = 7.8 Hz, 1H), 7.43 (s, 1H), 7.27 (m, 3H), 7.13 (s, 1H), 7.04 (s, 1H), 6.80 (s, 1H), 4.71-4.56 (m, 1H), 3.86 (m, 2H), 3.47-3.37 (m, 2H), 2.33 (s, 3H), 1.28 (d, J = 6.0 Hz, 6H).<br>(ESI+) m/z 436 (M + H)+<br>Retention time = 2.84 min (method 2) |
| 087 | 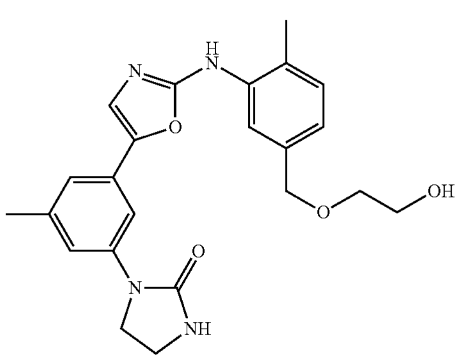 [SMILES: Cc1cc(-c2cnc(Nc3cc(COCCO)ccc3C)o2)cc(N2CCNC2=O)c1] | 1-(3-{2-[5-(2-Hydroxy-ethoxymethyl)-2-methyl-phenylamino]-oxazol-5-yl}-5-methyl-phenyl)-imidazolidin-2-one | (300 MHz, DMSO) δ 9.26 (s, 1H), 7.84 (s, 1H), 7.62 (s, 1H), 7.34 (s, 1H), 7.26 (s, 1H), 7.16 (d, J = 7.8 Hz, 1H), 7.06 (s, 1H), 7.01-6.90 (m, 2H), 4.61 (t, J = 5.5 Hz, 1H), 4.45 (s, 2H), 3.92-3.82 (m, 2H), 3.53 (dd, J = 10.6, 5.0 Hz, 2H), 3.48-3.36 (m, 4H), 2.31 (s, 3H), 2.28 (s, 3H).<br>(ESI+) m/z 423.2 (M + H)+<br>Retention time = 2.72 min (method 2) |

TABLE 1-continued

| Ex # | Chemical structure | Name | $^1$H NMR/LCMS |
|---|---|---|---|
| 088 | 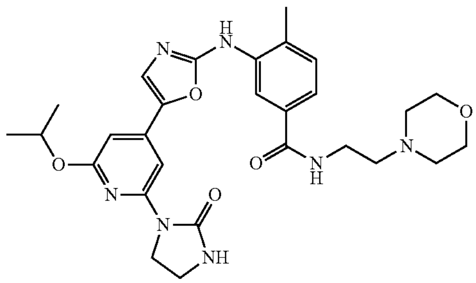 [SMILES: Cc1ccc(C(=O)NCCN2CCOCC2)cc1Nc1ncc(-c2cc(OC(C)C)nc(N3CCNC3=O)c2)o1] | 3-{5-[3-Isopropoxy-5-(2-oxo-imidazolidin-1-yl)-phenyl]-oxazol-2-ylamino}-4-methyl-N-(2-morpholin-4-yl-ethyl)-benzamide | (300 MHz, DMSO) δ 9.40 (s, 1H), 8.32 (m, 1H), 8.29 (m, 1H), 7.44 (m, 2H), 7.32-7.23 (m, 2H), 7.13 (t, J = 2.0 Hz, 1H), 7.03 (s, 1H), 6.81 (s, 1H), 4.64 (m, 1H), 3.94-3.81 (m, 2H), 3.64-3.51 (m, 4H), 3.45-3.30 (m, 4H), 2.45-2.35 (m, 4H), 2.33 (s, 3H), 1.28 (d, J = 6.0 Hz, 6H). (ESI+) m/z 549 (M + H)$^+$ Retention time = 2.32 min (method 2) |
| 089 | 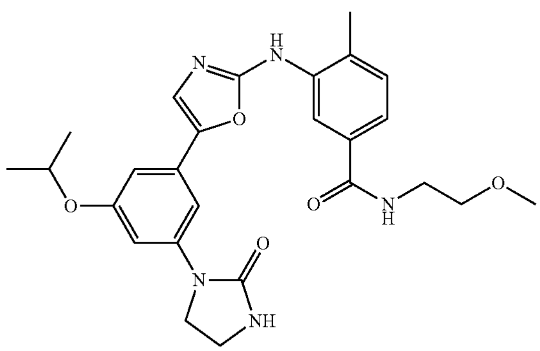 [SMILES: COCCNC(=O)c1ccc(C)c(Nc2ncc(-c3cc(OC(C)C)cc(N4CCNC4=O)c3)o2)c1] | 3-{5-[3-Isopropoxy-5-(2-oxo-imidazolidin-1-yl)-phenyl]-oxazol-2-ylamino}-N-(2-methoxy-ethyl)-4-methyl-benzamide | (300 MHz, DMSO) δ 9.39 (s, 1H), 8.42 (m, 1H), 8.33 (d, J = 1.4 Hz, 1H), 7.46 (dd, J = 7.9, 1.6 Hz, 1H), 7.43 (s, 1H), 7.30-7.24 (m, 2H), 7.14 (t, J = 2.0 Hz, 1H), 7.02 (s, 1H), 6.80 (s, 1H), 4.63 (m, 1H), 3.94-3.80 (m, 2H), 3.51-3.35 (m, 6H), 3.26 (s, 3H), 2.33 (s, 3H), 1.28 (d, J = 6.0 Hz, 6H). (ESI+) m/z 494 (M + H)+ Retention time = 2.99 min (method 2) |
| 090 | 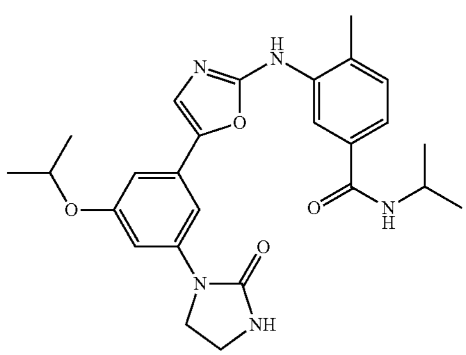 [SMILES: Cc1ccc(C(=O)NC(C)C)cc1Nc1ncc(-c2cc(OC(C)C)cc(N3CCNC3=O)c2)o1] | 3-{5-[3-Isopropoxy-5-(2-oxo-imidazolidin-1-yl)-phenyl]-oxazol-2-ylamino}-N-isopropyl-4-methyl-benzamide | (300 MHz, DMSO) δ 9.38 (s, 1H), 8.30 (d, J = 1.5 Hz, 1H), 8.12 (d, J = 7.8 Hz, 1H), 7.47 (dd, J = 7.8, 1.6 Hz, 1H), 7.42 (s, 1H), 7.30-7.24 (m, 2H), 7.14 (s, 1H), 7.02 (s, 1H), 6.79 (s, 1H), 4.63 (m, 1H), 4.18-3.97 (m, 1H), 3.93-3.80 (m, 2H), 3.40 (m, 2H), 2.32 (s, 3H), 1.28 (d, J = 6.0 Hz, 6H), 1.15 (d, J = 6.6 Hz, 6H). (ESI+) m/z 478 (M + H)+ Retention time = 3.16 min (method 2) |
| 091 | 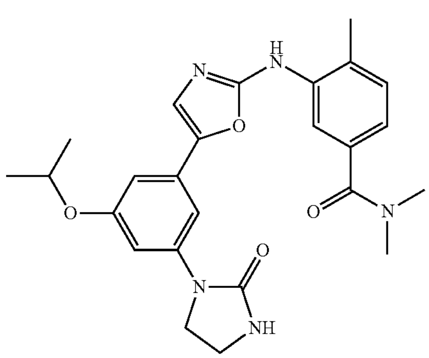 [SMILES: Cc1ccc(C(=O)N(C)C)cc1Nc1ncc(-c2cc(OC(C)C)cc(N3CCNC3=O)c2)o1] | 3-{5-[3-Isopropoxy-5-(2-oxo-imidazolidin-1-yl)-phenyl]-oxazol-2-ylamino}-4,N,N-trimethyl-benzamide | (300 MHz, DMSO) δ 9.41 (s, 1H), 7.99 (d, J = 1.5 Hz, 1H), 7.43 (s, 1H), 7.29 (s, 1H), 7.24 (d, J = 7.8 Hz, 1H), 7.12 (s, 1H), 7.02 (s, 1H), 6.99 (dd, J = 7.6, 1.7 Hz, 1H), 6.80 (s, 1H), 4.63 (m, 1H), 3.93-3.81 (m, 2H), 3.40 (m, 2H), 2.96 (s, 6H), 2.33 (s, 3H), 1.28 (d, J = 6.0 Hz, 6H). (ESI+) m/z 464 (M + H)+ Retention time = 3.02 min (method 2) |

TABLE 1-continued

| Ex # | Chemical structure | Name | ¹H NMR/LCMS |
|---|---|---|---|
| 092 | 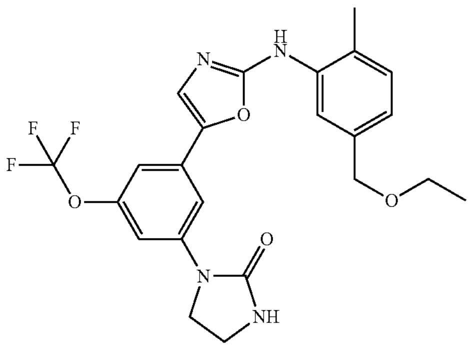 [SMILES: CCOCc1ccc(C)c(Nc2ncc(-c3cc(OC(F)(F)F)cc(N4CCNC4=O)c3)o2)c1] | 1-(3-(2-(5-(ethoxymethyl)-2-methylphenylamino)oxazol-5-yl)-5-(trifluoromethoxy)phenyl)imidazolidin-2-one | ¹H NMR (400 MHz, DMSO) δ 9.39 (s, 1H), 7.81 (s, 1H), 7.66 (d, J = 6.7 Hz, 1H), 7.57 (d, J = 2.1 Hz, 2H), 7.25 (s, 1H), 7.16 (d, J = 8.0 Hz, 2H), 6.94 (d, J = 7.6 Hz, 1H), 4.41 (s, 2H), 3.98-3.85 (m, 2H), 3.52-3.37 (m, 4H), 2.27 (s, 3H), 1.14 (t, J = 7.0 Hz, 3H). (ESI+) m/z 477.2 (M + H)⁺ Retention time = 3.65 min (method 2) |
| 093 | 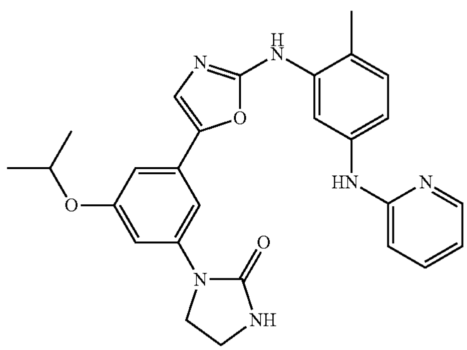 [SMILES: Cc1ccc(Nc2ccccn2)cc1Nc1ncc(-c2cc(OC(C)C)cc(N3CCNC3=O)c2)o1] | 1-(3-Isopropoxy-5-{2-[2-methyl-5-(pyridin-2-ylamino)-phenylamino]-oxazol-5-yl}-phenyl)-imidazolidin-2-one | (300 MHz, DMSO) δ 9.20 (s, 1H), 8.94 (s, 1H), 8.12-8.05 (m, 1H), 8.02 (d, J = 2.0 Hz, 1H), 7.58-7.48 (m, 1H), 7.44 (dd, J = 8.2, 2.1 Hz, 1H), 7.40 (s, 1H), 7.26 (s, 1H), 7.14 (d, J = 2.0 Hz, 1H), 7.06 (d, J = 8.3 Hz, 1H), 7.01 (s, 1H), 6.84 (d, J = 8.5 Hz, 1H), 6.80 (s, 1H), 6.68 (dd, J = 7.0, 5.1 Hz, 1H), 4.60 (m, 1H), 3.83 (m, 2H), 3.43-3.34 (m, 2H), 2.22 (s, 3H), 1.26 (d, J = 6.0 Hz, 6H). (ESI+) m/z 484 (M + H)+ Retention time = 2.55 min (method 2) |
| 094 | 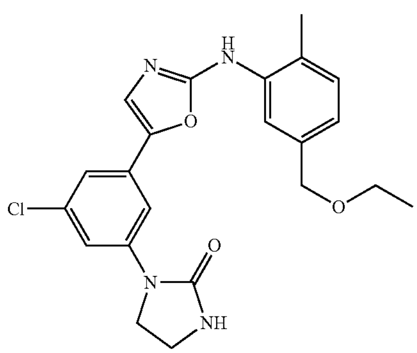 [SMILES: CCOCc1ccc(C)c(Nc2ncc(-c3cc(Cl)cc(N4CCNC4=O)c3)o2)c1] | 1-{3-Chloro-5-[2-(5-ethoxymethyl-2-methyl-phenylamino)-oxazol-5-yl]-phenyl}-imidazolidin-2-one | ¹H NMR (300 MHz, DMSO) δ 9.41 (s, 1H), 7.86 (s, 1H), 7.66 (d, J = 1.4 Hz, 2H), 7.58 (s, 1H), 7.29 (d, J = 9.4 Hz, 1H), 7.27-7.17 (m, 2H), 6.99 (d, J = 7.7 Hz, 1H), 4.46 (s, 2H), 4.02-3.89 (m, 2H), 3.51-3.48 (m, 4H), 2.32 (s, 3H), 1.18 (t, J = 1.0 Hz, 3H). (ESI+) m/z 427.2 (M + H)⁺ Retention time = 3.50 min (method 2) |
| 095 | 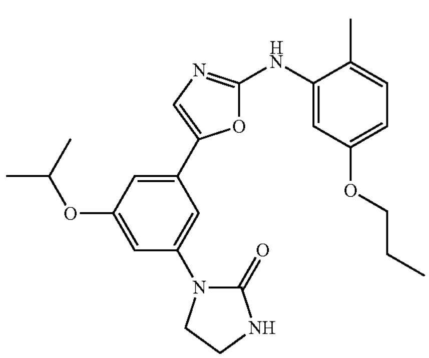 [SMILES: CCCOc1ccc(C)c(Nc2ncc(-c3cc(OC(C)C)cc(N4CCNC4=O)c3)o2)c1] | 1-{3-Isopropoxy-5-[2-(2-methyl-5-propoxy-phenylamino)-oxazol-5-yl]-phenyl)-imidazolidin-2-one | (300 MHz, DMSO) δ 9.22 (s, 1H), 7.59 (d, J = 2.4 Hz, 1H), 7.42 (s, 1H), 7.29 (s, 1H), 7.12 (s, 1H), 7.09-6.98 (m, 2H), 6.80 (s, 1H), 6.53 (dd, J = 8.3, 2.5 Hz, 1H), 4.62 (m, 1H), 3.95-3.78 (m, 4H), 3.48-3.37 (m, 2H), 2.21 (s, 3H), 1.72 (m, 2H), 1.28 (d, J = 6.0 Hz, 6H), 0.97 (t, J = 7.4 Hz, 3H). (ESI+) m/z 451 (M + H)⁺ Retention time = 3.76 min (method 2) |

TABLE 1-continued

| Ex # | Chemical structure | Name | ¹H NMR/LCMS |
|---|---|---|---|
| 096 | 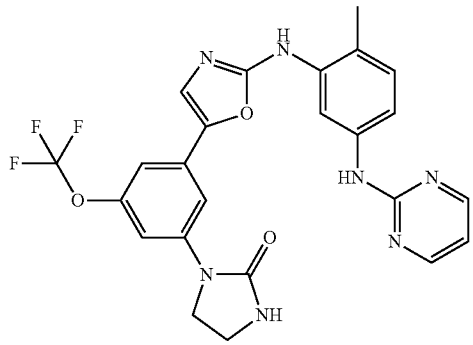 | 1-(3-{2-[2-Methyl-5-(pyrimidin-2-ylamino)-phenylamino]-oxazol-5-yl)-5-trifluoromethoxy-phenyl)-imidazolidin-2-one | (300 MHz, DMSO) δ 9.55 (s, 1H), 9.38 (s, 1H), 8.42 (d, J = 4.8 Hz, 2H), 8.14 (d, J = 1.8 Hz, 1H), 7.70 (s, 1H), 7.55 (s, 1H), 7.51 (s, 1H), 7.41 (dd, J = 8.2, 2.0 Hz, 1H), 7.23 (s, 1H), 7.14 (s, 1H), 7.10 (d, J = 8.4 Hz, 1H), 6.79 (t, J = 4.8 Hz, 1H), 3.88 (t, J = 7.7 Hz, 2H), 3.41 (t, J = 7.7 Hz, 2H), 2.22 (s, 3H). (ESI+) m/z 512 (M + H)+ Retention time = 3.32 min (method 2) |
| 097 | 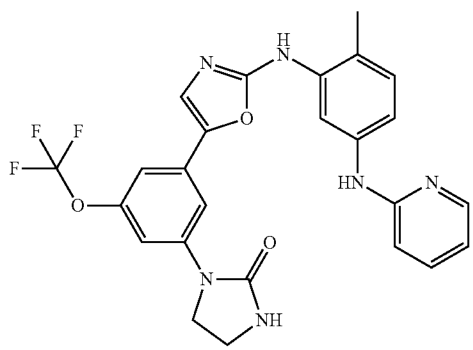 [SMILES: Cc1ccc(Nc2ccccn2)cc1Nc1ncc(-c2cc(OC(F)(F)F)cc(N3CCNC3=O)c2)o1] | 1-(3-{2-[2-Methyl-5-(pyridin-2-ylamino)-phenylamino]-oxazol-5-yl}-5-trifluoromethoxy-phenyl)-imidazolidin-2-one | (400 MHz, DMSO) δ 9.33 (s, 1H), 8.96 (s, 1H), 8.08 (dd, J = 4.9, 1.2 Hz, 1H), 8.04 (d, J = 1.9 Hz, 1H), 7.70 (s, 1H), 7.57 (s, 1H), 7.55-7.48 (m, 2H), 7.45 (dd, J = 8.3, 2.0 Hz, 1H), 7.24 (s, 1H), 7.16 (s, 1H), 7.07 (d, J = 8.4 Hz, 1H), 6.84 (d, J = 8.4 Hz, 1H), 6.68 (m, 1H), 3.88 (t, J = 7.9 Hz, 2H), 3.41 (t, J = 7.9 Hz, 2H), 2.22 (s, 3H). (ESI+) m/z 511 (M + H)+ Retention time = 2.64 min (method 2) |
| 098 | 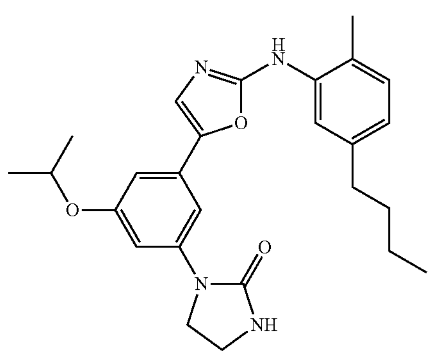 [SMILES: CCCCc1ccc(C)c(Nc2ncc(-c3cc(OC(C)C)cc(N4CCNC4=O)c3)o2)c1] | 1-{3-[2-5-Butyl-2-methyl-phenylamino)-oxazol-5-yl]-5-isopropoxy-phenyl}-imidazolidin-2-one | 1H NMR (400 MHz, DMSO) δ 9.22 (s, 1H), 7.66 (s, 1H), 7.40 (s, 1H), 7.27 (s, 1H), 7.13-7.00 (m, 3H), 6.84-6.72 (m, 2H), 4.67-4.55 (m, 1H), 3.85 (t, J = 7.9 Hz, 2H), 3.45-3.37 (m, 2H), 2.56-2.51 (m, 2H), 2.23 (s, 3H), 1.58-1.48 (m, 2H), 1.36-1.28 (m, 2H), 1.28 (s, 3H), 1.27 (s, 3H), 0.88 (t, J = 7.3 Hz, 3H). (ESI+) m/z 449.3 (M + H)+ Retention time = 4.00 min (method 2) |
| 099 | 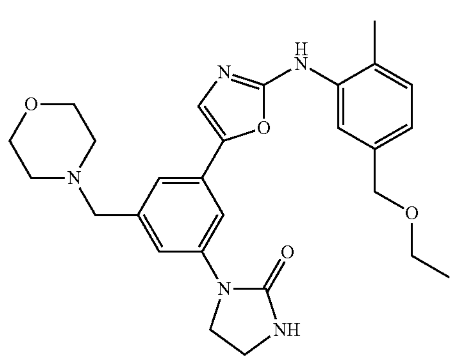 [SMILES: CCOCc1ccc(C)c(Nc2ncc(-c3cc(CN4CCOCC4)cc(N4CCNC4=O)c3)o2)c1] | 1-{3-[2-(5-Ethoxymethyl-2-methyl-phenylamino)-oxazol-5-yl]-5-morpholin-4-ylmethyl-phenyl}-imidazolidin-2-one | 1H NMR (400 MHz, DMSO) δ 9.27 (s, 1H), 7.84 (s, 1H), 7.65 (s, 1H), 7.43 (s, 1H), 7.37 (s, 1H), 7.18-7.14 (m, 2H), 7.00 (s, 1H), 6.94 (d, J = 7.7 Hz, 1H), 4.42 (s, 2H), 3.93-3.84 (m, 2H), 3.62-3.57 (m, 4H), 3.44 (dd, J = 18.4, 7.7 Hz, 5H), 2.38 (s, 4H), 2.28 (s, 3H), 1.19-1.09 (m, 3H). (ESI+) m/z 492.3 (M + H)+ Retention time = 2.29 min (method 2) |

TABLE 1-continued

| Ex # | Chemical structure | Name | ¹H NMR/LCMS |
|---|---|---|---|
| 100 | 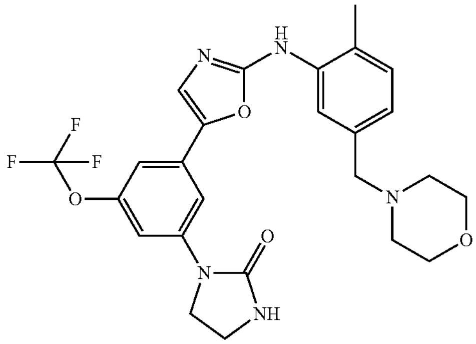 [SMILES: Cc1ccc(CN2CCOCC2)cc1Nc1ncc(-c2cc(OC(F)(F)F)cc(N3CCNC3=O)c2)o1] | 1-{3-[2-(2-Methyl-5-morpholin-4-ylmethyl-phenylamino)-oxazol-5-yl]-5-trifluoromethoxy-phenyl}-imidazolidin-2-one | 1H NMR (300 MHz, DMSO) δ 9.36 (s, 1H), 7.76 (s, 1H), 7.66 (s, 1H), 7.57 (s, 2H), 7.25 (s, 1H), 7.15 (d, J = 7.4 Hz, 2H), 6.94 (d, J = 7.7 Hz, 1H), 3.97-3.86 (m, 2H), 3.60-3.50 (m, 4H), 3.49-3.37 (m, 4H), 2.35 (s, 4H), 2.27 (s, 3H). (ESI+) m/z 518.3 (M + H)+ Retention time = 2.44 min (method 2) |

Among the compounds of formula I in which ring A is depicted above, the present invention is directed to compounds of the following formula III:

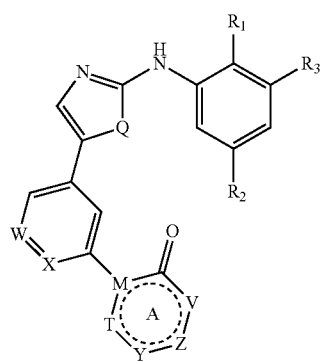

Wherein:

A ring is a six member heterocycle ring;

$R_1$ is hydrogen, halogen (selected from F, Cl, Br or I), an alkyl group containing from 1 to 10 carbon atoms or an alkoxy group;

$R_2$ is halogen (selected from F, Cl, Br or I), an aryl group, an haloalkyl or alkyl group containing from 1 to 10 carbon atoms optionally substituted with at least one heteroatom, notably oxygen or nitrogen, optionally substituted with an haloalkyl or alkyl group containing from 1 to 10 carbon atoms optionally substituted with a solubilising group; as well as an alkoxy group or an haloalkoxy group; as well as a —COOR, —NRR', —NR—CO—R', —CONRR' or —NR—SO$_2$—R' group wherein R and R' are each independently selected from hydrogen, aryl group, heteroaryl group, alkyl group optionally substituted with at least one heteroatom, notably oxygen or nitrogen, optionally substituted with an alkyl group containing from 1 to 10 carbon atoms optionally substituted with a solubilising group; as well as a heterocycle group or a solubilising group;

$R_3$ is hydrogen, halogen (selected from F, Cl, Br or I), cyano, an alkyl group containing from 1 to 10 carbon atoms or an alkoxy group; as well as CF$_3$, —NRR', —NR—CO—R', —CONRR' group wherein R and R' are each independently selected from hydrogen, alkyl group optionally substituted with at least one heteroatom, notably oxygen or nitrogen, optionally substituted with an alkyl group containing from 1 to 10 carbon atoms optionally substituted with a solubilising group; as well as a heterocycle group or a solubilising group;

Q is O or S;

W is N or CR$_4$;

$R_4$ is hydrogen, cyano, CF$_3$, halogen (selected from F, Cl, Br or I), an alkyl group containing from 1 to 10 carbon atoms optionally substituted with at least one heteroatom, notably oxygen or nitrogen, optionally substituted with an alkyl group containing from 1 to 10 carbon atoms optionally substituted with a solubilising group; as well as an alkoxy group or an haloalkoxy group, a solubilising group, an heterocycle, —CO—NRR', SO$_2$—NRR', —NRR', NR—CO—R' or NR—SO$_2$R' group wherein R and R' are each independently selected from hydrogen, alkyl group optionally substituted with at least one heteroatom, notably oxygen or nitrogen, optionally substituted with an alkyl group containing from 1 to 10 carbon atoms optionally substituted with a solubilising group or heterocycle group;

X is N or CR$_5$;

$R_5$ is hydrogen, cyano, halogen (selected from F, Cl, Br or I), an alkyl group containing from 1 to 10 carbon atoms, an alkoxy group, —CO—OR, —CO—NRR' group wherein R and R' are each independently selected from hydrogen, alkyl group optionally substituted with at least one heteroatom, notably oxygen or nitrogen, optionally substituted with an alkyl group containing from 1 to 10 carbon atoms optionally substituted with a solubilising group or heterocycle group;

M is C or N;

V is N, CH$_2$, CR$_7$ or NR$_7$;

$R_7$ is hydrogen, cyano or an alkyl group containing from 1 to 10 carbon atoms optionally substituted with a solubilising group or heterocycle group;

Y is N, CR$_8$ or CR$_8$R$_9$;

Z is N, CR$_8$ or CR$_8$R$_9$;

T is N, C=O, CR$_8$ or CR$_8$R$_9$;

$R_8$ is hydrogen, a halogen (selected from F, Cl, Br or I), an hydroxyl group, an alkyl group containing from 1 to 10 carbon atoms or an alkoxy group;

$R_9$ is hydrogen or an alkyl group containing from 1 to 10 carbon atoms.

In one embodiment the invention relates to compounds of formula III or pharmaceutically acceptable salts thereof, wherein $R_2$ is halogen (selected from F, Cl, Br or I), an aryl group, an haloalkyl or alkyl group containing from 1 to 10 carbon atoms optionally substituted with at least one heteroatom, notably oxygen or nitrogen, optionally substituted with an haloalkyl or alkyl group containing from 1 to 10 carbon atoms optionally substituted with a solubilising group; as well as an alkoxy group or an haloalkoxy group; as well as a —NRR', —NR—CO—R', —CONRR' or —NR—SO₂—R' group wherein R and R' are each independently selected from hydrogen, alkyl group optionally substituted with at least one heteroatom, notably oxygen or nitrogen, optionally substituted with an alkyl group containing from 1 to 10 carbon atoms optionally substituted with a solubilising group; as well as a heterocycle group or a solubilising group.

Examples of preferred compounds of the above formula are depicted in table 2 below:

TABLE 2

| Ex # | Chemical structure | Name | $^1$H NMR |
|---|---|---|---|
| 101 | 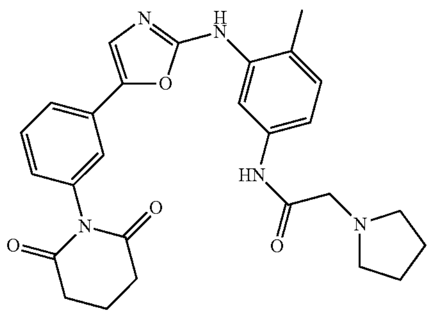 [SMILES: Cc1ccc(NC(=O)CN2CCCC2)cc1Nc1ncc(-c2cccc(N3C(=O)CCCC3=O)c2)o1] | N-(3-{5-[3-(2,6-Dioxo-piperidin-1-yl)-phenyl]-oxazol-2-yl-amino}-4-methyl-phenyl)-2-pyrrolidin-1-yl-acetamide | (400 MHz, DMSO) δ 9.96 (s, 1H), 9.64 (s, 1H), 9.27 (d, J = 12.2 Hz, 1H), 8.03 (d, J = 10.9 Hz, 1H), 7.94 (s, 1H), 7.54-7.46 (m, 1H), 7.35-7.27 (m, 3H), 7.10 (d, J = 8.2 Hz, 1H), 3.23 (s, 2H), 2.69 (t, J = 6.5 Hz, 4H), 2.63-2.56 (m, 4H), 2.23 (s, 3H), 2.12 (m, 2H), 1.74 (s, 4H). (ESI+) m/z 488 (M + H)⁺ Retention time = 2.26 min (method 1) |
| 102 | 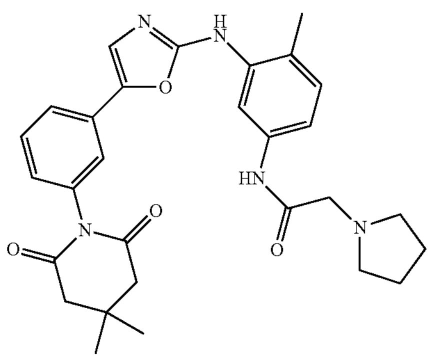 [SMILES: Cc1ccc(NC(=O)CN2CCCC2)cc1Nc1ncc(-c2cccc(N3C(=O)CC(C)(C)CC3=O)c2)o1] | N-(3-{5-[3-(4,4-Dimethyl-2,6-dioxo-piperidin-1-yl)-phenyl]-oxazol-2-ylamino}-4-methyl-phenyl)-2-pyrrolidin-1-yl-acetamide | (400 MHz, DMSO) δ 9.94 (s, 1H), 9.66 (s, 1H), 9.27 (d, J = 12.4 Hz, 1H), 8.06 (d, J = 10.7 Hz, 1H), 7.94 (s, 1H), 7.53-7.45 (m, 1H), 7.40-7.27 (m, 3H), 7.10 (d, J = 8.1 Hz, 1H), 3.22 (s, 2H), 2.69 (s, 4H), 2.63-2.54 (m, 4H), 2.23 (s, 3H), 1.74 (s, 4H), 1.14 (s, 3H), 1.10 (s, 3H). (ESI+) m/z 516 (M + H)⁺ Retention time = 2.72 min (method 1) |
| 103 | 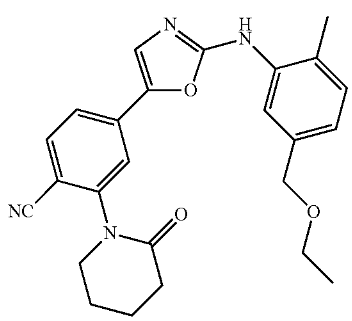 [SMILES: CCOCc1ccc(C)c(Nc2ncc(-c3ccc(C#N)c(N4CCCCC4=O)c3)o2)c1] | 4-[2-(5-(Ethoxymethyl)-2-methyl-phenylamino)-oxazol-5-yl]-2-(2-oxo-piperidin-1-yl)-benzonitrile | (300 MHz, CDCl₃) δ 7.93 (s, 1H), 7.67 (d, J = 8.2 Hz, 1H), 7.50 (dd, J = 8.2, 1.5 Hz, 1H), 7.44 (d, J = 1.3 Hz, 1H), 7.30 (s, 2H), 7.18 (d, J = 7.7 Hz, 1H), 7.03 (d, J = 8.0 Hz, 1H), 4.51 (s, 2H), 3.67 (m, 2H), 3.54 (q, J = 7.0 Hz, 2H), 2.61 (m, 2H), 2.31 (s, 3H), 2.01 (m, 4H), 1.20 (t, J = 7.0 Hz, 3H). |
| 104 | 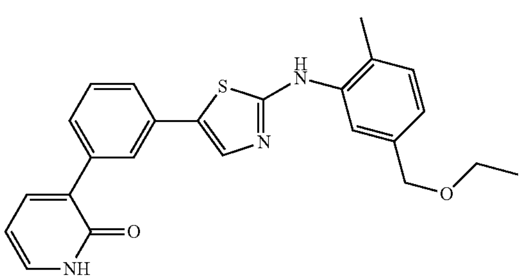 [SMILES: CCOCc1ccc(C)c(Nc2ncc(-c3cccc(-c4ccc[nH]c4=O)c3)s2)c1] | 3-{3-[2-(5-(Ethoxymethyl)-2-methyl-phenylamino)-thiazol-5-yl]-phenyl}-1H-pyridin-2-one | (400 MHz, DMSO-d₆) δ 11.81 (s, 1H), 9.39 (s, 1H), 7.81 (d, J = 11.8 Hz, 2H), 7.71 (dd, J = 6.9, 2.0 Hz, 1H), 7.63 (s, 1H), 7.56 (d, J = 7.6 Hz, 1H), 7.50-7.31 (m, 3H), 7.20 (d, J = 7.7 Hz, 1H), 6.98 (d, J = 7.6 Hz, 1H), 6.31 (t, J = 6.7 Hz, 1H), 4.42 (s, 2H), 3.48 (q, J = 7.0 Hz, 2H), 2.27 (s, 3H), 1.15 (t, J = 7.0 Hz, 3H). (ESI+) m/z 418 (M + H)⁺ Retention time = 3.53 min (method 1) |

TABLE 2-continued

| Ex # | Chemical structure | Name | ¹H NMR |
|---|---|---|---|
| 105 | 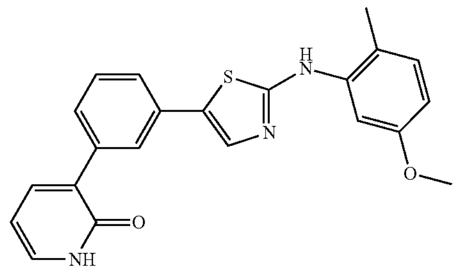 [SMILES: COc1ccc(C)c(Nc2ncc(-c3cccc(-c4ccc[nH]c4=O)c3)s2)c1] | 3-{3-[2-(5-Methoxy-2-methyl-phenylamino)-thiazol-5-yl]-phenyl}-1H-pyridin-2-one | (400 MHz, DMSO-$d_6$) δ ¹H NMR (400 MHz, DMSO) δ 11.82 (s, 1H), 9.44 (s, 1H), 7.85 (s, 1H), 7.72 (dd, J = 6.9, 1.9 Hz, 1H), 7.65 (s, 1H), 7.62-7.53 (m, 2H), 7.48-7.35 (m, 3H), 7.12 (d, J = 8.3 Hz, 1H), 6.61 (dd, J = 8.3, 2.6 Hz, 1H), 6.31 (t, J = 6.7 Hz, 1H), 3.73 (s, 3H), 2.21 (s, 3H). (ESI+) m/z 390 (M + H)⁺ Retention time = 3.42 min (method 1) |
| 106 | 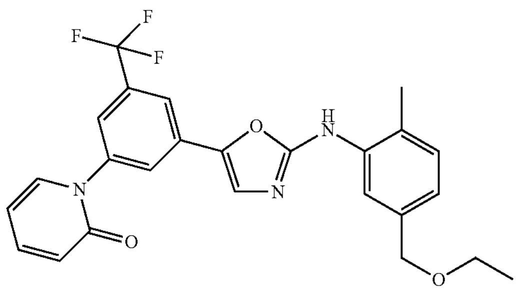 [SMILES: CCOCc1ccc(C)c(Nc2ncc(-c3cc(-n4ccccc4=O)cc(C(F)(F)F)c3)o2)c1] | 1-{3-[2-(5-(Ethoxymethyl)-2-methyl-phenylamino)-oxazol-5-yl]-5-trifluoromethyl-phenyl}-1H-pyridin-2-one | (300 MHz, DMSO-$d_6$) δ 9.43 (s, 1H), 7.94-7.91 (m, 1H), 7.86 (s, 1H), 7.81-7.74 (m, 2H), 7.71 (s, 1H), 7.60-7.53 (m, 1H), 7.17 (d, J = 7.8 Hz, 1H), 6.95 (d, J = 9.1 Hz, 1H), 6.53 (d, J = 9.2 Hz, 1H), 6.38 (t, J = 6.6 Hz, 1H), 4.41 (s, 2H), 3.46 (q, J = 6.9 Hz, 2H), 2.28 (s, 3H), 1.12 (t, J = 7.0 Hz, 3H). |
| 107 | 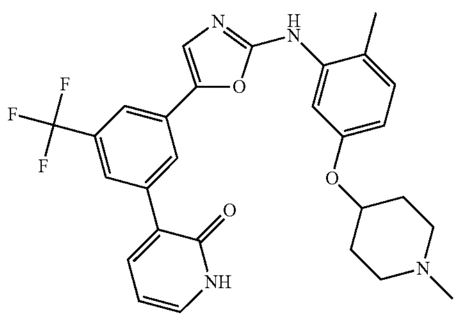 [SMILES: Cc1ccc(OC2CCN(C)CC2)cc1Nc1ncc(-c2cc(-c3ccc[nH]c3=O)cc(C(F)(F)F)c2)o1] | 3-(3-{2-[2-Methyl-5-(1-methyl-piperidin-4-yloxy)-phenylamino]-oxazol-5-yl}-5-trifluoromethyl-phenyl)-1H-pyridin-2-one | (400 MHz, DMSO-$d_6$) δ 12.00 (s, 1H), 9.36 (s, 1H), 8.18 (s, 1H), 8.00 (s, 1H), 7.89-7.82 (m, 2H), 7.71 (s, 1H), 7.62 (s, 1H), 7.52-7.47 (m, 1H), 7.06 (d, J = 8.1 Hz, 1H), 6.58 (d, J = 6.2 Hz, 1H), 6.39-6.33 (m, 1H), 4.32-4.22 (m, 1H), 2.64-2.58 (m, 2H), 2.23 (s, 3H), 2.17 (s, 3H), 2.16-2.06 (m, 2H), 1.96-1.85 (m, 2H), 1.68-1.56 (m, 2H). (ESI+) m/z 525 (M + H)⁺ Retention time = 3.08 min (method 1) |
| 108 | 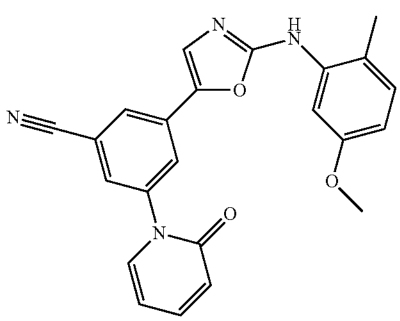 [SMILES: COc1ccc(C)c(Nc2ncc(-c3cc(C#N)cc(-n4ccccc4=O)c3)o2)c1] | 3-[2-(5-Methoxy-2-methyl-phenylamino)-oxazol-5-yl]-5-(2-oxo-2H-pyridin-1-yl)-benzonitrile | (300 MHz, DMSO-$d_6$) δ 9.40 (s, 1H), 8.10 (s, 1H), 7.93 (t, J = 1.6 Hz, 1H), 7.87-7.85 (m, 1H), 7.77 (dd, J = 6.7, 1.7 Hz, 1H), 7.73 (s, 1H), 7.62-7.53 (m, 2H), 7.09 (d, J = 8.4 Hz, 1H), 6.60-6.51 (m, 2H), 6.38 (td, J = 6.6, 0.9 Hz, 1H), 3.72 (s, 3H), 2.21 (s, 3H). (ESI+) m/z 399 (M + H)⁺ Retention time = 3.56 min (method 1) |
| 109 | 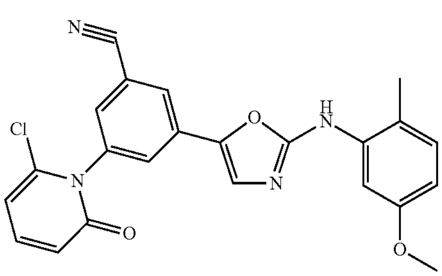 [SMILES: COc1ccc(C)c(Nc2ncc(-c3cc(C#N)cc(-n4c(Cl)cccc4=O)c3)o2)c1] | 3-(6-Chloro-2-oxo-2H-pyridin-1-yl)-5-[2-(5-methoxy-2-methyl-phenylamino)-oxazol-5-yl]-benzonitrile | (300 MHz, DMSO-$d_6$) δ 9.38 (s, 1H), 8.12 (t, J = 1.4 Hz, 1H), 7.89 (d, J = 1.4 Hz, 2H), 7.72 (s, 1H), 7.60-7.54 (m, 2H), 7.09 (d, J = 8.5 Hz, 1H), 6.66 (dd, J = 7.3, 0.9 Hz, 1H), 6.60-6.54 (m, 2H), 3.72 (s, 3H), 2.21 (s, 3H). (ESI+) m/z 433 (M + H)⁺ Retention time = 3.96 min (method 1) |

TABLE 2-continued

| Ex # | Chemical structure | Name | ¹H NMR |
|---|---|---|---|
| 110 | 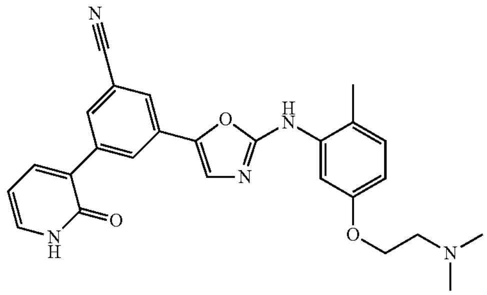 [SMILES: Cc1ccc(OCCN(C)C)cc1Nc1ncc(-c2cc(C#N)cc(-c3ccc[nH]c3=O)c2)o1] | 3-{2-[5-(2-Dimethylamino-ethoxy)-2-methyl-phenylamino]-oxazol-5-yl}-5-(2-oxo-1,2-dihydro-pyridin-3-yl)-benzonitrile | (300 MHz, DMSO-$d_6$) δ 12.02 (s, 1H), 9.38 (s, 1H), 8.25 (s, 1H), 8.03 (s, 1H), 7.99 (s, 1H), 7.84 (d, J = 7.2 Hz, 1H), 7.67 (s, 1H), 7.60 (d, J = 2.7 Hz, 1H), 7.50 (d, J = 7.3 Hz, 1H), 7.07 (d, J = 8.4 Hz, 1H), 6.54 (dd, J = 8.2, 2.6 Hz, 1H), 6.36 (t, J = 6.8 Hz, 1H), 4.00 (m, 2H), 2.60 (m, 2H), 2.22 (s, 3H), 2.20 (s, 6H). |
| 111 | 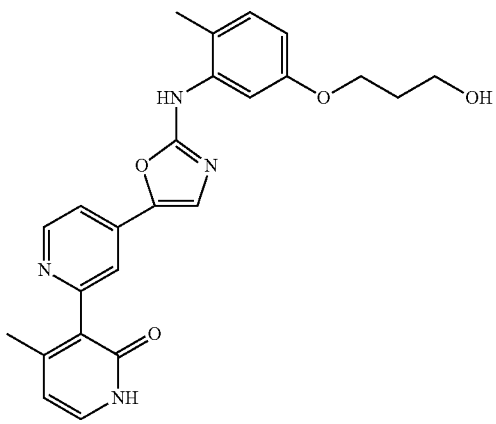 [SMILES: Cc1ccc(OCCCO)cc1Nc1ncc(-c2ccnc(-c3c(C)cc[nH]c3=O)c2)o1] | 4-{2-[5-(3-Hydroxy-propoxy)-2-methyl-phenylamino]-oxazol-5-yl}-4'-methyl-1'H-[2,3']bipyridinyl-2'-one | (300 MHz, DMSO-$d_6$) δ 11.67 (s, 1H), 9.45 (s, 1H), 8.60 (d, J = 5.4 Hz, 1H), 7.78 (s, 1H), 7.58 (d, J = 2.3 Hz, 1H), 7.55 (s, 1H), 7.43 (d, J = 5.5 Hz, 1H), 7.34 (d, J = 6.5 Hz, 1H), 7.08 (d, J = 8.5 Hz, 1H), 6.58 (dd, J = 8.4, 2.2 Hz, 1H), 6.18 (d, J = 6.7 Hz, 1H), 4.54 (t, J = 5.0 Hz, 1H), 3.99 (t, J = 6.5 Hz, 2H), 3.55 (q, J = 6.7 Hz, 2H), 2.22 (s, 3H), 2.03 (s, 3H), 1.85 (quint, J = 6.7 Hz, 2H). (ESI+) m/z 433 (M + H)⁺ Retention time = 2.19 min (method 1) |
| 112 | 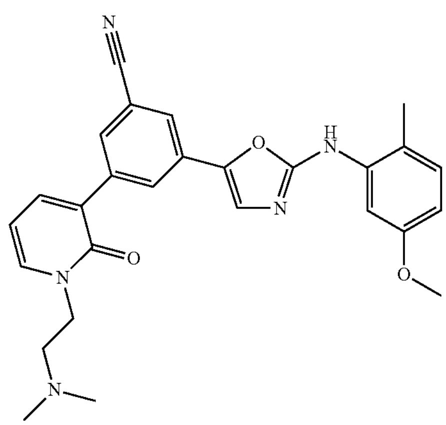 [SMILES: COc1ccc(C)c(Nc2ncc(-c3cc(C#N)cc(-c4cccn(CCN(C)C)c4=O)c3)o2)c1] | 3-[1-(2-Dimethylamino-ethyl)-2-oxo-1,2-dihydro-pyridin-3-yl]-5-[2-(5-methoxy-2-methyl-phenylamino)-oxazol-5-yl]-benzonitrile | (400 MHz, DMSO-$d_6$) δ 9.39 (s, 1H), 8.23 (t, J = 1.6 Hz, 1H), 8.01 (t, J = 1.6 Hz, 1H), 7.99 (t, J = 1.5 Hz, 1H), 7.85-7.76 (m, 2H), 7.67 (s, 1H), 7.61 (d, J = 2.7 Hz, 1H), 7.09 (d, J = 8.4 Hz, 1H), 6.58 (dd, J = 8.3, 2.6 Hz, 1H), 6.40 (t, J = 6.9 Hz, 1H), 4.08 (t, J = 6.4 Hz, 2H), 3.73 (s, 3H), 2.55 (t, J = 6.4 Hz, 2H), 2.23 (s, 3H), 2.20 (s, 6H). (ESI+) m/z 470 (M + H)⁺ Retention time = 2.99 min (method 1) |
| 113 | 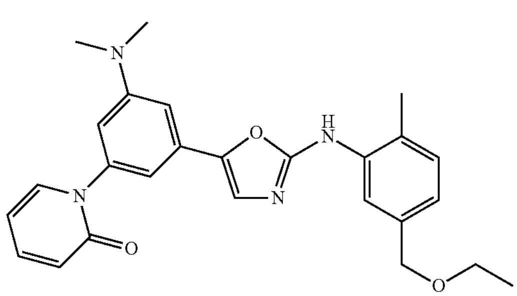 [SMILES: CCOCc1ccc(C)c(Nc2ncc(-c3cc(N(C)C)cc(-n4ccccc4=O)c3)o2)c1] | 1-{3-Dimethylamino-5-[2-(5-(ethoxymethyl)-2-methyl-phenylamino)-oxazol-5-yl]-phenyl}-1H-pyridin-2-one | (300 MHz, DMSO-$d_6$) δ 9.25 (s, 1H), 7.88 (s, 1H), 7.65 (d, J = 6.3 Hz, 1H), 7.59-7.44 (m, 2H), 7.16 (d, J = 7.4 Hz, 1H), 7.00-6.84 (m, 3H), 6.56 (s, 1H), 6.47 (d, J = 9.2 Hz, 1H), 6.30 (t, J = 6.6 Hz, 1H), 4.40 (s, 2H), 3.46 (dd, J = 14.0, 6.9 Hz, 2H), 2.98 (s, 6H), 2.28 (s, 3H), 1.13 (t, J = 7.0 Hz, 3H). (ESI+) m/z 445 (M + H)⁺ Retention time = 3.83 min (method 1) |

TABLE 2-continued

| Ex # | Chemical structure | Name | ¹H NMR |
|---|---|---|---|
| 114 | 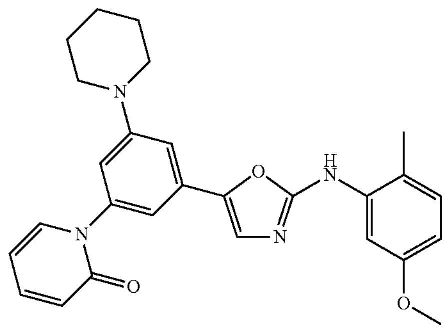 [SMILES: COc1ccc(C)c(Nc2ncc(-c3cc(N4CCCCC4)cc(-n4ccccc4=O)c3)o2)c1] | 1-{3-[2-(5-Methoxy-2-methyl-phenylamino)-oxazol-5-yl]-5-piperidin-1-yl-phenyl}-1H-pyridin-2-one | (300 MHz, DMSO-$d_6$) δ 9.20 (s, 1H), 7.69-7.63 (m, 2H), 7.55-7.47 (m, 2H), 7.16 (s, 1H), 7.07 (d, J = 8.3 Hz, 1H), 6.96 (s, 1H), 6.78 (s, 1H), 6.54 (dd, J = 8.2, 2.2 Hz, 1H), 6.47 (d, J = 9.2 Hz, 1H), 6.30 (t, J = 6.6 Hz, 1H), 3.71 (s, 3H), 3.24 (s, 4H), 2.21 (s, 3H), 1.60 (s, 6H). (ESI+) m/z 457 (M + H)⁺ Retention time = 3.94 min (method 1) |
| 115 | 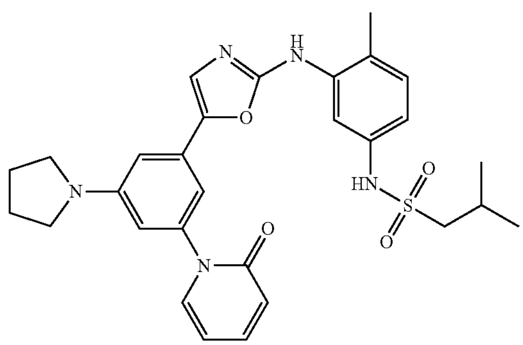 [SMILES: Cc1ccc(NS(=O)(=O)CC(C)C)cc1Nc1ncc(-c2cc(N3CCCC3)cc(-n3ccccc3=O)c2)o1] | 2-Methyl-propane-1-sulfonic acid (4-methyl-3-{5-[3-(2-oxo-2H-pyridin-1-yl)-5-pyrrolidin-1-yl-phenyl]-oxazol-2-ylamino}-phenyl)-amide | (300 MHz, DMSO-$d_6$) δ 9.66 (s, 1H), 9.27 (s, 1H), 7.84 (d, J = 1.4 Hz, 1H), 7.64 (dd, J = 6.9, 1.4 Hz, 1H), 7.55-7.46 (m, 2H), 7.11 (d, J = 8.1 Hz, 1H), 6.86-6.75 (m, 3H), 6.46 (d, J = 9.0 Hz, 1H), 6.37 (s, 1H), 6.30 (t, J = 6.6 Hz, 1H), 3.29 (s, 4H), 2.96 (d, J = 6.4 Hz, 2H), 2.23 (s, 3H), 2.18-2.07 (m, 1H), 1.98 (s, 4H), 0.99 (d, J = 6.7 Hz, 6H). (ESI+) m/z 548 (M + H)⁺ Retention time = 4.19 min (method 1) |
| 116 | 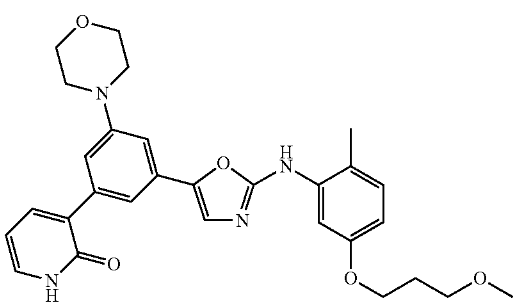 [SMILES: COCCCOc1ccc(C)c(Nc2ncc(-c3cc(-c4ccc[nH]c4=O)cc(N4CCOCC4)c3)o2)c1] | 3-(3-{2-[5-(3-Methoxy-propoxy)-2-methyl-phenylamino]-oxazol-5-yl}-5-morpholin-4-yl-phenyl)-1H-pyridin-2-one | (300 MHz, DMSO-$d_6$) δ 11.79 (s, 1H), 9.20 (s, 1H), 7.66 (s, 2H), 7.49-7.34 (m, 3H), 7.21-7.03 (m, 3H), 6.53 (dd, J = 8.3, 2.3 Hz, 1H), 6.30 (t, J = 6.6 Hz, 1H), 3.97 (t, J = 6.2 Hz, 2H), 3.77 (s, 4H), 3.46 (t, J = 6.1 Hz, 2H), 3.24 (s, 3H), 3.18 (s, 4H), 2.22 (s, 3H), 1.99-1.89 (m, 2H). (ESI+) m/z 517 (M + H)⁺ Retention time = 3.56 min (method 1) |
| 117 | 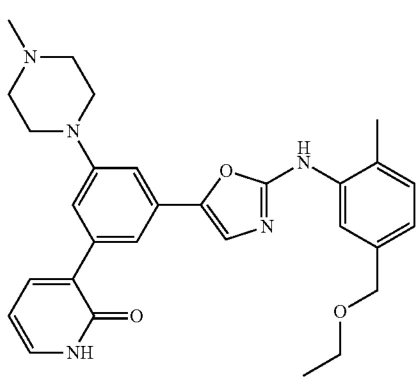 [SMILES: CCOCc1ccc(C)c(Nc2ncc(-c3cc(-c4ccc[nH]c4=O)cc(N4CCN(C)CC4)c3)o2)c1] | 3-[3-[2-(5-(Ethoxymethyl)-2-methyl-phenylamino)-oxazol-5-yl]-5-(4-methyl-piperazin-1-yl)-phenyl]-1H-pyridin-2-one | (400 MHz, DMSO) δ 11.77 (s, 1H), 9.22 (s, 1H), 7.89 (s, 1H), 7.67 (dd, J = 6.8, 2.1 Hz, 1H), 7.42 (s, 1H), 7.41-7.37 (m, 1H), 7.36 (s, 1H), 7.22-7.12 (m, 2H), 7.09 (s, 1H), 6.91 (d, J = 8.0 Hz, 1H), 6.29 (t, J = 6.8 Hz, 1H), 4.38 (s, 2H), 3.46 (q, J = 7.0 Hz, 2H), 3.27-3.14 (m, 4H), 2.49-2.46 (m, 4H), 2.28 (s, 3H), 2.24 (s, 3H), 1.13 (t, J = 7.0 Hz, 3H). (ESI+) m/z 500 (M + H)⁺ Retention time = 2.65 min (method 1) |

TABLE 2-continued

| Ex # | Chemical structure | Name | ¹H NMR |
|---|---|---|---|
| 118 | 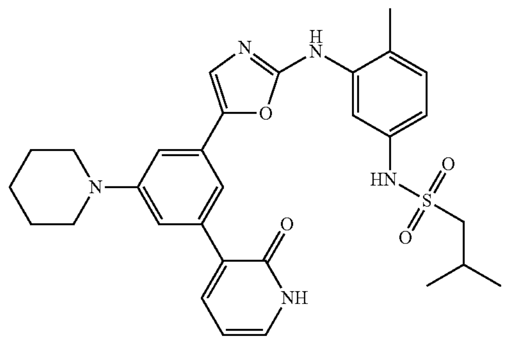 [SMILES: Cc1ccc(NS(=O)(=O)CC(C)C)cc1Nc1ncc(-c2cc(-c3ccc[nH]c3=O)cc(N3CCCCC3)c2)o1] | 2-Methyl-propane-1-sulfonic acid (4-methyl-3-{5-[3-(2-oxo-1,2-dihydro-pyridin-3-yl)-5-piperidin-1-yl-phenyl]-oxazol-2-ylamino}-phenyl)-amide | (400 MHz, DMSO) δ 11.75 (s, 1H), 9.66 (s, 1H), 9.24 (s, 1H), 7.84 (s, 1H), 7.66 (dd, J = 7.2, 2.4 Hz, 1H), 7.41 (s, 1H), 7.38 (dd, J = 7.8, 1.9 Hz, 1H), 7.32 (s, 1H), 7.16 (s, 1H), 7.12-7.03 (m, 2H), 6.78 (dd, J = 8.3, 1.9 Hz, 1H), 6.28 (t, J = 6.5 Hz, 1H), 3.24-3.11 (m, 4H), 2.96 (d, J = 6.7 Hz, 2H), 2.23 (s, 3H), 2.17-2.08 (m, 1H), 1.69-1.49 (m, 6H), 1.07-0.90 (m, 6H). (ESI+) m/z 562 (M + H)⁺ Retention time = 3.13 min (method 1) |
| 119 | 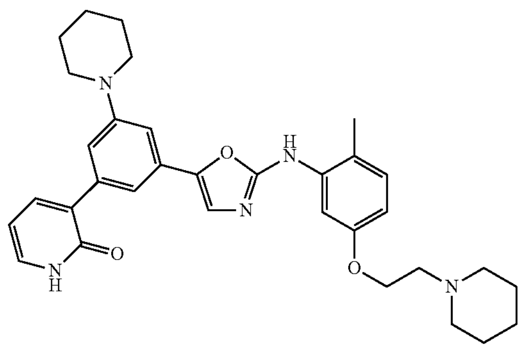 [SMILES: Cc1ccc(OCCN2CCCCC2)cc1Nc1ncc(-c2cc(-c3ccc[nH]c3=O)cc(N3CCCCC3)c2)o1] | 3-(3-{2-[2-Methyl-5-(2-piperidin-1-yl-ethoxy)-phenylamino]-oxazol-5-yl}-5-piperidin-1-yl-phenyl)-1H-pyridin-2-one | (400 MHz, DMSO) δ 11.69 (s, 1H), 9.14 (s, 1H), 7.71-7.61 (m, 2H), 7.42 (s, 1H), 7.41-7.37 (m, 1H), 7.34 (s, 1H), 7.17 (s, 1H), 7.12-7.02 (m, 2H), 6.54 (d, J = 8.3 Hz, 1H), 6.29 (t, J = 6.8 Hz, 1H), 4.07-3.98 (m, 2H), 3.22-3.16 (m, 4H), 2.69-2.59 (m, 2H), 2.45-2.41 (m, 4H), 2.23 (s, 3H), 1.61-1.31 (m, 12H). (ESI+) m/z 554 (M + H)⁺ Retention time = 2.38 min (method 1) |
| 120 | 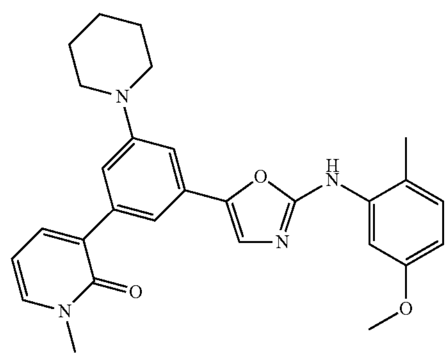 [SMILES: COc1ccc(C)c(Nc2ncc(-c3cc(-c4cccn(C)c4=O)cc(N4CCCCC4)c3)o2)c1] | 3-{3-[2-(5-Methoxy-2-methyl-phenylamino)-oxazol-5-yl]-5-piperidin-1-yl-phenyl}-1-methyl-1H-pyridin-2-one | (400 MHz, DMSO-d₆) δ 9.20 (s, 1H), 7.76 (dd, J = 6.6, 1.9 Hz, 1H), 7.68 (d, J = 2.5 Hz, 1H), 7.65 (dd, J = 7.0, 2.0 Hz, 1H), 7.44 (s, 1H), 7.32 (s, 1H), 7.15 (s, 1H), 7.10 (s, 1H), 7.07 (d, J = 8.3 Hz, 1H), 6.54 (dd, J = 8.3, 2.6 Hz, 1H), 6.33 (t, J = 6.8 Hz, 1H), 3.73 (s, 3H), 3.52 (s, 3H), 3.27-3.12 (m, 4H), 2.23 (s, 3H), 1.76-1.46 (m, 6H). (ESI+) m/z 471 (M + H)⁺ Retention time = 3.18 min (method 1) |
| 121 | 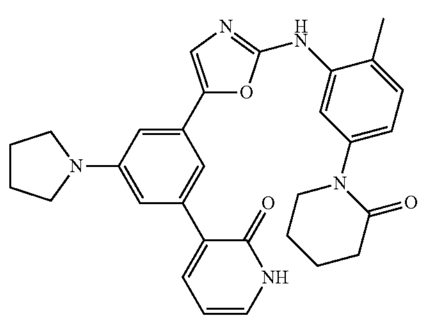 [SMILES: Cc1ccc(N2CCCCC2=O)cc1Nc1ncc(-c2cc(-c3ccc[nH]c3=O)cc(N3CCCC3)c2)o1] | 3-(3-{2-[2-Methyl-5-(2-oxo-piperidin-1-yl)-phenylamino]-oxazol-5-yl}-5-pyrrolidin-1-yl-phenyl)-1H-pyridin-2-one | (400 MHz, DMSO) δ 11.75 (s, 1H), 9.28 (s, 1H), 7.84 (s, 1H), 7.68 (d, J = 1.9 Hz, 1H), 7.64 (dd, J = 6.9, 2.0 Hz, 1H), 7.37 (s, 1H), 7.18 (d, J = 7.9 Hz, 1H), 7.14 (d, J = 7.8 Hz, 1H), 6.86 (dd, J = 5.9, 2.3 Hz, 1H), 6.78 (d, J = 8.2 Hz, 1H), 6.69 (dd, J = 8.0, 2.0 Hz, 1H), 6.35-6.29 (m, 1H), 3.59 (t, J = 5.3 Hz, 2H), 3.28-3.18 (m, 4H), 2.38 (t, J = 6.0 Hz, 2H), 2.32 (s, 3H), 1.99-1.88 (m, 4H), 1.83-1.72 (m, 4H). (ESI+) m/z 510 (M + H)⁺ Retention time = 3.44 min (method 1) |

TABLE 2-continued

| Ex # | Chemical structure | Name | $^1$H NMR |
|---|---|---|---|
| 122 | 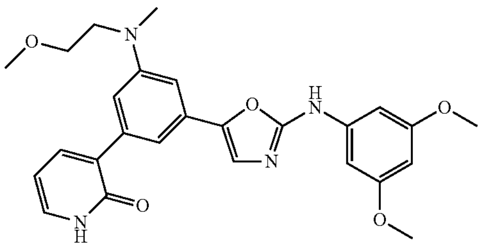 | 3-{3-[2-(3,5-Dimethoxy-phenylamino)-oxazol-5-yl]-5-[(2-methoxy-ethyl)-methyl-amino]-phenyl}-1H-pyridin-2-one | (300 MHz, CDCl$_3$) δ 12.44 (s, 1H), 7.61 (s, 1H), 7.58 (d, J = 6.9 Hz, 1H), 7.32 (d, J = 6.1 Hz, 1H), 7.18 (s, 1H), 7.12 (s, 1H), 6.89 (s, 1H), 6.84 (s, 1H), 6.74 (s, 2H), 6.32 (t, J = 6.7 Hz, 1H), 6.14 (s, 1H), 3.79 (s, 6H), 3.64-3.48 (m, 4H), 3.37 (s, 3H), 3.03 (s, 3H).<br>(ESI+) m/z 411 (M + H)$^+$<br>Retention time = 3.38 min (method 1) |
| 123 | 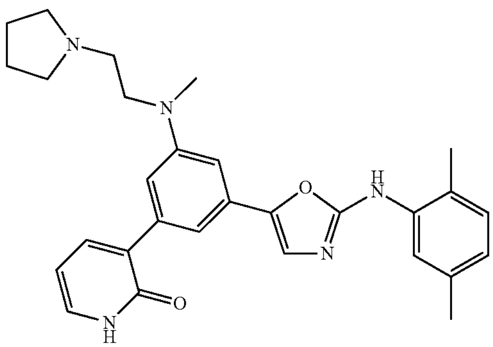 [SMILES: Cc1ccc(C)c(Nc2ncc(-c3cc(-c4ccc[nH]c4=O)cc(N(C)CCN4CCCC4)c3)o2)c1] | 3-{3-[2-(2,5-Dimethyl-phenylamino)-oxazol-5-yl]-5-[methyl-(2-pyrrolidin-1-yl-ethyl)-amino]-phenyl}-1H-pyridin-2-one | (300 MHz, CDCl$_3$) δ 11.30 (s, 1H), 7.92 (s, 1H), 7.62 (d, J = 6.7 Hz, 1H), 7.34-7.30 (m, 1H), 7.18 (s, 1H), 7.15 (s, 1H), 7.07 (d, J = 7.5 Hz, 1H), 6.99 (s, 1H), 6.91 (s, 1H), 6.80 (d, J = 7.2 Hz, 1H), 6.70 (s, 1H), 6.35 (t, J = 6.7 Hz, 1H), 3.70-3.55 (m, 2H), 3.06 (s, 3H), 2.86-2.55 (m, 6H), 2.37 (s, 3H), 2.32 (s, 3H), 1.91-1.78 (m, 4H).<br>(ESI+) m/z 484 (M + H)$^+$<br>Retention time = 2.89 min (method 1) |
| 124 | 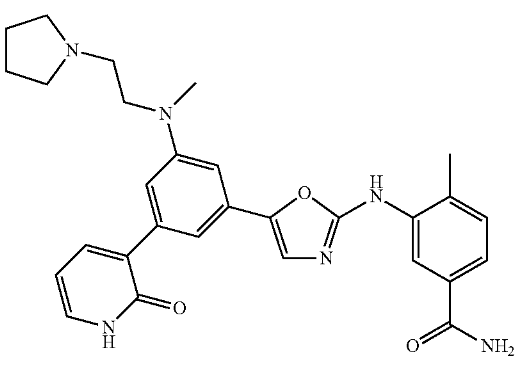 [SMILES: Cc1ccc(C(N)=O)cc1Nc1ncc(-c2cc(-c3ccc[nH]c3=O)cc(N(C)CCN3CCCC3)c2)o1] | 4-Methyl-3-{5-[3-[methyl-(2-pyrrolidin-1-yl-ethyl)-amino]-5-(2-oxo-1,2-dihydro-pyridin-3-yl)-phenyl]-oxazol-2-ylamino}-benzamide | (300 MHz, DMSO) δ 11.75 (s, 1H), 9.33 (s, 1H), 8.38 (s, 1H), 7.87 (s, 1H), 7.65 (d, J = 6.6 Hz, 1H), 7.48 (d, J = 7.3 Hz, 1H), 7.43-7.34 (m, 2H), 7.30-7.21 (m, 2H), 7.17 (s, 1H), 6.97 (s, 1H), 6.83 (s, 1H), 6.30 (t, J = 6.6 Hz, 1H), 3.53-3.44 (m, 2H), 2.97 (s, 3H), 2.74-2.53 (m, 6H), 2.33 (s, 3H), 1.75-1.56 (m, 4H).<br>(ESI+) m/z 513 (M + H)$^+$<br>Retention time = 2.17 min (method 1) |
| 125 | 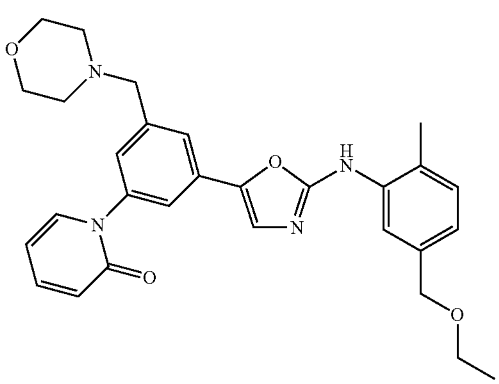 [SMILES: CCOCc1ccc(C)c(Nc2ncc(-c3cc(CN4CCOCC4)cc(-n4ccccc4=O)c3)o2)c1] | 1-{3-[2-(5-(Ethoxymethyl)-2-methyl-phenylamino)-oxazol-5-yl]-5-morpholin-4-ylmethyl-phenyl}-1H-pyridin-2-one | (300 MHz, DMSO-d$_6$) δ 9.32 (s, 1H), 7.86 (s, 1H), 7.70 (dd, J = 6.7, 1.6 Hz, 1H), 7.59-7.49 (m, 4H), 7.21-7.14 (m, 2H), 6.96-6.91 (m, 1H), 6.50 (d, J = 9.7 Hz, 1H), 6.37-6.31 (m, 1H), 4.40 (s, 2H), 3.62-3.55 (m, 4H), 3.53 (s, 2H), 3.46 (q, J = 7.0 Hz, 2H), 2.41 (s, 4H), 2.28 (s, 3H), 1.13 (t, J = 7.0 Hz, 3H).<br>(ESI+) m/z 501 (M + H)$^+$<br>Retention time = 2.65 min (method 1) |

TABLE 2-continued

| Ex # | Chemical structure | Name | ¹H NMR |
|---|---|---|---|
| 126 | 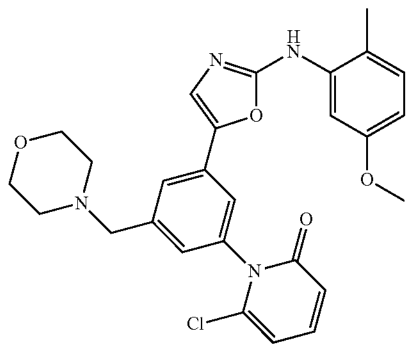 [SMILES: COc1ccc(C)c(Nc2ncc(-c3cc(CN4CCOCC4)cc(-n4c(Cl)cccc4=O)c3)o2)c1] | 6-Chloro-1-{3-[2-(5-methoxy-2-methyl-phenylamino)-oxazol-5-yl]-5-morpholin-4-ylmethyl-phenyl}-1H-pyridin-2-one | (300 MHz, DMSO-$d_6$) δ 9.27 (s, 1H), 7.65-7.57 (m, 2H), 7.57-7.51 (m, 2H), 7.46 (t, J = 1.7 Hz, 1H), 7.14-7.10 (m, 1H), 7.08 (d, J = 8.3 Hz, 1H), 6.62 (dd, J = 7.3, 1.0 Hz, 1H), 6.57 (d, J = 2.7 Hz, 1H), 6.55-6.50 (m, 1H), 3.72 (s, 3H), 3.63-3.56 (m, 4H), 3.54 (s, 2H), 2.39 (s, 4H), 2.22 (s, 3H). |
| 127 | 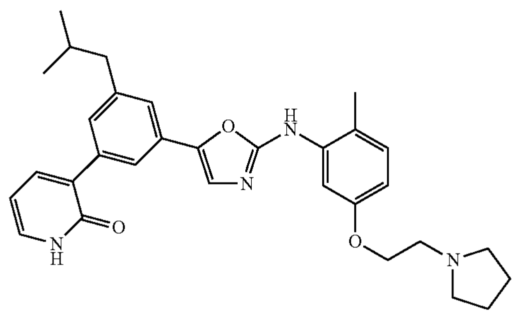 [SMILES: Cc1ccc(OCCN2CCCC2)cc1Nc1ncc(-c2cc(CC(C)C)cc(-c3ccc[nH]c3=O)c2)o1] | 3-(3-Isobutyl-5-{2-[2-methyl-5-(2-pyrrolidin-1-yl-ethoxy)-phenylamino]-oxazol-5-yl}-phenyl)-1H-pyridin-2-one | (400 MHz, DMSO) δ 11.82 (s, 1H), 9.22 (s, 1H), 7.79 (s, 1H), 7.73-7.62 (m, 2H), 7.44 (s, 1H), 7.41 (d, J = 7.3 Hz, 1H), 7.37 (d, J = 10.2 Hz, 2H), 7.06 (d, J = 8.5 Hz, 1H), 6.60-6.49 (m, 1H), 6.31 (t, J = 6.7 Hz, 1H), 4.02 (t, J = 5.8 Hz, 2H), 2.78 (t, J = 5.8 Hz, 2H), 2.50-2.49 (m, 4H), 2.48-2.37 (m, 2H), 2.23 (s, 3H), 1.93-1.86 (m, 1H), 1.78-1.55 (m, 4H), 0.92 (s, 3H), 0.89 (s, 3H). |
| 128 | 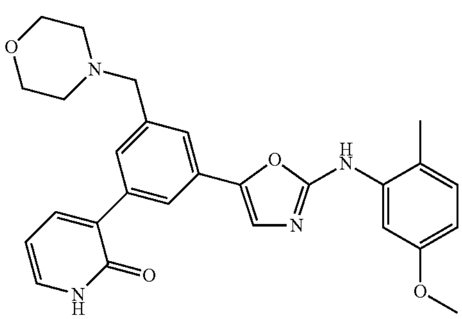 [SMILES: COc1ccc(C)c(Nc2ncc(-c3cc(CN4CCOCC4)cc(-c4ccc[nH]c4=O)c3)o2)c1] | 3-{3-[2-(5-Methoxy-2-methyl-phenylamino)-oxazol-5-yl]-5-morpholin-4-ylmethyl-phenyl}-1H-pyridin-2-one | (300 MHz, DMSO-$d_6$) δ 11.84 (s, 1H), 9.26 (s, 1H), 7.85 (s, 1H), 7.67 (s, 2H), 7.56-7.26 (m, 4H), 7.07 (d, J = 8.1 Hz, 1H), 6.55 (d, J = 7.0 Hz, 1H), 6.32 (t, J = 6.3 Hz, 1H), 3.73 (s, 3H), 3.59 (s, 4H), 3.50 (s, 2H), 2.39 (s, 4H), 2.23 (s, 3H). (ESI+) m/z 473 (M + H)⁺ Retention time = 2.52 min (method 1) |
| 129 | 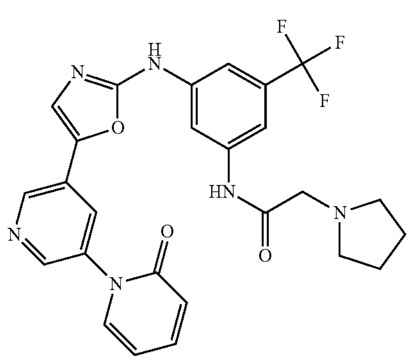 [SMILES: O=C(CN1CCCC1)Nc1cc(Nc2ncc(-c3cncc(-n4ccccc4=O)c3)o2)cc(C(F)(F)F)c1] | N-{3-[5-(2-Oxo-2H-[1,3']bipyridinyl-5'-yl)-oxazol-2-yl-amino]-5-trifluoromethyl-phenyl}-2-pyrrolidin-1-yl-acetamide | (300 MHz, DMSO-$d_6$) δ 10.93 (s, 1H), 10.11 (s, 1H), 8.88 (s, 1H), 8.54 (s, 1H), 8.24 (s, 1H), 8.15 (s, 1H), 7.87-7.75 (m, 3H), 7.70 (s, 1H), 7.63-7.48 (m, 1H), 6.55 (d, J = 9.3 Hz, 1H), 6.40 (t, J = 6.5 Hz, 1H), 3.26 (s, 2H), 2.59 (s, 4H), 1.75 (s, 4H). (ESI+) m/z 525 (M + H)⁺ Retention time = 2.48 min (method 1) |

TABLE 2-continued

| Ex # | Chemical structure | Name | ¹H NMR |
|---|---|---|---|
| 130 | 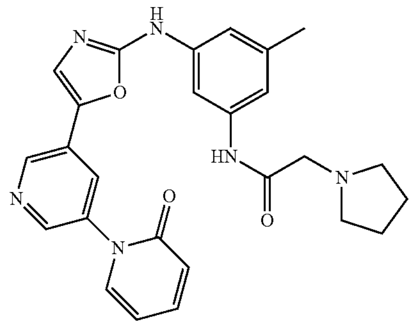 [SMILES: Cc1cc(NC(=O)CN2CCCC2)cc(Nc2ncc(-c3cncc(-n4ccccc4=O)c3)o2)c1] | N-{3-[5-(2-Oxo-2H-[1,3']bipyridinyl-5'-yl)-oxazol-2-yl-amino]-5-methyl-phenyl}-2-pyrrolidin-1-yl-acetamide | (300 MHz, DMSO-d₆) δ 10.43 (s, 1H), 9.64 (s, 1H), 8.87 (s, 1H), 8.51 (s, 1H), 8.13 (s, 1H), 7.86 (s, 1H), 7.80 (d, J = 6.6 Hz, 1H), 7.74 (s, 1H), 7.58 (t, J = 7.3 Hz, 1H), 7.14 (s, 1H), 7.07 (s, 1H), 6.55 (d, J = 9.3 Hz, 1H), 6.39 (t, J = 6.4 Hz, 1H), 3.21 (s, 2H), 2.58 (s, 4H), 2.26 (s, 3H), 1.75 (s, 4H).<br>(ESI+) m/z 471 (M + H)⁺<br>Retention time = 2.10 min (method 1) |
| 131 | 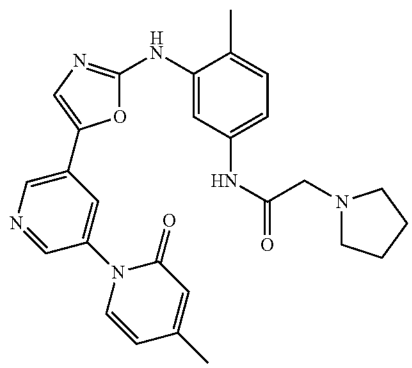 [SMILES: Cc1ccn(-c2cncc(-c3cnc(Nc4cc(NC(=O)CN5CCCC5)ccc4C)o3)c2)c(=O)c1] | N-{4-Methyl-3-[5-(4-methyl-2-oxo-2H-[1,3']bipyridinyl-5'-yl)-oxazol-2-ylamino]-phenyl}-2-pyrrolidin-1-yl-acetamide | (300 MHz, DMSO-d₆) δ 9.66 (s, 1H), 9.44 (s, 1H), 8.86 (d, J = 2.0 Hz, 1H), 8.47 (d, J = 2.2 Hz, 1H), 8.13 (d, J = 1.7 Hz, 1H), 8.07 (t, J = 2.1 Hz, 1H), 7.70-7.66 (m, 2H), 7.29 (dd, J = 8.1, 2.0 Hz, 1H), 7.11 (d, J = 8.4 Hz, 1H), 6.35 (s, 1H), 6.25 (dd, J = 7.0, 1.7 Hz, 1H), 3.19 (s, 2H), 2.57 (s, 4H), 2.23 (s, 3H), 2.21 (s, 3H), 1.76-1.70 (m, 4H). |
| 132 | 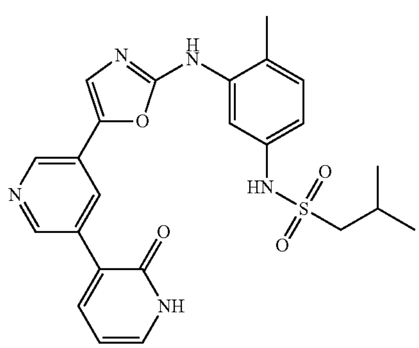 [SMILES: Cc1ccc(NS(=O)(=O)CC(C)C)cc1Nc1ncc(-c2cncc(-c3ccc[nH]c3=O)c2)o1] | 2-Methyl-propane-1-sulfonic acid {4-methyl-3-[5-(2'-oxo-1',2'-dihydro-[3,3']bipyridinyl-5-yl)-oxazol-2-yl-amino]-phenyl}-amide | (300 MHz, DMSO-d₆) δ 11.98 (s, 1H), 9.70 (s, 1H), 9.46 (s, 1H), 8.77 (d, J = 11.8 Hz, 2H), 8.31 (s, 1H), 7.84 (d, J = 6.7 Hz, 1H), 7.80 (s, 1H), 7.61 (s, 1H), 7.49 (s, 1H), 7.13 (d, J = 8.1 Hz, 1H), 6.83 (d, J = 8.0 Hz, 1H), 6.36 (t, J = 6.7 Hz, 1H), 2.97 (d, J = 6.4 Hz, 2H), 2.25 (s, 3H), 2.17-2.09 (m, 1H), 0.99 (d, J = 6.6 Hz, 6H).<br>(ESI+) m/z 480 (M + H)⁺<br>Retention time = 2.84 min (method 1) |
| 133 | 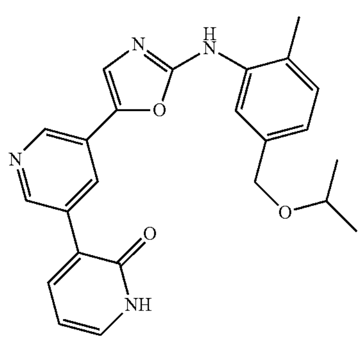 [SMILES: Cc1ccc(COC(C)C)cc1Nc1ncc(-c2cncc(-c3ccc[nH]c3=O)c2)o1] | 5'-[2-(5-(Isopropoxymethyl)-2-methyl-phenylamino)-oxazol-5-yl]-1H-[3,3']bipyridinyl-2-one | (300 MHz, DMSO-d₆) δ 11.98 (s, 1H), 9.41 (s, 1H), 8.76 (s, 1H), 8.73 (s, 1H), 8.31 (s, 1H), 7.92-7.71 (m, 2H), 7.60 (s, 1H), 7.49 (d, J = 5.4 Hz, 1H), 7.16 (d, J = 7.7 Hz, 1H), 6.95 (d, J = 7.7 Hz, 1H), 6.36 (t, J = 6.5 Hz, 1H), 4.43 (s, 2H), 3.63 (q, J = 6.0 Hz, 1H), 2.28 (s, 3H), 1.12 (d, J = 6.0 Hz, 6H).<br>(ESI+) m/z 417 (M + H)⁺<br>Retention time = 3.02 min (method 1) |

TABLE 2-continued

| Ex # | Chemical structure | Name | $^1$H NMR |
|---|---|---|---|
| 134 | 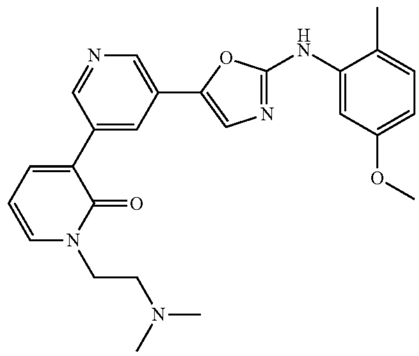 [SMILES: COc1ccc(C)c(Nc2ncc(-c3cncc(-c4cccn(CCN(C)C)c4=O)c3)o2)c1] | 1-(2-Dimethylamino-ethyl)-5'-[2-(5-methoxy-2-methyl-phenylamino)-oxazol-5-yl]-1H-[3,3']bipyridinyl-2-one | (300 MHz, CDCl$_3$) δ 8.66 (d, J = 2.2 Hz, 1H), 8.56 (d, J = 1.9 Hz, 1H), 8.08 (t, J = 2.2 Hz, 1H), 7.70 (m, 1H), 7.59 (s, 1H), 7.51 (dd, J = 7.0, 1.9 Hz, 1H), 7.43 (dd, J = 7.1, 1.9 Hz, 1H), 7.07 (d, J = 8.4 Hz, 1H), 6.96 (m, 1H), 6.65 (dd, J = 8.4, 2.6 Hz, 1H), 6.34 (t, J = 6.8 Hz, 1H), 4.12 (t, J = 6.3 Hz, 2H), 3.77 (s, 3H), 2.68 (t, J = 6.3 Hz, 2H), 2.29 (s, 6H), 2.15 (s, 3H). |
| 135 | 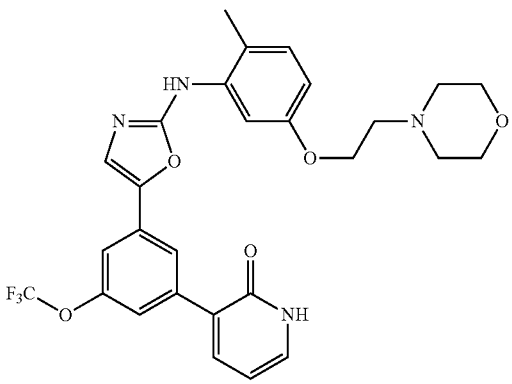 [SMILES: Cc1ccc(OCCN2CCOCC2)cc1Nc1ncc(-c2cc(OC(F)(F)F)cc(-c3ccc[nH]c3=O)c2)o1] | 3-(3-{2-[2-Methyl-5-(2-morpholin-4-yl-ethoxy)-phenylamino]-oxazol-5-yl}-5-trifluoromethoxy-phenyl)-1H-pyridin-2-one | (400 MHz, DMSO-d$_6$) δ 11.98 (s, 1H), 9.36 (s, 1H), 7.97 (s, 1H), 7.84 (d, J = 7.0 Hz, 1H), 7.76-7.57 (m, 3H), 7.50 (br s, 2H), 7.08 (d, J = 8.2 Hz, 1H), 6.58 (d, J = 8.2 Hz, 1H), 6.36 (t, J = 6.7 Hz, 1H), 4.05 (t, J = 5.7 Hz, 2H), 3.58 (t, J = 4.1 Hz, 4H), 2.68 (t, J = 5.7 Hz, 2H), 2.47 (s, 4H), 2.23 (s, 3H).<br>(ESI+) m/z 557 (M + H)$^+$<br>Retention time = 3.06 min (method 1) |
| 136 | 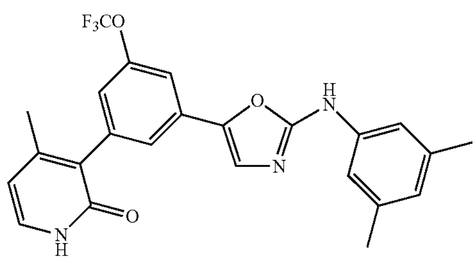 [SMILES: Cc1cc(C)cc(Nc2ncc(-c3cc(OC(F)(F)F)cc(-c4c(C)cc[nH]c4=O)c3)o2)c1] | 3-{3-[2-(3,5-Dimethyl-phenylamino)-oxazol-5-yl]-5-trifluoromethoxy-phenyl}-4-methyl-1H-pyridin-2-one | (400 MHz, DMSO) δ 11.65 (s, 1H), 10.21 (s, 1H), 7.64 (s, 1H), 7.50 (s, 1H), 7.46 (s, 1H), 7.33 (d, J = 6.6 Hz, 1H), 7.26 (s, 2H), 7.09 (s, 1H), 6.62 (s, 1H), 6.20 (d, J = 6.7 Hz, 1H), 2.25 (s, 6H), 2.05 (s, 3H).<br>(ESI+) m/z 456 (M + H)$^+$<br>Retention time = 4.66 min (method 1) |
| 137 | 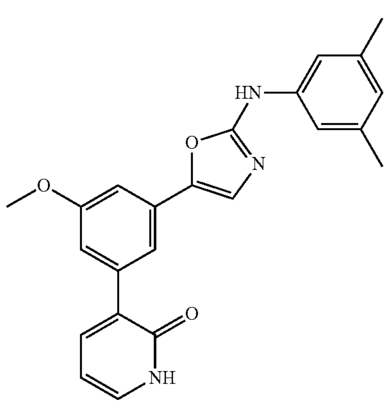 | 3-{3-[2-(3,5-Dimethyl-phenylamino)-oxazol-5-yl]-5-methoxy-phenyl}-1H-pyridin-2-one | (400 MHz, DMSO) δ 11.85 (s, 1H), 10.22 (s, 1H), 7.73 (dd, J = 6.9, 2.0 Hz, 1H), 7.56 (d, J = 1.4 Hz, 1H), 7.50 (s, 1H), 7.43 (d, J = 4.6 Hz, 1H), 7.25 (s, 2H), 7.19 (d, J = 1.4 Hz, 1H), 7.09 (s, 1H), 6.60 (s, 1H), 6.32 (t, J = 6.7 Hz, 1H), 3.82 (s, 3H), 2.17 (s, 6H).<br>(ESI+) m/z 388 (M + H)$^+$<br>Retention time = 3.90 min (method 1) |

TABLE 2-continued

| Ex # | Chemical structure | Name | ¹H NMR |
|---|---|---|---|
| 138 | 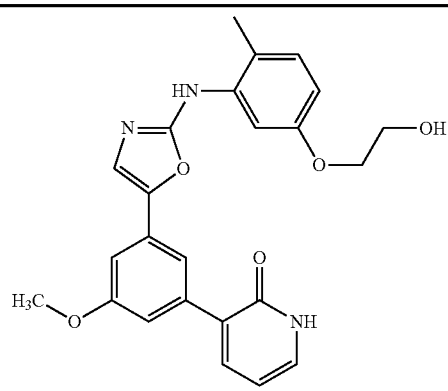 | 3-(3-{2-[5-(2-Hydroxy-ethoxy)-2-methyl-phenylamino]-oxazol-5-yl}-5-methoxy-phenyl)-1H-pyridin-2-one | (400 MHz, DMSO-$d_6$) δ 11.84 (s, 1H), 9.26 (s, 1H), 7.71 (dd, J = 6.9, 2.0 Hz, 1H), 7.69 (d, J = 2.5 Hz, 1H), 7.54 (s, 1H), 7.49 (s, 1H), 7.43 (d, J = 4.9 Hz, 1H), 7.19 (br s, 1H), 7.11 (br s, 1H), 7.06 (d, J = 8.4 Hz, 1H), 6.54 (dd, J = 8.3, 2.5 Hz, 1H), 6.32 (t, J = 6.6 Hz, 1H), 4.88 (t, J = 5.5 Hz, 1H), 3.94 (t, J = 5.0 Hz, 2H), 3.83 (s, 3H), 3.70 (q, J = 5.1 Hz, 2H), 2.23 (s, 3H). (ESI+) m/z 448 (M + H)⁺ Retention time = 3.07 min (method 1) |
| 139 | 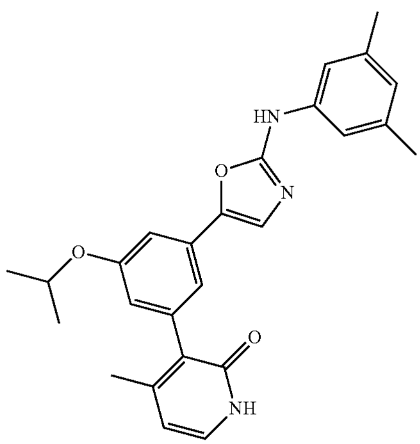 [SMILES: Cc1cc(C)cc(Nc2ncc(-c3cc(OC(C)C)cc(-c4c(C)cc[nH]c4=O)c3)o2)c1] | 3-{3-[2-(3,5-Dimethyl-phenylamino)-oxazol-5-yl]-5-isopropoxy-phenyl}-4-methyl-1H-pyridin-2-one | 1H NMR (400 MHz, DMSO-$d_6$) δ 11.57 (s, 1H), 10.18 (s, 1H), 7.50 (s, 1H), 7.29 (d, J = 6.7 Hz, 1H), 7.25 (s, 2H), 7.05 (s, 1H), 6.99 (s, 1H), 6.63 (s, 1H), 6.61 (s, 1H), 6.17 (d, J = 6.8 Hz, 1H), 4.75-4.59 (m, 1H), 2.25 (s, 6H), 2.03 (s, 3H), 1.31 (d, J = 6.0 Hz, 6H). (ESI+) m/z 430 (M + H)⁺ Retention time = 4.45 min (method 1) |
| 140 | 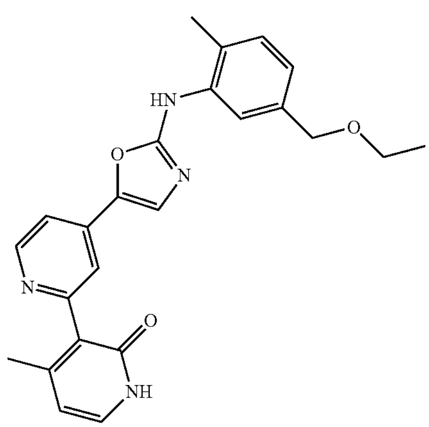 [SMILES: CCOCc1ccc(C)c(Nc2ncc(-c3ccnc(-c4c(C)cc[nH]c4=O)c3)o2)c1] | 4-[2-(5-(Ethoxymethyl)-2-methyl-phenylamino)-oxazol-5-yl]-4'-methyl-1'H-[2,3']bipyridinyl-2'-one | (300 MHz, DMSO-$d_6$) δ 11.67 (s, 1H), 9.51 (s, 1H), 8.59 (d, J = 5.3 Hz, 1H), 7.79 (s, 1H), 7.77 (s, 1H), 7.53 (s, 1H), 7.42 (dd, J = 5.3, 1.7 Hz, 1H), 7.34 (d, J = 6.6 Hz, 1H), 7.18 (d, J = 7.7 Hz, 1H), 6.96 (d, J = 7.6 Hz, 1H), 6.18 (d, J = 6.7 Hz, 1H), 4.40 (s, 2H), 3.46 (q, J = 7.0 Hz, 2H), 2.26 (s, 3H), 2.03 (s, 3H), 1.13 (t, J = 7.0 Hz, 3H). (ESI+) m/z 417 (M + H)⁺ Retention time = 2.53 min (method 1) |
| 141 | 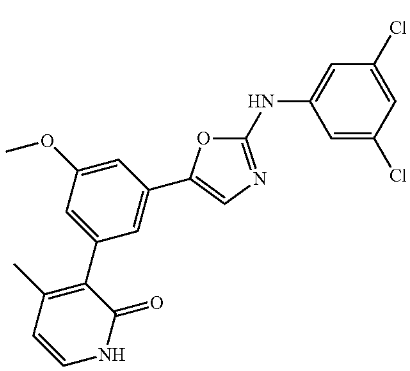 [SMILES: COc1cc(-c2cnc(Nc3cc(Cl)cc(Cl)c3)o2)cc(-c2c(C)cc[nH]c2=O)c1] | 3-{3-[2-(3,5-Dichloro-phenylamino)-oxazol-5-yl]-5-methoxy-phenyl}-4-methyl-1H-pyridin-2-one | (400 MHz, DMSO-$d_6$) δ 11.56 (s, 1H), 10.82 (s, 1H), 7.70 (s, 2H), 7.57 (s, 1H), 7.28 (d, J = 6.3 Hz, 1H), 7.14 (s, 1H), 7.08 (s, 1H), 7.05 (s, 1H), 6.68 (s, 1H), 6.16 (d, J = 6.7 Hz, 1H), 3.81 (s, 3H), 2.01 (s, 1H). (ESI+) m/z 442 (M + H)⁺ Retention time = 4.60 min (method 1) |

TABLE 2-continued

| Ex # | Chemical structure | Name | ¹H NMR |
|---|---|---|---|
| 142 | 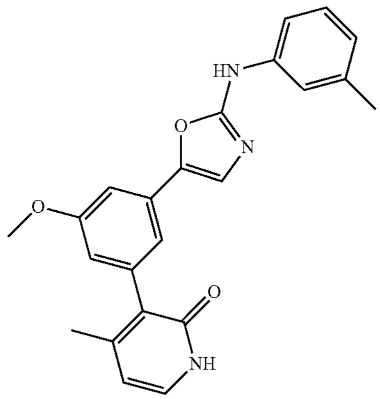 | 3-[3-Methoxy-5-(2-m-tolylamino-oxazol-5-yl)-phenyl]-4-methyl-1H-pyridin-2-one | (400 MHz, DMSO-$d_6$) δ 11.53 (s, 1H), 10.19 (s, 1H), 7.48 (s, 2H), 7.41 (d, J = 8.2 Hz, 1H), 7.28 (d, J = 6.6 Hz, 1H), 7.19 (t, J = 7.8 Hz, 1H), 7.07 (s, 1H), 7.03 (s, 1H), 6.77 (d, J = 7.3 Hz, 1H), 6.65 (s, 1H), 6.16 (d, J = 6.7 Hz, 1H), 3.82 (s, 3H), 2.30 (s, 3H), 2.02 (s, 3H). (ESI+) m/z 388 (M + H)⁺ Retention time = 3.74 min (method 1) |
| 143 | 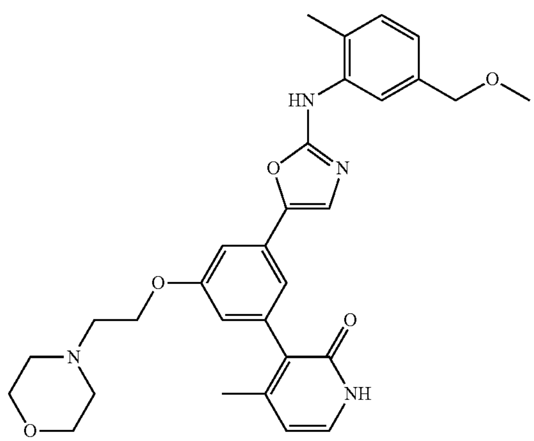 [SMILES: COCc1ccc(C)c(Nc2ncc(-c3cc(OCCN4CCOCC4)cc(-c4c(C)cc[nH]c4=O)c3)o2)c1] | 3-[3-[2-(5-(Methoxymethyl)-2-methyl-phenylamino)-oxazol-5-yl]-5-(2-morpholin-4-yl-ethoxy)-phenyl]-4-methyl-1H-pyridin-2-one | (400 MHz, DMSO) δ 11.58 (s, 1H), 9.22 (s, 1H), 7.89 (s, 1H), 7.49 (s, 1H), 7.29 (d, J = 6.6 Hz, 1H), 7.16 (d, J = 7.7 Hz, 1H), 7.10 (s, 1H), 7.01 (s, 1H), 6.91 (d, J = 8.6 Hz, 1H), 6.65 (s, 1H), 6.16 (d, J = 6.7 Hz, 1H), 4.36 (s, 2H), 4.13 (t, J = 5.7 Hz, 2H), 3.64-3.49 (m, 4H), 3.26 (s, 3H), 2.72 (t, J = 5.6 Hz, 2H), 2.50-2.46 (m, 4H), 2.26 (s, 3H), 2.01 (s, 3H). (ESI+) m/z 529 (M + H)⁺ Retention time = 2.61 min (method 1) |
| 144 | 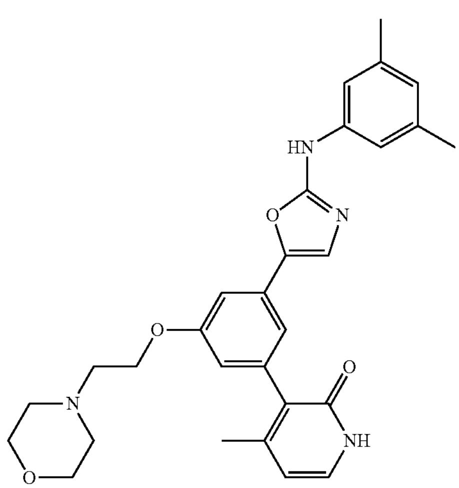 [SMILES: Cc1cc(C)cc(Nc2ncc(-c3cc(OCCN4CCOCC4)cc(-c4c(C)cc[nH]c4=O)c3)o2)c1] | 3-[3-[2-(3,5-Dimethyl-phenylamino)-oxazol-5-yl]-5-(2-morpholin-4-yl-ethoxy)-phenyl]-4-methyl-1H-pyridin-2-one | (400 MHz, DMSO) δ 11.54 (s, 1H), 10.10 (s, 1H), 7.49 (s, 1H), 7.28 (d, J = 6.7 Hz, 1H), 7.25 (s, 2H), 7.08 (s, 1H), 7.01 (s, 1H), 6.66 (s, 1H), 6.60 (s, 1H), 6.16 (d, J = 6.7 Hz, 1H), 4.14 (t, J = 5.7 Hz, 2H), 3.64-3.49 (m, 4H), 2.72 (t, J = 5.7 Hz, 2H), 2.58-2.53 (m, 4H), 2.24 (s, 6H), 2.00 (s, 3H). (ESI+) m/z 501 (M + H)⁺ Retention time = 2.97 min (method 1) |

TABLE 2-continued

| Ex # | Chemical structure | Name | $^1$H NMR |
|---|---|---|---|
| 145 | 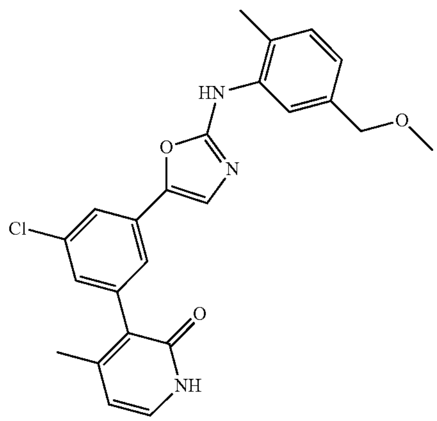 [SMILES: COCc1ccc(C)c(Nc2ncc(-c3cc(Cl)cc(-c4c(C)cc[nH]c4=O)c3)o2)c1] | 3-{3-Chloro-5-[2-(5-(methoxymethyl)-2-methyl-phenylamino)-oxazol-5-yl]-phenyl}-4-methyl-1H-pyridin-2-one | (400 MHz, DMSO) δ 11.62 (s, 1H), 9.29 (s, 1H), 7.86 (s, 1H), 7.66-7.50 (m, 2H), 7.38 (s, 1H), 7.32 (d, J = 6.7 Hz, 1H), 7.17 (d, J = 7.6 Hz, 1H), 7.14 (s, 1H), 6.93 (d, J = 7.1 Hz, 1H), 6.19 (d, J = 6.7 Hz, 1H), 4.37 (s, 2H), 3.27 (s, 3H), 2.28 (s, 3H), 2.02 (s, 3H). (ESI+) m/z 436 (M + H)$^+$ Retention time = 3.86 min (method 1) |
| 146 | 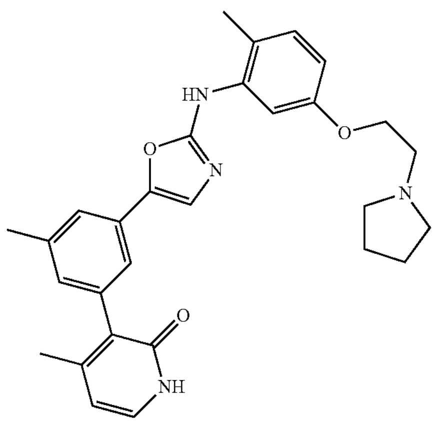 [SMILES: Cc1cc(-c2cnc(Nc3cc(OCCN4CCCC4)ccc3C)o2)cc(-c2c(C)cc[nH]c2=O)c1] | 4-Methyl-3-(3-methyl-5-{2-[2-methyl-5-(2-pyrrolidin-1-yl-ethoxy)-phenylamino]-oxazol-5-yl}-phenyl)-1H-pyridin-2-one | (300 MHz, DMSO) δ 11.54 (s, 1H), 9.16 (s, 1H), 7.66 (s, 1H), 7.43 (s, 1H), 7.36 (s, 1H), 7.30-7.22 (m, 2H), 7.05 (d, J = 8.3 Hz, 1H), 6.90 (s, 1H), 6.53 (dd, J = 8.2, 2.2 Hz, 1H), 6.16 (d, J = 6.6 Hz, 1H), 4.01 (t, J = 5.8 Hz, 2H), 2.76 (t, J = 5.8 Hz, 2H), 2.49 (m, 4H), 2.35 (s, 3H), 2.21 (s, 3H), 1.99 (s, 3H), 1.75-1.61 (m, 4H). (ESI+) m/z 485 (M + H)$^+$ Retention time = 2.85 min (method 1) |
| 147 | 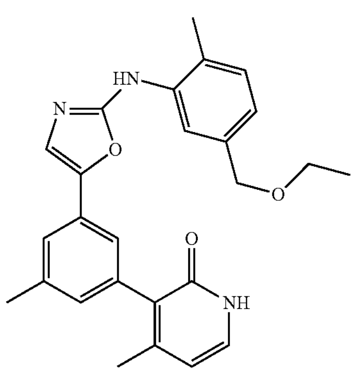 [SMILES: CCOCc1ccc(C)c(Nc2ncc(-c3cc(C)cc(-c4c(C)cc[nH]c4=O)c3)o2)c1] | 3-{3-[2-(5-(Ethoxymethyl)-2-methyl-phenylamino)-oxazol-5-yl]-5-methyl-phenyl}-4-methyl-1H-pyridin-2-one | (300 MHz, DMSO-d$_6$) δ 11.55 (s, 1H), 9.19 (s, 1H), 7.87 (s, 1H), 7.41 (s, 1H), 7.35 (s, 1H), 7.28 (d, J = 6.6 Hz, 1H), 7.22 (s, 1H), 7.15 (d, J = 7.6 Hz, 1H), 6.96-6.86 (m, 2H), 6.16 (d, J = 6.7 Hz, 1H), 4.40 (s, 2H), 3.46 (q, J = 7.0 Hz, 2H), 2.36 (s, 3H), 2.27 (s, 3H), 2.00 (s, 3H), 1.12 (t, J = 7.0 Hz, 3H). (ESI+) m/z 430 (M + H)$^+$ Retention time = 3.84 min (method 1) |
| 148 | 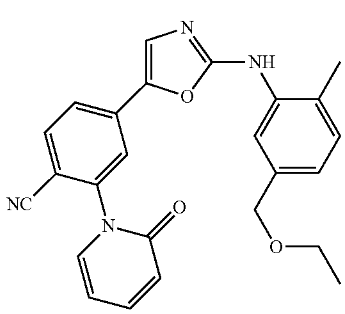 [SMILES: CCOCc1ccc(C)c(Nc2ncc(-c3ccc(C#N)c(-n4ccccc4=O)c3)o2)c1] | 4-[2-(5-(Ethoxymethyl)-2-methyl-phenylamino)-oxazol-5-yl]-2-(2-oxo-2H-pyridin-1-yl)-benzonitrile | (300 MHz, DMSO-d$_6$) δ 9.55 (s, 1H), 8.05 (d, J = 8.1 Hz, 1H), 7.77 (dd, J = 16.5, 10.7 Hz, 5H), 7.61 (t, J = 7.0 Hz, 1H), 7.18 (d, J = 7.6 Hz, 1H), 6.97 (d, J = 7.7 Hz, 1H), 6.57 (d, J = 9.2 Hz, 1H), 6.41 (t, J = 6.6 Hz, 1H), 4.41 (s, 2H), 3.46 (q, J = 7.0 Hz, 2H), 2.27 (s, 3H)), 1.13 (t, J = 7.0 Hz, 3H). (ESI+) m/z 427 (M + H)$^+$ Retention time = 3.61 min (method 1) |

TABLE 2-continued

| Ex # | Chemical structure | Name | ¹H NMR |
|---|---|---|---|
| 149 | 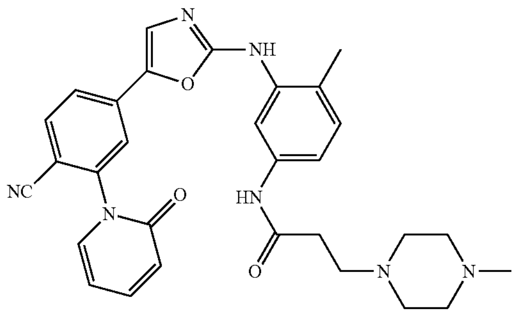 [SMILES: Cc1ccc(NC(=O)CCN2CCN(C)CC2)cc1Nc1ncc(-c2ccc(C#N)c(-n3ccccc3=O)c2)o1] | N-(3-{5-[4-Cyano-3-(2-oxo-2H-pyridin-1-yl)-phenyl]-oxazol-2-ylamino}-4-methyl-phenyl)-3-(4-methyl-piperazin-1-yl)-propionamide | (300 MHz, DMSO-$d_6$) δ 10.11 (s, 1H), 9.52 (s, 1H), 8.08 (s, 1H), 8.04 (d, J = 8.2 Hz, 1H), 7.90-7.69 (m, 4H), 7.60 (t, J = 7.1 Hz, 1H), 7.28 (d, J = 7.9 Hz, 1H), 7.11 (d, J = 8.1 Hz, 1H), 6.56 (d, J = 9.1 Hz, 1H), 6.41 (t, J = 6.5 Hz, 1H), 2.57 (d, J = 6.2 Hz, 2H), 2.43-2.05 (m, 16H). (ESI+) m/z 538 (M + H)⁺ Retention time = 2.17 min (method 1) |
| 150 | 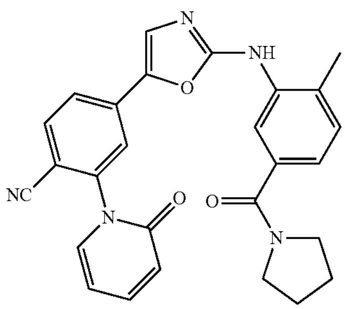 [SMILES: Cc1ccc(C(=O)N2CCCC2)cc1Nc1ncc(-c2ccc(C#N)c(-n3ccccc3=O)c2)o1] | 4-{2-[2-Methyl-5-(pyrrolidine-1-carbonyl)-phenylamino]-oxazol-5-yl}-2-(2-oxo-2H-pyridin-1-yl)-benzonitrile | (400 MHz, DMSO-$d_6$) δ 9.67 (s, 1H), 8.13-7.99 (m, 2H), 7.84 (s, 1H), 7.83-7.70 (m, 3H), 7.62 (t, J = 7.9 Hz, 1H), 7.27 (d, J = 7.8 Hz, 1H), 7.16 (d, J = 6.6 Hz, 1H), 6.57 (d, J = 9.2 Hz, 1H), 6.42 (t, J = 6.4 Hz, 1H), 3.54-3.37 (m, 4H), 2.33 (s, 3H), 1.99-1.68 (m, 4H). (ESI+) m/z 466 (M + H)⁺ Retention time = 3.09 min (method 1) |
| 151 | 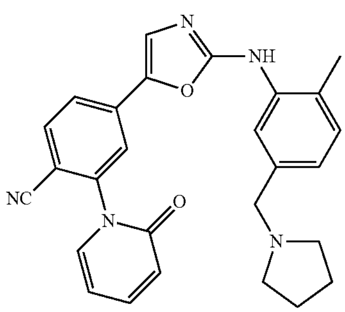 [SMILES: Cc1ccc(CN2CCCC2)cc1Nc1ncc(-c2ccc(C#N)c(-n3ccccc3=O)c2)o1] | 4-[2-(2-Methyl-5-pyrrolidin-1-ylmethyl-phenylamino)-oxazol-5-yl]-2-(2-oxo-2H-pyridin-1-yl)-benzonitrile | (300 MHz, DMSO-$d_6$) δ 9.53 (s, 1H), 8.04 (d, J = 8.1 Hz, 1H), 7.81 (s, 1H), 7.77-7.64 (m, 4H), 7.61 (t, J = 7.9 Hz, 1H), 7.14 (d, J = 7.8 Hz, 1H), 6.95 (d, J = 7.8 Hz, 1H), 6.56 (d, J = 9.3 Hz, 1H), 6.40 (t, J = 6.6 Hz, 1H), 3.51 (s, 2H), 2.46-2.34 (m, 4H), 2.25 (s, 3H), 1.72-1.60 (m, 4H). (ESI+) m/z 452 (M + H)⁺ Retention time = 2.35 min (method 1) |
| 152 | 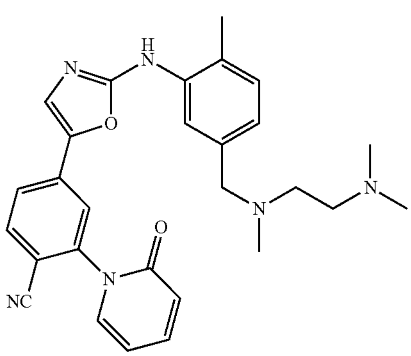 [SMILES: Cc1ccc(CN(C)CCN(C)C)cc1Nc1ncc(-c2ccc(C#N)c(-n3ccccc3=O)c2)o1] | 4-[2-(5-{[(2-Dimethylamino-ethyl)-methyl-amino]-methyl}-2-methyl-phenylamino)-oxazol-5-yl]-2-(2-oxo-2H-pyridin-1-yl)-benzonitrile | (300 MHz, CDCl₃) δ 7.87 (s, 1H), 7.76 (d, J = 8.2 Hz, 1H), 7.63 (d, J = 8.2 Hz, 1H), 7.56 (s, 1H), 7.45 (m, 1H), 7.34 (s, 1H), 7.28 (m, 1H), 7.14 (d, J = 7.7 Hz, 1H), 7.02 (d, J = 7.8 Hz, 1H), 6.70 (m, 2H), 6.32 (t, J = 6.8 Hz, 1H), 3.49 (s, 2H), 2.56-2.41 (m, 4H), 2.28 (s, 3H), 2.22 (s, 9H). (ESI+) m/z 483 (M + H)⁺ Retention time = 1.88 min (method 1) |

TABLE 2-continued

| Ex # | Chemical structure | Name | ¹H NMR |
|---|---|---|---|
| 153 | 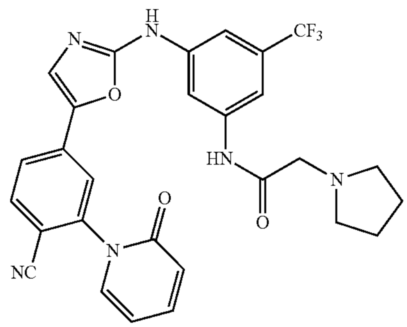 [SMILES: N#Cc1ccc(-c2cnc(Nc3cc(NC(=O)CN4CCCC4)cc(C(F)(F)F)c3)o2)cc1-n1ccccc1=O] | N-(3-{5-[4-Cyano-3-(2-oxo-2H-pyridin-1-yl)-phenyl]-oxazol-2-ylamino}-5-trifluoromethyl-phenyl)-2-pyrrolidin-1-yl-acetamide | (400 MHz, DMSO) δ 10.99 (s, 1H), 10.13 (s, 1H), 8.29 (s, 1H), 8.08 (d, J = 8.1 Hz, 1H), 7.92 (s, 1H), 7.90 (d, J = 1.5 Hz, 1H), 7.84-7.72 (m, 3H), 7.69 (s, 1H), 7.66-7.58 (m, 1H), 6.58 (d, J = 9.3 Hz, 1H), 6.43 (dd, J = 7.2, 6.0 Hz, 1H), 3.27 (s, 2H), 2.60 (s, 4H), 1.76 (s, 4H). (ESI+) m/z 549 (M + H)⁺ Retention time = 2.82 min (method 1) |
| 154 | 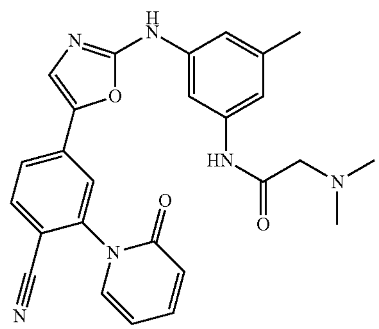 [SMILES: Cc1cc(NC(=O)CN(C)C)cc(Nc2ncc(-c3ccc(C#N)c(-n4ccccc4=O)c3)o2)c1] | N-(3-{5-[4-Cyano-3-(2-oxo-2H-pyridin-1-yl)-phenyl]-oxazol-2-ylamino}-5-methyl-phenyl)-2-dimethylamino-acetamide | (300 MHz, DMSO-d₆) δ 10.55 (s, 1H), 9.67 (s, 1H), 8.09 (d, J = 8.3 Hz, 1H), 7.98-7.87 (m, 3H), 7.82 (d, J = 8.5 Hz, 2H), 7.65 (t, J = 7.1 Hz, 1H), 7.16 (s, 1H), 7.11 (s, 1H), 6.61 (d, J = 9.4 Hz, 1H), 6.45 (t, J = 6.6 Hz, 1H), 3.07 (s, 2H), 2.31 (s, 6H), 2.29 (s, 3H). (ESI+) m/z 469 (M + H)⁺ Retention time = 2.34 min (method 1) |
| 155 | 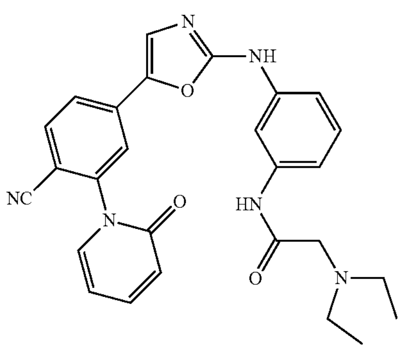 [SMILES: CCN(CC)CC(=O)Nc1cccc(Nc2ncc(-c3ccc(C#N)c(-n4ccccc4=O)c3)o2)c1] | N-(3-{5-[4-Cyano-3-(2-oxo-2H-pyridin-1-yl)-phenyl]-oxazol-2-ylamino}-phenyl)-2-diethylamino-acetamide | (300 MHz, DMSO-d6) δ 10.57 (s, 1H), 9.61 (s, 1H), 8.04 (d, J = 8.1 Hz, 1H), 7.86 (s, 2H), 7.77 (d, J = 7.9 Hz, 2H), 7.61 (t, J = 7.1 Hz, 1H), 7.32-7.08 (m, 3H), 6.57 (d, J = 9.3 Hz, 1H), 6.42 (t, J = 6.7 Hz, 1H), 3.12 (s, 2H), 2.60 (q, J = 7.0 Hz, 4H), 1.02 (t, J = 7.0 Hz, 6H). (ESI+) m/z 483 (M + H)⁺ Retention time = 2.30 min (method 1) |
| 156 | 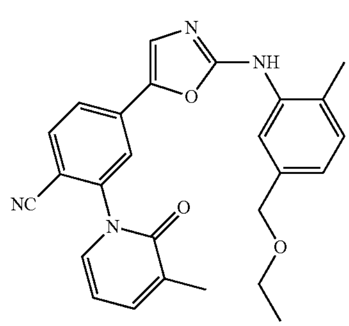 [SMILES: CCOCc1ccc(C)c(Nc2ncc(-c3ccc(C#N)c(-n4cccc(C)c4=O)c3)o2)c1] | 4-[2-(5-(Ethoxymethyl)-2-methyl-phenylamino)-oxazol-5-yl]-2-(3-methyl-2-oxo-2H-pyridin-1-yl)-benzonitrile | (300 MHz, DMSO-d₆) δ 9.55 (s, 1H), 8.05 (d, J = 8.0 Hz, 1H), 7.83-7.68 (m, 4H), 7.61 (d, J = 6.7 Hz, 1H), 7.48 (d, J = 6.6 Hz, 1H), 7.18 (d, J = 7.8 Hz, 1H), 6.97 (d, J = 7.4 Hz, 1H), 6.33 (t, J = 6.8 Hz, 1H), 4.41 (s, 2H), 3.46 (q, J = 7.0 Hz, 2H), 2.27 (s, 3H), 2.06 (d, J = 7.1 Hz, 3H), 1.12 (t, J = 7.0 Hz, 3H). (ESI+) m/z 441 (M + H)⁺ Retention time = 3.90 min (method 1) |

TABLE 2-continued

| Ex # | Chemical structure | Name | ¹H NMR |
|---|---|---|---|
| 157 | 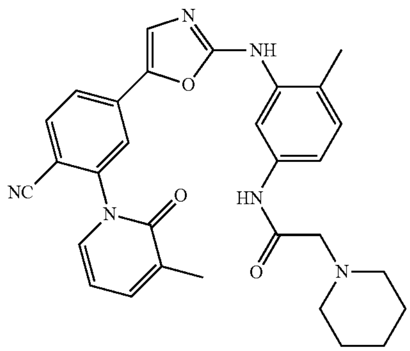 [SMILES: Cc1ccc(NC(=O)CN2CCCCC2)cc1Nc1ncc(-c2ccc(C#N)c(-n3cccc(C)c3=O)c2)o1] | N-(3-{5-[4-Cyano-3-(3-methyl-2-oxo-2H-pyridin-1-yl)-phenyl]-oxazol-2-ylamino}-4-methyl-phenyl)-2-piperidin-1-yl-acetamide | (300 MHz, DMSO-$d_6$) δ 9.62 (s, 1H), 9.55 (s, 1H), 8.13 (d, J = 1.5 Hz, 1H), 8.03 (d, J = 8.3 Hz, 1H), 7.83-7.75 (m, 3H), 7.61 (d, J = 6.7 Hz, 1H), 7.48 (d, J = 6.6 Hz, 1H), 7.27 (dd, J = 8.1, 1.8 Hz, 1H), 7.12 (d, J = 8.2 Hz, 1H), 6.33 (t, J = 6.8 Hz, 1H), 3.01 (s, 2H), 2.44 (s, 4H), 2.23 (s, 3H), 2.07 (s, 3H), 1.55 (s, 4H), 1.41-1.37 (m, 2H). |
| 158 | 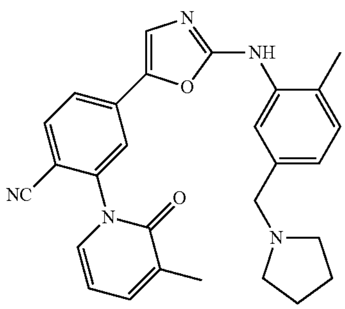 [SMILES: Cc1ccc(CN2CCCC2)cc1Nc1ncc(-c2ccc(C#N)c(-n3cccc(C)c3=O)c2)o1] | 2-(3-Methyl-2-oxo-2H-pyridin-1-yl)-4-[2-(2-methyl-5-pyrrolidin-1-ylmethyl-phenylamino)-oxazol-5-yl]-benzonitrile | (300 MHz, DMSO-$d_6$) δ 9.53 (s, 1H), 8.04 (d, J = 8.3 Hz, 1H), 7.81 (s, 1H), 7.77-7.68 (m, 3H), 7.61 (d, J = 6.5 Hz, 1H), 7.48 (d, J = 6.0 Hz, 1H), 7.14 (d, J = 7.6 Hz, 1H), 6.95 (d, J = 7.6 Hz, 1H), 6.33 (t, J = 6.7 Hz, 1H), 3.51 (s, 2H), 2.46-2.34 (m, 4H), 2.25 (s, 3H), 2.07 (s, 3H), 1.71-1.59 (m, 4H). (ESI+) m/z 466 (M + H)⁺ Retention time = 2.58 min (method 1) |
| 159 | 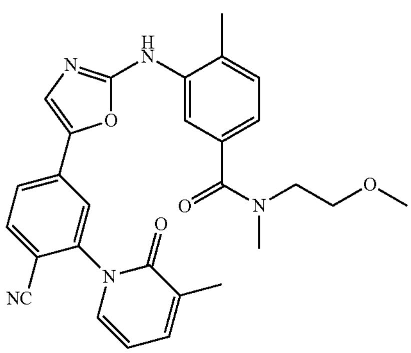 [SMILES: COCCN(C)C(=O)c1ccc(C)c(Nc2ncc(-c3ccc(C#N)c(-n4cccc(C)c4=O)c3)o2)c1] | 3-{5-[4-Cyano-3-(3-methyl-2-oxo-2H-pyridin-1-yl)-phenyl]-oxazol-2-ylamino}-N-(2-methoxy-ethyl)-4,N-dimethyl-benzamide | (400 MHz, DMSO) δ 9.67 (s, 1H), 8.07 (d, J = 8.1 Hz, 1H), 7.95 (s, 1H), 7.84 (s, 1H), 7.80-7.72 (m, 2H), 7.63 (d, J = 5.4 Hz, 1H), 7.49 (d, J = 6.6 Hz, 1H), 7.34-7.16 (m, 1H), 7.02 (d, J = 7.5 Hz, 1H), 6.34 (t, J = 6.8 Hz, 1H), 3.68-3.38 (m, 5H), 3.15 (m, 2H), 2.96 (s, 3H), 2.33 (s, 3H), 2.08 (s, 3H). (ESI+) m/z 498 (M + H)⁺ Retention time = 3.22 min (method 1) |
| 160 | 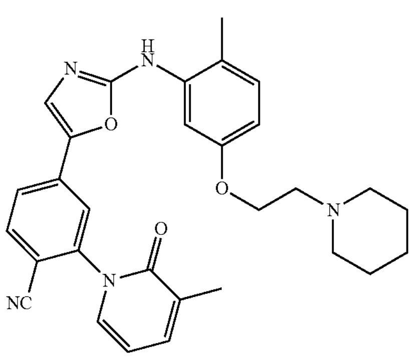 [SMILES: Cc1ccc(OCCN2CCCCC2)cc1Nc1ncc(-c2ccc(C#N)c(-n3cccc(C)c3=O)c2)o1] | 2-(3-Methyl-2-oxo-2H-pyridin-1-yl)-4-{2-[2-methyl-5-(2-piperidin-1-yl-ethoxy)-phenylamino]-oxazol-5-yl}-benzonitrile | (300 MHz, DMSO-$d_6$) δ 9.50 (s, 1H), 8.05 (d, J = 8.1 Hz, 1H), 7.83 (s, 1H), 7.76 (d, J = 9.8 Hz, 2H), 7.62 (d, J = 6.1 Hz, 1H), 7.55 (d, J = 2.3 Hz, 1H), 7.49 (d, J = 6.1 Hz, 1H), 7.08 (d, J = 8.4 Hz, 1H), 6.59 (dd, J = 8.4, 2.4 Hz, 1H), 6.34 (t, J = 6.8 Hz, 1H), 4.01 (t, J = 5.9 Hz, 2H), 2.62 (t, J = 5.9 Hz, 2H), 2.41 (s, 4H), 2.20 (s, 3H), 2.07 (s, 3H), 1.48 (d, J = 5.0 Hz, 4H), 1.37 (d, J = 4.6 Hz, 2H). (ESI+) m/z 510 (M + H)⁺ Retention time = 2.77 min (method 1) |

TABLE 2-continued

| Ex # | Chemical structure | Name | ¹H NMR |
|---|---|---|---|
| 161 | 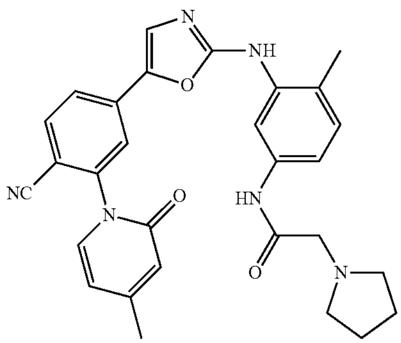 [SMILES: Cc1ccn(-c2cc(-c3cnc(Nc4cc(NC(=O)CN5CCCC5)ccc4C)o3)ccc2C#N)c(=O)c1] | N-(3-{5-[4-Cyano-3-(4-methyl-2-oxo-2H-pyridin-1-yl)-phenyl]-oxazol-2-ylamino}-4-methyl-phenyl)-2-pyrrolidin-1-yl-acetamide | (300 MHz, DMSO-$d_6$) δ 9.66 (s, 1H), 9.55 (s, 1H), 8.14 (d, J = 1.5 Hz, 1H), 8.02 (d, J = 8.2 Hz, 1H), 7.84-7.79 (m, 2H), 7.76 (dd, J = 8.3, 1.3 Hz, 1H), 7.65 (d, J = 7.0 Hz, 1H), 7.28 (dd, J = 8.1, 1.9 Hz, 1H), 7.12 (d, J = 8.3 Hz, 1H), 6.37 (s, 1H), 6.28 (dd, J = 7.1, 1.6 Hz, 1H), 3.18 (s, 2H), 2.57 (s, 4H), 2.23 (s, 6H), 1.74 (s, 4H). (ESI+) m/z 509 (M + H)⁺ Retention time = 2.50 min (method 1) |
| 162 | 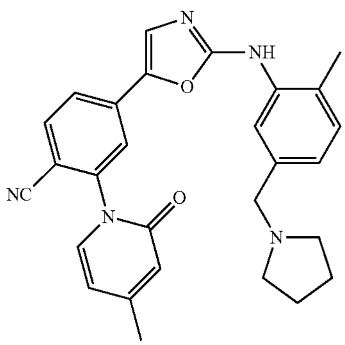 [SMILES: Cc1ccn(-c2cc(-c3cnc(Nc4cc(CN5CCCC5)ccc4C)o3)ccc2C#N)c(=O)c1] | 2-(4-Methyl-2-oxo-2H-pyridin-1-yl)-4-[2-(2-methyl-5-pyrrolidin-1-ylmethyl-phenylamino)-oxazol-5-yl]-benzonitrile | (300 MHz, DMSO-$d_6$) δ 9.53 (s, 1H), 8.02 (d, J = 8.1 Hz, 1H), 7.80 (s, 1H), 7.74-7.68 (m, 3H), 7.65 (d, J = 7.0 Hz, 1H), 7.14 (d, J = 7.6 Hz, 1H), 6.95 (d, J = 7.4 Hz, 1H), 6.38 (s, 1H), 6.28 (d, J = 7.0 Hz, 1H), 3.52 (s, 2H), 2.47-2.36 (m, 4H), 2.25 (s, 3H), 2.23 (s, 3H), 1.72-1.60 (m, 4H). (ESI+) m/z 466 (M + H)⁺ Retention time = 2.53 min (method 1) |
| 163 | 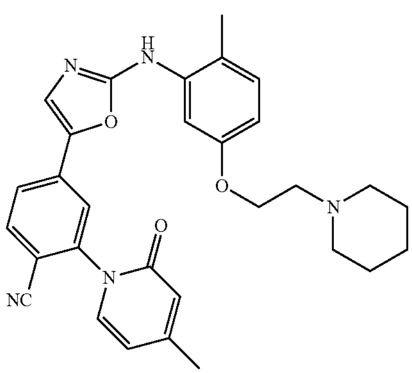 [SMILES: Cc1ccn(-c2cc(-c3cnc(Nc4cc(OCCN5CCCCC5)ccc4C)o3)ccc2C#N)c(=O)c1] | 2-(4-Methyl-2-oxo-2H-pyridin-1-yl)-4-{2-[2-methyl-5-(2-piperidin-1-yl-ethoxy)-phenylamino]-oxazol-5-yl}-benzonitrile | (300 MHz, DMSO-$d_6$) δ 9.50 (s, 1H), 8.04 (d, J = 8.5 Hz, 1H), 7.82 (s, 1H), 7.78-7.72 (m, 2H), 7.65 (d, J = 7.0 Hz, 1H), 7.55 (d, J = 2.1 Hz, 1H), 7.08 (d, J = 8.4 Hz, 1H), 6.59 (dd, J = 8.3, 2.2 Hz, 1H), 6.38 (s, 1H), 6.29 (d, J = 7.0 Hz, 1H), 4.01 (t, J = 5.8 Hz, 2H), 2.63 (t, J = 5.3 Hz, 2H), 2.42 (s, 4H), 2.23 (s, 3H), 2.21 (s, 3H), 1.54-1.44 (m, 4H), 1.39-1.31 (m, 2H). (ESI+) m/z 510 (M + H)⁺ Retention time = 2.70 min (method 1) |
| 164 | 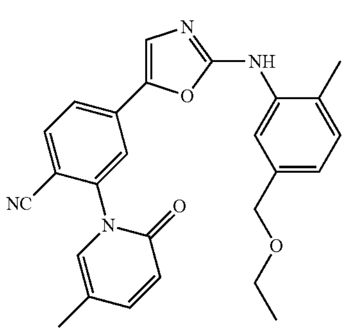 [SMILES: CCOCc1ccc(C)c(Nc2ncc(-c3ccc(C#N)c(-n4cc(C)ccc4=O)c3)o2)c1] | 4-[2-(5-(Ethoxymethyl)-2-methyl-phenylamino)-oxazol-5-yl]-2-(5-methyl-2-oxo-2H-pyridin-1-yl)-benzonitrile | (300 MHz, DMSO-$d_6$) δ 9.56 (s, 1H), 8.04 (d, J = 8.1 Hz, 1H), 7.83-7.70 (m, 4H), 7.57 (s, 1H), 7.49 (dd, J = 9.4, 2.3 Hz, 1H), 7.18 (d, J = 7.7 Hz, 1H), 6.97 (d, J = 7.8 Hz, 1H), 6.51 (d, J = 9.4 Hz, 1H), 4.41 (s, 2H), 3.46 (q, J = 7.0 Hz, 2H), 2.27 (s, 3H), 2.08 (s, 3H), 1.13 (t, J = 7.0 Hz, 3H). (ESI+) m/z 441 (M + H)⁺ Retention time = 3.83 min (method 1) |

TABLE 2-continued

| Ex # | Chemical structure | Name | $^1$H NMR |
|---|---|---|---|
| 165 | 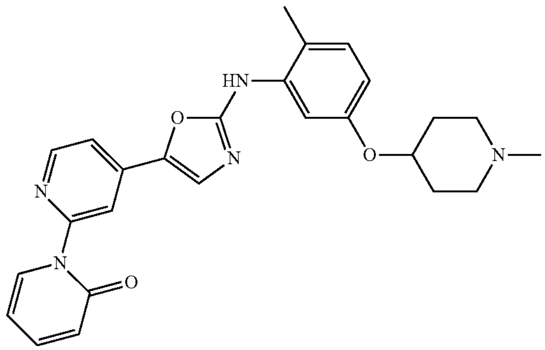 [SMILES: Cc1ccc(OC2CCN(C)CC2)cc1Nc1ncc(-c2ccnc(-n3ccccc3=O)c2)o1] | 4'-{2-[2-Methyl-5-(1-methyl-piperidin-4-yloxy)-phenylamino]-oxazol-5-yl}-[1,2']bipyridinyl-2-one | (300 MHz, DMSO-d$_6$) δ 9.58 (s, 1H), 8.57 (d, J = 5.4 Hz, 1H), 7.93-7.83 (m, 3H), 7.62-7.51 (m, 3H), 7.07 (d, J = 8.4 Hz, 1H), 6.61 (dd, J = 8.3, 2.5 Hz, 1H), 6.53 (d, J = 9.1 Hz, 1H), 6.38 (td, J = 6.9, 1.1 Hz, 1H), 4.37-4.10 (m, 1H), 2.68-2.53 (m, 2H), 2.21 (s, 3H), 2.15 (s, 3H), 2.13 (s, 2H), 1.89 (s, 2H), 1.76-1.49 (m, 2H). (ESI+) m/z 458 (M + H)$^+$ Retention time = 2.31 min (method 1) |
| 166 | 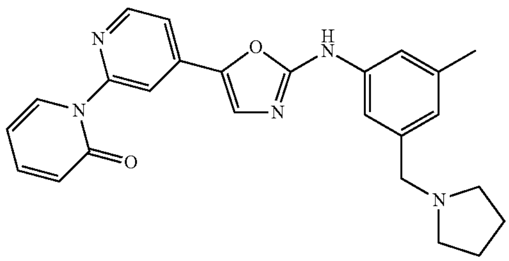 [SMILES: Cc1cc(CN2CCCC2)cc(Nc2ncc(-c3ccnc(-n4ccccc4=O)c3)o2)c1] | 4'-[2-(3-Methyl-5-pyrrolidin-1-ylmethyl-phenylamino)-oxazol-5-yl]-[1,2']bipyridinyl-2-one | (300 MHz, DMSO-d6) δ 10.51 (s, 1H), 8.58 (d, J = 5.1 Hz, 1H), 8.03-7.76 (m, 3H), 7.71-7.46 (m, 2H), 7.40 (s, 1H), 7.35 (s, 1H), 6.75 (s, 1H), 6.54 (d, J = 9.1 Hz, 1H), 6.39 (t, J = 6.6 Hz, 1H), 3.50 (s, 2H), 2.42 (s, 4H), 2.28 (s, 3H), 1.68 (s, 4H). (ESI+) m/z 428 (M + H)$^+$ Retention time = 2.27 min (method 1) |
| 167 | 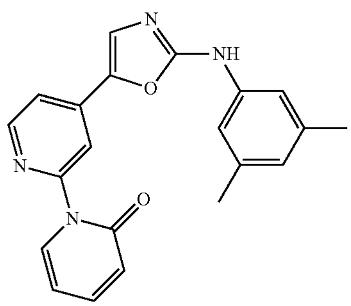 [SMILES: Cc1cc(C)cc(Nc2ncc(-c3ccnc(-n4ccccc4=O)c3)o2)c1] | 4'-[2-(3,5-Dimethyl-phenylamino)-oxazol-5-yl]-[1,2']bipyridinyl-2-one | (300 MHz, DMSO-d$_6$) δ 10.48 (s, 1H), 8.58 (d, J = 5.2 Hz, 1H), 7.91 (s, 3H), 7.71-7.42 (m, 2H), 7.27 (s, 2H), 6.64 (s, 1H), 6.54 (d, J = 9.2 Hz, 1H), 6.39 (t, J = 6.7 Hz, 1H), 2.26 (s, 6H). (ESI+) m/z 359 (M + H)$^+$ Retention time = 3.65 min (method 1) |
| 168 | 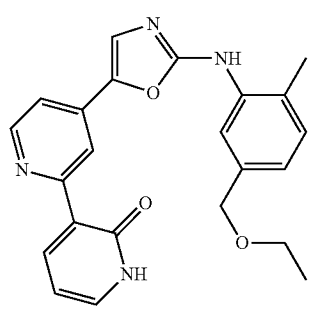 [SMILES: CCOCc1ccc(C)c(Nc2ncc(-c3ccnc(-c4ccc[nH]c4=O)c3)o2)c1] | 4-[2-(5-(Ethoxymethyl)-2-methyl-phenylamino)-oxazol-5-yl]-1'H-[2,3']bipyridinyl-2'-one | (300 MHz, DMSO-d$_6$) δ 11.91 (s, 1H), 9.61 (s, 1H), 8.73 (s, 1H), 8.58 (d, J = 5.0 Hz, 1H), 8.43 (d, J = 7.0 Hz, 1H), 7.78 (s, 1H), 7.71 (s, 1H), 7.55 (d, J = 5.0 Hz, 1H), 7.45 (d, J = 4.6 Hz, 1H), 7.18 (d, J = 7.4 Hz, 1H), 6.97 (d, J = 7.4 Hz, 1H), 6.41 (t, J = 6.6 Hz, 1H), 4.43 (s, 2H), 3.47 (q, J = 6.9 Hz, 2H), 2.29 (s, 3H), 1.14 (t, J = 6.9 Hz, 3H). (ESI+) m/z 403 (M + H)$^+$ Retention time = 2.58 min (method 1) |
| 169 | 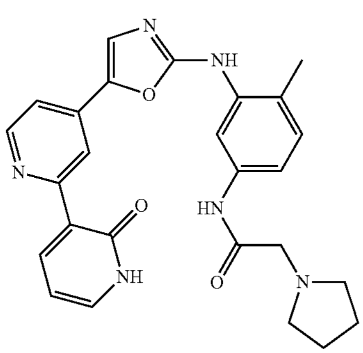 [SMILES: Cc1ccc(NC(=O)CN2CCCC2)cc1Nc1ncc(-c2ccnc(-c3ccc[nH]c3=O)c2)o1] | N-{4-Methyl-3-[5-(2'-oxo-1',2'-dihydro-[2,3']bipyridinyl-4-yl)-oxazol-2-ylamino]-phenyl}-2-pyrrolidin-1-yl-acetamide | (300 MHz, DMSO-d$_6$) δ 12.04 (s, 1H), 9.67 (s, 1H), 9.60 (s, 1H), 8.73 (s, 1H), 8.58 (d, J = 5.2 Hz, 1H), 8.43 (dd, J = 7.1, 2.0 Hz, 1H), 8.04 (d, J = 1.7 Hz, 1H), 7.70 (s, 1H), 7.55 (d, J = 4.9 Hz, 1H), 7.47 (dd, J = 5.1, 1.3 Hz, 1H), 7.37 (dd, J = 8.1, 1.7 Hz, 1H), 7.12 (d, J = 8.2 Hz, 1H), 6.41 (t, J = 6.7 Hz, 1H), 3.22 (s, 2H), 2.58 (s, 4H), 2.24 (s, 3H), 1.73 (s, 4H). (ESI+) m/z 471 (M + H)$^+$ Retention time = 1.62 min (method 1) |

TABLE 2-continued

| Ex # | Chemical structure | Name | ¹H NMR |
|---|---|---|---|
| 170 | 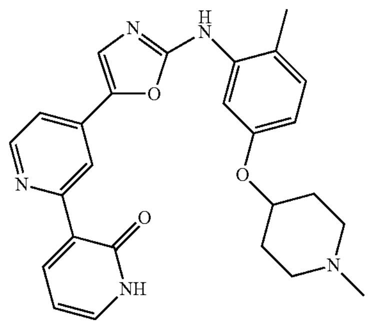 [SMILES: Cc1ccc(OC2CCN(C)CC2)cc1Nc1ncc(-c2ccnc(-c3ccc[nH]c3=O)c2)o1] | 4-{2-[2-Methyl-5-(1-methyl-piperidin-4-yloxy)-phenylamino]-oxazol-5-yl}-1'H-[2,3']bipyridinyl-2'-one | (400 MHz, DMSO-d$_6$) δ 12.04 (s, 1H), 9.57 (s, 1H), 8.69 (s, 1H), 8.59 (d, J = 5.3 Hz, 1H), 8.42 (dd, J = 7.1, 2.1 Hz, 1H), 7.71 (s, 1H), 7.61-7.49 (m, 2H), 7.46 (dd, J = 5.1, 1.7 Hz, 1H), 7.07 (d, J = 8.3 Hz, 1H), 6.60 (dd, J = 8.3, 2.5 Hz, 1H), 6.41 (t, J = 6.7 Hz, 1H), 4.39-4.16 (m, 1H), 2.67-2.53 (m, 2H), 2.24 (s, 3H), 2.14 (s, 3H), 2.14-2.01 (m, 2H), 2.00-1.81 (m, 2H), 1.75- 1.48 (m, 2H). (ESI+) m/z 458 (M + H)⁺ Retention time = 1.74 min (method 1) |
| 171 | 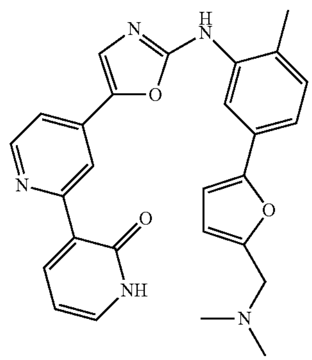 [SMILES: Cc1ccc(-c2ccc(CN(C)C)o2)cc1Nc1ncc(-c2ccnc(-c3ccc[nH]c3=O)c2)o1] | 4-{2-[5-(5-Dimethylaminomethyl-furan-2-yl)-2-methyl-phenylamino]-oxazol-5-yl}-1'H-[2,3']bipyridinyl-2'-one | (300 MHz, DMSO-d$_6$) δ 12.05 (s, 1H), 9.70 (s, 1H), 8.74 (s, 1H), 8.59 (d, J = 5.1 Hz, 1H), 8.43 (dd, J = 7.1, 2.1 Hz, 1H), 8.12 (d, J= 1.4 Hz, 1H), 7.73 (s, 1H), 7.55 (d, J = 4.5 Hz, 1H), 7.46 (dd, J = 5.1, 1.6 Hz, 1H), 7.34 (dd, J = 7.9, 1.4 Hz, 1H), 7.26 (d, J = 7.9 Hz, 1H), 6.79 (d, J = 3.2 Hz, 1H), 6.50-6.31 (m, 2H), 3.48 (s, 2H), 2.31 (s, 3H), 2.19 (s, 6H). (ESI+) m/z 468 (M + H)⁺ Retention time = 1.89 min (method 1) |
| 172 | 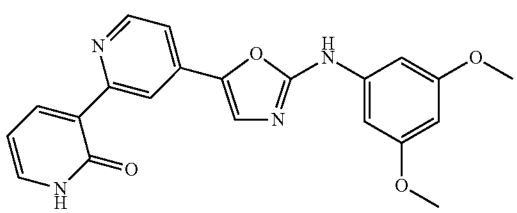 [SMILES: COc1cc(Nc2ncc(-c3ccnc(-c4ccc[nH]c4=O)c3)o2)cc(OC)c1] | 4-[2-(3,5-Dimethoxy-phenylamino)-oxazol-5-yl]-1'H-[2,3']bipyridinyl-2'-one | (300 MHz, DMSO-d$_6$) δ 12.04 (s, 1H), 10.60 (s, 1H), 8.77 (s, 1H), 8.59 (d, J = 5.2 Hz, 1H), 8.45 (d, J = 5.3 Hz, 1H), 7.77 (s, 1H), 7.53 (m, 1H), 7.47 (d, J = 5.2 Hz, 1H), 6.90 (m, 2H), 6.41 (m, 1H), 6.16 (s, 1H), 3.74 (s, 6H). (ESI+) m/z 391 (M + H)⁺ Retention time = 2.48 min (method 1) |
| 173 | 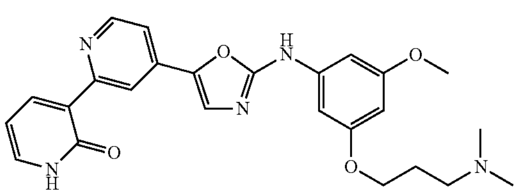 [SMILES: COc1cc(Nc2ncc(-c3ccnc(-c4ccc[nH]c4=O)c3)o2)cc(OCCCN(C)C)c1] | 4-{2-[3-(3-Dimethylamino-propoxy)-5-methoxy-phenylamino]-oxazol-5-yl}-1'H-[2,3']bipyridinyl-2'-one | (300 MHz, DMSO-d$_6$) δ 12.05 (s, 1H), 10.58 (s, 1H), 8.77 (s, 1H), 8.60 (d, J = 5.0 Hz, 1H), 8.45 (d, J = 7.0 Hz, 1H), 7.77 (s, 1H), 7.55 (d, J = 5.9 Hz, 1H), 7.47 (d, J = 5.1 Hz, 1H), 6.91 (s, 1H), 6.87 (s, 1H), 6.41 (t, J = 6.3 Hz, 1H), 6.14 (s, 1H), 3.97 (t, J = 6.1 Hz, 2H), 3.73 (s, 3H), 2.35 (t, J = 7.0 Hz, 2H), 2.15 (s, 6H), 1.90-1.78 (m, 2H). (ESI+) m/z 462 (M + H)⁺ Retention time = 1.76 min (method 1) |
| 174 | 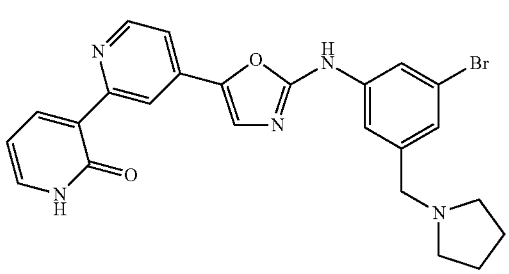 [SMILES: O=c1[nH]cccc1-c1cc(-c2cnc(Nc3cc(Br)cc(CN4CCCC4)c3)o2)ccn1] | 4-[2-(3-Bromo-5-pyrrolidin-1-ylmethyl-phenylamino)-oxazol-5-yl]-1'H-[2,3']bipyridinyl-2'-one | (300 MHz, DMSO-d$_6$) δ 12.04 (s, 1H), 10.85 (s, 1H), 8.79 (s, 1H), 8.61 (d, J = 5.0 Hz, 1H), 8.46 (d, J = 6.9 Hz, 1H), 7.89 (s, 1H), 7.80 (s, 1H), 7.61-7.43 (m, 3H), 7.10 (s, 1H), 6.42 (t, J = 6.5 Hz, 1H), 3.55 (s, 2H), 2.45 (s, 4H), 1.71 (s, 4H). (ESI+) m/z 492 (M + H)⁺ Retention time = 1.85 min (method 1) |

TABLE 2-continued

| Ex # | Chemical structure | Name | ¹H NMR |
|---|---|---|---|
| 175 | 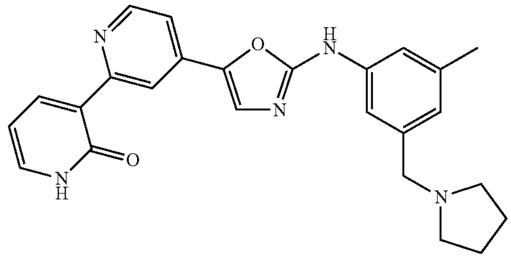 [SMILES: Cc1cc(CN2CCCC2)cc(Nc2ncc(-c3ccnc(-c4ccc[nH]c4=O)c3)o2)c1] | 4-[2-(3-Methyl-5-pyrrolidin-1-ylmethyl-phenylamino)-oxazol-5-yl]-1'H-[2,3']bipyridinyl-2'-one | (300 MHz, DMSO-$d_6$) δ 12.03 (s, 1H), 10.51 (s, 1H), 8.77 (s, 1H), 8.59 (d, J = 5.2 Hz, 1H), 8.45 (d, J = 5.7 Hz, 1H), 7.76 (s, 1H), 7.55 (d, J = 4.5 Hz, 1H), 7.47 (d, J = 5.3 Hz, 1H), 7.41 (s, 1H), 7.38 (s, 1H), 6.75 (s, 1H), 6.41 (t, J = 6.6 Hz, 1H), 3.51 (s, 2H), 2.43 (s, 4H), 2.29 (s, 3H), 1.69 (s, 4H). (ESI+) m/z 428 (M + H)⁺ Retention time = 1.70 min (method 1) |
| 176 | 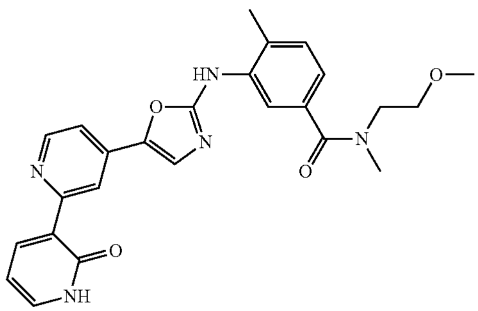 [SMILES: COCCN(C)C(=O)c1ccc(C)c(Nc2ncc(-c3ccnc(-c4ccc[nH]c4=O)c3)o2)c1] | N-(2-Methoxy-ethyl)-4,N-dimethyl-3-[5-(2'-oxo-1',2'-dihydro-[2,3']bipyridinyl-4-yl)-oxazol-2-ylamino]-benzamide | (300 MHz, DMSO-$d_6$) δ 12.01 (s, 1H), 9.73 (s, 1H), 8.74 (s, 1H), 8.59 (d, J = 5.3 Hz, 1H), 8.43 (d, J = 7.1 Hz, 1H), 7.95 (s, 1H), 7.73 (s, 1H), 7.55 (d, J = 4.8 Hz, 1H), 7.47 (d, J = 5.0 Hz, 1H), 7.26 (d, J = 7.6 Hz, 1H), 7.01 (d, J = 7.8 Hz, 1H), 6.41 (t, J = 6.3 Hz, 1H), 3.72-3.08 (m, 7H), 2.97 (s, 3H), 2.34 (s, 3H). (ESI+) m/z 460 (M + H)⁺ Retention time = 2.14 min (method 1) |
| 177 | 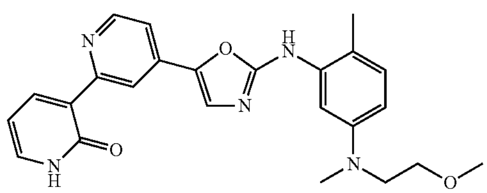 [SMILES: COCCN(C)c1ccc(C)c(Nc2ncc(-c3ccnc(-c4ccc[nH]c4=O)c3)o2)c1] | 4-(2-{5-[(2-Methoxy-ethyl)-methyl-amino]-2-methyl-phenylamino}-oxazol-5-yl)-1'H-[2,3']bipyridinyl-2'-one | (300 MHz, DMSO-$d_6$) δ 12.01 (s, 1H), 9.73 (s, 1H), 8.74 (s, 1H), 8.59 (d, J = 5.3 Hz, 1H), 8.43 (d, J = 7.1 Hz, 1H), 7.95 (s, 1H), 7.73 (s, 1H), 7.55 (d, J = 4.8 Hz, 1H), 7.47 (d, J = 5.0 Hz, 1H), 7.26 (d, J = 7.6 Hz, 1H), 7.01 (d, J = 7.8 Hz, 1H), 6.41 (t, J = 6.3 Hz, 1H), 3.64-3.08 (m, 7H), 2.97 (s, 3H), 2.34 (s, 3H). (ESI+) m/z 432 (M + H)⁺ Retention time = 2.01 min (method 1) |
| 178 | 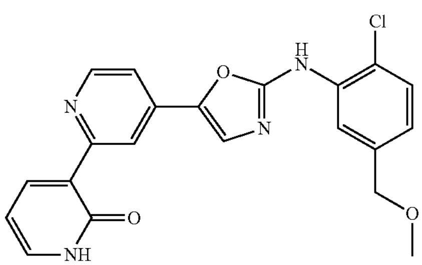 [SMILES: COCc1ccc(Cl)c(Nc2ncc(-c3ccnc(-c4ccc[nH]c4=O)c3)o2)c1] | 4-[2-(2-Chloro-5-(methoxymethyl)-phenylamino)-oxazol-5-yl]-1'H-[2,3']bipyridinyl-2'-one | (400 MHz, DMSO-$d_6$) δ 12.01 (s, 1H), 9.93 (s, 1H), 8.75 (s, 1H), 8.60 (d, J = 5.2 Hz, 1H), 8.43 (dd, J = 7.1, 2.0 Hz, 1H), 8.06 (s, 1H), 7.74 (s, 1H), 7.54 (d, J = 5.3 Hz, 1H), 7.47 (d, J = 7.4 Hz, 2H), 7.06 (d, J = 8.2 Hz, 1H), 6.41 (t, J = 6.7 Hz, 1H), 4.43 (s, 2H), 3.31 (s, 3H). (ESI+) m/z 409 (M + H)⁺ Retention time = 2.53 min (method 1) |
| 179 | 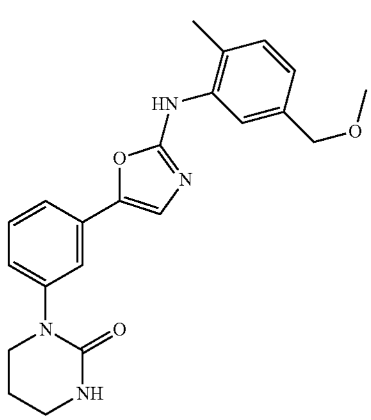 [SMILES: COCc1ccc(C)c(Nc2ncc(-c3cccc(N4CCCNC4=O)c3)o2)c1] | 1-{3-[2-((5-Methoxymethyl)-2-methyl-phenylamino)-oxazol-5-yl]-phenyl}-tetrahydro-pyrimidin-2-one | (300 MHz, DMSO-$d_6$) δ 9.32 (s, 1H), 7.88 (br s, 1H), 7.52 (br s, 1H), 7.43 (s, 1H), 7.35 (d, J = 4.2 Hz, 1H), 7.34 (s, 1H), 7.18 (s, 1H), 7.16 (s, 1H), 6.93 (dd, J = 7.9, 1.4 Hz, 1H), 6.64 (br s, 1H), 4.37 (s, 2H), 3.69-3.61 (m, 2H), 3.28 (s, 3H), 3.24 (t, J = 5.7 Hz, 2H), 2.28 (s, 3H), 1.96 (quint, J = 5.7 Hz, 2H). (ESI+) m/z 393 (M + H)⁺ Retention time = 3.15 min (method 1) |

TABLE 2-continued

| Ex # | Chemical structure | Name | $^1$H NMR |
|---|---|---|---|
| 180 | 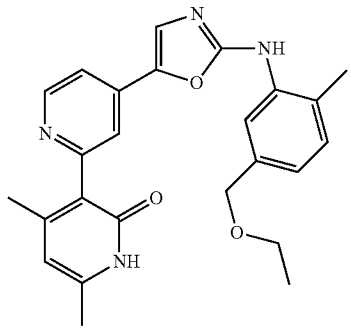 | 4',6'-Dimethyl-4-{2-[2-methyl-5-(ethoxymethyl)-phenylamino]-oxazol-5-yl}-1'H-[2,3']bipyridinyl-2'-one | (400 MHz, DMSO-d$_6$) δ 11.53 (s, 1H), 9.39 (s, 1H), 8.57 (d, J = 5.3 Hz, 1H), 7.76 (s, 1H), 7.70 (s, 1H), 7.52 (s, 1H), 7.39 (dd, J = 5.3, 1.7 Hz, 1H), 7.18 (d, J = 7.6 Hz, 1H), 6.98 (d, J = 6.3 Hz, 1H), 5.98 (s, 1H), 4.42 (s, 2H), 3.49 (q, J = 7.0 Hz, 2H), 2.29 (s, 3H), 2.20 (s, 3H), 2.01 (s, 3H), 1.14 (t, J = 7.0 Hz, 3H). (ESI+) m/z 431 (M + H)$^+$ Retention time = 2.64 min (method 1) |
| 181 | 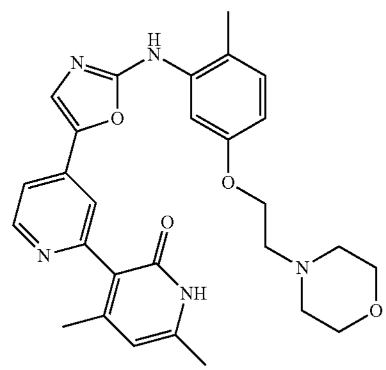 [SMILES: Cc1cc(C)c(-c2cc(-c3cnc(Nc4cc(OCCN5CCOCC5)ccc4C)o3)ccn2)c(=O)[nH]1] | 4',6'-Dimethyl-4-{2-[2-methyl-5-(2-morpholin-4-yl-ethoxy)-phenylamino]-oxazol-5-yl}-1'H-[2,3']bipyridinyl-2'-one | (400 MHz, DMSO-d$_6$) δ $^1$H NMR (400 MHz, DMSO) δ 11.68 (s, 1H), 9.48 (s, 1H), 8.58 (d, J = 5.2 Hz, 1H), 7.77 (s, 1H), 7.59 (d, J = 2.2 Hz, 1H), 7.54 (s, 1H), 7.42 (dd, J = 5.2, 1.4 Hz, 1H), 7.08 (d, J = 8.4 Hz, 1H), 6.59 (dd, J = 8.3, 2.3 Hz, 1H), 6.00 (s, 1H), 4.04 (t, J = 5.6 Hz, 2H), 3.57 (t, J = 4.3 Hz, 4H), 2.67 (t, J = 5.5 Hz, 2H), 2.48-2.43 (m, 4H), 2.20 (d, J = 10.5 Hz, 6H), 1.99 (s, 3H). (ESI+) m/z 502 (M + H)$^+$ Retention time = 1.75 min (method 1) |
| 182 | 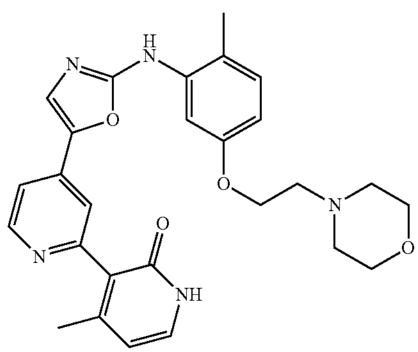 [SMILES: Cc1ccc(OCCN2CCOCC2)cc1Nc1ncc(-c2ccnc(-c3c(C)cc[nH]c3=O)c2)o1] | 4'-Methyl-4-{2-[2-methyl-5-(2-morpholin-4-yl-ethoxy)-phenylamino]-oxazol-5-yl}-1'H-[2,3']bipyridinyl-2'-one | (300 MHz, DMSO-d$_6$) δ 11.67 (s, 1H), 9.46 (s, 1H), 8.59 (d, J = 5.4 Hz, 1H), 7.78 (s, 1H), 7.59 (s, 1H), 7.55 (s, 1H), 7.43 (d, J = 5.1 Hz, 1H), 7.34 (d, J = 6.8 Hz, 1H), 7.08 (d, J = 8.3 Hz, 1H), 6.59 (d, J = 6.4 Hz, 1H), 6.18 (d, J = 6.7 Hz, 1H), 4.04 (t, J = 5.6 Hz, 2H), 3.64-3.50 (m, 4H), 2.67 (t, J = 5.6 Hz, 2H), 2.46 (s, 4H), 2.21 (s, 3H), 2.03 (s, 3H). (ESI+) m/z 488 (M + H)$^+$ Retention time = 1.65 min (method 1) |
| 183 | 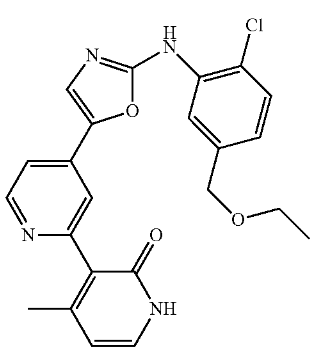 [SMILES: CCOCc1ccc(Cl)c(Nc2ncc(-c3ccnc(-c4c(C)cc[nH]c4=O)c3)o2)c1] | 4-[2-(2-Chloro-5-ethoxymethyl-phenylamino)-oxazol-5-yl]-4'-methyl-1'H-[2,3']bipyridinyl-2'-one | (400 MHz, DMSO-d$_6$) δ $^1$H NMR (400 MHz, DMSO) δ 11.69 (s, 1H), 9.84 (s, 1H), 8.61 (d, J = 5.2 Hz, 1H), 8.09 (d, J = 1.5 Hz, 1H), 7.82 (s, 1H), 7.56 (s, 1H), 7.50-7.43 (m, 2H), 7.35 (d, J = 6.6 Hz, 1H), 7.06 (dd, J = 8.2, 1.8 Hz, 1H), 6.19 (d, J = 6.7 Hz, 1H), 4.46 (s, 2H), 3.49 (q, J = 7.0 Hz, 2H), 2.03 (s, 3H), 1.15 (dd, J = 8.4, 5.5 Hz, 3H). (ESI+) m/z 437 (M + H)$^+$ Retention time = 2.73 min (method 1) |

TABLE 2-continued

| Ex # | Chemical structure | Name | $^1$H NMR |
|---|---|---|---|
| 184 | 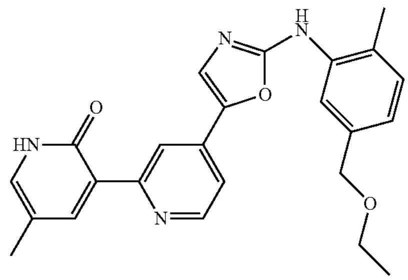 [SMILES: CCOCc1ccc(C)c(Nc2ncc(-c3ccnc(-c4cc(C)c[nH]c4=O)c3)o2)c1] | 4-[2-(5-Ethoxymethyl-2-methyl-phenylamino)-oxazol-5-yl]-5'-methyl-1'H-[2,3']bipyridinyl-2'-one | (400 MHz, DMSO-d$_6$) δ 11.82 (s, 1H), 9.61 (s, 1H), 8.76 (s, 1H), 8.58 (d, J = 5.2 Hz, 1H), 8.32 (d, J = 2.6 Hz, 1H), 7.79 (s, 1H), 7.70 (s, 1H), 7.45 (dd, J = 5.2, 1.6 Hz, 1H), 7.35 (s, 1H), 7.18 (d, J = 7.7 Hz, 1H), 6.98 (d, J = 7.7 Hz, 1H), 4.43 (s, 2H), 3.48 (q, J = 7.0 Hz, 2H), 2.29 (s, 3H), 2.13 (s, 3H), 1.14 (t, J = 7.0 Hz, 3H). (ESI+) m/z 417 (M + H)$^+$ Retention time = 2.16 min (method 1) |
| 185 | 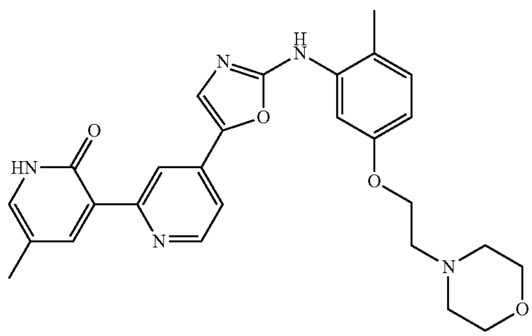 [SMILES: Cc1c[nH]c(=O)c(-c2cc(-c3cnc(Nc4cc(OCCN5CCOCC5)ccc4C)o3)ccn2)c1] | 5'-Methyl-4-{2-[2-methyl-5-(2-morpholin-4-yl-ethoxy)-phenylamino]-oxazol-5-yl}-1'H-[2,3']bipyridinyl-2'-one | (400 MHz, DMSO-d$_6$) δ 11.84 (s, 1H), 9.55 (s, 1H), 8.76 (s, 1H), 8.58 (d, J = 5.2 Hz, 1H), 8.31 (d, J = 2.7 Hz, 1H), 7.71 (s, 1H), 7.55 (d, J = 2.4 Hz, 1H), 7.45 (dd, J = 5.2, 1.5 Hz, 1H), 7.34 (s, 1H), 7.08 (d, J = 8.4 Hz, 1H), 6.60 (dd, J = 8.3, 2.4 Hz, 1H), 4.05 (t, J = 5.7 Hz, 2H), 3.58-3.54 (m, 4H), 2.68 (t, J = 5.7 Hz, 2H), 2.49-2.40 (m, 4H), 2.23 (s, 3H), 2.12 (s, 3H). (ESI+) m/z 488 (M + H)$^+$ Retention time = 1.78 min (method 1) |
| 186 | 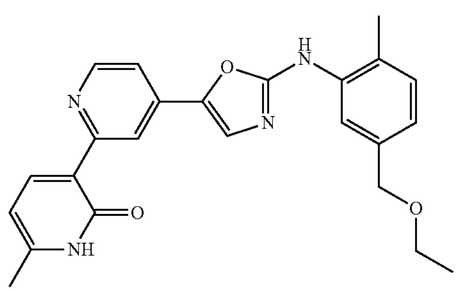 [SMILES: CCOCc1ccc(C)c(Nc2ncc(-c3ccnc(-c4ccc(C)[nH]c4=O)c3)o2)c1] | 4-[2-((5-Ethoxymethyl)-2-methyl-phenylamino)-oxazol-5-yl]-6'-methyl-1'H-[2,3']bipyridinyl-2'-one | (400 MHz, DMSO) δ 11.95 (s, 1H), 9.60 (s, 1H), 8.73 (s, 1H), 8.55 (d, J = 5.1 Hz, 1H), 8.36 (d, J = 7.3 Hz, 1H), 7.77 (s, 1H), 7.68 (s, 1H), 7.41 (d, J = 5.1 Hz, 1H), 7.18 (d, J = 7.6 Hz, 1H), 6.97 (d, J = 7.6 Hz, 1H), 6.22 (d, J = 7.2 Hz, 1H), 4.42 (s, 2H), 3.47 (q, J = 7.0 Hz, 2H), 2.29 (s, 2H), 2.27 (s, 3H), 1.13 (t, J = 6.9 Hz, 3H). (ESI+) m/z 417 (M + H)$^+$ Retention time = 2.71 min (method 1) |
| 187 | 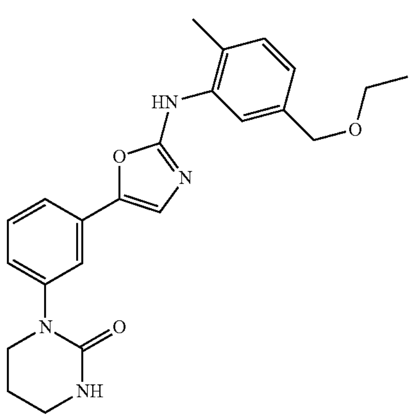 [SMILES: CCOCc1ccc(C)c(Nc2ncc(-c3cccc(N4CCCNC4=O)c3)o2)c1] | 1-{3-[2-((5-Ethoxymethyl)-2-methyl-phenylamino)-oxazol-5-yl]-phenyl}-tetrahydro-pyrimidin-2-one | (300 MHz, DMSO-d$_6$) δ 9.26 (s, 1H), 7.86 (s, 1H), 7.53 (s, 1H), 7.47-7.25 (m, 3H), 7.17 (s, 1H), 7.15 (s, 1H), 6.93 (d, J = 7.2 Hz, 1H), 6.65 (s, 1H), 4.41 (s, 2H), 3.65 (t, J = 6.5 Hz, 2H), 3.47 (q, J = 6.9 Hz, 2H), 3.24 (br t, J = 6.3 Hz, 2H), 2.28 (s, 3H), 2.04-1.84 (m, 2H), 1.15 (t, J = 7.0 Hz, 3H). (ESI+) m/z 407 (M + H)$^+$ Retention time = 3.41 min (method 1) |

TABLE 2-continued

| Ex # | Chemical structure | Name | ¹H NMR |
|---|---|---|---|
| 188 | 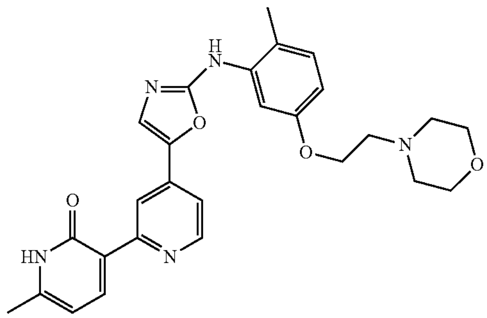 [SMILES: Cc1ccc(-c2cc(-c3cnc(Nc4cc(OCCN5CCOCC5)ccc4C)o3)ccn2)c(=O)[nH]1] | 6'-Methyl-4-{2-[2-methyl-5-(2-morpholin-4-yl-ethoxy)-phenylamino]-oxazol-5-yl}-1'H-[2,3']bipyridinyl-2'-one | (400 MHz, DMSO-$d_6$) δ 11.98 (s, 1H), 9.57 (s, 1H), 8.74 (s, 1H), 8.55 (d, J = 5.2 Hz, 1H), 8.36 (d, J = 7.3 Hz, 1H), 7.70 (s, 1H), 7.55 (s, 1H), 7.42 (dd, J = 5.1, 1.6 Hz, 1H), 7.08 (d, J = 8.3 Hz, 1H), 6.60 (d, J = 8.3 Hz, 1H), 6.22 (d, J = 7.3 Hz, 1H), 4.05 (t, J = 5.6 Hz, 2H), 3.60-3.51 (m, 4H), 2.67 (t, J = 5.7 Hz, 2H), 2.45 (s, 4H), 2.27 (s, 3H), 2.23 (s, 3H). (ESI+) m/z 488 (M + H)⁺ Retention time = 1.74 min (method 1) |
| 189 | 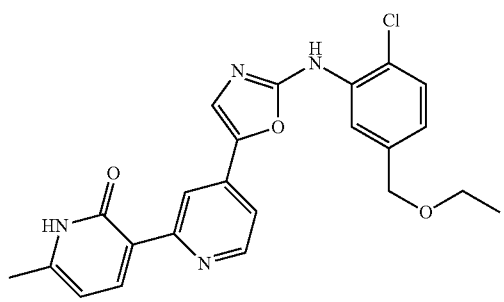 [SMILES: CCOCc1ccc(Cl)c(Nc2ncc(-c3ccnc(-c4ccc(C)[nH]c4=O)c3)o2)c1] | 4-[2-(2-Chloro-(5-ethoxymethyl)-phenylamino)-oxazol-5-yl]-6'-methyl-1'H-[2,3']bipyridinyl-2'-one | (400 MHz, DMSO-$d_6$) δ ¹H NMR (400 MHz, DMSO) δ 11.95 (s, 1H), 9.90 (s, 1H), 8.75 (s, 1H), 8.57 (d, J = 5.2 Hz, 1H), 8.36 (d, J = 7.3 Hz, 1H), 8.04 (s, 1H), 7.72 (s, 1H), 7.53-7.38 (m, 2H), 7.07 (dd, J = 8.1, 1.7 Hz, 1H), 6.22 (d, J = 7.2 Hz, 1H), 4.47 (s, 2H), 3.50 (q, J = 7.0 Hz, 2H), 2.27 (s, 3H), 1.15 (t, J = 7.0 Hz, 3H). (ESI+) m/z 437 (M + H)⁺ Retention time = 2.89 min (method 1) |
| 190 | 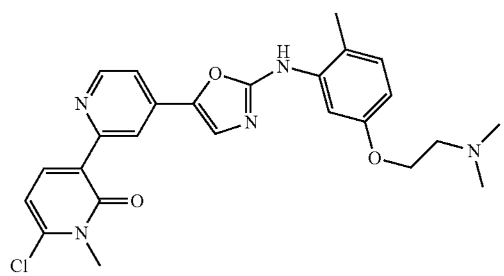 [SMILES: Cc1ccc(OCCN(C)C)cc1Nc1ncc(-c2ccnc(-c3ccc(Cl)n(C)c3=O)c2)o1] | 6'-Chloro-4-{2-[5-(2-dimethylamino-ethoxy)-2-methyl-phenylamino]-oxazol-5-yl}-1'-methyl-1'H-[2,3']bipyridinyl-2'-one | (300 MHz, DMSO-$d_6$) δ 9.59 (s, 1H), 8.65 (s, 1H), 8.60 (d, J = 5.2 Hz, 1H), 8.37 (d, J = 8.0 Hz, 1H), 7.75 (s, 1H), 7.57 (br s, 1H), 7.49 (d, J = 4.5 Hz, 1H), 7.09 (d, J = 8.2 Hz, 1H), 6.73 (d, J = 7.9 Hz, 1H), 6.60 (br d, J = 6.3 Hz, 1H), 4.01 (t, J = 5.6 Hz, 2H), 3.71 (s, 3H), 2.62 (t, J = 5.4 Hz, 2H), 2.23 (s, 3H), 2.21 (s, 6H). (ESI+) m/z 480 (M + H)⁺ Retention time = 1.94 min (method 1) |
| 191 | 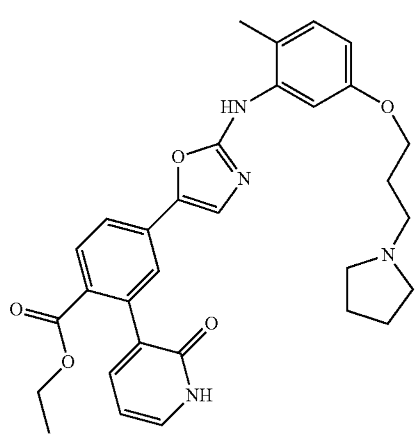 [SMILES: CCOC(=O)c1ccc(-c2cnc(Nc3cc(OCCCN4CCCC4)ccc3C)o2)cc1-c1ccc[nH]c1=O] | 4-{2-[2-Methyl-5-(2-pyrrolidin-1-yl-propyloxy)-phenylamino]-oxazol-5-yl}-2-(2-oxo-1,2-dihydro-pyridin-3-yl)-benzoic acid ethyl ester | (300 MHz, DMSO-$d_6$) δ 11.72 (s, 1H), 9.35 (s, 1H), 7.81 (dd, J = 8.1, 3.6 Hz, 1H), 7.70-7.57 (m, 3H), 7.52 (brs, 1H), 7.50 (brs, 1H), 7.40 (d, J = 4.3 Hz, 1H), 7.07 (d, J = 8.1 Hz, 1H), 6.55 (d, J = 8.1 Hz, 1H), 6.29 (t, J = 6.7 Hz, 1H), 4.07 (q, J = 7.3 Hz, 2H), 3.97 (t, J = 6.2 Hz, 2H), 3.54-3.34 (m, 2H), 2.43 (s, 4H), 2.22 (s, 3H), 1.94-1.79 (m, 2H), 1.67 (s, 4H), 1.09 (t, J = 7.3 Hz, 3H). (ESI+) m/z 543 (M + H)⁺ Retention time = 2.82 min (method 1) |

TABLE 2-continued

| Ex # | Chemical structure | Name | ¹H NMR |
|---|---|---|---|
| 192 | 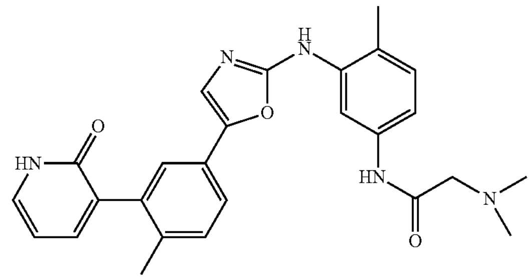 [SMILES: Cc1ccc(NC(=O)CN(C)C)cc1Nc1ncc(-c2ccc(C)c(-c3ccc[nH]c3=O)c2)o1] | 2-Dimethylamino-N-(3-{5-[4-methyl-3-(2-oxo-1,2-dihydro-pyridin-3-yl)-phenyl]-oxazol-2-ylamino}-phenyl)-acetamide | (300 MHz, DMSO-$d_6$) δ 11.78 (s, 1H), 9.63 (s, 1H), 9.16 (s, 1H), 8.11 (s, 1H), 7.54-7.17 (m, 7H), 7.09 (d, J = 8.5 Hz, 1H), 6.28 (t, J = 6.6 Hz, 1H), 3.04 (s, 2H), 2.27 (s, 6H), 2.23 (s, 3H), 2.16 (s, 3H).<br>(ESI+) m/z 458 (M + H)⁺<br>Retention time = 2.42 min (method 1) |
| 193 | 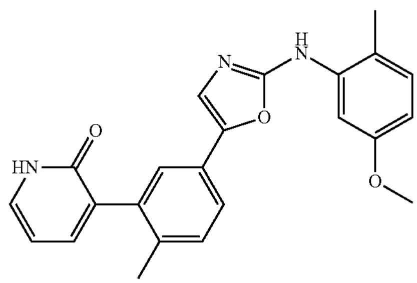 [SMILES: COc1ccc(C)c(Nc2ncc(-c3ccc(C)c(-c4ccc[nH]c4=O)c3)o2)c1] | 3-{5-[2-(5-Methoxy-2-methyl-phenylamino)-oxazol-5-yl]-2-methyl-phenyl}-1H-pyridin-2-one | (300 MHz, DMSO-d6) δ 11.79 (s, 1H), 9.16 (s, 1H), 7.66 (d, J = 2.5 Hz, 1H), 7.51-7.36 (m, 5H), 7.28 (d, J = 7.9 Hz, 1H), 7.07 (d, J = 8.6 Hz, 1H), 6.53 (dd, J = 8.4, 2.6 Hz, 1H), 6.29 (t, J = 6.5 Hz, 1H), 3.72 (s, 3H), 2.21 (s, 3H), 2.16 (s, 3H).<br>(ESI+) m/z 388 (M + H)⁺<br>Retention time = 3.50 min (method 1) |
| 194 | 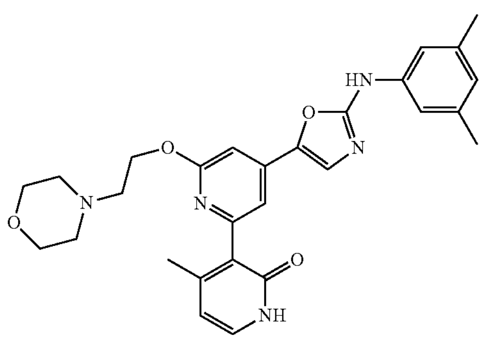 [SMILES: Cc1cc(C)cc(Nc2ncc(-c3cc(OCCN4CCOCC4)nc(-c4c(C)cc[nH]c4=O)c3)o2)c1] | 4-[2-(3,5-Dimethyl-phenylamino)-oxazol-5-yl]-4'-methyl-6-(2-morpholin-4-yl-ethoxy)-1'H-[2,3']bipyridinyl-2'-one | (400 MHz, DMSO-$d_6$) δ 11.64 (s, 1H), 10.29 (s, 1H), 7.77 (s, 1H), 7.33 (d, J = 6.7 Hz, 1H), 7.26 (s, 2H), 7.23 (d, J = 1.1 Hz, 1H), 6.83 (d, J = 1.2 Hz, 1H), 6.63 (s, 1H), 6.17 (d, J = 6.7 Hz, 1H), 4.36 (t, J = 5.8 Hz, 2H), 3.65-3.47 (m, 4H), 2.69 (t, J = 5.8 Hz, 2H), 2.49-2.39 (m, 4H), 2.25 (s, 6H), 2.09 (s, 3H).<br>(ESI+) m/z 502 (M + H)⁺<br>Retention time = 2.94 min (method 1) |
| 195 | 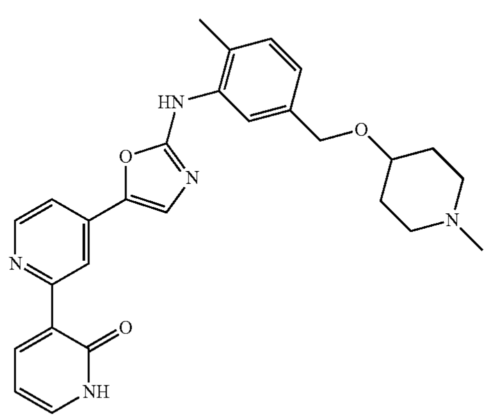 [SMILES: Cc1ccc(COC2CCN(C)CC2)cc1Nc1ncc(-c2ccnc(-c3ccc[nH]c3=O)c2)o1] | 4-{2-[2-Methyl-5-(1-methyl-piperidin-4-yloxymethyl)-phenylamino]-oxazol-5-yl}-1'H-[2,3']bipyridinyl-2'-one | (300 MHz, DMSO-$d_6$) δ 12.03 (s, 1H), 9.60 (s, 1H), 8.73 (s, 1H), 8.58 (d, J = 5.1 Hz, 1H), 8.43 (d, J = 7.3 Hz, 1H), 7.78 (s, 1H), 7.69 (s, 1H), 7.55 (br d, J = 5.3 Hz, 1H), 7.45 (d, J = 4.6 Hz, 1H), 7.18 (d, J = 7.5 Hz, 1H), 6.98 (d, J = 7.3 Hz, 1H), 6.41 (t, J = 6.4 Hz, 1H), 4.47 (s, 2H), 2.69-2.58 (m, 2H), 2.29 (s, 3H), 2.16 (s, 3H), 2.11-1.96 (m, 2H), 1.92-1.76 (m, 2H), 1.60-1.41 (m, 2H).<br>(ESI+) m/z 472 (M + H)⁺<br>Retention time = 1.76 min (method 1) |

TABLE 2-continued

| Ex # | Chemical structure | Name | $^1$H NMR |
|---|---|---|---|
| 196 | 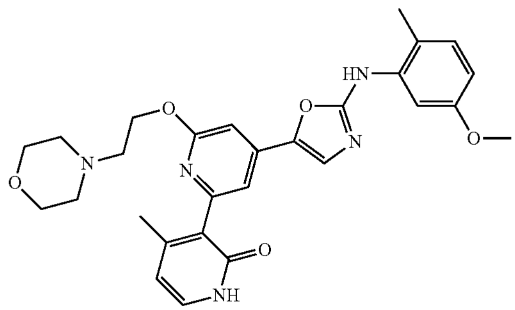 [SMILES: COc1ccc(C)c(Nc2ncc(-c3cc(OCCN4CCOCC4)nc(-c4c(C)cc[nH]c4=O)c3)o2)c1] | 4-[2-(5-Methoxy-2-methyl-phenylamino)-oxazol-5-yl]-4'-methyl-6-(2-morpholin-4-yl-ethoxy)-1'H-[2,3']bipyridinyl-2'-one | (400 MHz, DMSO-d$_6$) δ 11.63 (s, 1H), 9.40 (s, 1H), 7.75 (s, 1H), 7.57 (d, J = 2.5 Hz, 1H), 7.33 (d, J = 6.7 Hz, 1H), 7.21 (d, J = 0.9 Hz, 1H), 7.10 (d, J = 8.4 Hz, 1H), 6.84 (d, J = 0.8 Hz, 1H), 6.59 (dd, J = 8.3, 2.6 Hz, 1H), 6.17 (d, J = 6.7 Hz, 1H), 4.35 (t, J = 5.8 Hz, 2H), 3.73 (s, 3H), 3.63-3.48 (m, 4H), 2.69 (t, J = 5.8 Hz, 2H), 2.49-2.43 (m, 4H), 2.22 (s, 3H), 2.07 (s, 3H). (ESI+) m/z 518 (M + H)$^+$ Retention time = 2.64 min (method 1) |
| 197 | 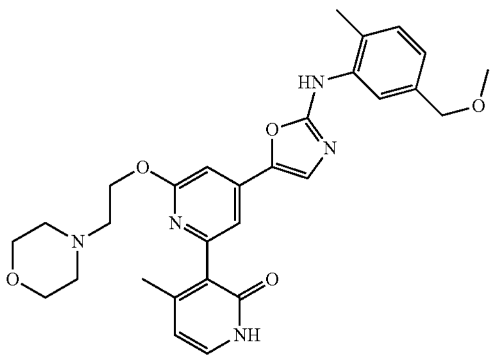 [SMILES: COCc1ccc(C)c(Nc2ncc(-c3cc(OCCN4CCOCC4)nc(-c4c(C)cc[nH]c4=O)c3)o2)c1] | 4-[2-((5-Methoxymethyl)-2-methyl-phenylamino)-oxazol-5-yl]-4'-methyl-6-(2-morpholin-4-yl-ethoxy)-1'H-[2,3']bipyridinyl-2'-one | (400 MHz, DMSO-d$_6$) δ 11.62 (s, 1H), 9.44 (s, 1H), 7.82 (s, 1H), 7.74 (s, 1H), 7.33 (d, J = 6.7 Hz, 1H), 7.19 (s, 1H), 7.19-7.15 (m, 1H), 6.95 (d, J = 7.5 Hz, 1H), 6.83 (s, 1H), 6.17 (d, J = 6.7 Hz, 1H), 4.41-4.28 (m, 4H), 3.61-3.52 (m, 4H), 3.27 (s, 3H), 2.68 (t, J = 5.7 Hz, 2H), 2.48-2.42 (m, 4H), 2.28 (s, 3H), 2.07 (s, 3H). (ESI+) m/z 532 (M + H)$^+$ Retention time = 2.656 min (method 1) |
| 198 | 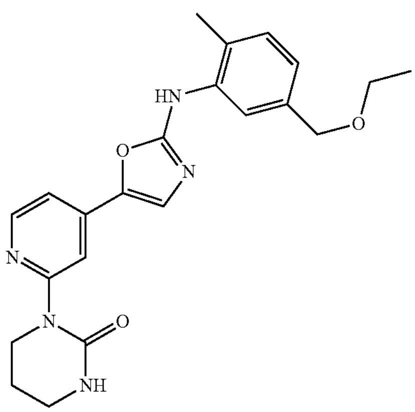 [SMILES: CCOCc1ccc(C)c(Nc2ncc(-c3ccnc(N4CCCNC4=O)c3)o2)c1] | 1-{4-[2-((5-Ethoxymethyl)-2-methyl-phenylamino)-oxazol-5-yl]-pyridin-2-yl}-tetrahydro-pyrimidin-2-one | (300 MHz, DMSO) δ 9.54 (s, 1H), 8.28 (d, J = 5.2 Hz, 1H), 7.99 (s, 1H), 7.79 (s, 1H), 7.66 (s, 1H), 7.24-7.10 (m, 2H), 7.00-6.86 (m, 2H), 4.41 (s, 2H), 3.92-3.80 (m, 2H), 3.47 (q, J = 6.9 Hz, 2H), 3.26-3.19 (m, 2H), 2.27 (s, 3H), 2.03-1.80 (m, 2H), 1.14 (t, J = 7.0 Hz, 3H). (ESI+) m/z 408 (M + H)$^+$ Retention time = 2.78 min (method 1) |
| 199 | 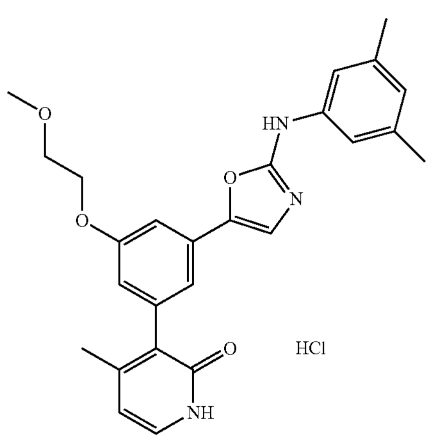 | 3-[3-[2-(3,5-Dimethyl-phenylamino)-oxazol-5-yl]-5-(2-methoxy-ethoxy)-phenyl]-4-methyl-1H-pyridin-2-one hydrochloride | 1H NMR (400 MHz, DMSO) δ 11.57 (br s, 1H), 10.21 (s, 1H), 7.52 (s, 1H), 7.29 (d, J = 6.8 Hz, 1H), 7.25 (s, 2H), 7.09 (s, 1H), 7.02 (s, 1H), 6.67 (s, 1H), 6.61 (s, 1H), 6.17 (d, J = 6.7 Hz, 1H), 4.41 (br s, 1H), 4.19-4.11 (m, 2H), 3.74-3.63 (m, 2H), 3.33 (s, 3H), 2.25 (s, 6H), 2.03 (s, 3H) (ESI+) m/z 446 (M + H)$^+$ Retention time = 3.95 min (method 1) |

TABLE 2-continued

| Ex # | Chemical structure | Name | ¹H NMR |
|---|---|---|---|
| 200 | 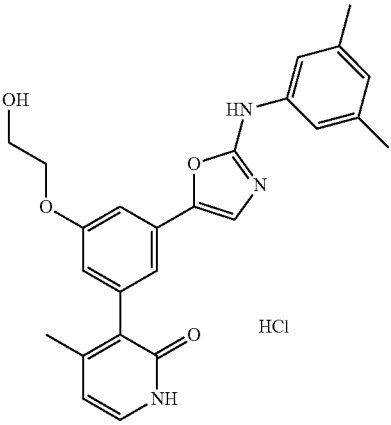 [SMILES: Cc1cc(C)cc(Nc2ncc(-c3cc(OCCO)cc(-c4c(C)cc[nH]c4=O)c3)o2)c1 ; Cl] | 3-[3-[2-(3,5-Dimethyl-phenylamino)-oxazol-5-yl]-5-(2-hydroxy-ethoxy)-phenyl]-4-methyl-1H-pyridin-2-one hydrochloride | 1H NMR (400 MHz, DMSO) δ 11.53 (br s, 1H), 10.21 (s, 1H), 7.51 (s, 1H), 7.29 (d, J = 6.4 Hz, 1H), 7.25 (s, 2H), 7.09 (s, 1H), 7.02 (s, 1H), 6.66 (s, 1H), 6.62 (s, 1H), 6.18 (d, J = 6.3 Hz, 1H), 4.07-4.04 (m, 2H), 3.98 (br s, 1H), 3.79-3.71 (m, 2H), 2.28 (s, 6H), 2.03 (s, 3H). (ESI+) m/z 432 (M + H)⁺ Retention time = 3.50 min (method 1) |
| 201 | 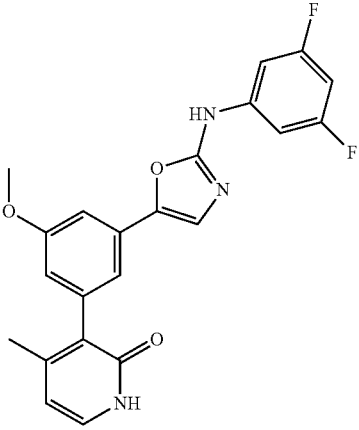 [SMILES: COc1cc(-c2cnc(Nc3cc(F)cc(F)c3)o2)cc(-c2c(C)cc[nH]c2=O)c1] | 3-{3-[2-(3,5-Difluoro-phenylamino)-oxazol-5-yl]-5-methoxy-phenyl}-4-methyl-1H-pyridin-2-one | 1H NMR (400 MHz, DMSO) δ 11.54 (s, 1H), 10.83 (s, 1H), 7.55 (s, 1H), 7.34 (d, J = 9.1 Hz, 2H), 7.28 (d, J = 5.9 Hz, 1H), 7.07 (s, 1H), 7.04 (s, 1H), 6.76 (t, J = 9.3 Hz, 1H), 6.67 (s, 1H), 6.16 (d, J = 5.1 Hz, 1H), 3.81 (s, 3H), 2.01 (s, 3H). |
| 202 | 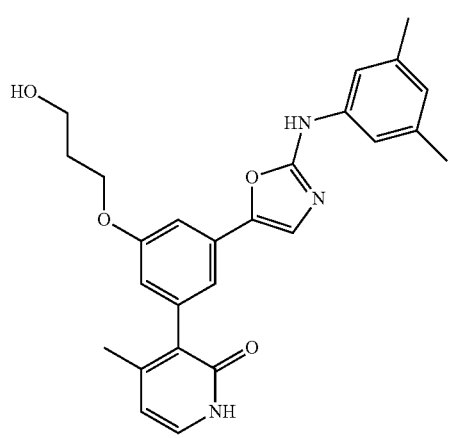 [SMILES: Cc1cc(C)cc(Nc2ncc(-c3cc(OCCCO)cc(-c4c(C)cc[nH]c4=O)c3)o2)c1] | 3-[3-[2-(3,5-Dimethyl-phenylamino)-oxazol-5-yl]-5-(3-hydroxy-propoxy)-phenyl]-4-methyl-1H-pyridin-2-one | ¹H NMR (400 MHz, DMSO) δ 11.53 (s, 1H), 10.10 (s, 1H), 7.48 (s, 1H), 7.34-7.21 (m, 3H), 7.07 (s, 1H), 7.01 (s, 1H), 6.64 (s, 1H), 6.60 (s, 1H), 6.16 (d, J = 6.7 Hz, 1H), 4.56 (t, J = 5.1 Hz, 1H), 4.09 (t, J = 6.3 Hz, 2H), 3.59 (dd, J = 11.5, 6.0 Hz, 2H), 2.27 (s, 6H), 2.01 (s, 3H), 1.95-1.82 (m, 2H). (ESI+) m/z 446 (M + H)⁺ Retention time = 3.63 min (method 1) |

| Ex # | Chemical structure | Name | ¹H NMR |
|---|---|---|---|
| 203 | 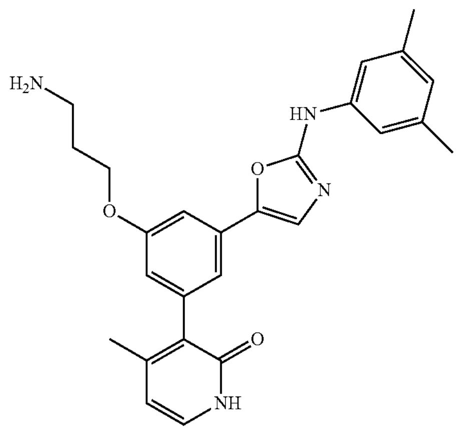 [SMILES: Cc1cc(C)cc(Nc2ncc(-c3cc(OCCCN)cc(-c4c(C)cc[nH]c4=O)c3)o2)c1] | 3-{3-(3-Amino-propoxy)-5-[2-(3,5-dimethyl-phenylamino)-oxazol-5-yl]-phenyl}-4-methyl-1H-pyridin-2-one | ¹H NMR (400 MHz, DMSO) δ 11.57 (s, 1H), 10.15 (s, 1H), 7.49 (s, 1H), 7.37-7.20 (m, 3H), 7.09 (s, 1H), 7.04 (s, 1H), 6.69 (s, 1H), 6.60 (s, 1H), 6.17 (d, J = 6.6 Hz, 1H), 4.22-4.02 (m, 2H), 3.10-3.03 (m, 2H), 2.22 (s, 6H), 2.02 (s, 3H), 1.85-1.70 (m, 2H). |
| 204 | 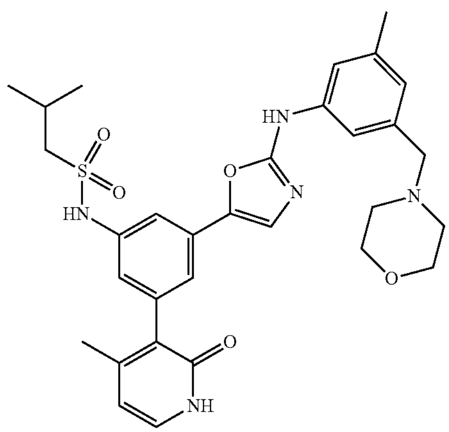 [SMILES: Cc1cc(CN2CCOCC2)cc(Nc2ncc(-c3cc(NS(=O)(=O)CC(C)C)cc(-c4c(C)cc[nH]c4=O)c3)o2)c1] | 2-Methyl-propane-1-sulfonic acid [3-[2-(3-methyl-(5-morpholin-4-ylmethyl)-phenylamino)-oxazol-5-yl]-5-(4-methyl-2-oxo-1,2-dihydro-pyridin-3-yl)-phenyl]-amide | ¹H NMR (400 MHz, DMSO) δ 11.59 (s, 1H), 10.25 (s, 1H), 9.91 (s, 1H), 7.46 (s, 1H), 7.44-7.34 (m, 3H), 7.31 (d, J = 6.5 Hz, 1H), 7.22 (s, 1H), 6.90 (s, 1H), 6.74 (s, 1H), 6.18 (d, J = 6.7 Hz, 1H), 3.66-3.52 (m, 4H), 3.41 (s, 2H), 3.04 (d, J = 6.4 Hz, 2H), 2.43-2.32 (m, 4H), 2.29 (s, 3H), 2.21-2.14 (m, 1H), 2.01 (s, 3H), 1.03 (d, J = 9.2 Hz, 6H). (ESI+) m/z 592 (M + H)⁺ Retention time = 2.77 min (method 1) |
| 205 | 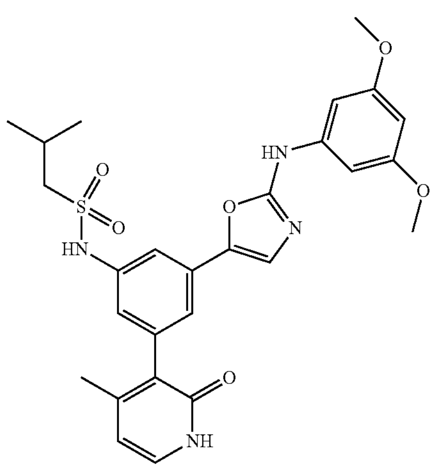 [SMILES: COc1cc(Nc2ncc(-c3cc(NS(=O)(=O)CC(C)C)cc(-c4c(C)cc[nH]c4=O)c3)o2)cc(OC)c1] | 2-Methyl-propane-1-sulfonic acid [3-[2-(3,5-dimethoxy-phenylamino)-oxazol-5-yl]-5-(4-methyl-2-oxo-1,2-dihydro-pyridin-3-yl)-phenyl]-amide | ¹H NMR (400 MHz, DMSO) δ 11.58 (s, 1H), 10.31 (s, 1H), 9.92 (s, 1H), 7.46 (s, 1H), 7.36 (s, 1H), 7.30 (d, J = 6.8 Hz, 1H), 7.20 (s, 1H), 6.93-6.85 (m, 3H), 6.18 (d, J = 6.8 Hz, 1H), 6.14 (t, J = 2.2 Hz, 1H), 3.73 (s, 6H), 3.03 (d, J = 6.4 Hz, 2H), 2.19-2.11 (m, 1H), 2.02 (s, 3H), 1.01 (d, J = 6.7 Hz, 6H). (ESI+) m/z 539 (M + H)⁺ Retention time = 3.72 min (method 1) |

TABLE 2-continued

| Ex # | Chemical structure | Name | ¹H NMR |
|---|---|---|---|
| 206 | 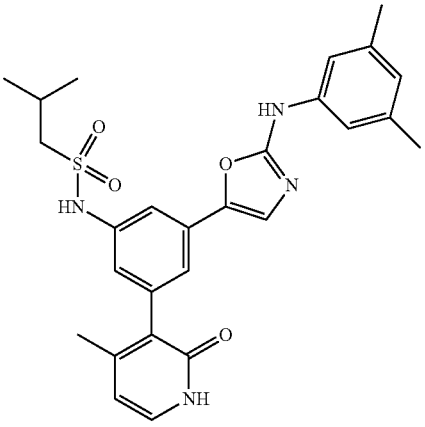 [SMILES: Cc1cc(C)cc(Nc2ncc(-c3cc(NS(=O)(=O)CC(C)C)cc(-c4c(C)cc[nH]c4=O)c3)o2)c1] | 2-Methyl-propane-1-sulfonic acid [3-[2-(3,5-dimethyl-phenylamino)-oxazol-5-yl]-5-(4-methyl-2-oxo-1,2-dihydro-pyridin-3-yl)-phenyl]-amide | ¹H NMR (400 MHz, DMSO) δ 11.62 (s, 1H), 10.22 (s, 1H), 9.94 (s, 1H), 7.46 (s, 1H), 7.39-7.34 (m, 1H), 7.31 (d, J = 6.7 Hz, 1H), 7.29-7.24 (m, 2H), 7.21 (s, 1H), 6.88 (s, 1H), 6.61 (s, 1H), 6.18 (d, J = 6.7 Hz, 1H), 3.03 (d, J = 6.3 Hz, 2H), 2.22 (s, 6H), 2.17-2.11 (m, 1H), 2.01 (s, 3H), 1.03 (d, J = 6.9 Hz, 6H). (ESI+) m/z 507 (M + H)⁺ Retention time = 4.10 min (method 1) |
| 207 | 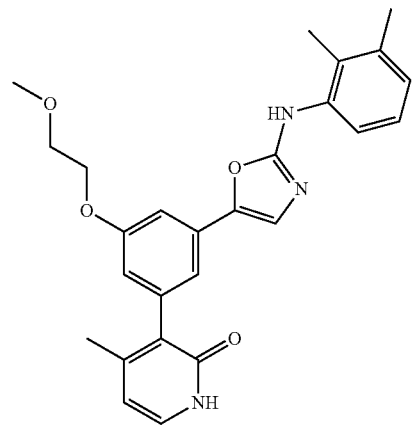 [SMILES: COCCOc1cc(-c2cnc(Nc3cccc(C)c3C)o2)cc(-c2c(C)cc[nH]c2=O)c1] | 3-[3-[2-(2,3-Dimethyl-phenylamino)-oxazol-5-yl]-5-(2-methoxy-ethoxy)-phenyl]-4-methyl-1H-pyridin-2-one | ¹H NMR (400 MHz, DMSO) δ 11.55 (s, 1H), 9.19 (s, 1H), 7.58 (d, J = 8.0 Hz, 1H), 7.41 (s, 1H), 7.28 (d, J = 6.7 Hz, 1H), 7.13-7.02 (m, 2H), 6.98 (s, 1H), 6.93 (d, J = 7.5 Hz, 1H), 6.63 (s, 1H), 6.16 (d, J = 6.7 Hz, 1H), 4.19-4.08 (m, 2H), 3.73-3.63 (m, 2H), 3.33 (s, 4H), 2.26 (s, 3H), 2.16 (s, 3H), 2.01 (s, 3H). (ESI+) m/z 446 (M + H)⁺ Retention time = 3.56 min (method 1) |
| 208 | 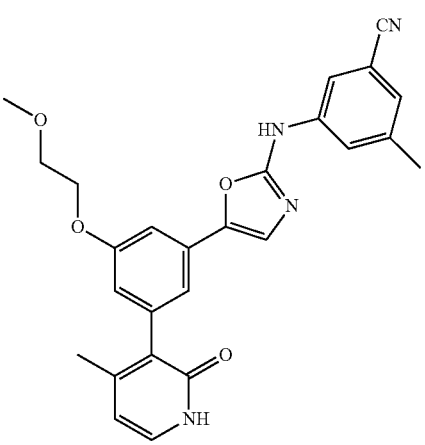 | 3-{5-[3-(2-Methoxy-ethoxy)-5-(4-methyl-2-oxo-1,2-dihydro-pyridin-3-yl)-phenyl]-oxazol-2-ylamino}-5-methyl-benzonitrile hydrochloride | 1H NMR (400 MHz, DMSO) δ 11.64 (br s, 1H), 10.74 (s, 1H), 7.92 (s, 1H), 7.70 (s, 1H), 7.57 (s, 1H), 7.30 (d, J = 6.7 Hz, 1H), 7.25 (s, 1H), 7.11 (d, J = 2.2 Hz, 1H), 7.04 (s, 1H), 6.69 (d, J = 1.2 Hz, 1H), 6.18 (d, J = 6.8 Hz, 1H), 5.12 (br s, 1H), 4.29-4.05 (m, 2H), 3.78-3.60 (m, 2H), 2.35 (s, 3H), 2.03 (s, 3H). (ESI+) m/z 457 (M + H)⁺ Retention time = 3.77 min (method 1) |

TABLE 2-continued

| Ex # | Chemical structure | Name | ¹H NMR |
|---|---|---|---|
| 209 | 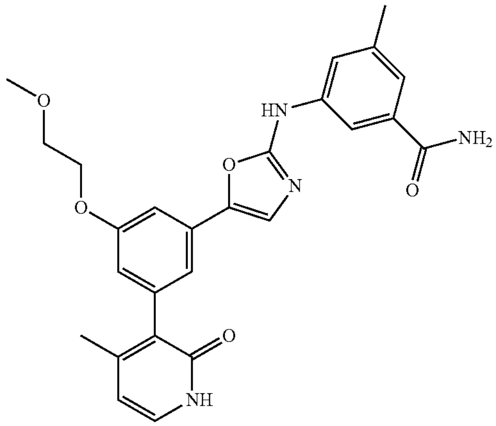 [SMILES: COCCOc1cc(-c2cnc(Nc3cc(C)cc(C(N)=O)c3)o2)cc(-c2c(C)cc[nH]c2=O)c1] | 3-{5-[3-(2-Methoxy-ethoxy)-5-(4-methyl-2-oxo-1,2-dihydro-pyridin-3-yl)-phenyl]-oxazol-2-ylamino}-5-methyl-benzamide | ¹H NMR (400 MHz, DMSO) δ 11.55 (s, 1H), 10.32 (s, 1H), 7.89 (s, 1H), 7.86-7.78 (m, 1H), 7.62 (s, 1H), 7.52 (s, 1H), 7.35-7.20 (m, 3H), 7.11 (s, 1H), 7.03 (s, 1H), 6.66 (s, 1H), 6.17 (d, J = 6.6 Hz, 1H), 4.23-4.10 (m, 2H), 3.74-3.65 (m, 2H), 3.34 (s, 3H), 2.35 (s, 3H), 2.03 (s, 3H). (ESI+) m/z 475 (M + H)⁺ Retention time = 2.91 min (method 1) |
| 210 | 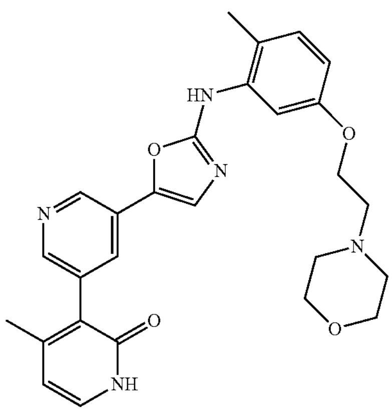 [SMILES: Cc1ccc(OCCN2CCOCC2)cc1Nc1ncc(-c2cncc(-c3c(C)cc[nH]c3=O)c2)o1] | 4-Methyl-5'-{2-[2-methyl-5-(2-morpholin-4-yl-ethoxy)-phenylamino]-oxazol-5-yl}-1H-[3,3']bipyridinyl-2-one | 1H NMR (400 MHz, DMSO) δ 11.68 (s, 1H), 9.30 (s, 1H), 8.76 (s, 1H), 8.29 (s, 1H), 7.84 (s, 1H), 7.61 (s, 2H), 7.34 (d, J = 6.6 Hz, 1H), 7.07 (d, J = 8.3 Hz, 1H), 6.57 (d, J = 8.2 Hz, 1H), 6.22 (d, J = 6.7 Hz, 1H), 4.04 (t, J = 5.5 Hz, 2H), 3.64-3.52 (m, 4H), 2.68 (t, J = 5.4 Hz, 2H), 2.46 (s, 4H), 2.22 (s, 3H), 2.06 (s, 3H). (ESI+) m/z 488 (M + H)⁺ Retention time = 2.04 min (method 1) |
| 211 | 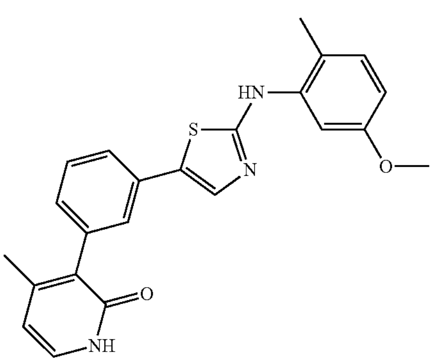 | 3-{3-[2-(5-Methoxy-2-methyl-phenylamino)-thiazol-5-yl]-phenyl}-4-methyl-1H-pyridin-2-one | 1H NMR (400 MHz, DMSO) δ 11.53 (s, 1H), 9.35 (s, 1H), 7.64 (s, 1H), 7.57 (d, J = 2.4 Hz, 2H), 7.45-7.35 (m, 2H), 7.32 (s, 1H), 7.27 (d, J = 6.8 Hz, 1H), 7.11 (d, J = 8.3 Hz, 1H), 7.06 (d, J = 7.3 Hz, 1H), 6.59 (dd, J = 8.4, 2.7 Hz, 1H), 6.16 (d, J = 6.7 Hz, 1H), 3.71 (s, 3H), 2.20 (s, 3H), 2.00 (s, 3H). (ESI+) m/z 404 (M + H)⁺ Retention time = 3.49 min (method 1) |

TABLE 2-continued

| Ex # | Chemical structure | Name | $^1$H NMR |
|---|---|---|---|
| 212 | 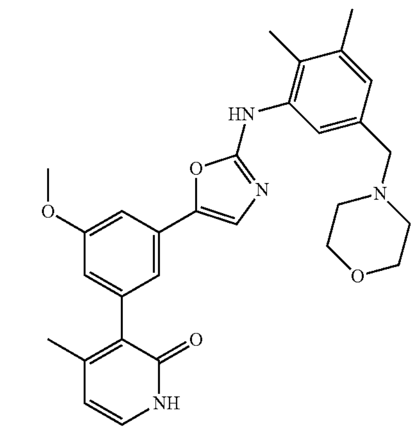 [SMILES: COc1cc(-c2cnc(Nc3cc(CN4CCOCC4)cc(C)c3C)o2)cc(-c2c(C)cc[nH]c2=O)c1] | 3-{3-[2-(2,3-Dimethyl-(5-morpholin-4-ylmethyl)-phenylamino)-oxazol-5-yl]-5-methoxy-phenyl}-4-methyl-1H-pyridin-2-one | $^1$H NMR (400 MHz, DMSO) δ 11.56 (s, 1H), 9.22 (s, 1H), 7.51 (s, 1H), 7.43 (s, 1H), 7.28 (d, J = 6.8 Hz, 1H), 7.04 (s, 1H), 6.97 (d, J = 1.2 Hz, 1H), 6.87 (s, 1H), 6.69-6.57 (m, 1H), 6.16 (d, J = 6.7 Hz, 1H), 3.80 (s, 3H), 3.63-3.48 (m, 4H), 3.36 (s, 2H), 2.41-2.27 (m, 4H), 2.25 (s, 3H), 2.14 (s, 3H), 2.01 (s, 3H). (ESI+) m/z 501 (M + H)$^+$ Retention time = 2.74 min (method 1) |
| 213 | 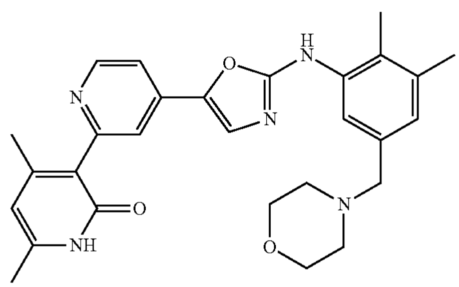 [SMILES: Cc1cc(C)c(-c2cc(-c3cnc(Nc4cc(CN5CCOCC5)cc(C)c4C)o3)ccn2)c(=O)[nH]1] | 4-[2-(2,3-Dimethyl-5-(morpholin-4-ylmethyl)-phenylamino)-oxazol-5-yl]-4',6'-dimethyl-1'H-[2,3']bipyridinyl-2'-one | $^1$H NMR (400 MHz, DMSO) δ 11.67 (s, 1H), 9.51 (s, 1H), 8.55 (d, J = 5.3 Hz, 1H), 7.72 (s, 1H), 7.45 (d, J = 8.3 Hz, 2H), 7.36 (dd, J = 5.2, 1.6 Hz, 1H), 6.91 (s, 1H), 5.99 (s, 1H), 3.60-3.49 (m, 4H), 3.37 (s, 2H), 2.41-2.29 (m, 4H), 2.25 (s, 3H), 2.18 (s, 3H), 2.13 (s, 3H), 1.99 (s, 3H). (ESI+) m/z 486 (M + H)$^+$ Retention time = 1.82 min (method 1) |

In one embodiment, which can be combined with other embodiments of the invention, the invention relates to compounds of formula I or pharmaceutically acceptable salts thereof wherein:

$R_1$ is H or a ($C_1$-$C_6$)alkyl;

$R_2$ is H;
a halogen;
COOH;
a ($C_1$-$C_6$)alkyl optionally substituted by a group —$NR_{10}R_{11}$, by OH or by a ($C_1$-$C_4$)alkoxy optionally substituted by OH where $R_{10}$ and $R_{11}$ are each independently H or ($C_1$-$C_4$)alkyl optionally substituted with amino, ($C_1$-$C_4$)alkylamino or di($C_1$-$C_4$)alkylamino; or $R_{10}$ and $R_{11}$ form, together with the nitrogen atom to which they are bonded, a 5- or 6-membered heterocycloalkyl containing 1 or 2 heteroatoms selected from O, S and N, in particular pyrrolidine, piperidine, piperazine and morpholine;
a ($C_1$-$C_6$)alkoxy optionally substituted by OH, a ($C_1$-$C_4$) alkoxy or a group —$NR_{12}R_{13}$ where $R_{12}$ and $R_{13}$ are each independently H or ($C_1$-$C_4$)alkyl; or $R_{12}$ and $R_{13}$ form, together with the nitrogen atom to which they are bonded, a 5- or 6-membered heterocycloalkyl containing 1 or 2 heteroatoms selected from O, S and N, in particular pyrrolidine, piperidine, piperazine and morpholine, said heterocycloalkyl being optionally substituted with 1 to 3 ($C_1$-$C_4$)alkyls;
a group —$OR_{14}$ where $R_{14}$ is a 5- or 6-membered heterocycloalkyl containing 1 or 2 heteroatoms selected from O, S and N, in particular pyrrolidine, piperidine, piperazine and morpholine, said heterocycloalkyl being optionally substituted with 1 to 3 ($C_1$-$C_4$)alkyls;
a group —$CONR_{15}R_{16}$ where $R_{15}$ and $R_{16}$ are each independently H or a ($C_1$-$C_4$)alkyl optionally substituted with a ($C_1$-$C_4$)alkoxy or with a 5- or 6-membered heterocycloalkyl containing 1 or 2 heteroatoms selected from O, S and N, in particular morpholine; or $R_{15}$ and $R_{16}$ form, together with the nitrogen atom to which they are bonded, a 5- or 6-membered heterocycloalkyl containing 1 or 2 heteroatoms selected from O, S and N, in particular pyrrolidine, piperidine, piperazine and morpholine;
a group —$NR_{17}R_{18}$ where $R_{17}$ is H or ($C_1$-$C_4$)alkyl and $R_{18}$ is H; a ($C_1$-$C_4$)alkyl optionally substituted with a ($C_1$-$C_4$)alkoxy; or a 5- or 6-membered heteroaryl containing 1 to 3 heteroatoms selected from O, S and N, in particular pyridine, pyrimidine and thiazole;
a group —$NR_{19}COR_{20}$ where $R_{19}$ is H or ($C_1$-$C_4$)alkyl and $R_{20}$ is H or a ($C_1$-$C_4$)alkyl optionally substituted with amino, ($C_1$-$C_4$)alkylamino or di($C_1$-$C_4$)alkylamino or with a 5- or 6-membered heterocycloalkyl containing 1 or 2 heteroatoms selected from O, S and N, in particular pyrrolidine, piperidine, piperazine and morpholine, said heterocycloalkyl being optionally substituted with 1 to 3 ($C_1$-$C_4$)alkyls; or
a 5- or 6-membered heterocycloalkyl or heteroaryl containing 1 or 2 heteroatoms selected from O and N, in particular piperidine and furane, said heterocycloalkyl or heteroaryl being optionally substituted with an oxo group or with a ($C_1$-$C_4$)alkyl optionally substituted with amino, ($C_1$-$C_4$)alkylamino or di($C_1$-$C_4$)alkylamino;

$R_3$ is H; cyano; $CF_3$; a halogen; a ($C_1$-$C_4$)alkyl; or a ($C_1$-$C_4$)alkoxy;

Q is O or S, preferably Q is O;

W is N or $CR_{21}$ where $R_{21}$ is
H;
a halogen;
CN;
$CF_3$;
$OCF_3$;
a ($C_1$-$C_4$)alkyl optionally substituted with a 5- or 6-membered heterocycloalkyl containing 1 or 2 heteroatoms selected from O and N, in particular pyrrolidine, piperidine, piperazine and morpholine;
a ($C_1$-$C_4$)alkoxy;
a group —O($CH_2$)$_n$$R_{22}$ where n is 0, 1, 2 or 3 and $R_{22}$ is H; a ($C_1$-$C_4$)alkoxy; a group —$NR_{22a}R_{22b}$ where $R_{22a}$ and $R_{22b}$ are each independently H or a ($C_1$-$C_4$)alkyl; or a 5- or 6-membered heterocycloalkyl containing 1 or 2 heteroatoms selected from O and N, in particular pyrrolidine, piperidine, piperazine and morpholine, said heterocycloalkyl being optionally substituted with 1 to 3 ($C_1$-$C_4$)alkyls;
a group —$NR_{23}R_{24}$ where $R_{23}$ and $R_{24}$ are each independently H or a ($C_1$-$C_4$)alkyl optionally substituted with a ($C_1$-$C_4$)alkoxy; $R_{24}$ can also represent a group —$SO_2$($C_1$-$C_4$)alkyl; or $R_{23}$ and $R_{24}$ form, together with the nitrogen atom to which they are bonded, a 5- or 6-membered heterocycloalkyl or heteroaryl containing 1 or 2 heteroatoms selected from O, S and N, in particular pyrrolidine, piperidine, piperazine, morpholine and pyrazole, said heterocycloalkyl being optionally substituted with 1 to 3 ($C_1$-$C_4$)alkyls;
X is N or $CR_{25}$ where $R_{25}$ is H; CN; a ($C_1$-$C_4$)alkyl; or a group —COO($C_1$-$C_4$)alkyl; and
A is a 5- or 6-membered heterocycloalkyl or heteroaryl containing 1 to 3 heteroatoms selected from O and N, in particular piperidine, piperazine, pyrrolidine, morpholine, imidazolidine, dihydroimidazole, triazole, dihydropyridine and tetrahydropyridine, said heterocycloalkyl or heteroaryl being optionally substituted with 1 to 3 substituents selected from: an oxo group; a halogen; a ($C_1$-$C_4$)alkyl optionally substituted with amino, ($C_1$-$C_4$)alkylamino, di($C_1$-$C_4$)alkylamino or a 5- or 6-membered heterocycloalkyl containing 1 or 2 heteroatoms selected from O and N, in particular piperidine; and a ($C_1$-$C_4$)alkoxy. Within this family of compounds those where $R_2$, $R_3$ and W are as defined below are preferred:
$R_2$ is H;
a halogen;
a ($C_1$-$C_6$)alkyl optionally substituted by a group —$NR_{10}R_{11}$ or by a ($C_1$-$C_4$)alkoxy optionally substituted by OH where $R_{10}$ and $R_{11}$ are each independently H or ($C_1$-$C_4$)alkyl optionally substituted with amino, ($C_1$-$C_4$)alkylamino or di($C_1$-$C_4$)alkylamino; or $R_{10}$ and $R_{11}$ form, together with the nitrogen atom to which they are bonded, a 5- or 6-membered heterocycloalkyl containing 1 or 2 heteroatoms selected from O, S and N, in particular pyrrolidine, piperidine, piperazine and morpholine;
a ($C_1$-$C_6$)alkoxy optionally substituted by OH, a ($C_1$-$C_4$)alkoxy or a group —$NR_{12}R_{13}$ where $R_{12}$ and $R_{13}$ are each independently H or ($C_1$-$C_4$)alkyl; or $R_{12}$ and $R_{13}$ form, together with the nitrogen atom to which they are bonded, a 5- or 6-membered heterocycloalkyl containing 1 or 2 heteroatoms selected from O, S and N, in particular pyrrolidine, piperidine, piperazine and morpholine, said heterocycloalkyl being optionally substituted with 1 to 3 ($C_1$-$C_4$)alkyls;
a group —$OR_{14}$ where $R_{14}$ is a 5- or 6-membered heterocycloalkyl containing 1 or 2 heteroatoms selected from O, S and N, in particular pyrrolidine, piperidine, piperazine and morpholine, said heterocycloalkyl being optionally substituted with 1 to 3 ($C_1$-$C_4$)alkyls;
a group —$CONR_{15}R_{16}$ where $R_{15}$ and $R_{16}$ are each independently H or a ($C_1$-$C_4$)alkyl optionally substituted with a ($C_1$-$C_4$)alkoxy; or $R_{15}$ and $R_{16}$ form, together with the nitrogen atom to which they are bonded, a 5- or 6-membered heterocycloalkyl containing 1 or 2 heteroatoms selected from O, S and N, in particular pyrrolidine, piperidine, piperazine and morpholine;
a group —$NR_{17}R_{18}$ where $R_{17}$ is H or ($C_1$-$C_4$)alkyl and $R_{18}$ is H; a ($C_1$-$C_4$)alkyl optionally substituted with a ($C_1$-$C_4$)alkoxy; or a 5- or 6-membered heteroaryl containing 1 to 3 heteroatoms selected from O and N, in particular pyridine;
a group —$NR_{19}COR_{20}$ where $R_{19}$ is H or ($C_1$-$C_4$)alkyl and $R_{20}$ is H or a ($C_1$-$C_4$)alkyl optionally substituted with amino, ($C_1$-$C_4$)alkylamino or di($C_1$-$C_4$)alkylamino or with a 5- or 6-membered heterocycloalkyl containing 1 or 2 heteroatoms selected from O, S and N, in particular pyrrolidine, piperidine, piperazine and morpholine, said heterocycloalkyl being optionally substituted with 1 to 3 ($C_1$-$C_4$)alkyls; or
a 5- or 6-membered heterocycloalkyl or heteroaryl containing 1 or 2 heteroatoms selected from O and N, in particular piperidine and furane, said heterocycloalkyl or heteroaryl being optionally substituted with an oxo group or with a ($C_1$-$C_4$)alkyl optionally substituted with amino, ($C_1$-$C_4$)alkylamino or di($C_1$-$C_4$)alkylamino;
$R_3$ is H; $CF_3$; a halogen; a ($C_1$-$C_4$)alkyl; or a ($C_1$-$C_4$)alkoxy;
W is N or $CR_{21}$ where $R_{21}$ is
H;
a halogen;
CN;
$CF_3$;
$OCF_3$;
a ($C_1$-$C_4$)alkyl optionally substituted with a 5- or 6-membered heterocycloalkyl containing 1 or 2 heteroatoms selected from O and N, in particular pyrrolidine, piperidine, piperazine and morpholine;
a ($C_1$-$C_4$)alkoxy;
a group —O($CH_2$)$_n$$R_{22}$ where n is 0, 1 or 2 and $R_{22}$ is a 5- or 6-membered heterocycloalkyl containing 1 or 2 heteroatoms selected from O and N, in particular pyrrolidine, piperidine, piperazine and morpholine, said heterocycloalkyl being optionally substituted with 1 to 3 ($C_1$-$C_4$)alkyls;
a group —$NR_{23}R_{24}$ where $R_{23}$ and $R_{24}$ are each independently H or a ($C_1$-$C_4$)alkyl optionally substituted with a ($C_1$-$C_4$)alkoxy; or $R_{23}$ and $R_{24}$ form, together with the nitrogen atom to which they are bonded, a 5- or 6-membered heterocycloalkyl or heteroaryl containing 1 or 2 heteroatoms selected from O, S and N, in particular pyrrolidine, piperidine, piperazine, morpholine and pyrazole, said heterocycloalkyl being optionally substituted with 1 to 3 ($C_1$-$C_4$)alkyls.

In another embodiment, which can be combined with other embodiments of the invention, compounds of formula I or pharmaceutically acceptable salts thereof are contemplated wherein:
$R_1$ is H or a ($C_1$-$C_4$)alkyl;
$R_2$ is H; a ($C_1$-$C_4$)alkyl optionally substituted by a ($C_1$-$C_4$)alkoxy; a ($C_1$-$C_4$)alkoxy optionally substituted by OH or a group —$NR_{12}R_{13}$ where $R_{12}$ and $R_{13}$ are each independently H or ($C_1$-$C_4$)alkyl or $R_{12}$ and $R_{13}$ form, together with the nitrogen atom to which they are bonded, a 5- or 6-membered heterocycloalkyl containing 1 or 2 heteroatoms selected from O, and N, in particular morpholine; or a group —CONR$_{15}$R$_{16}$ where R$_{15}$ and R$_{16}$ are each independently H or a (C$_1$-C$_4$)alkyl;

R$_3$ is H or a (C$_1$-C$_4$)alkyl;

Q is O;

W is N or CR$_{21}$ where R$_{21}$ is H; OCF$_3$; a (C$_1$-C$_4$)alkyl; a (C$_1$-C$_4$)alkoxy; or a group —O(CH$_2$)$_n$R$_{22}$ where n is 0, 1 or 2, preferably n is 2, and R$_{22}$ is a 5- or 6-membered heterocycloalkyl containing 1 or 2 heteroatoms selected from O and N, in particular morpholine;

X is N or CH; and

A is a 5- or 6-membered heterocycloalkyl or heteroaryl containing 1 or 2 nitrogen atoms, in particular imidazolidine and dihydropyridine, said heterocycloalkyl or heteroaryl being optionally substituted with 1 to 3 (C$_1$-C$_4$)alkyls.

Preferred compounds of the invention are selected from those of examples 1 to 225 and pharmaceutically acceptable salts thereof.

The following compounds are especially preferred:

1-{4-[2-((5-Ethoxymethyl)-2-methyl-phenylamino)-oxazol-5-yl]-pyridin-2-yl}-imidazolidin-2-one;

1-{3-[2-((5-Ethoxymethyl)-2-methyl-phenylamino)-oxazol-5-yl]-5-methoxy-phenyl}-4,4-dimethyl-imidazolidin-2-one;

1-(3-{2-[5-(2-Hydroxy-ethoxy)-2-methyl-phenylamino]-oxazol-5-yl}-5-methyl-phenyl)-imidazolidin-2-one;

1-(4-{2-[5-(2-Hydroxy-ethoxy)-2-methyl-phenylamino]-oxazol-5-yl}-pyridin-2-yl)-imidazolidin-2-one;

1-(4-{2-[2-Methyl-5-(2-morpholin-4-yl-ethoxy)-phenylamino]-oxazol-5-yl}-pyridin-2-yl)-imidazolidin-2-one;

1-[4-[2-((5-Methoxymethyl)-2-methyl-phenylamino)-oxazol-5-yl]-pyridin-2-yl]-4-methyl-imidazolidin-2-one;

4-Methyl-1-(4-{2-[2-methyl-5-(2-morpholin-4-yl-ethoxy)-phenylamino]-oxazol-5-yl}-pyridin-2-yl)-imidazolidin-2-one;

1-(3-Methyl-5-{2-[2-methyl-5-(2-morpholin-4-yl-ethoxy)-phenylamino]-oxazol-5-yl}-phenyl)-imidazolidin-2-one;

1-(4-{2-[2-Methyl-5-(3-morpholin-4-yl-propoxy)-phenylamino]-oxazol-5-yl}-pyridin-2-yl)-imidazolidin-2-one;

1-{3-[2-((5-Ethoxymethyl)-2-methyl-phenylamino)-oxazol-5-yl]-5-methoxy-phenyl}-imidazolidin-2-one;

1-(3-Methoxy-5-{2-[2-methyl-5-(2-morpholin-4-yl-ethoxy)-phenylamino]-oxazol-5-yl}-phenyl)-imidazolidin-2-one;

1-{3-[2-((5-Ethoxymethyl)-2-methyl-phenylamino)-oxazol-5-yl]-5-methoxy-phenyl}-4-methyl-imidazolidin-2-one;

1-{3-tert-Butoxy-5-[2-((5-methoxymethyl)-2-methyl-phenylamino)-oxazol-5-yl]-phenyl}-imidazolidin-2-one;

1-(3-{2-[5-(2-Hydroxy-ethoxy)-2-methyl-phenylamino]-oxazol-5-yl}-5-methoxy-phenyl)-imidazolidin-2-one;

1-(3-Methoxy-5-{2-[2-methyl-5-(2-morpholin-4-yl-ethoxy)-phenylamino]-oxazol-5-yl}-phenyl)-4-methyl-imidazolidin-2-one;

1-{3-Isopropoxy-5-[2-((5-methoxymethyl)-2-methyl-phenylamino)-oxazol-5-yl]-phenyl}-imidazolidin-2-one;

1-(3-{2-[5-(2-Hydroxy-ethoxy)-2-methyl-phenylamino]-oxazol-5-yl}-5-isopropoxy-phenyl)-imidazolidin-2-one;

1-(3-Isopropoxy-5-{2-[5-(2-methoxy-ethyl)-2-methyl-phenylamino]-oxazol-5-yl}-phenyl)-imidazolidin-2-one;

1-(3-(2-(2-methyl-5-(2-morpholinoethoxy)phenylamino)oxazol-5-yl)-5-(trifluoromethoxy)phenyl)imidazolidin-2-one;

1-(3-(2-(5-methoxy-2-methylphenylamino)oxazol-5-yl)-5-(trifluoromethoxy)phenyl)imidazolidin-2-one;

1-(3-{2-[5-(2-Hydroxy-ethoxymethyl)-2-methyl-phenylamino]-oxazol-5-yl}-5-methyl-phenyl)-imidazolidin-2-one;

3-{5-[3-Isopropoxy-5-(2-oxo-imidazolidin-1-yl)-phenyl]-oxazol-2-ylamino}-N-(2-methoxy-ethyl)-4-methyl-benzamide;

1-(3-(2-(5-(ethoxymethyl)-2-methylphenylamino)oxazol-5-yl)-5-(trifluoromethoxy)phenyl)imidazolidin-2-one;

3-{3-[2-(3,5-Dimethyl-phenylamino)-oxazol-5-yl]-5-trifluoromethoxy-phenyl}-4-methyl-1H-pyridin-2-one;

3-{3-[2-(3,5-Dimethyl-phenylamino)-oxazol-5-yl]-5-methoxy-phenyl}-1H-pyridin-2-one;

3-{3-[2-(3,5-Dimethyl-phenylamino)-oxazol-5-yl]-5-isopropoxy-phenyl}-4-methyl-1H-pyridin-2-one;

4-[2-(5-(Ethoxymethyl)-2-methyl-phenylamino)-oxazol-5-yl]-4'-methyl-1'H-[2,3]bipyridinyl-2'-one;

3-[3-[2-(3,5-Dimethyl-phenylamino)-oxazol-5-yl]-5-(2-morpholin-4-yl-ethoxy)-phenyl]-4-methyl-1H-pyridin-2-one;

4'-Methyl-4-{2-[2-methyl-5-(2-morpholin-4-yl-ethoxy)-phenylamino]-oxazol-5-yl}-1'H-[2,3]bipyridinyl-2'-one;

4-[2-(3,5-Dimethyl-phenylamino)-oxazol-5-yl]-4'-methyl-6-(2-morpholin-4-yl-ethoxy)-1'H-[2,3]bipyridinyl-2'-one;

1-{3-[2-((5-Ethoxymethyl)-2-methyl-phenylamino)-oxazol-5-yl]-5-isopropoxy-phenyl}-imidazolidin-2-one;

4'-Methyl-4-{2-[2-methyl-5-(3-morpholin-4-yl-propoxy)-phenylamino]-oxazol-5-yl}-1'H-[2,3]bipyridinyl-2'-one; and pharmaceutically acceptable salts thereof.

The compounds of the present invention may be prepared using the general protocol as follows.

The synthesis of the aminooxazole derivatives was undergone by firstly reacting aromatic aldehydes I with p-toluenesulfonylmethyl isocyanide (TosMIC) to prepare the corresponding arylsubstitued oxazole derivatives II using the method of Van Leusen et. al. (*Tetrahedron Lett.*, 1972, 23, 2369) (Scheme 1). The non-commercial aldehydes were prepared using literature methods to introduce the aldehyde group either from the corresponding brominated aromatic compound using an organometallic reagent and DMF or from the oxidation of corresponding toluene according the method of Frey et. al. (*Tetrahedron Lett.*, 2001, 39, 6815).

Secondly, those compounds II were then further functionalised by deprotonation of the oxazole moiety by a suitable organic base and subsequent electrophilic chlorination was used to prepare the 2-chlorooxazole coumpounds III. A direct nucleophilic displacement reaction by aniline compounds IV (wherein R' is hydrogen), in the presence of a suitable solvent such as alcohol and with heating in elevated temperature, should generally afford the final target compounds V. Compounds V can also obtained by reacting compounds IV (wherein R' is an acetyl group) and compounds III in the presence of sodium hydride and in a suitable solvent such as tetrahydrofurane or dimethylformamide (WO 2007/131953).

Scheme 1

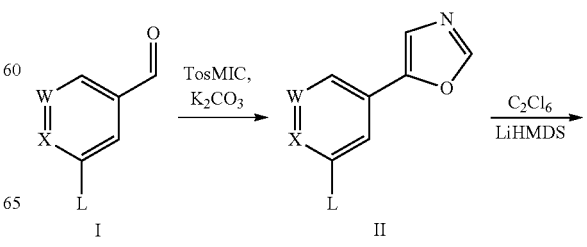

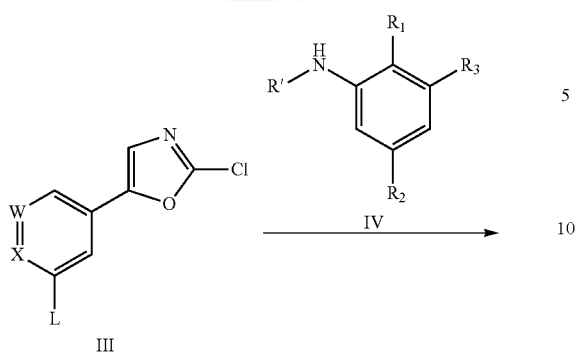

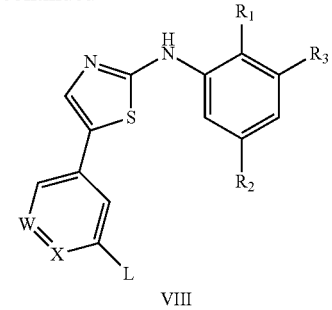

Scheme 2 depicts the synthesis of the aminothiazole derivatives VIII undergone firstly by reacting aromatic aldehydes I with (methoxymethyl)triphenyl phosphonium chloride to prepare the corresponding arylsubstitued enol ether derivatives VI using Wittig reaction described by Iwao et. al. (*J. Org. Chem.* 2009, 74, 8143). Secondly, a cyclisation was perfomed with the enol ether VI, thiourea derivatives VII and N-bromosuccinimide (NBS) using the method of Zhao et. al. (*Tetrahedron Lett.*, 2001, 42, 2101).

Scheme 2

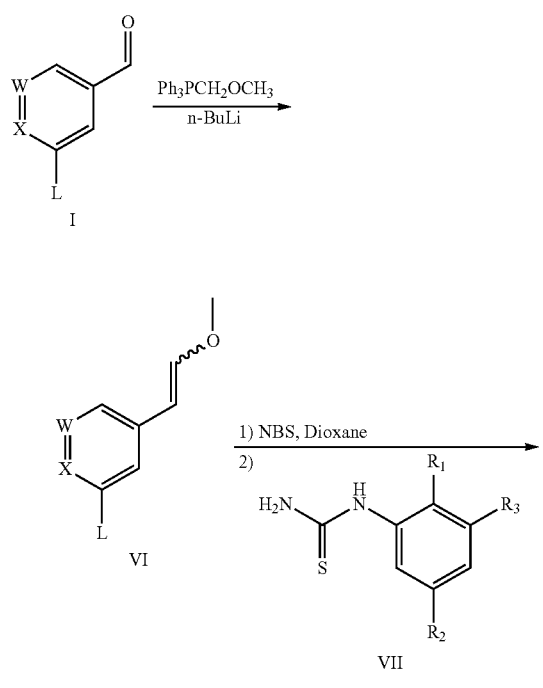

The invention is now illustrated by Examples which represent currently preferred embodiments which make up a part of the invention but which in no way are to be used to limit the scope of it.

Examples of Compound Synthesis

The invention will be more fully understood by reference to the following preparative examples, but they should not be construed as limiting the scope of the invention.

General: All chemicals used were commercial reagent grade products. Solvents were of anhydrous commercial grade and were used without further purification. The progress of the reactions was monitored by thin layer chromatography using precoated silica gel 60F 254, Merck TLC plates, which were visualized under UV light. Multiplicities in $^1$H NMR spectra are indicated as singlet (s), broad singlet (br s), doublet (d), triplet (t), quadruplet (q), and multiplet (m) and the NMR spectrum were performed either on a Bruker Avance 300, 360 or 400 MHz spectrometer. Mass spectra were performed by Electrospray Ionisation Mass Spectrometry (ESI MS) in positive mode or by Atmospheric Pressure Chemical Ionization Mass Spectrometry (APCI MS) in positive mode.

LCMS methods: Method 1: This method was run on a Ultra-high performance liquid chromatography (UPLC) ACQUITY Waters instrument coupled to a TQD mass spectrometer. The gradient used was: starting at t=0.0 min with 5% of $CH_3CN$+0.1% Formic acid in Water+0.1% Formic acid until t=0.5 min; then a linear gradient from t=0.5 min to t=7.0 min reaching 100% $CH_3CN$+0.1% Formic acid; then staying at this state from t=7.0 min until t=10.0 min. The column used was a Waters HSS C18 1.8 μm, 2.1×50 mm. The detection instrument used was the triple quadrupole mass spectrometer (TQD) using ESI positive mode.

Method 2: This method was run on HPLC 2695 Alliance, Waters coupled to a ZMD mass spectrometer instrument. The gradient used was: starting at t=0.0 min with 0% of $CH_3CN$+0.04% Formic acid in water (10 mM); then a linear gradient to t=3.1 min reaching 100% of $CH_3CN$+0.04% Formic acid; then staying at this state to t=3.8 min and decreasing to =4.8 min to 0% of $CH_3CN$+0.04% Formic acid in water. The column used was a Sunfire 2.1×50 mm dp: 3.5 μm.

Abbreviations
AcCl Acetyl chloride
$Al_2O_3$ Alumina gel
APCI MS Atmospheric Pressure Chemical Ionization Mass Spectrometer
BINAP 2,2'-Bis(diphenylphosphino)-1,1'-binaphthalene
nBuLi n-Butyllithium
tBuONO Tert-butylnitrite
$C_2Cl_6$ Hexachloroethane
$CDCl_3$ Deuterochloroform
$CH_3I$ Iodomethane mCPBA 3-Chloroperoxybenzoic acid
Davephos 2-Dicyclohexylphosphino-2'-(N,N-dimethylamino)biphenyl
DCM Dichloromethane
DCE 1,2-Dichloroethylene
DMF N,N-Dimethylformamide
DMSO-$d_6$ Hexadeuterodimethyl sulfoxide
EDCI 1-Ethyl-3-(3-Dimethylaminopropyl)carbodiimide
EI-MS Electron impact ionisation mass spectrometry
ES-MS Electrospray mass spectrometry
$Et_2O$ Diethylether
EtOAc Ethyl acetate
EtOH Ethanol
h Hour(s)
$H_2O_2$ Hydrogen peroxyde
HOBT N-Hydroxybenzotriazole
$K_2CO_3$ Potassium carbonate
$K_3PO_4$ Potassium phosphate tribasic
KOtBu Potassium tert-butoxide
KSCN Potassium thiocyanate
LiHMDS Lithium bis(trimethylsilyl)amide
MeOH Methanol
$MgSO_4$ Magnesium sulfate
min Minutes
NaH Sodium hydride
$NaHCO_3$ Sodium bicarbonate
NaI Sodium iodide
NaOH Sodium hydroxyde
NaOtBu Sodium tert-butoxide
NaOEt Sodium ethoxide
NaOMe Sodium methoxide
NBS N-bromosuccinimide
$NEt_3$ Triethylamine
$Pd_2(dba)_3$ Tris(dibenzylideneacetone)palladium(0)
$Pd(PPh_3)_4$ Tetrakis(triphenylphoshine)palladium(0)
iPrOH 2-Propanol
$SiO_2$ Silica gel
$SnCl_2 \cdot 2H_2O$ Tin(II) chloride dihydrate
TosMIC p-Toluenesulfonylmethyl isocyanide
THF Tetrahydrofuran
Xantphos 4,5-Bis(diphenylphosphino)-9,9-dimethylxanthene Example 214

Synthetic Approach of Example 214

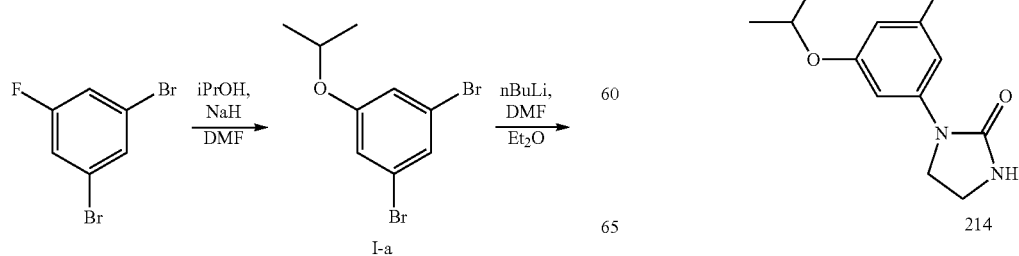

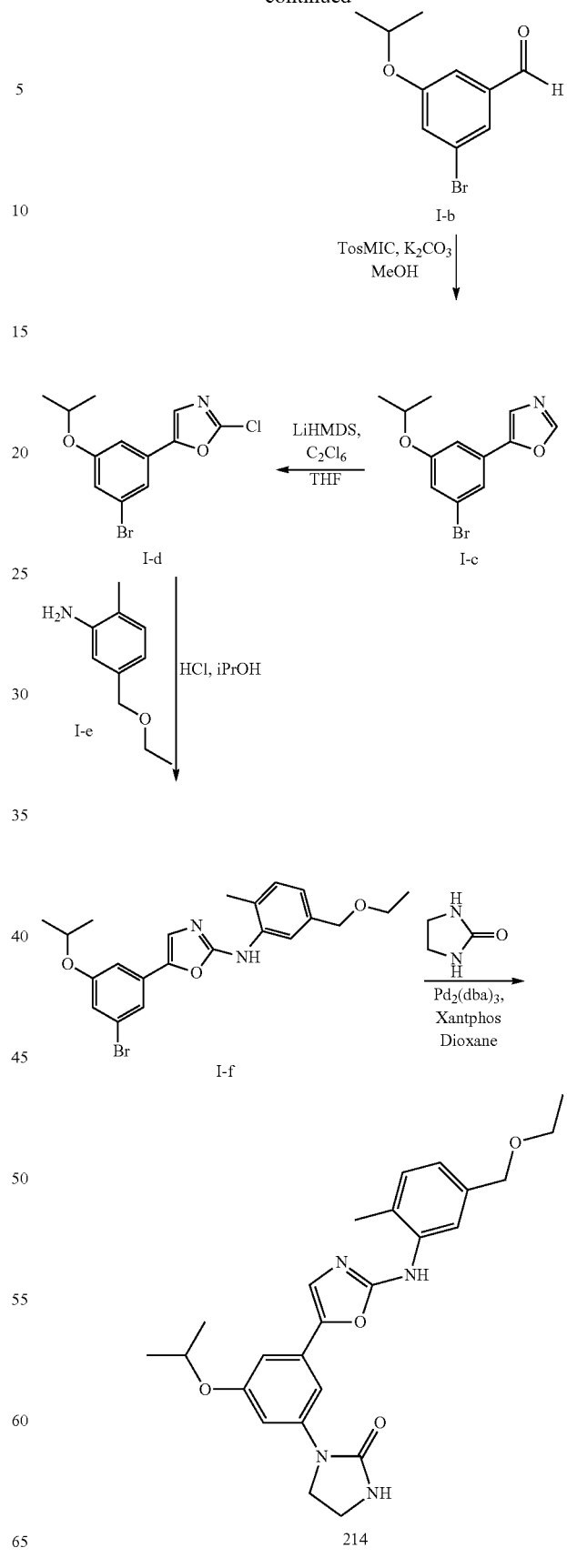

Synthetic Approach of Intermediate I-e

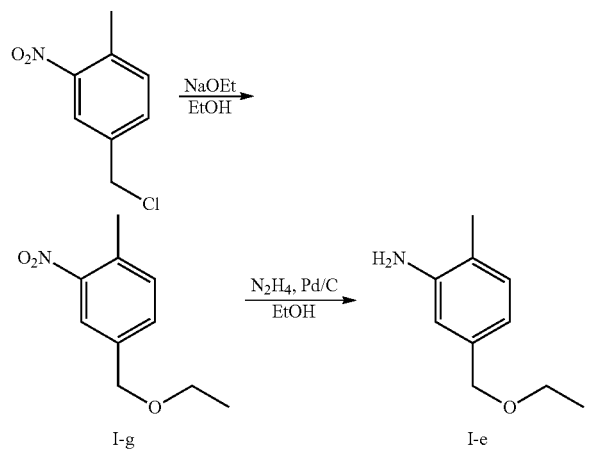

Synthesis of intermediate I-a: 1,3-dibromo-5-isopropoxy-benzene

To a solution of NaH 60% dispersion in mineral oil (1.89 g, 47.25 mmol) in dry DMF (20 mL) under inert atmosphere was added dropwise at 0° C. i-PrOH (3.62 mL, 47.25 mmol). The mixture was stirred at 0° C. for 15 min. Then, a solution of 1,3-dibromo-5-fluoro-benzene (1.98 mL, 15.75 mmol) in dry DMF (20 mL) was added dropwise at 0° C. The reaction mixture was stirred for 16 h at room temperature. A saturated solution of NaHCO$_3$ was added dropwise and the crude product was extracted with Et$_2$O (2 times), the organic layer was washed with a saturated solution of NaHCO$_3$ (3 times), then with a saturated solution of NaCl, dried over MgSO$_4$ and concentrated to give I-a as yellow oil in quantitative yield. $^1$H RMN (300 MHz, CDCl$_3$) δ 7.21 (t, J=1.4 Hz, 1H), 6.97 (d, J=1.5 Hz, 2H), 4.61-4.40 (m, 1H), 1.32 (d, J=6.0 Hz, 6H).

Synthesis of intermediate I-b: 3-bromo-5-isopropoxy-benzaldehyde

To a solution of I-a (4.630 g, 15.75 mmol) in dry Et$_2$O (60 mL) under inert atmosphere was added dropwise at −78° C. a solution of n-butyl lithium in dry Et$_2$O (6.3 mL, 15.75 mmol). The reaction mixture was stirred at −78° C. for 0.5 h. Then, dry DMF (1.35 mL) was added dropwise at −78° C. and the temperature was allowed to reach −40° C. over 1.5 h. A solution of HCl (3N) was added and the crude product was extracted with Et$_2$O (2 times), the organic layer was washed with water, then with a saturated solution of NaCl, dried over MgSO$_4$ and concentrated to give I-b as yellow oil in 82% yield. $^1$H RMN (300 MHz, CDCl$_3$) δ 9.89 (s, 1H), 7.54 (m, 1H), 7.29 (m, 2H), 4.60 (dt, J=12.1, 6.0 Hz, 1H), 1.36 (t, J=6.0 Hz, 6H).

Synthesis of intermediate I-c: 5-(3-bromo-5-isopropoxy-phenyl)-oxazole

To a solution of I-b (6.925 g, 28.50 mmol) in MeOH (125 mL) were added successively K$_2$CO$_3$ (11.811 g, 85.50 mmol) and TosMIC (6.674 g, 34.20 mmol). The reaction mixture was stirred at room temperature for 16 h. Then, the solvent was removed under reduce pressure, water was added and the crude product was extracted with EtOAc (2 times), the organic layer was washed with water, then with a saturated solution of NaCl, dried over MgSO$_4$ and concentrated. The final product was purified by silica gel chromatography using 5 to 30% EtOAc/cyclohexane as eluent to give I-c as yellow oil in 86% yield. $^1$H RMN (300 MHz, CDCl$_3$) δ 7.90 (s, 1H), 7.34 (m, 2H), 7.09 (m, 1H), 7.00 (m, 1H), 4.56 (dt, J=12.1, 6.0 Hz, 1H), 1.49-1.26 (m, 6H).

Synthesis of intermediate I-d: 5-(3-bromo-5-isopropoxy-phenyl)-2-chloro-oxazole To a solution of I-c (6.921 g, 24.50 mmol) in dry THF (130 mL) under inert atmosphere was added dropwise at −78° C. a solution of LiHMDS in dry THF (29 mL, 29.00 mmol). The reaction mixture was stirred at −78° C. for 0.5 hour. Then, C$_2$Cl$_6$ (8.712 g, 36.75 mmol) was added at −78° C. and the reaction mixture was stirred at room temperature for 16 h. Water was added and the crude product was extracted with EtOAc (2 times), the organic layer was washed with water, then with a saturated solution of NaCl, dried over MgSO$_4$ and concentrated. The final product was purified by silica gel chromatography using 0 to 20% EtOAc/cyclohexane as eluent to give I-d as yellow oil in 92% yield. $^1$H NMR (300 MHz, CDCl$_3$) δ 7.29 (t, J=1.5 Hz, 1H), 7.27 (s, 1H), 7.02 (d, J=1.4 Hz, 2H), 4.57 (dt, J=12.1, 6.0 Hz, 1H), 1.36 (s, 3H), 1.34 (s, 3H).

Synthesis of intermediate I-f: [5-(3-Bromo-5-isopropoxy-phenyl)-oxazol-2-yl]-((5-ethoxymethyl)-2-methyl-phenyl)-amine To a solution of I-d (1.556 g, 4.915 mmol) and I-e (0.812 g, 4.915 mmol) in i-PrOH (45 mL) under inert atmosphere was added dropwise a solution of HCl in dry Et$_2$O (0.98 mL, 0.98 mmol). The reaction mixture was stirred at 80° C. for 16 h. Then, the solvent was removed under reduced pressure and a solution of NaOH (2.5 N) was added. The crude product was extracted with EtOAc (2 times) and the organic layer was washed with water, then with a saturated solution of NaCl, dried over MgSO$_4$ and concentrated. The final product was purified by silica gel chromatography using 0 to 30% EtOAc/cyclohexane as eluent to give I-f as white solid in 64% yield. $^1$H RMN (300 MHz, DMSO-d$_6$) δ 9.30 (s, 1H), 7.81 (s, 1H), 7.56 (s, 1H), 7.30 (s, 1H), 7.16 (d, J=7.7 Hz, 1H), 7.09 (d, J=1.4 Hz, 1H), 7.00 (d, J=1.7 Hz, 1H), 6.94 (d, J=7.8 Hz, 1H), 4.69 (dt, J=12.0, 5.9 Hz, 1H), 4.41 (s, 2H), 3.47 (q, J=7.0 Hz, 2H), 2.27 (s, 3H), 1.39 (s, 3H), 1.27 (d, J=6.0 Hz, 6H), 1.14 (t, J=7.0 Hz, 3H).

Synthesis of intermediate I-g: 4-ethoxymethyl-1-methyl-2-nitro-benzene

To a solution of NaOEt in dry EtOH (45 mL, 114.90 mmol) under inert atmosphere was added 4-chloromethyl-1-methyl-2-nitro-benzene (7.0 g, 38.30 mmol). The reaction mixture was stirred at room temperature for 16 hours. Water was added and ethanol was removed under reduced pressure. The crude product was extracted with DCM (2 times) and the organic layer was washed with water, then with a saturated solution of NaCl, dried over MgSO$_4$ and concentrated to give I-g as brown oil in 96% yield. $^1$H NMR (300 MHz, CDCl$_3$) δ 7.95 (s, 1H), 7.48 (d, J=7.8 Hz, 1H), 7.31 (d, J=7.9 Hz, 1H), 4.52 (s, 2H), 3.56 (q, J=7.0 Hz, 2H), 2.57 (d, J=10.1 Hz, 3H), 1.26 (t, J=7.0 Hz, 3H).

Synthesis of intermediate I-e: 5-ethoxymethyl-2-methyl-phenylamine

To a solution of I-g (7.21 g, 36.93 mmol) in EtOH (238 mL) were added successively Pd/C (2.432 g) and at 0° C. hydrazine monohydrate (4.84 mL, 99.71 mmol) dropwise. The reaction mixture was stirred at 80° C. for 2 h. Then, the hot mixture was filtrated over celite pad and washed with EtOH. The filtrate was concentrated under reduced pressure to give I-e as yellow oil in quantitative yield. $^1$H NMR (300 MHz, CDCl$_3$) δ 6.99 (d, J=7.6 Hz, 1H), 6.67 (d, J=7.5 Hz, 2H), 4.41 (s, 2H), 3.52 (q, J=7.0 Hz, 3H), 2.18 (s, 3H), 1.04 (t, J=8.5 Hz, 3H).

Synthesis of example 214: 1-{3-[2-((5-Ethoxymethyl)-2-methyl-phenylamino)-oxazol-5-yl]-5-isopropoxy-phenyl}-imidazolidin-2-one In a sealed tube, to a solution of I-f (872 mg, 1.56 mmol) in dry dioxane (13 mL) were added successively imidazolidin-2-one (674 mg, 7.84 mmol), cesium carbonate (1.595 g, 4.90 mmol), Pd$_2$(dba)$_3$ (113 mg, 0.20 mmol), and Xantphos (54 mg, 0.06 mmol). The reaction mixture was stirred at 110° C. for 16 h. Water was added, the crude product was extracted with EtOAc (2 times) and the organic layer was washed with water, then with a saturated solution of NaCl, dried over MgSO$_4$ and concentrated. The final product was purified by silica gel chromatography using 50 to 100% EtOAc/cyclohexane as eluent to give compound 214 as white solid in 50% yield. $^1$H NMR (300 MHz, DMSO-d$_6$) δ 9.26 (s, 1H), 7.81 (s, 1H), 7.40 (s, 1H), 7.29 (s, 1H), 7.15 (d, J=7.7 Hz, 1H), 7.11 (t, J=2.0 Hz, 1H), 7.01 (s, 1H), 6.92 (d, J=7.7 Hz, 1H), 6.78 (s, 1H), 4.62 (dt, J=12.1, 6.0 Hz, 1H), 4.41 (s, 2H), 3.92-3.81 (m, 2H), 3.53-3.34 (m, 4H), 2.27 (s, 3H), 1.29 (s, 3H), 1.27 (s, 3H), 1.14 (t, J=7.0 Hz, 3H).

(ESI+) m/z 451.2 (M+H)$^+$.
Retention time=3.52 min (method 2).

Example 215

Synthetic Approach of Example 215

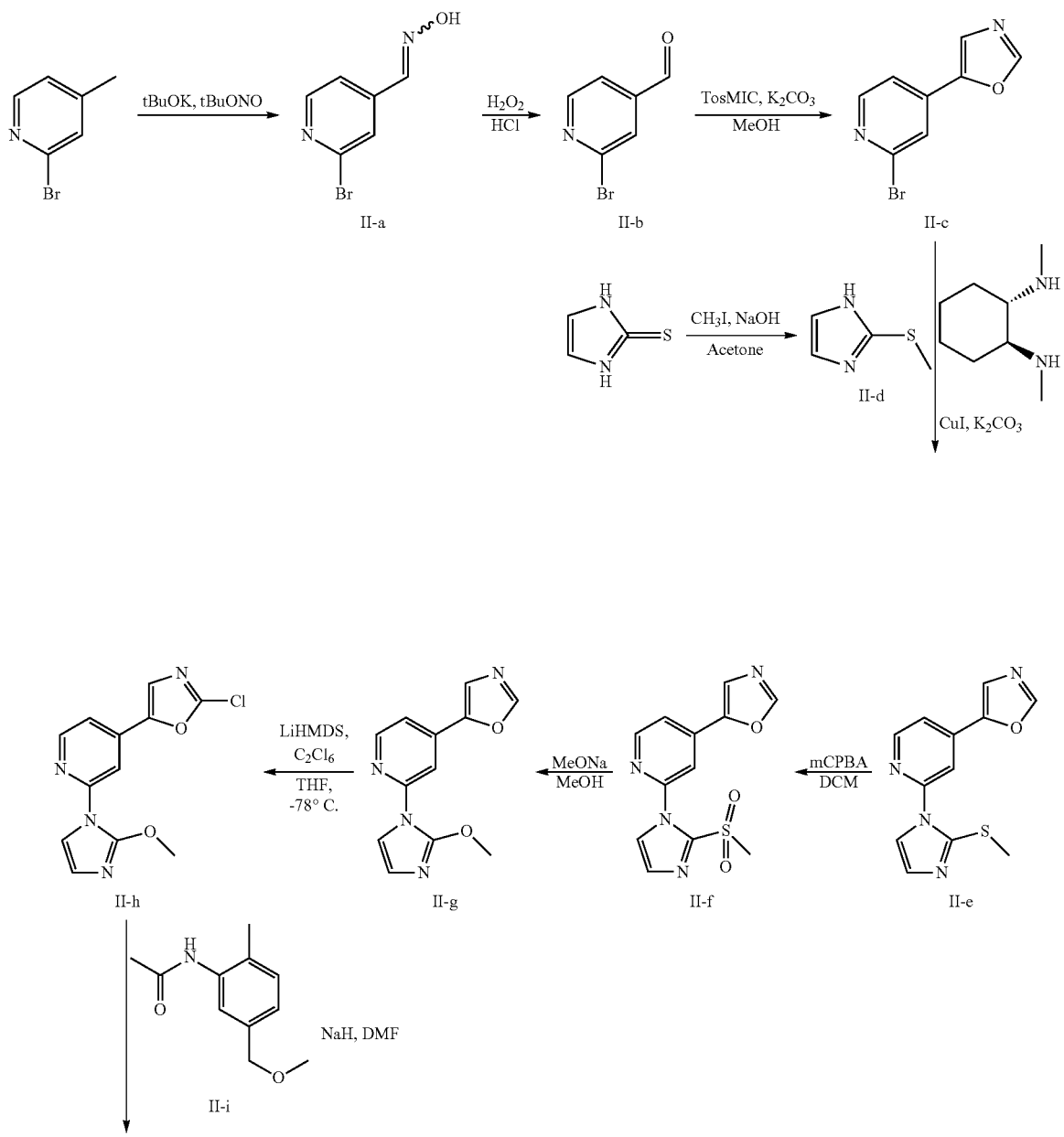

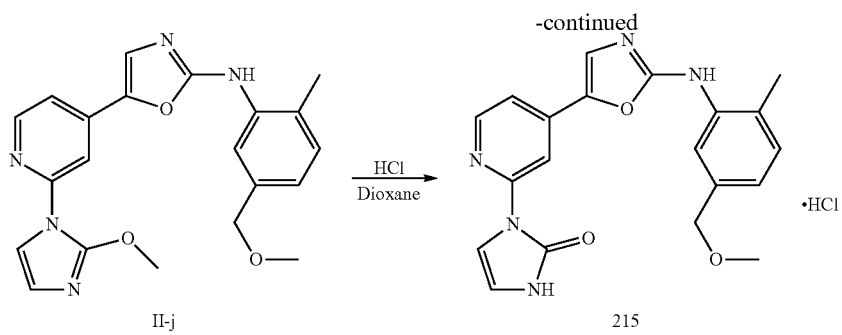

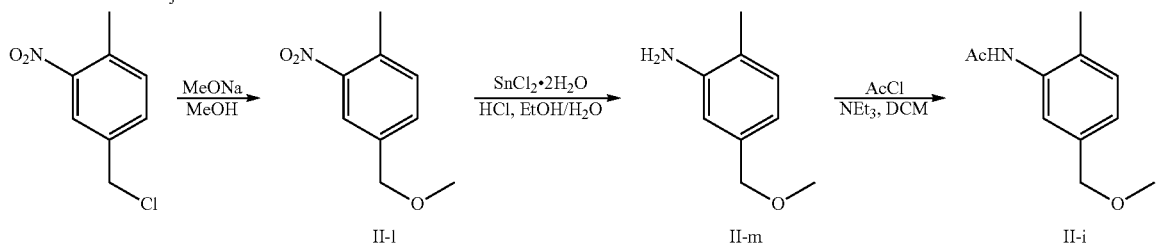

Synthesis of intermediate II-a: 2-Bromo-pyridine-4-carbaldehyde oxime

To a solution of 2-bromo-4-methylpyidine (10.0 g, 58.13 mmol) in dry THF (60 mL) under inert atmosphere were added successivelly dropwise at −10° C. tert-butylnitrite (12.5 mL, 104.63 mmol) and a solution of KOtBu in dry THF (88 mL, 87.20 mmol). The reaction mixture was stirred at −10° C. for 3 h. Then, a saturated solution of $NH_4Cl$ was added and a solution of HCl (4N) was added until pH=6-7. The crude product was extracted with EtOAc (2 times) and the organic layer was washed with water, then with a saturated solution of NaCl, dried over $MgSO_4$ and concentrated to give II-a as yellow oil in 90% yield. The crude product was directly engaged in the next step. $^1H$ NMR (300 MHz, DMSO-$d_6$) δ 12.47 (s, 1H), 8.49 (d, J=5.1 Hz, 1H), 8.12 (s, 1H), 7.90 (dd, J=5.1, 1.0 Hz, 1H), 7.55 (s, 1H).

Synthesis of intermediate II-b: 2-Bromo-pyridine-4-carbaldehyde

To a suspension of II-a (10.5 g, 52.23 mmol) in water (50 mL) were added successively dropwise at −10° C. concentrated solution of HCl (50 mL) and a solution of formaldehyde (50 mL) in water (37% w/w). The reaction mixture was stirred at −10° C. for 4 h. Then, a solution of NaOH (2 N) was added until pH=6-7. The crude product was extracted with EtOAc (2 times) and the organic layer was washed with water, then with a saturated solution of NaCl, dried over $MgSO_4$ and concentrated to give II-b as brownish oil in 97% yield. $^1H$ NMR (300 MHz, DMSO-$d_6$) δ 10.03 (s, 1H), 8.68 (d, J=4.9 Hz, 1H), 8.07 (s, 1H), 7.84 (d, J=4.9 Hz, 1H).

Synthesis of intermediate II-c: 2-Bromo-4-oxazol-5-yl-pyridine

To a solution of II-b (9.4 g, 50.53 mmol) in MeOH (100 mL) were added successively $K_2CO_3$ (13.97 g, 101.06 mmol) and TosMIC (14.80 g, 75.8 mmol). The reaction mixture was stirred at room temperature for 16 h. Then, the solvent was removed under reduce pressure, water was added and the crude product was extracted with EtOAc (2 times), the organic layer was washed with water, then with a saturated solution of NaCl, dried over $MgSO_4$ and concentrated. The dark brown solid was triturated in cold ether, filtered and washed with more ether to get the final product II-c as pale brown solid in 73% yield. $^1H$ NMR (300 MHz, $CDCl_3$) δ 8.42 (d, J=5.2 Hz, 1H), 8.02 (s, 1H), 7.73 (s, 1H), 7.60 (s, 1H), 7.48 (dd, J=5.2, 1.3 Hz, 1H).

Synthesis of intermediate II-d: 2-Methylsulfanyl-1H-imidazole

To a solution of 2-mercaptoimidazole (5.0 g, 49.93 mmol) in water (200 mL) was added NaOH (2.4 g, 59.91 mmol). The reaction mixture was stirred at room temperature for 0.5 h. Then, acetone (200 mL) and MeI (3.4 mL, 54.92 mmol) were added. The reaction mixture was stirred at room temperature for 16 h. Then, the solvent was removed under reduce pressure, water was added and the crude product was extracted with EtOAc (5 times), the organic layer was washed with water, then with a saturated solution of NaCl, dried over $MgSO_4$ and concentrated. The orange solid was triturated several times with petroleum ether and filtered to give compound II-d as pale brown solid in 88% yield. $^1H$ NMR (300 MHz, DMSO-$d_6$) δ 12.16 (s, 1H), 7.14 (s, 1H), 6.91 (s, 1H), 2.50 (s, 3H).

Synthesis of intermediate II-e: 2-(2-Methylsulfanyl-imidazol-1-yl)-4-oxazol-5-yl-pyridine In a sealed tube were charged II-d (1.98 g, 17.33 mmol), II-c (3.0 g, 13.33 mmol), $K_2CO_3$ (3.87 g, 27.99 mmol), CuI (253 mg, 1.33 mmol), N,N'-dimethylcyclohexane-1,2-diamine (420 µL, 2.66 mmol) in dry toluene (19 mL). The reaction mixture was stirred at 110° C. for 4 days. Then, water was added and the crude product was extracted with EtOAc (2 times), the organic layer was washed with water, then with a saturated solution of NaCl, dried over $MgSO_4$ and concentrated. The brown solid was triturated in cold ether, filtered and washed with more ether to get the final product We as pale brown solid in 70% yield. $^1H$ NMR (300 MHz, DMSO-$d_6$) δ 8.67 (s, 1H), 8.60 (d, J=5.2 Hz, 1H), 8.13 (s, 1H), 7.97 (s, 1H), 7.96 (s, 1H), 7.70 (dd, J=5.2, 1.4 Hz, 1H), 7.15 (d, J=1.5 Hz, 1H), 2.52 (s, 3H).

Synthesis of intermediate II-f: 2-(2-Methanesulfonyl-imidazol-1-yl)-4-oxazol-5-yl-pyridine To a solution of II-e (2.17 g, 7.83 mmol) in DCM (260 mg) was added mCPBA (2.97 g, 17.23 mmol). The mixture was stirred at room temperature for 16 h. Then, a saturated solution of NaHCO$_3$ was added and the crude product was extracted with DCM (2 times) and the organic layer was washed with saturated solution of NaHCO$_3$ (3 times), with water, then with a saturated solution of NaCl, dried over MgSO$_4$ and concentrated. The final product was purified by silica gel chromatography using 5 to 10% MeOH/EtOAc as eluent to give II-f as solid in 84% yield. $^1$H NMR (300 MHz, DMSO-d$_6$) δ 8.69 (m, 2H), 8.14 (s, 1H), 8.06 (d, J=0.7 Hz, 1H), 8.00 (d, J=1.2 Hz, 1H), 7.89 (dd, J=5.2, 1.5 Hz, 1H), 7.38 (d, J=1.2 Hz, 1H), 3.53 (s, 3H).

Synthesis of intermediate II-g: 2-(2-Methoxy-imidazol-1-yl)-4-oxazol-5-yl-pyridine To a solution of II-f (600 mg, 2.07 mmol) in dry MeOH/THF (1/1, 6 mL) was added at 0° C. a solution of NaOMe in MeOH (6.2 mL, 3.10 mmol). The reaction mixture was stirred at 50° C. for 16 h. Water was added and the crude product was extracted with EtOAc (2 times) and the organic layer was washed with water, then with a saturated solution of NaCl, dried over MgSO$_4$ and concentrated to give compound II-g as pale brown solid in 98% yield. $^1$H NMR (300 MHz, DMSO-d$_6$) δ 8.66 (s, 1H), 8.58 (d, J=5.3 Hz, 1H), 8.11 (s, 1H), 8.03 (s, 1H), 7.68 (dd, J=5.2, 1.4 Hz, 1H), 7.51 (d, J=1.9 Hz, 1H), 6.70 (d, J=1.9 Hz, 1H), 4.09 (s, 3H).

Synthesis of intermediate II-h: 4-(2-Chloro-oxazol-5-yl)-2-(2-methoxy-imidazol-1-yl)-pyridine To a solution of intermediate II-g (366 mg, 1.51 mmol) in dry THF (15 mL) under inert atmosphere was added dropwise at −78° C. a solution of LiHMDS in dry THF (2.3 mL, 2.27 mmol). The reaction mixture was stirred at −78° C. for 0.5 h. Then, C$_2$Cl$_6$ (537 mg, 2.27 mmol) was added at −78° C. and the reaction mixture was stirred at room temperature for 16 h. Water was added and the crude product was extracted with EtOAc (2 times), the organic layer was washed with water, then with a saturated solution of NaCl, dried over MgSO$_4$ and concentrated. The final product was purified by silica gel chromatography using 0 to 10% MeOH/EtOAc as eluent to give intermediate II-h as white solid in 74% yield. $^1$H NMR (300 MHz, CDCl$_3$) δ 8.51 (dd, J=5.2, 0.8 Hz, 1H), 7.95 (dd, J=1.4, 0.8 Hz, 1H), 7.55 (s, 1H), 7.52 (d, J=1.9 Hz, 1H), 7.33 (dd, J=5.2, 1.5 Hz, 1H), 6.75 (d, J=2.0 Hz, 1H), 4.21 (s, 3H).

Synthesis of intermediate II-l: 4-Methoxymethyl-1-methyl-2-nitro-benzene

To a solution of NaOMe (1.6 g, 29.63 mmol) in dry MeOH (40 mL) under inert atmosphere was added 4-chloromethyl-1-methyl-2-nitro-benzene (5.0 g, 26.94 mmol). The reaction mixture was stirred at room temperature for 16 h. Water was added and EtOH was removed under reduced pressure. The crude product was extracted with DCM (2 times) and the organic layer was washed with water, then with a saturated solution of NaCl, dried over MgSO$_4$ and concentrated to give intermediate II-l as yellow oil. $^1$H NMR (300 MHz, CDCl$_3$) δ 7.94 (s, 1H), 7.47 (d, J=7.8 Hz, 1H), 7.32 (d, J=7.8 Hz, 1H), 4.48 (s, 2H), 3.41 (s, 3H), 2.58 (s, 3H).

Synthesis of intermediate II-m: 5-Methoxymethyl-2-methyl-phenylamine

To a solution of intermediate II-l (4.77 g, 26.32 mmol) in EtOH/H$_2$O: 9/1 (150 mL) were added successively, SnCl$_2$.2H$_2$O (29.70 g, 131.60 mmol) and hydrochloric acid 37% (15 mL) dropwise. The reaction mixture was stirred at room temperature for 16 h. EtOH was removed under reduced pressure and to the resulting aqueous solution was added a solution of NaOH (10 N) until pH=6-7. Then, the crude product was extracted with DCM (2 times) and the organic layer was washed with water, then with a saturated solution of NaCl, dried over MgSO$_4$ and concentrated. The final product was purified by silica gel chromatography using 0 to 30% EtOAc/cyclohexane as eluent to give intermediate II-m as yellow oil. $^1$H NMR (300 MHz, DMSO-d$_6$) δ 6.88 (d, J=7.5 Hz, 1H), 6.58 (s, J=17.6 Hz, 1H), 6.41 (d, J=7.5 Hz, 1H), 4.80 (s, 2H), 4.24 (s, 2H), 3.23 (s, 3H), 2.03 (s, 3H).

Synthesis of intermediate II-i: N-(5-Methoxymethyl-2-methyl-phenyl)-acetamide To a solution of II-m (2.0 g, 13.23 mmol) in dry DCM (45 mL) was added successively dry NEt$_3$ (2.3 mL, 15.88 mmol) and at 0° C. AcCl (1.0 mL, 14.55 mmol) dropwise. The reaction mixture was stirred at room temperature for 2 h. Water was added and the crude product was extracted with DCM (2 times) and the organic layer was washed with water, then with a saturated solution of NaCl, dried over MgSO$_4$ and concentrated. The final product was purified by silica gel chromatography using 50 to 80% EtOAc/cyclohexane as eluent to give intermediate II-i as pale yellow solid in 88% yield over the 3 steps. $^1$H NMR (300 MHz, DMSO-d$_6$) δ 9.27 (s, 1H), 7.36 (s, 1H), 7.16 (d, J=7.7 Hz, 1H), 7.00 (d, J=7.6 Hz, 1H), 4.34 (s, 2H), 3.26 (s, 3H), 2.18 (s, 3H), 2.05 (s, 4H).

Synthesis of intermediate II-j: {5-[2-(2-Methoxy-imidazol-1-yl)-pyridin-4-yl]-oxazol-2-yl}-(5-methoxymethyl-2-methyl-phenyl)-amine To a solution of NaH 60% dispersion in mineral oil (237 mg, 6.16 mmol) in dry DMF (20 mL) was added dropwise at 0° C. a solution of intermediate II-i (595 mg, 3.08 mmol) in dry DMF (20 mL). The reaction mixture was stirred at room temperature for 1 h and a solution of intermediate II-h (852 mg, 3.08 mmol) in dry DMF (20 mL) was added dropwise at 0° C. The reaction mixture was stirred for 3 h at 0° C. Water was added and the crude product was extracted with EtOAc (2 times), the organic layer was washed with a saturated solution of NaHCO$_3$ (3 times), then with a saturated solution of NaCl, dried over MgSO₄ and concentrated. The final product was purified by silica gel chromatography using 0 to 20% EtOAc/cyclohexane as eluent to give intermediate II-j as white solid in 44% yield. ¹H NMR (300 MHz, DMSO-d₆) δ 9.65 (s, 1H), 8.45 (d, J=5.3 Hz, 1H), 7.86 (s, 1H), 7.79 (s, 1H), 7.72 (s, 1H), 7.46 (dd, J=5.1, 3.6 Hz, 2H), 7.21 (d, J=7.7 Hz, 1H), 7.00 (d, J=7.7 Hz, 1H), 6.68 (d, J=1.8 Hz, 1H), 4.38 (s, 2H), 4.05 (s, 3H), 3.28 (s, 3H), 2.29 (s, 3H).

Synthesis of example 215: 1-{4-[2-((5-Methoxymethyl)-2-methyl-phenylamino)-oxazol-5-yl]-pyridin-2-yl}-1,3-dihydro-imidazol-2-one hydrochloride To a solution of II-j (100 mg, 0.26 mmol) in dry dioxane (4 mL) was added dropwise at 0° C. a solution of HCl in dry ether (546 μL, 0.55 mmol). The reaction mixture was stirred at 60° C. for 2 h and at room temperature for 16 h. Then, the solvent was removed under reduce pressure, the crude product was triturated with ether and filtrated to give compound 215 as white solid in 57% yield. ¹H NMR (300 MHz, CD₃OD) δ 10.04-9.95 (m, 1H), 9.46 (s, 1H), 9.15 (s, 1H), 9.03 (d, J=4.6 Hz, 1H), 8.95-8.87 (m, 1H), 8.78 (d, J=7.8 Hz, 1H), 8.19 (d, J=3.2 Hz, 1H), 6.04 (s, 2H), 4.97 (s, 3H), 3.91 (s, 3H).

Example 216

Synthetic Approach of Compound 216

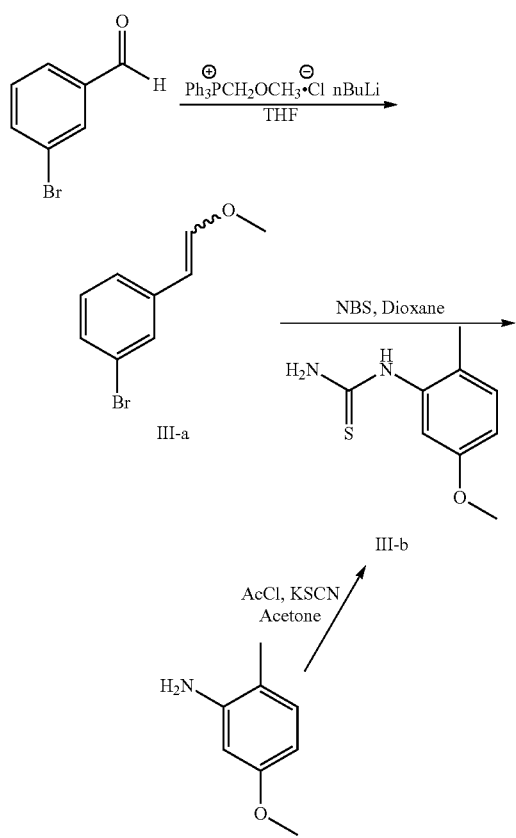

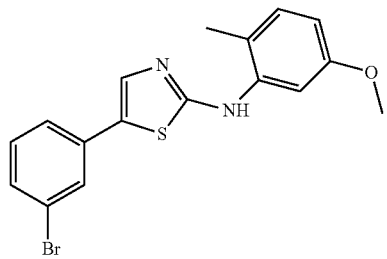

III-c

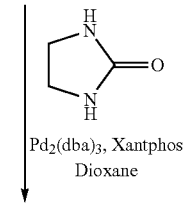

Pd₂(dba)₃, Xantphos
Dioxane

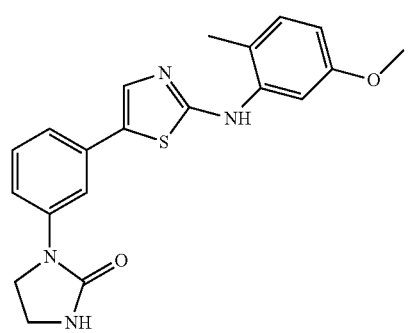

216

Synthesis of intermediate III-a:
1-Bromo-3-(2-methoxy-vinyl)-benzene

To a solution of (methoxymethyl)triphosphonium chloride (5.56 g, 16.21 mmol) in dry THF (13 mL) under inter atmosphere was added dropwise at 0° C. a solution of nBuLi in dry THF (22 mL, 21.62 mmol). The reaction mixture was stirred at room temperature for 1 h. Then, a solution of 3-bromobenzaldehyde (2.0 g; 10.81 mmol) in dry THF (20 mL) was added dropwise at 0° C. The reaction mixture was stirred at room temperature for 16 h. A saturated solution of NH₄Cl was added and the crude product was extracted with EtOAc (2 times) and the organic layer was washed with water, then with a saturated solution of NaCl, dried over MgSO₄ and concentrated. The final product was purified by silica gel chromatography using 10 to 15% EtOAc/cyclohexane as eluent to give III-a as yellow oil in 66% yield. ¹H NMR (300 MHz, CDCl₃) δ 7.79 (s, J=1.5 Hz, 1H), 7.48-7.24 (m, 5H), 7.20-7.12 (m, 2H), 7.06 (d, J=13.0 Hz, 1H), 6.19 (d, J=7.0 Hz, 1H), 5.75 (d, J=13.0 Hz, 1H), 5.17 (d, J=7.0 Hz, 1H), 3.82 (s, 3H), 3.71 (s, 3H).

Synthesis of intermediate III-b: (5-Methoxy-2-methyl-phenyl)-thiourea

To a solution of KSCN (780 mg, 8.02 mmol) in acetone (10 mL) was added dropwise at room temperature as solution of AcCl (900 µL, 8.02 mmol) in acetone (10 mL). The reaction mixture was stirred for 15 min at 50° C. Then, a solution of 5-methoxy-2-methylaniline (1.0 g, 7.29 mmol) in acetone (10 mL) was added and the reaction mixture was stirred at 50° C. for 15 min. Water was added and the solid was filtered, washed with more water and ether to give a white solid. A solution of the latter with K$_2$CO$_3$ (2.0 g, 14.58 mmol) in MeOH (20 mL) was stirred at room temperature for 3 h. MeOH was removed under reduced pressure and the solid was washed with water and ether to give III-b as a white solid in 78% yield. $^1$H NMR (300 MHz, DMSO-d$_6$) δ 9.20 (s, 1H), 7.13 (d, J=8.4 Hz, 1H), 6.81 (d, J=2.4 Hz, 1H), 6.75 (dd, J=8.3, 2.6 Hz, 1H), 3.71 (s, 3H), 2.10 (s, 3H).

Synthesis of intermediate III-c: [5-(3-Bromo-phenyl)-thiazol-2-yl]-(5-methoxy-2-methyl-phenyl)-amine To a solution of III-a (300 mg, 1.41 mmol) in dioxane/water (1/1, 6 mL) was added NBS (276 mg, 1.55 mmol). The reaction mixture was stirred at room temperature for 1 h. Then, III-b (277 mg, 1.41 mmol) was added and the reaction mixture was stirred at 80° C. for 16 h. Water followed by saturated solution of NH$_4$Cl were added and the crude product was extracted with EtOAc (2 times) and the organic layer was washed with water, then with a saturated solution of NaCl, dried over MgSO$_4$ and concentrated. The final product was purified by silica gel chromatography using 0 to 35% EtOAc/cyclohexane as eluent to give III-c as pale yellow solid in 69% yield. $^1$H NMR (300 MHz, DMSO-d$_6$) δ 9.48 (s, 1H), 7.77-7.69 (m, 2H), 7.54 (d, J=2.1 Hz, 1H), 7.46 (dd, J=7.6, 0.9 Hz, 1H), 7.40 (dd, J=7.9, 1.0 Hz, 1H), 7.30 (t, J=7.9 Hz, 1H), 7.11 (d, J=8.3 Hz, 1H), 6.60 (dd, J=8.3, 2.5 Hz, 1H), 3.71 (s, 3H), 2.19 (s, 3H).

Synthesis of example 216: 1-{3-[2-(5-Methoxy-2-methyl-phenylamino)-thiazol-5-yl]-phenyl}-imidazolidin-2-one In a sealed tube, to a solution of III-c (200 mg, 0.53 mmol) in dry dioxane (10 mL) were added successively 2-imidazolidinone (275 mg, 3.20 mmol), cesium carbonate (432 mg, 1.33 mmol), Pd$_2$(dba)$_3$ (46 mg, 0.05 mmol), 4,5-Xantphos (61 mg, 0.11 mmol). The reaction mixture was stirred at 110° C. for 16 h. Water was added and the crude product was extracted with EtOAc (2 times) and the organic layer was washed with water, then with a saturated solution of NaCl, dried over MgSO$_4$ and concentrated. The final product was purified by silica gel chromatography using 0 to 30% MeOH/EtOAc as eluent to give compound 216 as yellow solid in 41% yield. $^1$H NMR (300 MHz, DMSO-d$_6$) δ 9.36 (s, 1H), 7.75 (s, 1H), 7.63-7.56 (m, 2H), 7.37 (d, J=8.2 Hz, 1H), 7.29 (t, J=7.9 Hz, 1H), 7.15 (d, J=7.5 Hz, 1H), 7.11 (d, J=8.4 Hz, 1H), 7.01 (s, 1H), 6.59 (dd, J=8.3, 2.6 Hz, 1H), 3.93-3.83 (m, 2H), 3.72 (s, 3H), 3.44-3.37 (m, 2H), 2.20 (s, 3H).

Example 217

Synthetic Approach of Example 217

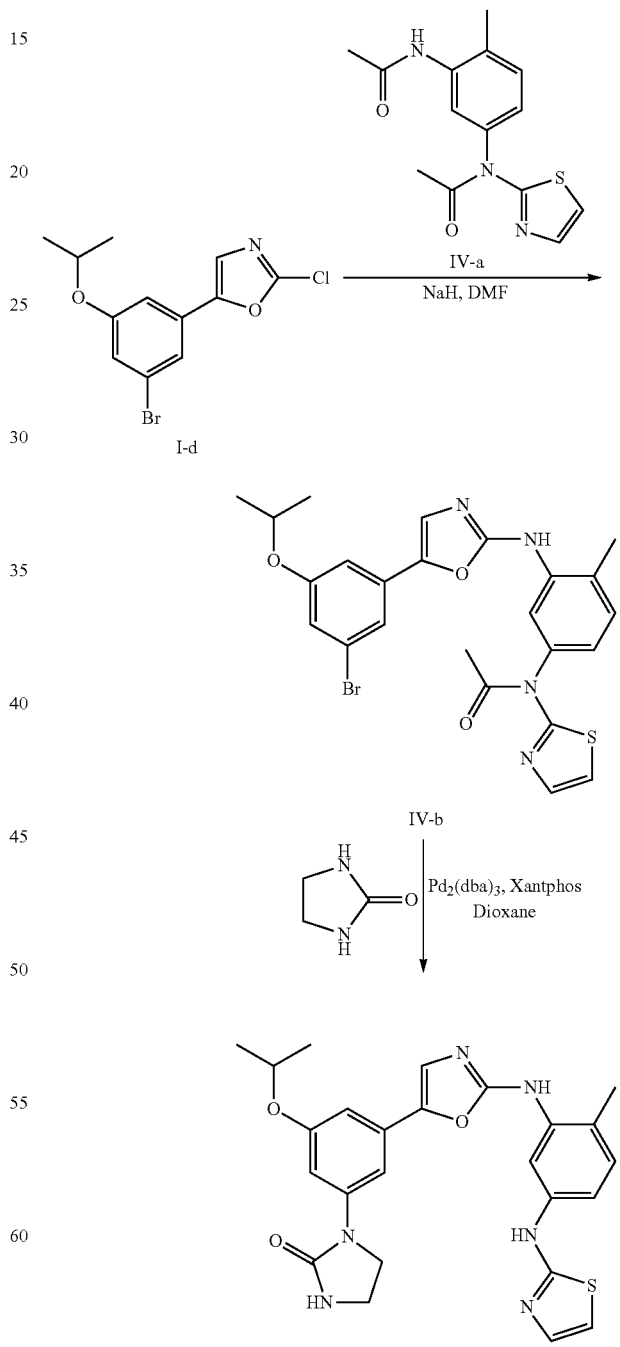

Synthetic Approach of Intermediate IV-a

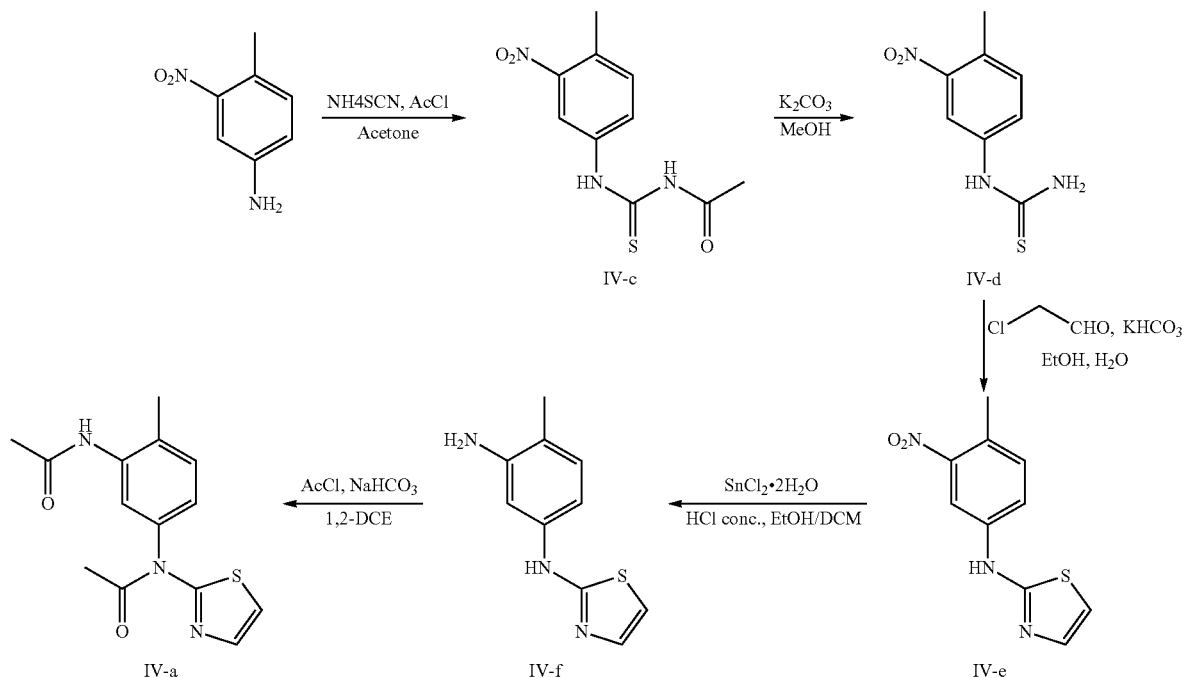

Synthesis of intermediate IV-c: 1-Acetyl-3-(4-methyl-3-nitro-phenyl)-thiourea To a solution of ammonium thiocyanate (1.05 g, 13.85 mmol) in acetone (21 mL) was added dropwise acetyl chloride (0.90 mL 12.70 mmol). The reaction mixture was stirred at 40° C. for 30 min. Then, a solution of 4-methyl-3-nitroaniline (1.76 g, 11.54 mmol) in acetone (7 mL) was added and the reaction mixture was stirred at room temperature for 4 h. The reaction mixture was poured into ice-water and the precipitate was filtered, washed with more water and cyclohexane to give compound IV-c as brown solid in 50% yield. (300 MHz, DMSO) δ 12.45 (s, 1H), 11.53 (s, 1H), 8.38 (d, J=2.0 Hz, 1H), 7.69 (dd, J=8.3, 2.0 Hz, 1H), 7.43 (d, J=8.3 Hz, 1H), 2.44 (s, 3H), 2.09 (s, 3H).

Synthesis of intermediate IV-d: (4-Methyl-3-nitro-phenyl)-thiourea

To a solution of IV-c (873 mg, 3.45 mmol) in methanol (5 mL) was added $K_2CO_3$ (953 mg, 6.90 mmol). The reaction mixture was stirred at room temperature for 16 h. Then, the solvent was removed under reduce pressure, water was added and the crude product was extracted with EtOAc (twice), the organic layer was washed with water, then with a saturated solution of NaCl, dried over $MgSO_4$, and concentrated. The final product was purified by silica gel chromatography using 0 to 50% EtOAc/cyclohexane as eluent to give compound IV-d as yellow solid in 60% yield. (300 MHz, DMSO) δ 9.95 (s, 1H), 8.28 (d, J=2.1 Hz, 1H), 8.00-7.70 (m, 3H), 7.42 (d, J=8.3 Hz, 1H), 2.47 (s, 3H).

Synthesis of intermediate IV-e: (4-Methyl-3-nitro-phenyl)-thiazol-2-yl-amine To a suspension of IV-d (377 mg, 1.79 mmol) in EtOH (7 mL) were added a solution of chloroacetaldehyde ((1.41 g, 17.93 mmol) in water (50% w/w) and $KHCO_3$ (539 mg, 5.37 mmol). The reaction mixture was stirred at 70° C. for 16 h. Then, the solvent was removed under reduce pressure, water was added and the crude product was extracted with EtOAc (3 times), the organic layer was washed with water, then with a saturated solution of NaCl, dried over $MgSO_4$, and concentrated. The final product was purified by silica gel chromatography using 0 to 70% EtOAc/cyclohexane as eluent to give compound IV-e as yellow solid in 40% yield. (300 MHz, DMSO) δ 10.58 (s, 1H), 8.55 (d, J=2.4 Hz, 1H), 7.69 (dd, J=8.4, 2.4 Hz, 1H), 7.41 (d, J=8.5 Hz, 1H), 7.33 (d, J=3.7 Hz, 1H), 7.00 (d, J=3.7 Hz, 1H), 2.45 (s, 3H).

Synthesis of intermediate IV-f: 4-Methyl-N1-thiazol-2-yl-benzene-1,3-diamine To a solution of IV-e (737 mg, 3.13 mmol) in EtOH/DCM: (30/13 mL) were added successively, $SnCl_2.2H_2O$ (3.54 g, 15.65 mmol) and hydrochloric acid 37% (3 mL) dropwise. The reaction mixture was stirred at room temperature for 16 h. EtOH was removed under reduced pressure and to the resulting aqueous solution was added a solution of NaOH (10 N) until pH=6-7. Then, the crude product was extracted with DCM (twice) and the organic layer was washed with water, then with a saturated solution of NaCl, dried over $MgSO_4$ and concentrated. The final product was purified by silica gel chromatography using 0 to 30% EtOAc/cyclohexane as eluent to give intermediate IV-f as yellow oil in 95% yield. (300 MHz, DMSO) δ 9.74 (s, 1H), 7.18 (d, J=3.7 Hz, 1H), 6.90 (d, J=2.0 Hz, 1H), 6.85-6.77 (m, 2H), 6.66 (dd, J=8.0, 2.0 Hz, 1H), 4.83 (brs, 2H), 1.99 (s, 3H).

Synthesis of intermediate IV-a: N-[5-(Acetyl-thiazol-2-yl-amino)-2-methyl-phenyl]-acetamide To a solution of IV-f (610 mg, 2.97 mmol) and $NaHCO_3$ (2.50 g, 29.71 mmol) in dry DCE (10 mL), was added dropwise at 0° C. actyl chloride (0.634 mL, 8.91 mmol). The reaction mixture was stirred at 50° C. for 5 h. Then, water was added and the crude product was extracted with DCM (3 times) and the organic layer was washed with water, then with a saturated solution of NaCl, dried over MgSO$_4$ and concentrated. The final product was purified by silica gel chromatography using 30% EtOAc/cyclohexane as eluent to give intermediate IV-a as yellow solid in 75% yield. (300 MHz, DMSO) δ 9.39 (s, 1H), 7.54 (d, J=1.7 Hz, 1H), 7.40-7.32 (m, 2H), 7.29 (d, J=3.6 Hz, 1H), 7.13 (dd, J=7.9, 1.9 Hz, 1H), 2.28 (s, 3H), 2.07 (s, 3H), 1.99 (s, 3H).

Synthesis of intermediate IV-b: N-{3-[5-(3-Bromo-5-isopropoxy-phenyl)-oxazol-2-ylamino]-4-methyl-phenyl}-N-thiazol-2-yl-acetamide To a solution of NaH 60% dispersion in mineral oil (83 mg, 2.08 mmol) in dry DMF (3 mL) was added dropwise at 0° C. a solution of intermediate IV-a (300 mg, 1.04 mmol) in dry DMF (3 mL). The reaction mixture was stirred at room temperature for 1 h and a solution of intermediate I-d (328 mg, 1.04 mmol) in dry DMF (3 mL) was added dropwise at 0° C. The reaction mixture was stirred for 16 h at room temperature. Water was added and the crude product was extracted with EtOAc (twice), the organic layer was washed with a saturated solution of NaHCO$_3$ (3 times), then with a saturated solution of NaCl, dried over MgSO$_4$ and concentrated. The final product was purified by silica gel chromatography using 0 to 35% EtOAc/cyclohexane as eluent to give intermediate IV-b as beige solid in 46% yield. (300 MHz, DMSO) δ 9.63 (s, 1H), 8.08 (d, J=2.1 Hz, 1H), 7.65 (s, 1H), 7.47 (d, J=2.2 Hz, 1H), 7.45 (d, J=2.5 Hz, 1H), 7.42-7.38 (m, 2H), 7.19 (t, J=2.0 Hz, 1H), 7.15 (dd, J=7.9, 2.2 Hz, 1H), 7.11 (t, J=2.0 Hz, 1H), 4.78 (septuplet, J=5.8 Hz, 1H), 2.49 (s, 3H), 2.14 (s, 3H), 1.37 (d, J=6.0 Hz, 6H).

Synthesis of example 217: 1-(3-Isopropoxy-5-{2-[2-methyl-5-(thiazol-2-ylamino)-phenylamino]-oxazol-5-yl}-phenyl)-imidazolidin-2-one In a sealed tube, to a solution of IV-b (219 mg, 0.42 mmol) in dry dioxane (5 mL) were added successively imidazolidin-2-one (286 mg, 3.36 mmol), cesium carbonate (162 mg, 0.50 mmol), Pd$_2$(dba)$_3$ (11 mg, 0.01 mmol), and Xantphos (24 mg, 0.04 mmol). The reaction mixture was stirred at 110° C. for 16 h. Water was added, the crude product was extracted with EtOAc (twice) and the organic layer was washed with water, then with a saturated solution of NaCl, dried over MgSO$_4$ and concentrated. The final product was purified by silica gel chromatography using 50 to 100% EtOAc/cyclohexane as eluent to give compound 217 as beige solid in 49% yield. (300 MHz, DMSO) δ 10.12 (brs, 1H), 9.25 (s, 1H), 8.04 (d, J=2.1 Hz, 1H), 7.42 (s, 1H), 7.38 (dd, J=8.3, 2.1 Hz, 1H), 7.25 (brs, 1H), 7.19 (d, J=3.7 Hz, 1H), 7.15 (t, J=1.9 Hz, 1H), 7.10 (d, J=8.4 Hz, 1H), 7.01 (s, 1H), 6.85 (d, J=3.6 Hz, 1H), 6.81 (s, 1H), 4.61 (m, 1H), 3.84 (m, 2H), 3.38 (m, 2H), 2.23 (s, 3H), 1.27 (d, J=6.0 Hz, 6H).

(ESI+) m/z 491 (M+H)$^+$
Retention time=3.13 min (method 2)

Example 218

Synthetic Approach of Example 218

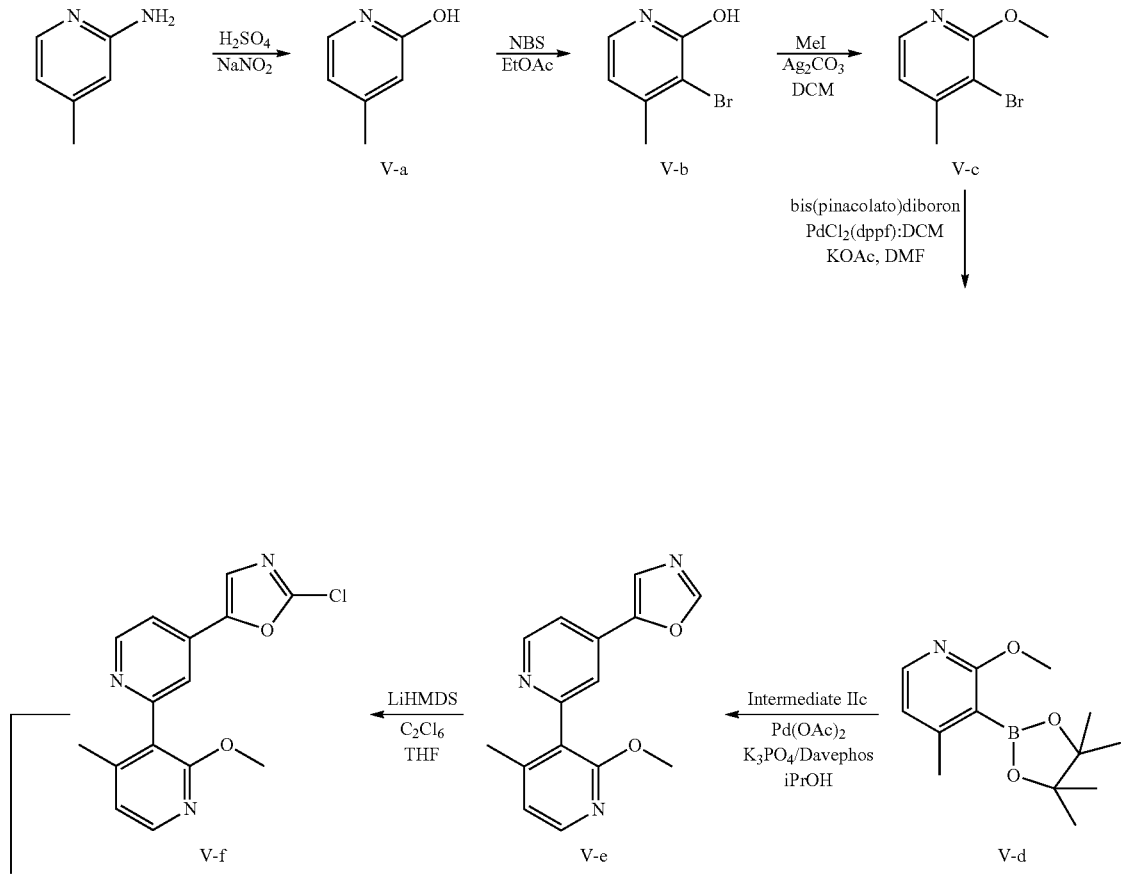

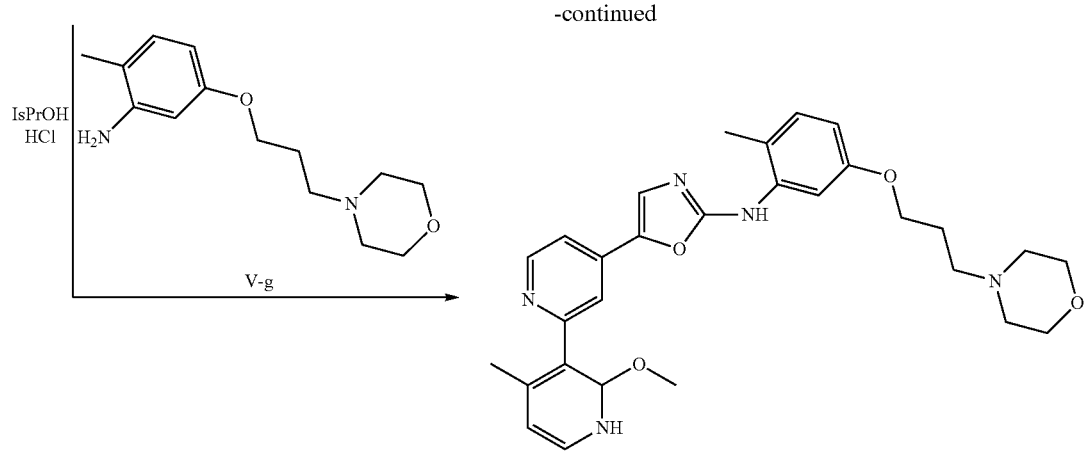

Synthetic Approach of Intermediate V-h

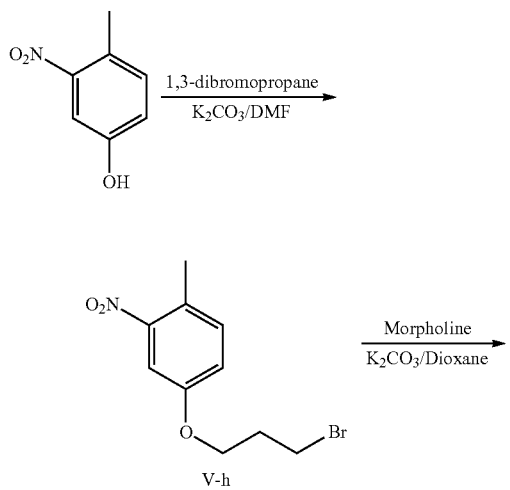

Synthesis of intermediate V-a: 4-Methyl-pyridin-2-ol

Intermediate V-a was prepared using the method of Adger et al, in *J. Chem. Soc. Perkin Trans.* 1, 1988, p2791-2796. A 1L flask containing water (240 mL) was treated with conc. $H_2SO_4$ (32 mL) and cooled to 0° C. then treated with the 2-amino-4-picoline in one portion (30 g, 277 mmol). A solution of $NaNO_2$ (20.6 g, 299 mmol) in water (40 mL) was added dropwise over 1 h such that the internal temperature never rose above 5° C. The reaction was stirred at 0° C. for 1 h then heated to 95° C. and after 15 min at this temperature cooled to room temperature. The solution was taken to pH 6-7 with 50% NaOH aq (exotherm) and extracted whilst hot with EtOAc (4×120 mL). The combined organics were dried ($MgSO_4$), filtered and evaporated to afford a beige crystalline solid (24.5 g, 81%) of intermediate V-a. $^1$H NMR (300 MHz, DMSO-$d_6$) δ 11.31 (s, 1H), 7.23 (d, J=6.7 Hz, 1H), 6.10 (s, 1H), 6.00 (dd, J=6.7, 1.2 Hz, 1H), 2.10 (s, 3H).

Synthesis of intermediate V-b: 3-Bromo-4-methyl-pyridin-2-ol

A solution of 4-methyl-pyridin-2-ol V-a (25 g, 229 mmol) in glacial acetic acid (350 mL) and EtOAc (680 mL) was treated with NBS (37.4 g, 210 mmol) and stirred at room temperature for 30 min. The mixture was then taken to pH 8 with aqueous ammonia and extracted with EtOAc. The separated organics were washed with 1:1 $H_2O$/brine then dried ($MgSO_4$), filtered and evaporated before purification by silica column chromatography (1-4% EtOH/DCM) to afford the desired product V-b as a white solid (8.66 g). $^1$H NMR (300 MHz, DMSO) δ 11.90 (s, 1H), 7.32 (d, J=6.6 Hz, 1H), 6.19 (d, J=6.6 Hz, 1H), 2.25 (s, 3H).

Synthesis of intermediate V-c: 3-Bromo-2-methoxy-4-methyl-pyridine

A solution of 3-bromo-4-methyl-2-pyridone V-b (2.20 g, 11.7 mmol), in DCM (80 mL) was treated with MeI (7.29 mL, 117 mmol) and $Ag_2CO_3$ (6.47 g, 23.5 mmol). The flask was stoppered and stirred under argon for 6 days. The mixture was filtered and purified by column chromatography ($SiO_2$, 10% EtOAc in cyclohexane) to afford the desired product V-c as a clear mobile oil (1.83 g, 80%). $^1$H NMR (300 MHz, $CDCl_3$) δ 7.94 (d, J=5.0 Hz, 1H), 6.77 (d, J=5.1 Hz, 1H), 4.00 (s, 3H), 2.39 (s, 3H).

Synthesis of intermediate V-d: 2-Methoxy-4-methyl-3-(4,4,5,5-tetramethyl-[1,3,2]dioxaborolan-2-yl)-pyridine A dry sealed tube under argon was charged with 3-bromo-2-methoxy-4-methylpyridine V-c (813 mg, 4.02 mmol), bis(pinacolato)diboron (1.12 g, 4.41 mmol), PdCl$_2$(dppf):DCM (146 mg, 0.20 mmol), KOAc (1.18 g, 12.0 mmol) and dry DMF (10 mL). After 1.5 h at 100° C., the mixture was cooled to room temperature and a further portion of catalyst (75 mg, 0.092 mmol) was added. The tube was sealed and the mixture stirred at 100° C. overnight. The mixture was cooled, the solvent evaporated and the mixture taken up in DCM before washing with water. The separated organics were dried (MgSO$_4$), filtered and evaporated before purification by column chromatography (SiO$_2$, 10% to 20% EtOAc in cyclohexane) to afford the intermediate V-d as a mobile yellow oil (2.14 g, 51%). $^1$H NMR (300 MHz, CDCl$_3$) δ 8.00 (d, J=5.3 Hz, 1H), 6.65 (d, J=5.3 Hz, 1H), 3.89 (s, 3H), 2.33 (s, 3H), 1.40 (d, J=11.1 Hz, 12H).

Synthesis of intermediate V-e: 2'-Methoxy-4'-methyl-4-oxazol-5-yl-[2,3']bipyridinyl An oven-dried flask under argon was charged with the 2-bromo-4-oxazol-5-yl-pyridine (Intermediate II-c, 461 mg, 2.07 mmol), 2-methoxy-4-methyl-3-(4,4,5,5-tetramethyl-[1,3,2]dioxaborolan-2-yl)-pyridine V-d (510 mg, 2.07 mmol), K$_3$PO$_4$ (2.82 g, 13.3 mmol), Pd(OAc)$_2$ (51 mg, 0.225 mmol), Davephos (89 mg, 0.225 mmol) in iPrOH (5 mL) and water (3 mL). After 40 min at 100° C., the mixture was cooled to room temperature, diluted with water and extracted with EtOAc then washed with brine. The organics were dried (MgSO$_4$), filtered and evaporated before purification by column chromatography (SiO$_2$, 30% to 100% EtOAc in cyclohexane) to afford the desired product V-e as an off-white solid (240 mg, 43%). $^1$H NMR (300 MHz, CDCl$_3$) δ 8.78 (d, J=4.8 Hz, 1H), 8.10 (d, J=4.8 Hz, 1H), 8.01 (s, 1H), 7.59 (d, J=4.9 Hz, 2H), 7.51 (d, J=4.9 Hz, 1H), 6.86 (d, J=4.9 Hz, 1H), 3.88 (s, 3H), 2.16 (s, 3H).

Synthesis of intermediate V-f: 4-(2-Chloro-oxazol-5-yl)-4'-methyl-1'H-[2,3']bipyridinyl-2'-one 4-(2-Chloro-oxazol-5-yl)-4'-methyl-1'H-[2,3]bipyridinyl-2'-one V-f was prepared as for I-d above from 4'-methyl-4-oxazol-5-yl-1H-[2,3']bipyridinyl-2'-one V-e (467 mg, 1.74 mmol) using LiHMDS (1M in THF, 2.62 mL, 2.62 mmol) and C$_2$Cl$_6$ (496 mg, 2.10 mmol) in dry THF. The crude product was purified by column chromatography (SiO$_2$; eluting with 30% to 50% EtOAc in cyclohexane) to afford the intermediate V-f as white solid (261 mg, 50%). $^1$H NMR (300 MHz, DMSO-d$_6$) δ 8.76 (d, J=5.3 Hz, 1H), 8.12 (d, J=4.4 Hz, 2H), 7.70 (s, 1H), 7.64 (dd, J=5.2, 1.7 Hz, 1H), 7.00 (d, J=5.2 Hz, 1H), 3.78 (s, 3H), 2.06 (s, 3H).

Synthesis of intermediate V-h: 4-(3-Bromo-propoxy)-1-methyl-2-nitro-benzene

A solution of 4-methyl-3-nitrophenol (1.00 g, 6.53 mmol) in DMF (6 mL) was treated with K$_2$CO$_3$ (0.903 g, 6.53 mmol) and 1,3-dibromopropane (6.63 mL, 65.3 mmol) and heated to 100° C. for 2.5 h. The cooled mixture was diluted with water and extracted with DCM. The combined organics were dried (MgSO$_4$), filtered and evaporated before purification by column chromatography (SiO$_2$; eluting with 20% EtOAc in cyclohexane) to afford the desired product V-h as a mobile yellow oil (1.05 g, 59%). $^1$H NMR (300 MHz, CDCl$_3$) δ 7.52 (d, J=2.7 Hz, 1H), 7.23 (d, J=8.5 Hz, 1H), 7.06 (dd, J=8.5, 2.7 Hz, 1H), 4.14 (t, J=5.8 Hz, 2H), 3.60 (t, J=6.4 Hz, 2H), 2.53 (s, 3H), 2.40-2.24 (m, 2H).

Synthesis of intermediate V-i: 4-[3-(4-Methyl-3-nitro-phenoxy)-propyl]-morpholine A solution of the 4-(3-bromo-propoxy)-1-methyl-2-nitro-benzene V-h (500 mg, 1.82 mmol) in dry dioxane (30 mL) was treated with K$_2$CO$_3$ (1.01 g, 7.28 mmol) and morpholine (319 μl, 3.65 mmol) and heated to 100° C. for 6 h. The cooled mixture was diluted with water and extracted with DCM. The combined organics were dried (MgSO$_4$), filtered and evaporated before purification by column chromatography (SiO$_2$; eluting with 2% EtOH in DCM) to afford the desired product as a yellow-orange oil V-i (356 mg, 70%). $^1$H NMR (300 MHz, CDCl$_3$) δ 7.51 (d, J=2.7 Hz, 1H), 7.21 (d, J=8.5 Hz, 1H), 7.05 (dd, J=8.5, 2.7 Hz, 1H), 4.06 (t, J=6.3 Hz, 2H), 3.79-3.66 (m, 4H), 2.49 (dt, J=9.0, 5.1 Hz, 9H), 2.07-1.88 (m, 2H).

Synthesis of intermediate V-g: 2-Methyl-5-(3-morpholin-4-yl-propoxy)-phenylamine A solution of the 4-[3-(4-methyl-3-nitro-phenoxy)-propyl]-morpholine V-i (350 mg, 1.25 mmol) in 90% EtOH (15 mL) was treated with SnCl$_2$.H$_2$O (1.58 g, 6.24 mmol) and conc. HCl (1.04 mL, 12.5 mmol) and heated to reflux for 1 h. The cooled solution was concentrated under reduced pressure and taken to pH=8 with a saturated solution of NaHCO$_3$ then extracted with EtOAc. The combined organics were dried (MgSO$_4$), filtered and evaporated to the desired product V-g as a viscous yellow oil (306 mg, 98%). $^1$H NMR (300 MHz, CDCl$_3$) δ 6.92 (d, J=8.8 Hz, 1H), 6.30-6.24 (m, 2H), 3.96 (t, J=6.3 Hz, 2H), 3.76-3.69 (m, 4H), 3.58 (s, 2H), 2.57-2.42 (m, 6H), 2.09 (s, 3H), 1.93 (dt, J=13.3, 6.5 Hz, 3H).

Synthesis of example 218: 4'-Methyl-4-{2-[2-methyl-5-(3-morpholin-4-yl-propoxy)-phenylamino]-oxazol-5-yl}-1'H-[2,3']bipyridinyl-2'-one A solution of 4-(2-chloro-oxazol-5-yl)-4'-methyl-1'H-[2,3']bipyridinyl-2'-one V-f (50 mg, 0.159 mmol) in iPrOH (4 mL) was treated with 2-methyl-5-(3-morpholin-4-yl-propoxy)-phenylamine V-g (48 mg, 0.191 mmol) and HCl (2M in ether, 120 μL, 0.240 mmol) and heated to reflux for 18 h. The solution was treated with a further 150 μL of HCl (2M in ether, 150 μL, 0.300 mmol) and heated for a further 2 h. The mixture was cooled to room temperature then the solvent was evaporated under reduced pressure. The residue was treated with ether and the white precipitate was filtered off to afford the compound 218 (31 mg, 39%). $^1$H NMR (300 MHz, DMSO) δ 11.62 (s, 1H), 9.40 (s, 1H), 8.55 (d, J=5.3 Hz, 1H), 7.73 (s, 1H), 7.55-7.48 (m, 2H), 7.38 (dd, J=5.2, 1.7 Hz, 1H), 7.29 (d, J=6.7 Hz, 1H), 7.03 (d, J=8.8 Hz, 1H), 6.52 (dd, J=8.3, 2.5 Hz, 1H), 6.13 (d, J=6.7 Hz, 1H), 3.92 (t, J=6.4 Hz, 2H), 3.56-3.44 (m, 4H), 2.40-2.25 (m, 6H), 2.16 (s, 3H), 1.98 (s, 3H), 1.86-1.75 (m, 2H). ESI$^+$ MS m/z 502 (M+H)$^+$. Retention time=1.76 min (method 1).

Example 219

Synthetic Approach of Example 219

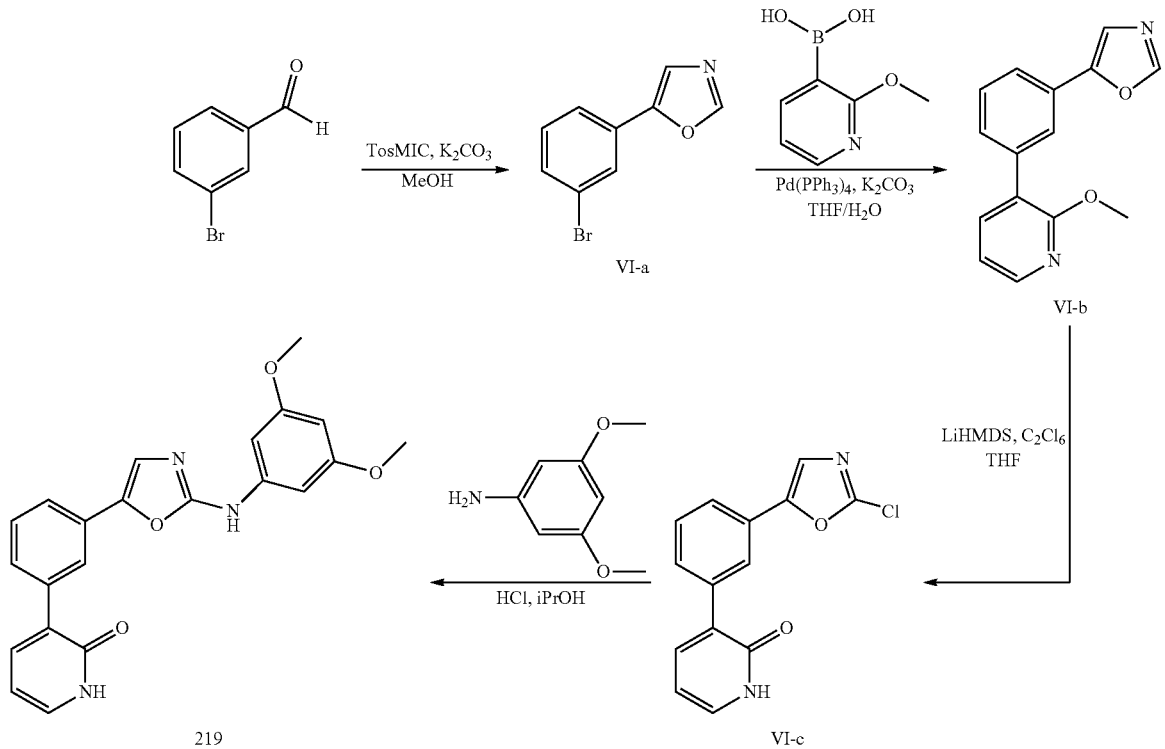

Synthesis of intermediate VI-a: 5-(3-Bromo-phenyl)-oxazole 5-(3-Bromo-phenyl)-oxazole VI-a was prepared as described for intermediate I-c using 3-Bromo-benzaldehyde (10 g, 54 mmol), TosMIC (12.7 g, 65 mmol) and $K_2CO_3$ (8.97 g) in MeOH to give the desired intermediate VI-a as a brownish solid (12.1 g, 100%). $^1$H NMR (300 MHz, CDCl$_3$) δ 7.92 (s, 1H), 7.80 (s, 1H), 7.57 (d, J=7.7 Hz, 1H), 7.46 (d, J=8.0 Hz, 1H), 7.37 (s, 1H), 7.29 (d, J=7.9 Hz, 1H).

Synthesis of intermediate VI-b: 2-Methoxy-3-(3-oxazol-5-yl-phenyl)-1,2-dihydro-pyridine A mixture of 5-(3-bromo-phenyl)-oxazole VI-a (1.33 g, 5.94 mmol), 2-methoxy-3-pyridinylboronic acid (1.00 g, 6.53 mmol), Pd(PPh$_3$)$_4$ and $K_2CO_3$ (1.81 g, 13.1 mmol) in THF (20 mL) and water (10 mL) was heated to reflux for 4 h. The mixture was cooled, then diluted with water and extracted with EtOAc. The combined organics were dried (MgSO$_4$), filtered and the residue purified by column chromatography (SiO$_2$; eluting with 30% EtOAc in cyclohexane) to afford the desired product VI-b as brown oil which crystallized on standing (1.37 g, 91%). $^1$H NMR (300 MHz, CDCl$_3$) δ 8.18 (dd, J=1.8, 5.0 Hz, 1H), 7.91 (s, 1H), 7.81 (s, 1H), 7.64 (d, J=6.9 Hz, 2H), 7.53-7.44 (m, 2H), 7.37 (s, 1H), 6.99 (dd, J=5.0, 7.2 Hz, 1H), 3.97 (s, 3H).

Synthesis of intermediate VI-c: 3-[3-(2-Chloro-oxazol-5-yl)-phenyl]-2-methoxy-1,2-dihydro-pyridine 3-[3-(2-Chloro-oxazol-5-yl)-phenyl]-2-methoxy-pyridine VI-c was prepared as for intermediate I-d above from 2-methoxy-3-(3-oxazol-5-yl-phenyl)-pyridine (1.37 g, 5.43 mmol), LiHMDS (1M in THF, 5.97 mL, 5.97 mmol) and $C_2Cl_6$ (1.54 g, 6.52 mmol) in dry THF (50 mL) to give the desired product VI-c as a white solid after purification by column chromatography (SiO$_2$; eluting with 10% to 30% EtOAc in cyclohexane) (1.24 g, 84%). $^1$H NMR (400 MHz, CDCl$_3$) δ 8.20 (dd, J=5.0, 1.9 Hz, 1H), 7.76 (t, J=1.6 Hz, 1H), 7.63 (dd, J=7.3, 2.0 Hz, 1H), 7.59-7.45 (m, 3H), 7.31 (s, 1H), 6.99 (dd, J=7.3, 5.0 Hz, 1H), 3.99 (s, 3H).

Synthesis of example 219: 3-{3-[2-(3,5-Dimethoxy-phenylamino)-oxazol-5-yl]-phenyl}-1H-pyridin-2-one 3-{3-[2-(3,5-Dimethoxy-phenylamino)-oxazol-5-yl]-phenyl}-1H-pyridin-2-one 219 was prepared as for intermediate I-f above from 3-[3-(2-chloro-oxazol-5-yl)-phenyl]-2-methoxy-pyridine VI-c (40 mg, 0.150 mmol) with 3,5-dimethoxyaniline (29 mg, 0.190 mmol) and HCl (2M in ether, 120 µL, 0.23 mmol) in iPrOH (4 mL). The crude reaction mixture was evaporated under reduced pressure and the residue treated with a saturated solution of NaHCO$_3$ and EtOAc. A precipitate formed from the biphasic mixture and was filtered off and dried to give the compound 219 product as a beige solid (19 mg, 33%). $^1$H NMR (300 MHz, DMSO-d$_6$) δ 11.86 (s, 1H), 10.35 (s, 1H), 7.96 (s, 1H), 7.70 (dd, J=2.0, 6.9 Hz, 1H), 7.60-7.41 (m, 5H), 6.89 (d, J=2.0 Hz, 2H), 6.32 (t, J=6.7 Hz, 1H), 6.13 (s, 1H), 3.73 (s, 6H). ESI$^+$ MS m/z 390 (M+H)$^+$. Retention time=3.45 min (method 1).

Example 220

Synthetic Approach of Example 220

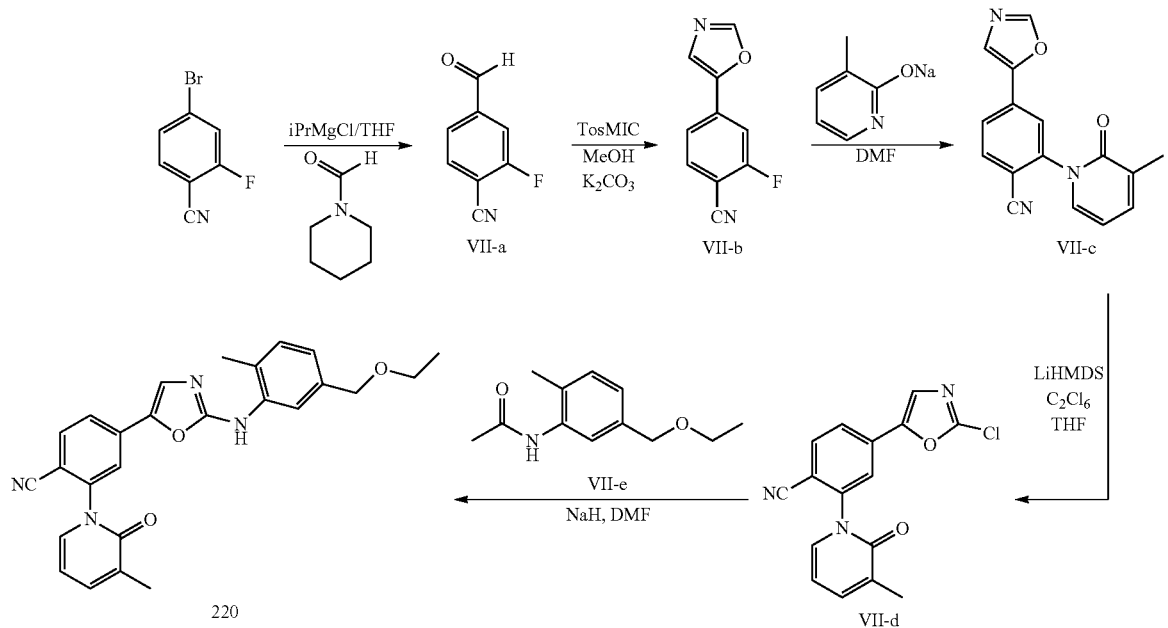

Synthesis of intermediate VII-a: 2-Fluoro-4-formyl-benzonitrile

A solution of 4-bromo-2-fluorobenzonitrile (5.00 g, 25 mmol) in dry THF (50 mL) at −10° C. under argon was treated with a solution of isopropylmagnesium chloride (2M in THF, 15.0 mL, 30.0 mmol) dropwise before stirring at this temperature for 3 h. A solution of N-formylpiperidine (3.89 g, 35.0 mmol) in dry THF (15 mL) was added dropwise and the mixture allowed to warm to room temperature before stirring for 1.5 h. The resultant solution was treated with 4M aq HCl (250 mL each) and the organics extracted with EtOAc. The combined organics were dried ($MgSO_4$), filtered and evaporated before purification of the residue by column chromatography ($SiO_2$; eluting with 30% to 50% EtOAc in cyclohexane) to afford 2-fluoro-4-formyl-benzonitrile VII-a as a pale yellow solid (2.73 g, 73%). $^1$H NMR (300 MHz, $CDCl_3$) δ 10.07 (d, J=1.7 Hz, 1H), 7.90-7.79 (m, 2H), 7.74 (dd, J=8.5, 0.8 Hz, 1H).

Synthesis of intermediate VII-b: 2-Fluoro-4-oxazol-5-yl-benzonitrile 5-(3-Bromo-phenyl)-oxazole VII-b was prepared as described for intermediate I-c using 2-Fluoro-4-formyl-benzonitrile VII-a (2 g, 13.43 mmol), TosMIC (2.85 g, 14.77 mmol) and $K_2CO_3$ (2.41 g, 1.86 mmol) in MeOH (40 mL) to give the desired intermediate VII-b as a yellow solid (1.46 g, 58%). $^1$H NMR (300 MHz, $CDCl_3$) δ 7.94 (s, 1H), 7.62 (dd, J=8.0, 6.5 Hz, 1H), 7.52-7.37 (m, 3H).

Synthesis of intermediate VII-c: 2-(3-Methyl-2-oxo-2H-pyridin-1-yl)-4-oxazol-5-yl-benzonitrile A solution of 3-methyl-1H-pyridin-2-one (1.43 g, 13.1 mmol) in absolute EtOH (100 mL) was treated with KOH (735 mg, 13.1 mmol) and heated to reflux with vigorous stirring for 2 h before cooling to room temperature and evaporation of the solvent under reduced pressure. The orange solid residue was taken up in dry DMF (100 mL) and treated with 2-fluoro-4-oxazol-5-yl-benzonitrile VII-b (2.24 g, 11.9 mmol) and stirred at 100° C. for 3 h. The solvent was evaporated under reduced pressure and the residue treated with a saturated solution of $NaHCO_3$ and extracted with DCM. The combined organics were dried ($MgSO_4$), filtered and evaporated and the residue purified by column chromatography ($SiO_2$, eluting with 50% EtOAc in cyclohexane) to give the desired intermediate VII-c as an off-white solid (2.55 g, 77%). $^1$H NMR (300 MHz, DMSO-$d_6$) δ 8.62 (s, 1H), 8.15 (d, J=8.1 Hz, 1H), 8.04 (s, 2H), 7.99 (dd, J=8.1, 1.6 Hz, 1H), 7.62 (dd, J=6.9, 1.1 Hz, 1H), 7.49 (d, J=6.6 Hz, 1H), 6.34 (t, J=6.8 Hz, 1H), 2.07 (s, 3H).

Synthesis of intermediate VII-d: 4-(2-Chloro-oxazol-5-yl)-2-(3-methyl-2-oxo-2H-pyridin-1-yl)-benzonitrile A solution of the 2-(3-methyl-2-oxo-2H-pyridin-1-yl)-4-oxazol-5-yl-benzonitrile VII-c (2.55 g, 9.19 mmol) in dry distilled THF (160 mL) at −78° C. under argon was treated dropwise with LiHMDS (1M in THF, 11.0 mL, 11.0 mmol) to give an opaque yellow slurry. After 1 h at this temperature, $C_2Cl_6$ (3.26 g, 13.8 mmol) was added in one portion and the mixture was allowed to warm to room temperature. This mixture was treated with water and extracted with DCM. The combined organics were dried ($MgSO_4$), filtered and evaporated and the residue purified by column chromatography ($SiO_2$; eluting with 50% EtOAc in cyclohexane) to give the desired product VII-d as a pink solid (1.51 g, 52%). $^1$H NMR (300 MHz, DMSO-$d_6$) δ 8.16 (d, J=8.2 Hz, 1H), 8.10 (s, 1H), 8.02 (d, J=1.4 Hz, 1H), 7.96 (dd, J=8.1, 1.5 Hz, 1H), 7.61 (d, J=6.9 Hz, 1H), 7.49 (d, J=6.7 Hz, 1H), 6.35 (t, J=6.8 Hz, 1H), 2.07 (s, 3H).

Synthesis of intermediate VII-e:
N-(5-ethoxymethyl-2-methyl-phenyl)-acetamide

N-(5-ethoxymethyl-2-methyl-phenyl)-acetamide VII-e was prepared as described for intermediate II-i using 5-ethoxymethyl-2-methyl-phenylamine I-e (5 g, 30.26 mmol), dry triethylamine (12.23 mL), DCM (60 mL) and AcCl (4.32 mL) to give the desired intermediate VII-e as a white solid (5.39 g, 86%). $^1$H NMR (300 MHz, CDCl$_3$) δ 7.69 (s, 1H), 7.15 (d, J=7.7 Hz, 1H), 7.07 (d, J=8.2 Hz, 1H), 4.46 (s, 2H), 3.53 (q, J=7.0 Hz, 2H), 2.23 (s, 3H), 2.18 (s, 3H), 1.23 (t, J=7.0 Hz, 3H).

Synthesis of example 220: 4-[2-((5-Ethoxymethyl)-2-methyl-phenylamino)-oxazol-5-yl]-2-(3-methyl-2-oxo-2H-pyridin-1-yl)-benzonitrile A mixture of N-(5-ethoxymethyl-2-methyl-phenyl)-acetamide VII-e (74 mg, 0.361 mmol), dry THF (3 mL) and NaH (60% in oil, 29 mg 0.722 mmol) under argon was stirred at room temperature for 1 h. A suspension of 4-(2-chloro-oxazol-5-yl)-2-(3-methyl-2-oxo-2H-pyridin-1-yl)-benzonitrile VII-d (75 mg, 0.241 mmol) in dry THF (3 mL) was added dropwise at 0° C. before warming to room temperature over 2 h. The mixture was treated with water, and extracted with EtOAc. The combined organics were dried (MgSO$_4$), filtered and evaporated and the residue purified by column chromatography (SiO$_2$; eluting with 50% EtOAc in cyclohexane) to give the desired product 220 as a pink solid (61 mg, 56%). $^1$H NMR (300 MHz, DMSO-d$_6$) δ 9.55 (s, 1H), 8.05 (d, J=8.0 Hz, 1H), 7.83-7.68 (m, 4H), 7.61 (d, J=6.7 Hz, 1H), 7.48 (d, J=6.6 Hz, 1H), 7.18 (d, J=7.8 Hz, 1H), 6.97 (d, J=7.4 Hz, 1H), 6.33 (t, J=6.8 Hz, 1H), 4.41 (s, 2H), 3.46 (q, J=7.0 Hz, 2H), 2.27 (s, 3H), 2.06 (d, J=7.1 Hz, 3H), 1.12 (t, J=7.0 Hz, 3H).

Example 221

Synthetic Approach of Example 221

Synthesis of intermediate VIII-a:
3-Bromo-5-oxazol-5-yl-pyridine 5-(3-Bromo-phenyl)-oxazole VIII-a was prepared as described for intermediate I-c using 2-5-bromo-pyridine-3-carbaldehyde (0.260 g, 1.4 mmol), TosMIC (0.273 g, 1.54 mmol) and K$_2$CO$_3$ (0.580 g, 4.2 mmol) in MeOH (15 mL) to give the desired intermediate VIII-a as a beige solid (0.16 g, 50%). $^1$H NMR (300 MHz, DMSO) δ 8.95 (s, 1H), 8.70 (s, 1H), 8.59 (s, 1H), 8.43 (s, 1H), 7.95 (s, 1H).

Synthesis of intermediate VIII-b:
5'-Oxazol-5-yl-[1,3']bipyridinyl-2-one

To an oven-dried sealed tube containing a solution of 3-bromo-5-oxazol-5-yl-pyridine VIII-a (1.00 g, 4.44 mol) in degassed 1,4-dioxane (20 mL) was added 2-hydroxypyridine (507 mg, 5.33 mmol), K$_2$CO$_3$ (1.23 g, 1.78 mmol), CuI (169 mg, 0.899 mmol) and rac-trans-N,N'-dimethylcyclohexane diamine (280 µL, 1.78 mmol). The tube was flushed with argon and sealed then heated in an oil bath at 120° C. overnight. After cooling to RT, the mixture was filtered and the filter cake washed with 1,4-dioxane. The mixture was evaporated and the residue purified by column chromatography (2% to 5% EtOH in DCM) to give the desired product VIII-b as a beige solid (752 mg, 71%). $^1$H NMR (300 MHz, DMSO-d$_6$) δ 9.06 (s, 1H), 8.68 (s, 1H), 8.60 (s, 1H), 8.29 (s, 1H), 7.95 (s, 1H), 7.80 (dd, J=6.8, 1.6 Hz, 1H), 7.57 (ddd, J=8.8, 6.6, 1.9 Hz, 1H), 6.54 (d, J=9.2 Hz, 1H), 6.39 (t, J=6.7 Hz, 1H).

Synthesis of intermediate VIII-c: 5'-(2-Chloro-oxazol-5-yl)-[1,3']bipyridinyl-2-one 5'-(2-Chloro-oxazol-5-yl)-[1,3']bipyridinyl-2-one VIII-c was prepared as described for I-d above from 5'-oxazol-5-yl-[1,3']bipyridinyl-2-one VIII-d (740 mg, 3.09 mmol) using LiHMDS (1M in THF, 4.64 mL, 4.64 mmol) and C$_2$Cl$_6$ (1.10 g, 4.64 mmol) in dry THF. The crude product was purified by column chromatography (SiO$_2$; eluting with 2% to 5% EtOH

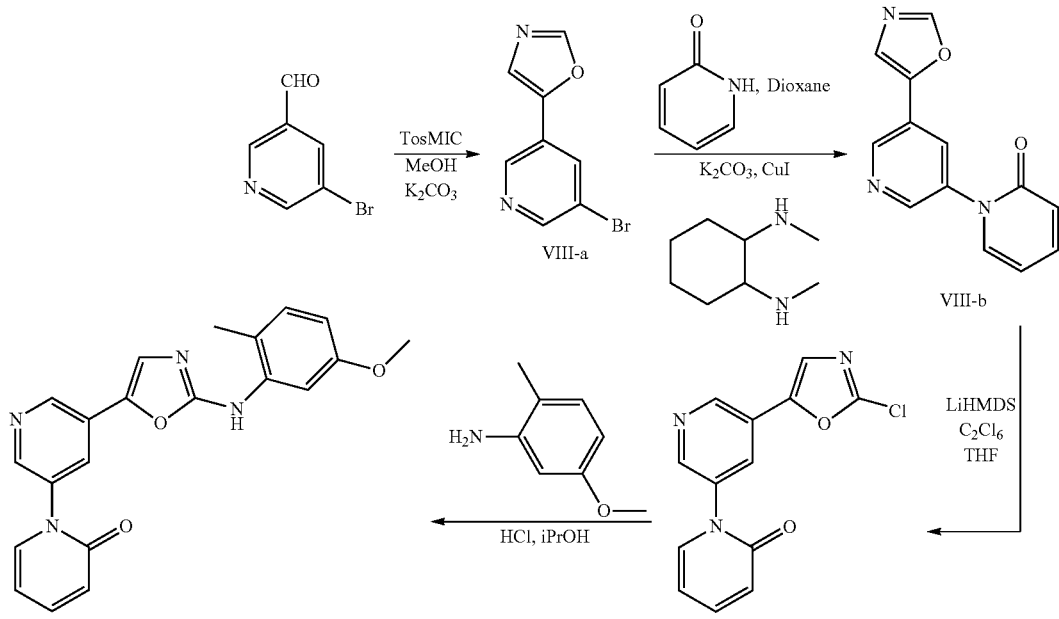

in DCM) to afford the desired product VIII-c as a white solid (393 mg, 47%). ¹H NMR (300 MHz, CDCl₃) δ 8.91 (s, 1H), 8.61 (s, 1H), 8.06 (t, J=2.2 Hz, 1H), 7.50-7.42 (m, 2H), 7.35 (dd, J=6.9, 1.9 Hz, 1H), 6.70 (d, J=9.3 Hz, 1H), 6.34 (td, J=6.8, 1.2 Hz, 1H).

Synthesis of example 221: 5'-[2-(5-Methoxy-2-methyl-phenylamino)-oxazol-5-yl]-[1,3']bipyridinyl-2-one 5'-[2-(5-Methoxy-2-methyl-phenylamino)-oxazol-5-yl]-[1,3']bipyridinyl-2-one 221 was prepared as described for I-f above from 5'-(2-Chloro-oxazol-5-yl)-[1,3']bipyridinyl-2-one VIII-c (68 mg, 0.250 mmol), and 5-methoxy-2-methylaniline (35 mg, 0.250 mmol) in iPrOH (3 mL) to afford the title compound 221 after column chromatography (SiO₂; eluting with 2% to 5% EtOH in DCM) as an orange solid (28 mg, 30%). (300 MHz, CDCl₃) δ 8.83 (d, J=1.9 Hz, 1H), 8.45 (d, J=2.3 Hz, 1H), 7.93 (t, J=2.1 Hz, 1H), 7.73 (d, J=2.4 Hz, 1H), 7.41 (m, 1H), 7.34 (m, 1H), 7.30 (s, 1H), 7.07 (d, J=8.3 Hz, 1H), 6.78 (s, 1H), 6.68 (d, J=9.3 Hz, 1H), 6.55 (dd, J=8.3, 2.5 Hz, 1H), 6.30 (t, J=5.6 Hz, 1H), 3.81 (s, 3H), 2.25 (s, 3H). ESL MS m/z 375 (M+H)⁺. Retention time=2.99 min (method 1).

Example 222

Synthesis of example 222: 3-{3-[2-(3,5-Dimethoxy-phenylamino)-oxazol-5-yl]-phenyl}-1-(2-dimethylamino-ethyl)-1H-pyridin-2-one

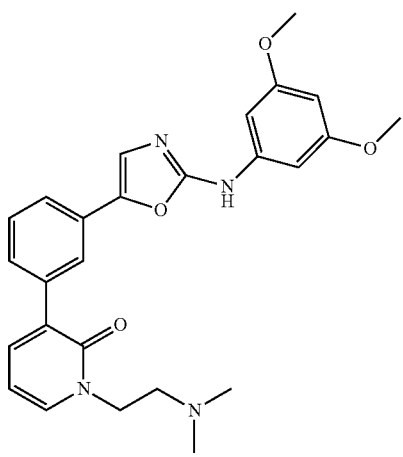

222

A mixture of 3-{3-[2-(3,5-Dimethoxy-phenylamino)-oxazol-5-yl]-phenyl}-1H-pyridin-2-one 219 (39 mg, 0.10 mmol), (2-chloro-ethyl)-dimethyl-amine hydrochloride (17.5 mg, 0.11 mmol), K₂CO₃ (31 mg, 0.22 mmol) and potassium iodide (19 mg, 0.11 mmol) in DMF (4 mL) was heated at 50° C. for 16 h. After evaporation of DMF, the mixture was treated with water and extracted with EtOAc. The combined organics were dried (MgSO₄), filtered and evaporated and the residue purified by column chromatography (Al₂O₃; eluting with 1% EtOH in DCM) to give the desired product 222 as a yellow solid (23 mg, 50%). ¹H NMR (300 MHz, DMSO) δ 10.32 (s, 1H), 7.95 (s, 1H), 7.72 (d, J=6.7 Hz, 1H), 7.66 (dd, J=6.9, 1.6 Hz, 1H), 7.58-7.31 (m, 4H), 6.90 (s, 1H), 6.89 (s, 1H), 6.35 (t, J=6.8 Hz, 1H), 6.13 (s, 1H), 4.07 (t, J=6.3 Hz, 2H), 3.73 (s, 6H), 2.55 (t, J=6.3 Hz, 2H), 2.20 (s, 6H). ESL MS m/z 461 (M+H)⁺. Retention time=2.90 min (method 1).

Example 223

Synthetic Approach of Example 223

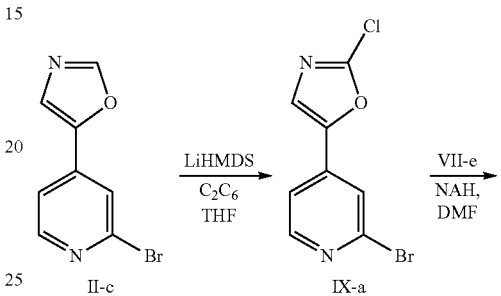

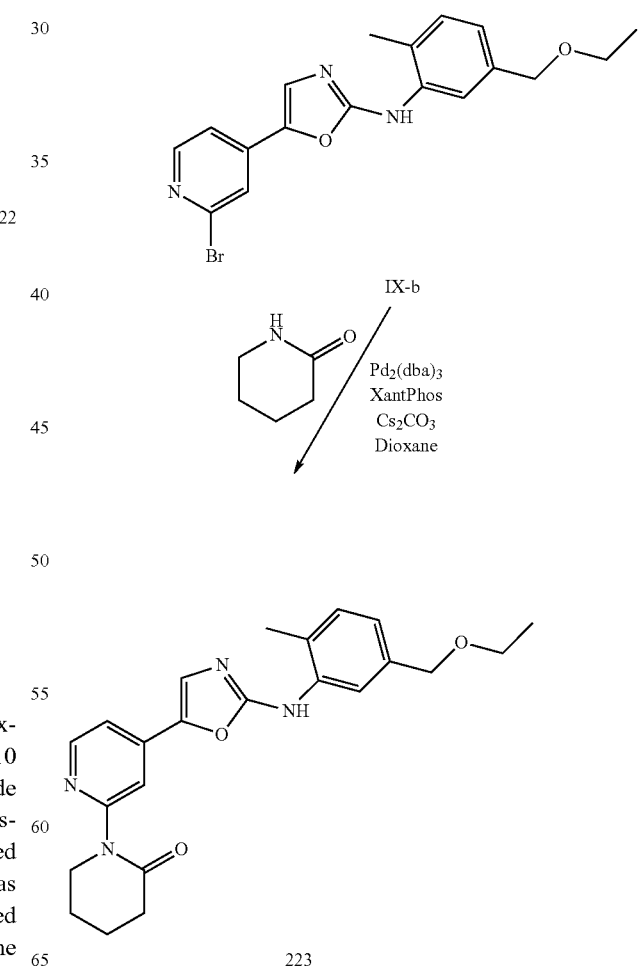

223

Synthesis of intermediate IX-a: 2-Bromo-4-(2-chloro-oxazol-5-yl)-pyridine

2-Bromo-4-(2-chloro-oxazol-5-yl)-pyridine IX-a was prepared as for example I-d using 2-Bromo-4-oxazol-5-yl-pyridine (450 mg, 2 mmol), LiHMDS (2.2 mL, 2.2 mmol) and $C_2Cl_6$ (568 mg, 2.4 mmol) in THF to give intermediate IX-a as a yellow-orange solid (465 mg, 90%). $^1$H NMR (300 MHz, CDCl$_3$) δ 8.43 (d, J=5.1 Hz, 1H), 7.68 (s, 1H), 7.53 (s, 1H), 7.46-7.36 (m, 1H).

Synthesis of intermediate IX-b: [5-(2-Bromo-pyridin-4-yl)-oxazol-2-yl]-(5-ethoxymethyl-2-methyl-phenyl)-amine

[5-(2-Bromo-pyridin-4-yl)-oxazol-2-yl]-(5-ethoxymethyl-2-methyl-phenyl)-amine IX-b was prepared as for example 220 using intermediate VII-e (169 mg, 0.65 mmol), N-(5-ethoxymethyl-2-methyl-phenyl)-acetamide (162 mg, 0.78 mmol) and NaH (65 mg, 1.6 mmol) in DMF to give intermediate IX-b as a yellow solid (162 mg, 64%). $^1$H NMR (300 MHz, CDCl$_3$) δ 8.32 (d, J=5.1 Hz, 1H), 7.94 (s, 1H), 7.56 (s, 1H), 7.42 (s, 1H), 7.32 (d, J=5.2 Hz, 1H), 7.21 (d, J=7.6 Hz, 1H), 7.06 (d, J=7.7 Hz, 1H), 6.91 (s, 1H), 4.54 (s, 2H), 3.58 (q, J=7.0 Hz, 2H), 2.34 (s, 3H), 1.27 (t, J=7.0 Hz, 3H).

Synthesis of example 223: 4'-[2-(5-Ethoxymethyl-2-methyl-phenylamino)-oxazol-5-yl]-3,4,5,6-tetrahydro-[1,2']bipyridinyl-2-one A mixture of intermediate IX-b (51 mg, 0.13 mmol), δ-valerolactam (16 mg, 0.16 mmol), cesium carbonate (60 mg, 0.18 mmol), Pd$_2$(dba)$_3$ (4 mg, 0.004 mmol) and Xant-Phos (7 mg, 0.012 mmol) in dioxane (2.5 mL) was refluxed for 1 h, until no starting material remained (reaction monitored by TLC). The reaction mixture was then evaporated, and the crude oil was directly chromatographed (SiO$_2$, eluting with 1 to 10% EtOH in DCM) to give example 223 as a yellow solid (22 mg, 42%). $^1$H NMR (300 MHz, CDCl$_3$) δ 8.39 (d, J=5.3 Hz, 1H), 7.99 (s, 1H), 7.94 (s, 1H), 7.39 (s, 1H), 7.25-7.12 (m, 3H), 7.05 (d, J=7.6 Hz, 1H), 4.54 (s, 2H), 4.02-3.89 (m, 2H), 3.57 (q, J=6.9 Hz, 2H), 2.69-2.56 (m, 2H), 2.34 (s, 3H), 2.02-1.89 (m, 4H), 1.26 (t, J=7.0 Hz, 3H). ESI-MS m/z 407 (M+H)$^+$. Retention time=3.48 min (method 1).

Example 224

Synthesis of example 224: 1-{4-[2-((5-Ethoxymethyl)-2-methyl-phenylamino)-oxazol-5-yl]-pyridin-2-yl}-tetrahydro-pyrimidin-2-one

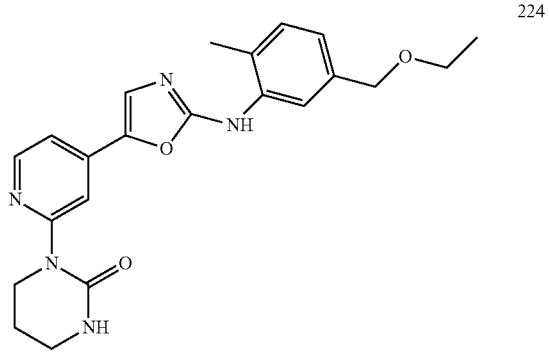 [SMILES: CCOCc1ccc(C)c(Nc2ncc(-c3ccnc(N4CCCNC4=O)c3)o2)c1]

224

A mixture of intermediate IX-b (50 mg, 0.13 mmol), N,N'-trimethyleneurea (130 mg, 1.3 mmol), cesium carbonate (46 mg, 0.14 mmol), Pd$_2$(dba)$_3$ (4 mg, 0.004 mmol) and Xant-Phos (7 mg, 0.012 mmol) in dioxane (2.5 mL) was refluxed for 1 h30. The reaction mixture was then evaporated, dissolved in ethyl acetate, washed several times with water, dried over MgSO$_4$, and concentrated. The crude oil was chromatographed (SiO$_2$, eluting with 1 to 10% EtOH in DCM) to give example 224 as a yellow-orange solid (16 mg, 31%). $^1$H NMR (300 MHz, DMSO-d$_6$) δ 9.54 (s, 1H), 8.28 (d, J=5.2 Hz, 1H), 7.99 (s, 1H), 7.79 (s, 1H), 7.66 (s, 1H), 7.24-7.10 (m, 2H), 7.00-6.86 (m, 2H), 4.41 (s, 2H), 3.92-3.80 (m, 2H), 3.47 (q, J=6.9 Hz, 2H), 3.26-3.19 (m, 2H), 2.27 (s, 3H), 2.03-1.80 (m, 2H), 1.14 (t, J=7.0 Hz, 3H).

Example 225

Synthetic Approach of Example 225

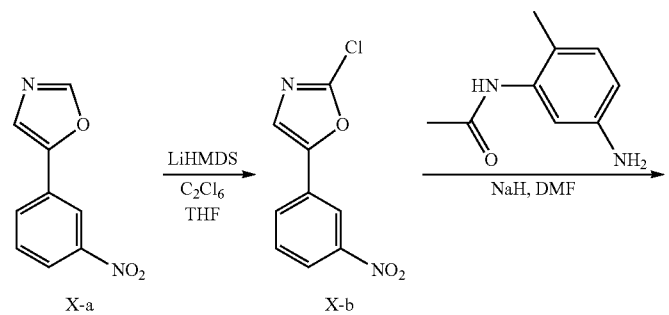

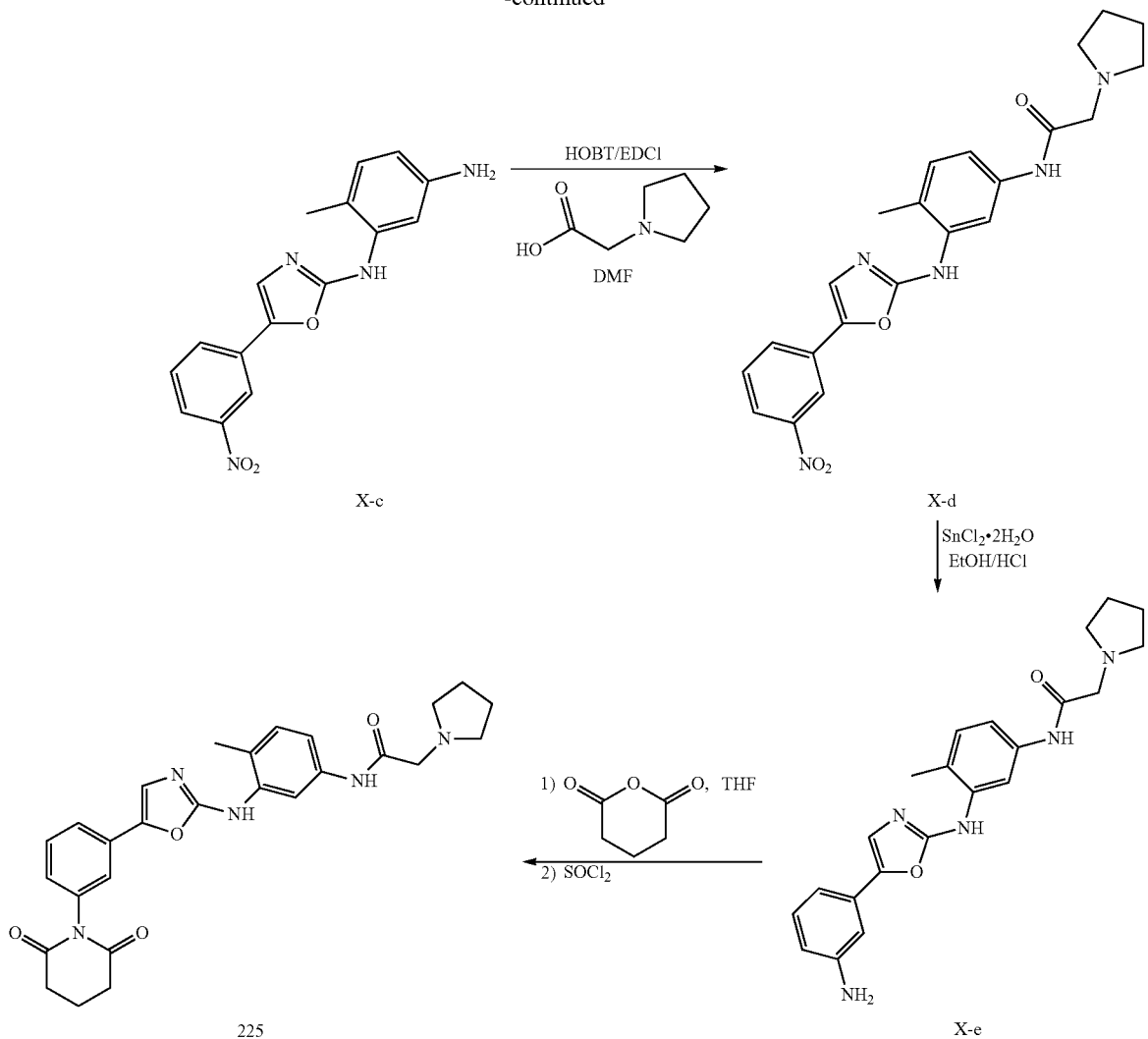

Synthesis of intermediate X-a:
5-(3-Nitro-phenyl)-oxazole

Intermediate X-a was prepared as for example I-c using 3-nitrobenzaldehyde (4 g, 26 mmol), TosMIC (5.7 g, 29 mmol) and $K_2CO_3$ (4.4 g, 32 mmol) in MeOH to give intermediate X-a as a yellow solid (4.7 g, 93%). $^1$H NMR (400 MHz, DMSO-$d_6$) δ 8.56 (s, 1H), 8.50 (t, J=1.9 Hz, 1H), 8.21 (ddd, J=8.2, 2.3, 1.0 Hz, 1H), 8.17 (ddd, J=7.8, 1.6, 1.0 Hz, 1H), 7.99 (s, 1H), 7.78 (t, J=8.0 Hz, 1H).

Synthesis of intermediate X-b:
2-Chloro-5-(3-nitro-phenyl)-oxazole

Intermediate X-b was prepared as for example I-d using intermediate X-a (3.2 g, 17 mmol), LiHMDS (20.2 mL, 20 mmol) and $C_2Cl_6$ (4.78 g, 20 mmol) in THF to give the desired intermediate X-b as a yellow solid (3.13 g, 82%). $^1$H NMR (400 MHz, DMSO-$d_6$) δ 8.48 (d, J=1.5 Hz, 1H), 8.24 (d, J=8.2 Hz, 1H), 8.14 (d, J=7.8 Hz, 1H), 8.09 (d, J=1.9 Hz, 1H), 7.80 (td, J=8.1, 1.9 Hz, 1H).

Synthesis of intermediate X-c: 4-Methyl-N3-[5-(3-nitro-phenyl)-oxazol-2-yl]-benzene-1,3-diamine Intermediate X-c was prepared as for example 220 using intermediate X-b (448 mg, 2 mmol), N-(5-Amino-2-methyl-phenyl)-acetamide (394 mg, 2.4 mmol) and NaH (160 mg, 4 mmol) in THF to give intermediate X-c as an orange solid (236 mg, 64%). $^1$H NMR (300 MHz, DMSO-$d_6$) δ 9.17 (s, 1H), 8.32 (s, 1H), 8.07 (d, J=7.5 Hz, 1H), 8.00 (d, J=7.7 Hz, 1H), 7.72 (m, 2H), 7.11 (s, 1H), 6.82 (d, J=8.0 Hz, 1H), 6.24 (d, J=7.4 Hz, 1H), 4.91 (s, 2H), 2.11 (s, 3H).

Synthesis of intermediate X-d: N-{4-Methyl-3-[5-(3-nitro-phenyl)-oxazol-2-ylamino]-phenyl}-2-pyrrolidin-1-yl-acetamide A mixture of intermediate X-c (226 mg, 0.72 mmol), 1-pyrrolidinyl acetic acid hydrochloride (158 mg, 0.94 mmol), 1-hydroxybenzotriazole hydrate (148 mg, 1.1 mmol), N-(3-dimethylaminopropyl)-N'-ethylcarbodiimide hydrochloride (252 mg, 1.3 mmol) and $NEt_3$ (360 μL, 2.6 mmol) in DMF (15 mL) was stirred at room temperature overnight. The reaction mixture was then evaporated, diluted with ethyl acetate, washed with water, dried over MgSO$_4$, and concentrated to a minimum volume for allowing crystallisation. The title compound was then collected by filtration to afford intermediate X-d as a yellow solid (224 mg, 72%). $^1$H NMR (300 MHz, DMSO-d$_6$) δ 9.66 (s, 1H), 9.43 (s, 1H), 8.35 (s, 1H), 8.03 (d, J=7.3 Hz, 1H), 7.89 (d, J=7.9 Hz, 1H), 7.70 (m, 2H), 7.04 (s, 1H), 6.89 (d, J=8.1 Hz, 1H), 6.26 (d, J=7.5 Hz, 1H), 3.24 (s, 2H), 2.63-2.54 (m, 4H), 2.22 (s, 3H), 1.76-1.69 (m, 4H).

Synthesis of intermediate X-e: N-{3-[5-(3-Aminophenyl)-oxazol-2-ylamino]-4-methyl-phenyl}-2-pyrrolidin-1-yl-acetamide A mixture of intermediate X-d (220 mg, 0.52 mmol), SnCl$_2$.2H$_2$O (590 mg, 2.6 mmol) and concentrated hydrochloric acid (735 μL, 5.2 mmol) in a mixture ethanol/eau (9 mL/1 mL) was stirred at 40° C. for 4 h. The reaction mixture was then evaporated, diluted with ethyl acetate and aqueous NaOH. The aqueous layer was extracted twice with ethyl acetate, then the combined organic layers were washed with water, dried over MgSO$_4$, and concentrated. The crude oil was chromatographed (Al$_2$O$_3$, eluting with 0.5% EtOH in DCM) to give intermediate X-e as a yellow-beige solid (147 mg, 72%). $^1$H NMR (300 MHz, DMSO-d$_6$) δ 9.68 (s, 1H), 9.40 (s, 1H), 8.21 (s, 1H), 7.95 (d, J=7.8 Hz, 1H), 7.88 (d, J=7.3 Hz, 1H), 7.56 (s, 1H), 7.32 (s, 1H), 7.05 (s, 1H), 6.91 (d, J=7.3 Hz, 1H), 6.19 (d, J=7.6 Hz, 1H), 4.85 (s, 2H), 3.28 (s, 2H), 2.67-2.56 (m, 4H), 2.23 (s, 3H), 1.78-1.68 (m, 4H).

Synthesis of example 225: N-(3-{5-[3-(2,6-Dioxo-piperidin-1-yl)-phenyl]-oxazol-2-ylamino}-4-methyl-phenyl)-2-pyrrolidin-1-yl-acetamide To a solution of intermediate X-e (70 mg, 0.18 mmol) in anhydrous THF (4 mL) under argon at 0° C. was added glutaric anhydride (20 mg, 0.18 mmol) in several portions. The mixture was stirred at ambient temperature for 1 h, then refluxed overnight. The solid formed was collected by filtration, then washed with THF and diethyl ether, to give a white solid (52 mg), which was treated in anhydrous 1,2-dichloroethane (8 mL) with SOCl$_2$ (30 μL, 0.4 mmol) over a period of 10 min. The mixture was refluxed for at least 4 h, until no starting material remained, then diluted with DCM, washed with aqueous NaHCO$_3$ and water, dried over MgSO$_4$, and concentrated. The residue was chromatographed (Al$_2$O$_3$, eluting with 0.5 to 1% EtOH in DCM) to give compound 225 as a beige solid (23 mg, 45%). $^1$H NMR (300 MHz, DMSO-d$_6$) δ 9.96 (s, 1H), 9.64 (s, 1H), 9.27 (d, J=12.2 Hz, 1H), 8.03 (d, J=10.9 Hz, 1H), 7.94 (s, 1H), 7.54-7.46 (m, 1H), 7.35-7.27 (m, 3H), 7.10 (d, J=8.2 Hz, 1H), 3.23 (s, 2H), 2.69 (t, J=6.5 Hz, 4H), 2.63-2.56 (m, 4H), 2.23 (s, 3H), 2.12 (m, 2H), 1.74 (s, 4H).

In another embodiment, the invention relates to a pharmaceutical composition comprising a compound as depicted above.

Such a pharmaceutical composition can be adapted for oral administration, and can be formulated using pharmaceutically acceptable carriers well known in the art in suitable dosages. Such carriers enable the pharmaceutical compositions to be formulated as tablets, pills, dragees, capsules, liquids, gels, syrups, slurries, suspensions, and the like, for ingestion by the patient. In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

The composition of the invention can also take the form of a pharmaceutical or cosmetic composition for topical administration.

Such compositions may be presented in the form of a gel, paste, ointment, cream, lotion, liquid suspension aqueous, aqueous-alcoholic or, oily solutions, or dispersions of the lotion or serum type, or anhydrous or lipophilic gels, or emulsions of liquid or semi-solid consistency of the milk type, obtained by dispersing a fatty phase in an aqueous phase or vice versa, or of suspensions or emulsions of soft, semi-solid consistency of the cream or gel type, or alternatively of microemulsions, of microcapsules, of microparticles or of vesicular dispersions to the ionic and/or nonionic type. These compositions are prepared according to standard methods.

The composition according to the invention comprises any ingredient commonly used in dermatology and cosmetic. It may comprise at least one ingredient selected from hydrophilic or lipophilic gelling agents, hydrophilic or lipophilic active agents, preservatives, emollients, viscosity enhancing polymers, humectants, surfactants, preservatives, antioxidants, solvents, and fillers, antioxidants, solvents, perfumes, fillers, screening agents, bactericides, odor absorbers and coloring matter.

As oils which can be used in the invention, mineral oils (liquid paraffin), vegetable oils (liquid fraction of shea butter, sunflower oil), animal oils, synthetic oils, silicone oils (cyclomethicone) and fluorinated oils may be mentioned. Fatty alcohols, fatty acids (stearic acid) and waxes (paraffin, carnauba, beeswax) may also be used as fatty substances.

As emulsifiers, glycerols, polysorbates, glycerides, and PEGs can be used in the invention.

As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned, and as lipophilic gelling agents, modified clays such as bentones, metal salts of fatty acids such as aluminum stearates and hydrophobic silica, or alternatively ethylcellulose and polyethylene may be mentioned.

As hydrophilic active agents, proteins or protein hydrolysates, amino acids, polyols, urea, allantoin, sugars and sugar derivatives, vitamins, starch and plant extracts, in particular those of Aloe vera may be used.

As lipophilic active, agents, retinol (vitamin A) and its derivatives, tocopherol (vitamin E) and its derivatives, essential fatty acids, ceramides and essential oils may be used. These agents add extra moisturizing or skin softening features when utilized.

In addition, a surfactant can be included in the composition so as to provide deeper penetration of the compound capable of depleting mast cells, such as a tyrosine kinase inhibitor, preferably a c-kit inhibitor.

Among the contemplated ingredients, the invention embraces penetration enhancing agents selected for example from the group consisting of mineral oil, water, ethanol, triacetin, glycerin and propylene glycol; cohesion agents selected for example from the group consisting of polyisobutylene, polyvinyl acetate and polyvinyl alcohol, and thickening agents.

Chemical methods of enhancing topical absorption of drugs are well known in the art. For example, compounds with penetration enhancing properties include sodium lauryl sulfate (Dugard, P. H. and Sheuplein, R. J., "Effects of Ionic Surfactants on the Permeability of Human Epidermis An Electrometric Study," J. West. Dermatol., V.60, pp. 263-69, 1973), lauryl amine oxide (Johnson et. al., U.S. Pat. No. 4,411,893), azone (Rajadhyaksha, U.S. Pat. Nos. 4,405,616 and 3,989,816) and decylmethyl sulfoxide (Sekura, D. L. and Scala, J., "The Percutaneous Absorption of Alkylmethyl Sulfides," Pharmacology of the Skin, Advances In Biolocy of Skin, (Appleton-Century Craft) V. 12, pp. 257-69, 1972). It has been observed that increasing the polarity of the head group in amphoteric molecules increases their penetration-enhancing properties but at the expense of increasing their skin irritating properties (Cooper, E. R. and Berner, B., "Interaction of Surfactants with Epidermal Tissues: Physiochemical Aspects," Surfactant Science Series, V. 16, Reiger, M. M. ed. (Marcel Dekker, Inc.) pp. 195-210, 1987).

A second class of chemical enhancers are generally referred to as co-solvents. These materials are absorbed topically relatively easily, and, by a variety of mechanisms, achieve permeation enhancement for some drugs. Ethanol (Gale et. al., U.S. Pat. No. 4,615,699 and Campbell et. al., U.S. Pat. Nos. 4,460,372 and 4,379,454), dimethyl sulfoxide (U.S. Pat. Nos. 3,740,420 and 3,743,727, and U.S. Pat. No. 4,575,515), and glycerine derivatives (U.S. Pat. No. 4,322,433) are a few examples of compounds which have shown an ability to enhance the absorption of various compounds.

The pharmaceutical compositions of the invention can also be intended for administration as an aerosolized formulation to target areas of a patient's respiratory tract.

Devices and methodologies for delivering aerosolized bursts of a formulation of a drug is disclosed in U.S. Pat. No. 5,906,202. Formulations are preferably solutions, e.g. aqueous solutions, ethanoic solutions, aqueous/ethanoic solutions, saline solutions, colloidal suspensions and microcrystalline suspensions. For example aerosolized particles comprise the active ingredient mentioned above and a carrier, (e.g., a pharmaceutically active respiratory drug and carrier) which are formed upon forcing the formulation through a nozzle which nozzle is preferably in the form of a flexible porous membrane. The particles have a size which is sufficiently small such that when the particles are formed they remain suspended in the air for a sufficient amount of time such that the patient can inhale the particles into the patient's lungs.

The invention encompasses the systems described in U.S. Pat. No. 5,556,611:
liquid gas systems (a liquefied gas is used as propellent gas (e.g. low-boiling FCHC or propane, butane) in a pressure container,
suspension aerosol (the active substance particles are suspended in solid form in the liquid propellent phase),
pressurized gas system (a compressed gas such as nitrogen, carbon dioxide, dinitrogen monoxide, air is used.

Thus, according to the invention the pharmaceutical preparation is made in that the active substance is dissolved or dispersed in a suitable nontoxic medium and said solution or dispersion atomized to an aerosol, i.e. distributed extremely finely in a carrier gas. This is technically possible for example in the form of aerosol propellent gas packs, pump aerosols or other devices known per se for liquid misting and solid atomizing which in particular permit an exact individual dosage.

Therefore, the invention is also directed to aerosol devices comprising the compound as defined above and such a formulation, preferably with metered dose valves.

The pharmaceutical compositions of the invention can also be intended for intranasal administration.

In this regard, pharmaceutically acceptable carriers for administering the compound to the nasal mucosal surfaces will be readily appreciated by the ordinary artisan. These carriers are described in the Remington's Pharmaceutical Sciences" 16th edition, 1980, Ed. By Arthur Osol, the disclosure of which is incorporated herein by reference.

The selection of appropriate carriers depends upon the particular type of administration that is contemplated. For administration via the upper respiratory tract, the composition can be formulated into a solution, e.g., water or isotonic saline, buffered or unbuffered, or as a suspension, for intra-nasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's, Id. at page 1445). Of course, the ordinary artisan can readily determine a suitable saline content and pH for an innocuous aqueous carrier for nasal and/or upper respiratory administration.

Common intranasal carriers include nasal gels, creams, pastes or ointments with a viscosity of, e.g., from about 10 to about 3000 cps, or from about 2500 to 6500 cps, or greater, may also be used to provide a more sustained contact with the nasal mucosal surfaces. Such carrier viscous formulations may be based upon, simply by way of example, alkylcelluloses and/or other biocompatible carriers of high viscosity well known to the art (see e.g., Remington's, cited supra. A preferred alkylcellulose is, e.g., methylcellulose in a concentration ranging from about 5 to about 1000 or more mg per 100 ml of carrier. A more preferred concentration of methyl cellulose is, simply by way of example, from about 25 to about mg per 100 ml of carrier.

Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. For nasal administration of solutions or suspensions according to the invention, various devices are available in the art for the generation of drops, droplets and sprays.

A premeasured unit dosage dispenser including a dropper or spray device containing a solution or suspension for delivery as drops or as a spray is prepared containing one or more doses of the drug to be administered and is another object of the invention. The invention also includes a kit containing one or more unit dehydrated doses of the compound, together with any required salts and/or buffer agents, preservatives, colorants and the like, ready for preparation of a solution or suspension by the addition of a suitable amount of water.

Another aspect of the invention is directed to the use of said compound to manufacture a medicament. In other words, the invention embraces a method for treating a disease related to unregulated c-kit transduction comprising administering an effective amount of a compound as defined above to a mammal in need of such treatment.

More particularly, the invention is aimed at a method for treating a disease selected from autoimmune diseases, allergic diseases, bone loss, cancers such as leukemia and GIST, tumor angiogenesis, inflammatory diseases, inflammatory bowel diseases (IBD), interstitial cystitis, mastocytosis, infections diseases, metabolic disorders, fibrosis, diabetes and CNS disorders comprising administering an effective amount a compound depicted above to a mammal in need of such treatment.

The above described compounds are useful for manufacturing a medicament for the treatment of diseases related to unregulated c-kit transduction, including, but not limited to:

neoplastic diseases such as mastocytosis, canine mastocytoma, solid tumours, human gastrointestinal stromal tumor ("GIST"), small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, solid tumors and astrocytomas.

tumor angiogenesis.

metabolic diseases such as diabetes mellitus and its chronic complications; obesity; diabete type II; hyperlipidemias and dyslipidemias; atherosclerosis; hypertension; and cardiovascular disease.

allergic diseases such as asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation.

interstitial cystitis.

bone loss (osteoporosis).

inflammatory diseases such as rheumatoid arthritis, conjunctivitis, rheumatoid spondylitis, osteoarthritis, gouty arthritis and other arthritic conditions.

autoimmune diseases such as multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, as well as proliferative glomerulonephritis.

graft-versus-host disease or graft rejection in any organ transplantation including kidney, pancreas, liver, heart, lung, and bone marrow.

Other autoimmune diseases embraced by the invention active chronic hepatitis and chronic fatigue syndrome.

subepidermal blistering disorders such as pemphigus.

Vasculitis.

HIV infection.

melanocyte dysfunction associated diseases such as hypermelanosis resulting from melanocyte dysfunction and including lentigines, solar and senile lentigo, Dubreuilh melanosis, moles as well as malignant melanomas. In this regard, the invention embraces the use of the compounds defined above to manufacture a medicament or a cosmetic composition for whitening human skin.

CNS disorders such as psychiatric disorders, migraine, pain, memory loss and nerve cells degeneracy. More particularly, the method according to the invention is useful for the treatment of the following disorders: Depression including dysthymic disorder, cyclothymic disorder, bipolar depression, severe or "melancholic" depression, atypical depression, refractory depression, seasonal depression, anorexia, bulimia, premenstrual syndrome, post-menopause syndrome, other syndromes such as mental slowing and loss of concentration, pessimistic worry, agitation, self-deprecation, decreased libido, pain including, acute pain, postoperative pain, chronic pain, nociceptive pain, cancer pain, neuropathic pain, psychogenic pain syndromes, anxiety disorders including anxiety associated with hyperventilation and cardiac arrhythmias, phobic disorders, obsessive-compulsive disorder, posttraumatic stress disorder, acute stress disorder, generalized anxiety disorder, psychiatric emergencies such as panic attacks, including psychosis, delusional disorders, conversion disorders, phobias, mania, delirium, dissociative episodes including dissociative amnesia, dissociative fugue and dissociative identity disorder, depersonalization, catatonia, seizures, severe psychiatric emergencies including suicidal behaviour, self-neglect, violent or aggressive behaviour, trauma, borderline personality, and acute psychosis, schizophrenia including paranoid schizophrenia, disorganized schizophrenia, catatonic schizophrenia, and undifferentiated schizophrenia, neurodegenerative diseases including Alzheimer's disease, Parkinson's disease, Huntington's disease, the prion diseases, Motor Neurone Disease (MND), and Amyotrophic Lateral Sclerosis (ALS).

substance use disorders as referred herein include but are not limited to drug addiction, drug abuse, drug habituation, drug dependence, withdrawal syndrome and overdose.

Cerebral ischemia.

Fibrosis.

Duchenne muscular dystrophy.

Regarding mastocytosis, the invention contemplates the use of the compounds as defined above for treating the different categories which can be classified as follows:

Category I is composed by two sub-categories (IA and IB). Category IA is made by diseases in which mast cell infiltration is strictly localized to the skin. This category represents the most frequent form of the disease and includes: i) urticaria pigmentosa, the most common form of cutaneous mastocytosis, particularly encountered in children, ii) diffuse cutaneous mastocytosis, iii) solitary mastocytoma and iv) some rare subtypes like bullous, erythrodermic and teleangiectatic mastocytosis. These forms are characterized by their excellent prognosis with spontaneous remissions in children and a very indolent course in adults. Long term survival of this form of disease is generally comparable to that of the normal population and the translation into another form of mastocytosis is rare. Category IB is represented by indolent systemic disease (SM) with or without cutaneous involvement. These forms are much more usual in adults than in children. The course of the disease is often indolent, but sometimes signs of aggressive or malignant mastocytosis can occur, leading to progressive impaired organ function.

Category II includes mastocytosis with an associated hematological disorder, such as a myeloproliferative or myelodysplastic syndrome, or acute leukemia. These malignant mastocytosis does not usually involve the skin. The progression of the disease depends generally on the type of associated hematological disorder that conditiones the prognosis.

Category III is represented by aggressive systemic mastocytosis in which massive infiltration of multiple organs by abnormal mast cells is common. In patients who pursue this kind of aggressive clinical course, peripheral blood features suggestive of a myeloproliferative disorder are more prominent. The progression of the disease can be very rapid, similar to acute leukemia, or some patients can show a longer survival time.

Finally, category IV of mastocytosis includes the mast cell leukemia, characterized by the presence of circulating mast cells and mast cell progenitors representing more than 10% of the white blood cells. This entity represents probably the rarest type of leukemia in humans, and has a very poor prognosis, similar to the rapidly progressing variant of malignant mastocytosis. Mast cell leukemia can occur either de novo or as the terminal phase of urticaria pigmentosa or systemic mastocytosis.

The invention also contemplates the method as depicted for the treatment of recurrent bacterial infections, resurging infections after asymptomatic periods such as bacterial cystitis. More particularly, the invention can be practiced for treating FimH expressing bacteria infections such as Gram-negative enterobacteria including *E. coli, Klebsiella pneumoniae, Serratia marcescens, Citrobactor freudii* and *Salmonella typhimurium*.

In this method for treating bacterial infection, separate, sequential or concomitant administration of at least one antibiotic selected bacitracin, the cephalosporins, the penicillins, the aminoglycosides, the tetracyclines, the streptomycins and the macrolide antibiotics such as erythromycin; the fluoroquinolones, actinomycin, the sulfonamides and trimethoprim, is of interest.

In one preferred embodiment, the invention is directed to a method for treating neoplastic diseases such as mastocytosis, canine mastocytoma, solid tumours, human gastrointestinal stromal tumor ("GIST"), small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, and astrocytomas comprising administering a compound as defined herein to a human or mammal, especially dogs and cats, in need of such treatment.

In one other preferred embodiment, the invention is directed to a method for treating allergic diseases such as asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation comprising administering a compound as defined herein to a human or mammal, especially dogs and cats, in need of such treatment.

In still another preferred embodiment, the invention is directed to a method for treating inflammatory diseases such as rheumatoid arthritis, conjunctivitis, rheumatoid spondylitis, osteoarthritis, gouty arthritis and other arthritic conditions comprising administering a compound as defined herein to a human in need of such treatment.

In still another preferred embodiment, the invention is directed to a method for treating autoimmune diseases such as multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, as well as proliferative glomerulonephritis comprising administering a compound as defined herein to a human in need of such treatment.

In still another preferred embodiment, the invention is directed to a method for treating graft-versus-host disease or graft rejection in any organ transplantation including kidney, pancreas, liver, heart, lung, and bone marrow comprising administering a compound as defined herein to a human in need of such treatment.

In yet a further embodiment, the compounds of the invention or pharmaceutically acceptable salts thereof can be administered in combination with one or more other active pharmaceutical agents in amounts sufficient to provide a therapeutic effect. In one implementation, the co-administration of the compounds of the invention and the other agent(s) is simultaneous. In another implementation, the co-administration of the compounds of the invention and the other agent(s) is sequential. In a further implementation, the co-administration of the compounds of the invention and the other agent(s) is made over a period of time, Examples of in vitro TK Inhibition Assays Procedures C-Kit WT and Mutated C-Kit (D816V) Assay Proliferation Assays Colorimetric cell proliferation and viability assay (reagent CellTiter-Blue purchased from Promega cat No G8081) was performed on BaF3 Kit WT or Kit D816 cell lines as well as on human and murine mastocytoma and mast leukemia cell lines.

A total of $2.9 \cdot 10^4$ cells/50 µl were seeded per well of a 96-wells plate. Treatment was initiated by addition of a 2× drug solution of ½ serial dilutions ranging from 0 to 10 µM. After incubating for 48 hours at 37° C., 10 µl of a ½ dilution of CellTiter-Blue reagent was added to each well and the plates were returned to the incubator for an additional 4 hours.

The fluorescence intensity from the CellTiter-Blue reagent is proportional to the number of viable cells and data were recorded ($544_{Ex}/590_{Em}$) using a POLARstar OMEGA microplate reader (BMG LabteckSarl). A background control without cells was used as a blank. The positive control of the assay corresponds to the cell proliferation obtained in the absence of drug treatment (100% proliferation). Each sample was done in triplicate. The results were expressed as a percentage of the proliferation obtained in absence of treatment.

All drugs were prepared as 20 mM stock solutions in DMSO and conserved at −80° C. Drug dilutions were made fresh in medium before each experiment. A DMSO control was included in each experiment.

-Cells

Human Kit WT and human Kit D816V are derived from the murine IL-3 dependent Ba/F3 proB lymphoid cells. While Ba/F3 Kit WT are stimulated with 250 ng/ml of recombinant murine SCF, cells expressing Kit D816V are independent of cytokines for their growth. The FMA3 and P815 cell lines are mastocytoma cells expressing endogenous mutated forms of Kit, i.e., frame deletion in the murine juxtamembrane coding region of the receptor-codons 573 to 579 (FMA3) and activating D814Y mutation in the kinase domain (P815). The human leukaemic MC line HMC-1 expresses two single point mutations in the c-Kit gene, V560G in the juxtamembrane domain and D816V in the kinase domain.

-Immunoprecipitation Assays and Western Blotting Analysis:

For each assay, $5 \cdot 10^6$ Ba/F3 cells and Ba/F3-derived cells expressing various c-kit mutations were lysed and immunoprecipitated as described (Beslu et al., 1996). Briefly, cell lysates were immunoprecipitated using rabbit immunsera directed toward the cytoplasmic domain of either anti murine KIT (Rottapel et al., 1991) or anti human KIT (Santa Cruz). Western blot was hybridized with the 4G10 anti-phosphotyrosine antibody (UBI), the corresponding rabbit immunsera anti KIT or antibodies directed against signaling molecules. The membrane was then incubated either with HRP-conjugated goat anti mouse IgG antibody or with HRP-conjugated goat anti rabbit IgG antibody (Immunotech), Proteins of interest were then visualized by incubation with ECL reagent (Amersham).

Experimental Results

The experimental results for various compounds according to the invention using the above-described protocols are set forth in Table 3:

TABLE 3 in vitro inhibitions of various compounds against c-kit WT and c-kit D816V

| Target | IC$_{50}$ (microM) | Compounds |
|---|---|---|
| c-kit WT | IC$_{50}$ ≤ 1 | 001; 013; 014; 015; 016; 020; 021; 024; 025; 026; 029; 031; 038; 041; 052; 054; 055; 056; 058; 059; 060; 061; 063; 064; 065; 066; 067; 068; 069; 070; 071; 072; 075; 076; 077; 079; 080; 081; 084; 086; 087; 092; 093; 094; 096; 097; 110; 122; 123; 126; 128; 135; 137; 138; 139; 140; 142; 145; 147; 168; 169; 171; 173; 177; 178; 181; 183; 186; 195; 199; 202; 212; 213; 214; 217; 218; 219; 222 |
| c-kit WT | 1 < IC$_{50}$ < 10 | 002; 003; 004; 005; 006; 007; 008; 009; 010; 011; 012; 017; 018; 019; 022; 023; 027; 028; 030; 032; 033; 034; 035; 036; 037; 039; 040; 042; 043; 044; 045; 046; 047; 048; 049; 050; 051; 053; 057; 062; 073; 074; 078; 082; 083; 085; 088; 089; 090; 091; 095; 099; 100; 101; 102; 103; 104; 105; 106; 107; 108; 109; 111; 112; 113; 114; 115; 116; 117; 118; 119; 120; 120; 124; 125; 127; 129; 130; 131; 132; 133; 134; 136; 141; 143; 144; 146; 148; 149; 150; 151; 152; 153; 154; 155; 156; 157; 158; 159; 160; 161; 162; 163; 164; 165; 166; 167; 170; 172; 174; 175; 176; 179; 180; 182; 184; 185; 187; 188; 189; 190; 191; 192; 193; 194; 196; 197; 198; 200; 204; 205; 206; 207; 208; 210; 211; 215; 216; 220; 221; 223; 224; 225 |
| c-kit D816V | IC$_{50}$ ≤ 1 | 001; 002; 007; 008; 009; 010; 014; 016; 020; 021; 022; 024; 025; 026; 027; 028; 029; 030; 031; 032; 033; 034; 035; 036; 038; 040; 042; 043; 044; 048; 049; 051; 052; 053; 054; 055; 056; 057; 058; 059; 060; 061; 062; 063; 064; 065; 066; 067; 068; 069; 070; 071; 072; 073; 074; 075; 076; 077; 078; 079; 081; 082; 083; 084; 085; 086; 087; 088; 089; 090; 091; 092; 093; 094; 095; 096; 097; 098; 099; 100; 103; 107; 110; 111; 114; 116; 119; 122; 123; 126; 127; 128; 130; 131; 132; 133; 135; 136; 137; 138; 139; 140; 142; 143; 144; 145; 146; 147; 148; 153; 154; 155; 156; 160; 161; 168; 169; 170; 171; 173; 177; 178; 179; 180; 182; 183; 184; 186; 188; 189; 192; 193; 194; 195; 196; 199; 200; 202; 206; 207; 208; 210; 212; 213; 214; 215; 216; 217; 218; 219; 220; 222 |
| c-kit D816V | 1 < IC$_{50}$ < 10 | 003; 004; 005; 006; 011; 012; 013; 015; 017; 018; 019; 023; 037; 039; 041; 045; 046; 047; 050; 080; 101; 102; 104; 105; 106; 108; 109; 112; 113; 115; 117; 118; 120; 121; 124; 125; 129; 134; 141; 149; 150; 151; 152; 157; 158; 159; 162; 163; 164; 165; 166; 167; 172; 174; 175; 176; 181; 185; 187; 190; 191; 197; 198; 201; 203; 204; 205; 209; 211; 221; 223; 224; 225 |

The inventors observed a very effective inhibition of a protein kinase and more particularly of native and/or mutant c-kit by the class of compounds of formula I of the invention. The listed compounds in Table 3 are well representing the class of compounds of formula I.

The invention claimed is:

1. A compound of formula (I):

(I)

or a pharmaceutically acceptable salt thereof, wherein:

A is five or six member heterocycle ring;

$R_1$ is
  hydrogen;
  halogen;
  a ($C_1$-$C_{10}$)alkyl group;
  a thio($C_1$-$C_{10}$)alkyl group; or
  a ($C_1$-$C_{10}$)alkoxy group;

$R_2$ is
  halogen;
  an aryl group;
  a halo($C_1$-$C_{10}$)alkyl group;
  a ($C_1$-$C_{10}$)alkyl group,
    wherein the $C_1$-$C_{10}$ carbons are optionally substituted with at least one heteroatom optionally substituted with a halo($C_1$-$C_{10}$)alkyl or a ($C_1$-$C_{10}$)alkyl, wherein the $C_1$-$C_{10}$ carbons are optionally substituted with a solubilising group;
  a ($C_1$-$C_{10}$) alkoxy group;
  a thio($C_1$-$C_{10}$) alkyl group;
  an halo($C_1$-$C_{10}$)alkoxy group;
  —COOR;
  —NRR';
  —NR—CO—R';
  —CONRR';
  —SO$_2$NRR';
  —NR—SO$_2$—R'
    wherein R and R' are each independently selected from the group consisting of
    hydrogen,
    aryl group,
    heteroaryl group, and
    a ($C_1$-$C_{10}$)alkyl group optionally substituted with at least one heteroatom optionally substituted with a ($C_1$-$C_{10}$)alkyl group optionally substituted with a solubilising group;
  a heterocycle group; or
  a solubilising group;

$R_3$ is
  hydrogen;
  halogen;
  cyano;
  a ($C_1$-$C_{10}$)alkyl group;
  a ($C_1$-$C_{10}$)alkoxy group;

—$CF_3$;
—$NRR'$;
—NR—CO—$R'$;
—$CONRR'$;
—$SO_2NRR'$;
a heterocycle group; or
a solubilising group;
 wherein R and R' are each independently hydrogen or a ($C_1$-$C_{10}$)alkyl group optionally substituted with at least one heteroatom optionally substituted with a ($C_1$-$C_{10}$)alkyl group optionally substituted with a solubilising group;
Q is O or S;
W is N or $CR_4$;
 wherein $R_4$ is
 hydrogen;
 cyano;
 —$CF_3$;
 halogen;
 a thio($C_1$-$C_{10}$)alkyl group;
 a ($C_1$-$C_{10}$)alkyl group that is optionally substituted with at least one heteroatom optionally substituted with a ($C_1$-$C_{10}$)alkyl group that is optionally substituted with a solubilising group;
 a ($C_1$-$C_{10}$)alkoxy group;
 a halo($C_1$-$C_{10}$)alkoxy group;
 a solubilising group;
 an heterocycle;
 —CO—$NRR'$;
 —$SO_2$—$NRR'$;
 —$NRR'$;
 —NR—CO—$R'$; or
 —NR—$SO_2R'$,
  wherein R and R' are each independently
   hydrogen,
   a ($C_1$-$C_{10}$)alkyl group optionally substituted with at least one heteroatom optionally substituted with a ($C_1$-$C_{10}$)alkyl group that is optionally substituted with a solubilising group, or
   a heterocycle group;
X is N or $CR_5$; and
 wherein $R_5$ is
  hydrogen;
  cyano;
  halogen;
  a ($C_1$-$C_{10}$)alkyl group;
  a ($C_1$-$C_{10}$)alkoxy group;
  —CO—OR; or
  —CO—$NRR'$,
   wherein R and R' are each independently selected from
    hydrogen,
    ($C_1$-$C_{10}$)alkyl group optionally substituted with at least one heteroatom optionally substituted with a ($C_1$-$C_{10}$)alkyl group optionally substituted with a solubilising group or
    a heterocycle group.

2. A compound according to claim 1 of formula (II):

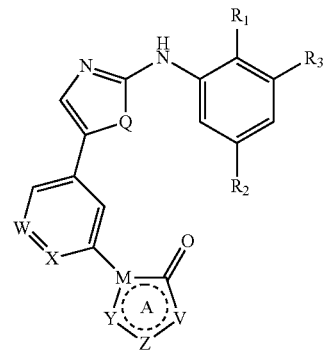

(II)

or a pharmaceutically acceptable salt thereof, wherein ring A is a five member heterocycle ring;
$R_1$ is
 hydrogen;
 halogen; a
 ($C_1$-$C_{10}$)alkyl group; or
 a ($C_1$-$C_{10}$)alkoxy group;
$R_2$ is
 halogen;
 an aryl group;
 a halo($C_1$-$C_{10}$)alkyl group; or
 a ($C_1$-$C_{10}$)alkyl group that is optionally substituted with at least one heteroatom optionally substituted with a halo($C_1$-$C_{10}$)alkyl or a ($C_1$-$C_{10}$)alkyl group optionally substituted with a solubilising group;
 a($C_1$-$C_{10}$) alkoxy group;
 a halo($C_1$-$C_{10}$)alkoxy group; a
 —COOR;
 —NR—CO—$R'$;
 —$CONRR'$;
 —NR—$SO_2$—$R'$;
 a heterocycle group; or
 a solubilising group,
  wherein R and R' are each independently selected from the group consisting of
   hydrogen,
   an aryl group,
   a heteroaryl group, and
   a ($C_1$-$C_{10}$)alkyl group that is optionally substituted with at least one heteroatom optionally substituted with a ($C_1$-$C_{10}$)alkyl group that is optionally substituted with a solubilising group;
$R_3$ is
 hydrogen;
 halogen;
 cyano;
 a ($C_1$-$C_{10}$)alkyl group;
 a ($C_1$-$C_{10}$)alkoxy group;
 —$CF_3$;
 —$NRR'$;
 —NR—CO—$R'$;
 —$CONRR'$;
 a heterocycle group; or
 a solubilising group;
  wherein R and R' are each independently hydrogen or a ($C_1$-$C_{10}$) alkyl group optionally substituted with at least one heteroatom optionally substituted with a (C$_1$-C$_{10}$)alkyl group that is optionally substituted with a solubilising group;

Q is O or S;

W is N or CR$_4$;
  wherein R$_4$ is
    hydrogen;
    cyano;
    —CF$_3$;
    halogen;
    a (C$_1$-C$_{10}$)alkyl group that is optionally substituted with at least one heteroatom optionally substituted with a (C$_1$-C$_{10}$)alkyl group that is optionally substituted with a solubilising group;
    a (C$_1$-C$_{10}$)alkoxy group;
    a halo(C$_1$-C$_{10}$)alkoxy group;
    a solubilising group;
    a heterocycle;
    —CO—NRR';
    —SO$_2$—NRR';
    NRR';
    —NR—CO—R'; or
    —NR—SO$_2$R';
      wherein R and R' are each independently hydrogen or a (C$_1$-C$_{10}$)alkyl group that is optionally substituted with at least one heteroatom optionally substituted with a (C$_1$-C$_{10}$)alkyl group that is optionally substituted with a solubilising group or a heterocycle group;

X is N or CR$_5$;
  wherein R$_5$ is
    hydrogen;
    cyano;
    halogen;
    a (C$_1$-C$_{10}$)alkyl group;
    a (C$_1$-C$_{10}$)alkoxy group;
    —CO—OR; or
    —CO—NRR';
      wherein R and R' are each independently hydrogen or a (C$_1$-C$_{10}$)alkyl group optionally substituted with at least one heteroatom optionally substituted with a (C$_1$-C$_{10}$)alkyl that is optionally substituted with a solubilising group or a heterocycle group;

M is C or N;

V is CH$_2$; CR$_7$; or NR$_7$;
  wherein R$_7$ is hydrogen or a (C$_1$-C$_{10}$)alkyl group optionally substituted with a solubilising group or a heterocycle group;

Y is N; CR$_8$; or CR$_8$R$_9$;

Z is
  N;
  NR$_8$;
  CR$_8$; or
  CR$_8$R$_9$,
    wherein R$_8$ is
      hydrogen;
      a (C$_1$-C$_{10}$)alkyl group; or
      a (C$_1$-C$_{10}$)alkoxy group; and
    R$_9$ is hydrogen or a (C$_1$-C$_{10}$)alkyl group.

3. A compound according to claim 1 of formula (III):

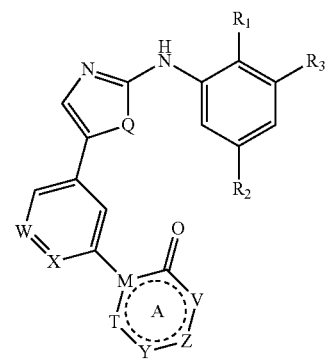

(III)

or a pharmaceutically acceptable salt thereof, wherein
ring A is a six member heterocycle ring;

R$_1$ is
  hydrogen;
  halogen;
  a (C$_1$-C$_{10}$)alkyl group; or
  a (C$_1$-C$_{10}$)alkoxy group;

R$_2$ is
  halogen;
  an aryl group;
  a halo(C$_1$-C$_{10}$)alkyl;
  a (C$_1$-C$_{10}$)alkyl group that is optionally substituted with at least one heteroatom optionally substituted with a halo(C$_1$-C$_{10}$)alkyl or (C$_1$-C$_{10}$)alkyl group that is optionally substituted with a solubilising group;
  a (C$_1$-C$_{10}$)alkoxy group;.
  a halo(C$_1$-C$_{10}$)alkoxy group;
  —COOR;
  NRR';
  —NR—CO—R';
  —CONRR';
  —NR—SO$_2$—R';
  a heterocycle group; or
  a solubilising group,
    wherein R and R' are each independently selected from the group consisting of
      hydrogen,
      an aryl group,
      a heteroaryl group, and
      a (C$_1$-C$_{10}$)alkyl group that is optionally substituted with at least one heteroatom optionally substituted with a (C$_1$-C$_{10}$)alkyl group that is optionally substituted with a solubilising group;

R$_3$ is
  hydrogen;
  halogen;
  cyano;
  a (C$_1$-C$_{10}$)alkyl group;
  a (C$_1$-C$_{10}$)alkoxy group;
  —CF$_3$;
  NRR';
  NR—CO—R';
  —CONRR';
  a heterocycle group; or
  a solubilising group,
    wherein R and R' are each independently hydrogen or (C$_1$-C$_{10}$)alkyl group that is optionally substituted with at least one heteroatom optionally substituted with a (C$_1$-C$_{10}$)alkyl group that is optionally substituted with a solubilising group;

Q is O or S;
W is N or CR$_4$;
  wherein R$_4$ is
    hydrogen;
    cyano;
    —CF$_3$;
    halogen;
    a (C$_1$-C$_{10}$)alkyl group optionally substituted with at least one heteroatom optionally substituted with a (C$_1$-C$_{10}$)alkyl group optionally substituted with a solubilising group;
    a (C$_1$-C$_{10}$)alkoxy group;
    a halo(C$_1$-C$_{10}$)alkoxy group;
    a solubilising group;
    a heterocycle;
    —CO—NRR';
    —SO$_2$—NRR';
    —NR—CO—R'; or
    —NR—SO$_2$R',
      wherein R and R' are each independently hydrogen or (C$_1$-C$_{10}$)alkyl group optionally substituted with at least one heteroatom optionally substituted with a (C$_1$-C$_{10}$)alkyl group optionally substituted with a solubilising group or a heterocycle group;
X is N or CR$_5$;
  wherein R$_5$ is
    hydrogen;
    cyano;
    halogen;
    a (C$_1$-C$_{10}$)alkyl group;
    a (C$_1$-C$_{10}$)alkoxy group;
    —CO—OR; or
    —CO—NRR',
      wherein R and R' are each independently hydrogen or a (C$_1$-C$_{10}$)alkyl group that is optionally substituted with at least one heteroatom optionally substituted with a (C$_1$-C$_{10}$)alkyl group that is optionally substituted with a solubilising group or a heterocycle group;
M is C or N;
V is
  N;
  CH$_2$;
  CR$_7$; or
  NR$_7$;
    wherein R$_7$ is
      hydrogen;
      cyano; or
      a (C$_1$-C$_{10}$)alkyl group optionally substituted with a solubilising group or a heterocycle group;
Y is N; CR$_8$; or CR$_8$R$_9$;
Z is N; CR$_8$; or CR$_8$R$_9$;
T is
  N;
  C=O;
  CR$_8$; or
  CR$_8$R$_9$;
    wherein R$_8$ is
      hydrogen;
      halogen;
      a hydroxyl group;
      a (C$_1$-C$_{10}$)alkyl group; or
      a (C$_1$-C$_{10}$)alkoxy; and
R$_9$ is hydrogen or a (C$_1$-C$_{10}$)alkyl group.

4. A compound according to claim 1, or a pharmaceutically acceptable salt thereof, wherein:
R$_1$ is H or a (C$_1$-C$_6$)alkyl;
R$_2$ is
  a halogen;
  COOH;
  a (C$_1$-C$_6$)alkyl optionally substituted with
    a —NR$_{10}$R$_{11}$ group,
    OH, or
    a (C$_1$-C$_4$)alkoxy optionally substituted with OH,
      wherein R$_{10}$ and R$_{11}$ are each independently H, (C$_1$-C$_4$)alkyl optionally substituted with amino, (C$_1$-C$_4$)alkylamino, or di(C$_1$-C$_4$)alkylamino, or
      R$_{10}$ and R$_{11}$ form, together with nitrogen to which they are bonded, a 5- or 6-membered heterocycloalkyl group containing 1 or 2 heteroatoms selected from the group consisting of O, S, and N;
  (C$_1$-C$_6$)alkoxy optionally substituted with OH, a (C$_1$-C$_4$)alkoxy, or a —NR$_{12}$R$_{13}$ group,
    wherein R$_{12}$ and R$_{13}$ are each independently H or (C$_1$-C$_4$)alkyl, or
    R$_{12}$ and R$_{13}$ form, together with nitrogen to which they are bonded, a 5- or 6-membered heterocycloalkyl group containing 1 or 2 heteroatoms selected from the group consisting of O, S, and N, said heterocycloalkyl being optionally substituted with from 1 to 3 (C$_1$-C$_4$)alkyl groups;
  a —OR$_{14}$ group,
    wherein R$_{14}$ is a 5- or 6-membered heterocycloalkyl group containing 1 or 2 heteroatoms selected from the group consisting of O, S, and N, said heterocycloalkyl being optionally substituted with from 1 to 3 (C$_1$-C$_4$) alkyl groups;
  a —CONR$_{15}$R$_{16}$ group;
    wherein R$_{15}$ and R$_{16}$ are each independently H or a (C$_1$-C$_4$)alkyl optionally substituted with a (C$_1$-C$_4$) alkoxy or with a 5- or 6-membered heterocycloalkyl group containing 1 or 2 heteroatoms selected from the group consisting of O, S, and N, or
    R$_{15}$ and R$_{16}$ form, together with nitrogen to which they are bonded, a 5- or 6-membered heterocycloalkyl group containing 1 or 2 heteroatoms selected from the group consisting of O, S, and N;
  a —NR$_{17}$R$_{18}$ group;
    wherein R$_{17}$ is H or (C$_1$-C$_4$)alkyl, and
    R$_{18}$ is H;
    a (C$_1$-C$_4$)alkyl optionally substituted with (C$_1$-C$_4$) alkoxy; or a 5- or 6-membered heteroaryl group containing from 1 to 3 heteroatoms selected from the group consisting of O, S, and N;
  a —NR$_{19}$COR$_{20}$ group,
    wherein R$_{19}$ is H or (C$_1$-C$_4$)alkyl, and
    R$_{20}$ is
      H or
      a (C$_1$-C$_4$)alkyl optionally substituted with
        amino,
        a (C$_1$-C$_4$)alkylamino,
        di(C$_1$-C$_4$)alkylamino, or
        a 5- or 6-membered heterocycloalkyl group containing 1 or 2 heteroatoms selected from the group consisting of O, S, and N, said heterocycloalkyl being optionally substituted with 1 to 3 (C$_1$-C$_4$)alkyls; or
  a 5- or 6-membered heterocycloalkyl or heteroaryl group containing 1 or 2 heteroatoms selected from the group consisting of O and N, said heterocycloalkyl or the heteroaryl being optionally substituted with an oxo group or with a ($C_1$-$C_4$)alkyl group optionally substituted with amino, ($C_1$-$C_4$)alkylamino, or di($C_1$-$C_4$)alkylamino;

$R_3$ is
H;
cyano;
$CF_3$;
halogen;
a ($C_1$-$C_4$)alkylgroup; or
a ($C_1$-$C_4$)alkoxy group;

Q is O or S;
W is N or $CR_{21}$,
wherein $R_{21}$ is
H,
halogen,
CN,
$CF_3$,
$OCF_3$,
a ($C_1$-$C_4$)alkyl optionally substituted with a 5- or 6-membered heterocycloalkyl group containing 1 or 2 heteroatoms selected from the group consisting of O and N,
a ($C_1$-$C_4$)alkoxy,
a —O($CH_2$)$_n$$R_{22}$ group;
wherein n is 0, 1, 2, or 3, and
$R_{22}$ is
H,
a ($C_1$-$C_4$)alkoxy,
a —$NR_{22a}R_{22b}$ group,
wherein $R_{22a}$ and $R_{22b}$ are each independently H or a ($C_1$-$C_4$)alkyl, or
5- or 6-membered heterocycloalkyl group containing 1 or 2 heteroatoms selected from the group consisting of O and N, said heterocycloalkyl being optionally substituted with 1 to 3 ($C_1$-$C_4$) alkyl groups,
a —$NR_{23}R_{24}$ group,
wherein $R_{23}$ and $R_{24}$ are each independently H or a ($C_1$-$C_4$)alkyl optionally substituted with a ($C_1$-$C_4$) alkoxy group,
$R_{24}$ can also represent a —$SO_2$($C_1$-$C_4$)alkyl group, or
$R_{23}$ and $R_{24}$ form, together with nitrogen to which they are bonded, a 5- or 6-membered heterocycloalkyl or heteroaryl group containing 1 or 2 heteroatoms selected from the group consisting of O, S, and N, said heterocycloalkyl being optionally substituted with from 1 to 3 ($C_1$-$C_4$)alkyl groups;

X is N or $CR_{25}$,
wherein $R_{25}$ is
H,
CN,
a ($C_1$-$C_4$)alkylgroup, or
a —COO($C_1$-$C_4$)alkyl group; and A is
a 5- or 6-membered heterocycloalkyl or heteroaryl group containing from 1 to 3 heteroatoms selected from the group consisting of O and N, said heterocycloalkyl or the heteroaryl being optionally substituted with from 1 to 3 substituents selected from the group consisting of
an oxo group,
a halogen,
a ($C_1$-$C_4$)alkyl optionally substituted with amino, ($C_1$-$C_4$)alkylamino, di($C_1$-$C_4$)alkylamino, or a 5- or 6-membered heterocycloalkyl group containing 1 or 2 heteroatoms selected from the group consisting of O and N; or
a ($C_1$-$C_4$)alkoxy group.

5. A compound according to claim 1, or a pharmaceutically acceptable salt thereof, wherein:
$R_1$ is H or a ($C_1$-$C_4$)alkylgroup;
$R_2$ is
a ($C_1$-$C_4$)alkyl group optionally substituted with ($C_1$-$C_4$)alkoxy;
a ($C_1$-$C_4$)alkoxy group optionally substituted with OH or a —$NR_{12}R_{13}$ group,
wherein $R_{12}$ and $R_{13}$ are each independently H or ($C_1$-$C_4$)alkyl, or
$R_{12}$ and $R_{13}$ form, together with nitrogen to which they are bonded, a 5- or 6-membered heterocycloalkyl group containing 1 or 2 heteroatoms selected from the group consisting of O and N; or
a —$CONR_{15}R_{16}$ group,
wherein $R_{15}$ and $R_{16}$ are each independently H or a ($C_1$-$C_4$)alkyl;
$R_3$ is H or a ($C_1$-$C_4$)alkyl;
Q is O;
W is N or $CR_{21}$,
wherein $R_{21}$ is H,
$OCF_3$,
a ($C_1$-$C_4$)alkyl group,
a ($C_1$-$C_4$)alkoxy group, or
a O($CH_2$)$_n$$R_{22}$ group,
wherein n is 0, 1, or 2, and
$R_{22}$ is a 5- or 6-membered heterocycloalkyl group containing 1 or 2 heteroatoms selected from the group consisting of O and N;
X is N or CH; and
A is a 5- or 6-membered heterocycloalkyl group or a heteroaryl group containing 1 or 2 nitrogen atoms, said heterocycloalkyl or the heteroaryl being optionally substituted with from 1 to 3 ($C_1$-$C_4$)alkyl groups.

6. A compound according to claim 1, wherein the solubilising group is selected from the group consisting of morpholinyl, piperidinyl, N—($C_1$-$C_6$)alkyl piperidinyl, N-(4-piperidinyl)piperidinyl, 4-(1-piperidinyl)piperidinyl, 1-pyrrolidinylpiperidinyl, 4-morpholinopiperidinyl, 4-(N-methyl-1-piperazinyl)piperidinyl, piperazinyl, N—($C_1$-$C_6$) alkylpiperazinyl, N-($C_3$-$C_6$)cycloalkyl piperazinyl, pyrrolidinyl, N—($C_1$-$C_6$)alkyl pyrrolidinyl, diazepinyl, N—($C_1$-$C_6$)alkyl azepinyl, homopiperazinyl, N-methyl homopiperazinyl, N-ethyl homopiperazinyl, and imidazolyl.

7. A compound according to claim 1, or a pharmaceutically acceptable salt thereof, selected from the group consisting of:
1- {4-[2-((5-Ethoxymethyl)-2-methyl-phenylamino)-oxazol-5-yl]-pyridin-2-yl}-imidazolidin-2-one;
1-{3-[2-((5-Ethoxymethyl)-2-methyl-phenylamino)-oxazol-5-yl]-5-methoxy-phenyl}-4,4-dimethyl-imidazolidin-2-one;
1-(3-{2-[5-(2-Hydroxy-ethoxy)-2-methyl-phenylamino]-oxazol-5-yl}-5-methyl-phenyl) -imidazolidin-2-one;
1-(4-{2-[5-(2-Hydroxy-ethoxy)-2-methyl-phenylamino]-oxazol-5-yl}-pyridin-2-yl) -imidazolidin-2-one;
1-(4-{2-[2-Methyl-5-(2-morpholin-4-yl-ethoxy) -phenylamino]-oxazol-5-yl}-pyridin-2-yl)-imidazolidin-2-one;
1-{4-[2-((5-Methoxymethyl)-2-methyl-phenylamino)-oxazol-5-yl]-pyridin-2-yl}-4-methyl-imidazolidin-2-one;
4-Methyl-1-(4-{2-[2-methyl-5-(2-morpholin-4-yl-ethoxy)-phenylamino]-oxazol-5-yl}-pyridin-2-yl)-imidazolidin-2-one;

1-(3-Methyl-5-{2-[2-methyl-5-(2-morpholin-4-yl-ethoxy)-phenylamino]-oxazol-5-yl}-phenyl)-imidazolidin-2-one;

1-(4-{2-[2-Methyl-5-(3-morpholin-4-yl-propoxy)-phenylamino]-oxazol-5-yl}-pyridin-2-yl)-imidazolidin-2-one;

1-{3-[2-((5-Ethoxymethyl)-2-methyl-phenylamino)-oxazol-5-yl]-5-methoxy-phenyl}-imidazolidin-2-one;

1-(3-Methoxy-5-{2-[2-methyl-5-(2-morpholin-4-yl-ethoxy)-phenylamino]-oxazol-5-yl}-phenyl)-imidazolidin-2-one;

1-{3-[2-((5-Ethoxymethyl)-2-methyl-phenylamino)-oxazol-5-yl]-5-methoxy-phenyl}-4-methyl-imidazolidin-2-one;

1-{3-tert-Butoxy-5-[2-((5-methoxymethyl)-2-methyl-phenylamino)-oxazol-5-yl]-phenyl}-imidazolidin-2-one;

1-(3-{2-[5-(2-Hydroxy-ethoxy)-2-methyl-phenylamino]-oxazol-5-yl}-5-methoxy-phenyl)-imidazolidin-2-one;

1-(3-Methoxy-5-{2-[2-methyl-5-(2-morpholin-4-yl-ethoxy)-phenylamino]-oxazol-5-yl}-phenyl)-4-methyl-imidazolidin-2-one;

1-{3-Isopropoxy-5-[2-((5-methoxymethyl)-2-methyl-phenylamino)-oxazol-5-yl]-phenyl}-imidazolidin-2-one;

1-(3-{2-[5-(2-Hydroxy-ethoxy)-2-methyl-phenylamino]-oxazol-5-yl}-5-isopropoxy-phenyl)-imidazolidin-2-one;

1-(3-Isopropoxy-5-{2-[5-(2-methoxy-ethyl)-2-methyl-phenylamino]-oxazol-5-yl}-phenyl)-imidazolidin-2-one;

1-(3-(2-(2-methyl-5-(2-morpholinoethoxy)phenylamino)oxazol-5-yl)-5-(trifluoromethoxy)phenyl)imidazolidin-2-one;

1-(3-(2-(5-methoxy-2-methylphenylamino)oxazol-5-yl)-5-(trifluoromethoxy)phenyl)imidazolidin-2-one;

1-(3-{2-[5-(2-Hydroxy-ethoxymethyl)-2-methyl-phenylamino]-oxazol-5-yl}-5-methyl-phenyl)-imidazolidin-2-one;

3-{5-[3-Isopropoxy-5-(2-oxo-imidazolidin-1-yl)-phenyl]-oxazol-2-ylamino}-N-(2-methoxy-ethyl)-4-methyl-benzamide;

1-(3-(2-(5-(ethoxymethyl)-2-methylphenylamino)oxazol-5-yl)-5-(trifluoromethoxy)phenyl)imidazolidin-2-one;

3-{3-[2-(3,5-Dimethyl-phenylamino)-oxazol-5-yl]-5-trifluoromethoxy-phenyl}-4-methyl-1H-pyridin-2-one;

3-{3-[2-(3,5-Dimethyl-phenylamino)-oxazol-5-yl]-5-methoxy-phenyl}-1H-pyridin-2-one;

3-{3-[2-(3,5-Dimethyl-phenylamino)-oxazol-5-yl]-5-isopropoxy-phenyl}-4-methyl-1H-pyridin-2-one;

4-[2-(5-(Ethoxymethyl)-2-methyl-phenylamino)-oxazol-5-yl]-4'-methyl-1'H-[2,3]bipyridinyl-2'-one;

3-[3-[2-(3,5-Dimethyl-phenylamino)-oxazol-5-yl]-5-(2-morpholin-4-yl-ethoxy)-phenyl]-4-methyl-1H-pyridin-2-one;

4'-Methyl-4-{2-[2-methyl-5-(2-morpholin-4-yl-ethoxy)-phenylamino]-oxazol-5-yl}-1'H-[2,3]bipyridinyl-2'-one;

4-[2-(3,5-Dimethyl-phenylamino)-oxazol-5-yl]-4'-methyl-6-(2-morpholin-4-yl-ethoxy)-1'H-[2,3]bipyridinyl-2'-one;

1-{3-[2-((5-Ethoxymethyl)-2-methyl-phenylamino)-oxazol-5-yl]-5-isopropoxy-phenyl}-imidazolidin-2-one; and 4'-Methyl-4-{2-[2-methyl-5-(3-morpholin-4-yl-propoxy)-phenylamino]-oxazol-5-yl}-1'H-[2,3]bipyridinyl-2'-one; and pharmaceutically acceptable salts thereof.

8. A pharmaceutical composition comprising a compound according to claim 1 or a pharmaceutically acceptable salt thereof, and at least one pharmaceutically acceptable excipient.

9. A cosmetic composition for topical administration comprising a compound according to claim 1 or a salt thereof, which is acceptable for cosmetics, and at least one excipient, which is acceptable for cosmetics.

10. The pharmaceutical composition according to claim 8, further comprising another active pharmaceutical agent.

11. A method for treating a protein kinase-related disease comprising administering to a subject in need thereof an effective amount of a compound capable of inhibiting at least one type selected from the group consisting of a wild type c-Kit and mutant c-Kit, wherein said compound is a compound according to claim 1 or a pharmaceutically acceptable salt thereof.

12. The method according to claim 11, further comprising simultaneously or sequentially administering to said subject an effective amount of another active pharmaceutical agent.

13. The compound according to claim 4, wherein Q is O.

14. The method according to claim 11, wherein the mutant c-Kit is c-Kit D816V.

15. The method according to claim 11, wherein the disease is mastocytosis, mast cell leukemia, acute myelocytic leukemia, or testicular cancer.

* * * * *